US010844114B2

(12) United States Patent
DiGiandomenico et al.

(10) Patent No.: US 10,844,114 B2
(45) Date of Patent: Nov. 24, 2020

(54) **ANTI-*PSEUDOMONAS* PSL BINDING MOLECULES AND USES THEREOF**

(71) Applicant: MedImmune Limited, Cambridge (GB)

(72) Inventors: Antonio DiGiandomenico, Gaithersburg, MD (US); Paul G. Warrener, Gaithersburg, MD (US); Charles K. Stover, Gaithersburg, MD (US); Bret Sellman, Gaithersburg, MD (US); Sandrine Guillard, Cambridge (GB); Ralph Minter, Cambridge (GB); Steven Rust, Cambridge (GB); Mladen Tomich, New York, NY (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 16/400,818

(22) Filed: May 1, 2019

(65) Prior Publication Data

US 2019/0322726 A1 Oct. 24, 2019

Related U.S. Application Data

(62) Division of application No. 15/192,072, filed on Jun. 24, 2016, now Pat. No. 10,370,436, which is a division of application No. 14/125,073, filed as application No. PCT/US2012/041538 on Jun. 8, 2012, now Pat. No. 9,403,901.

(60) Provisional application No. 61/613,317, filed on Mar. 20, 2012, provisional application No. 61/530,461, filed on Sep. 2, 2011, provisional application No. 61/495,460, filed on Jun. 10, 2011.

(51) Int. Cl.

| C12N 15/87 | (2006.01) |
|---|---|
| C12N 15/00 | (2006.01) |
| C12N 5/00 | (2006.01) |
| C12N 5/02 | (2006.01) |
| C12N 1/20 | (2006.01) |
| C07K 16/12 | (2006.01) |
| A61K 47/68 | (2017.01) |
| A61K 38/00 | (2006.01) |
| A61K 39/00 | (2006.01) |

(52) U.S. Cl.
CPC ...... *C07K 16/1214* (2013.01); *A61K 47/6811* (2017.08); *A61K 47/6835* (2017.08); *A61K 38/00* (2013.01); *A61K 2039/505* (2013.01); *C07K 2317/21* (2013.01); *C07K 2317/622* (2013.01); *C07K 2317/64* (2013.01); *C07K 2317/71* (2013.01); *C07K 2317/73* (2013.01); *C07K 2317/76* (2013.01); *C07K 2317/92* (2013.01)

(58) Field of Classification Search
CPC ........ C12N 15/70; C12N 15/86; A61K 38/00; A61K 39/00
See application file for complete search history.

(56) References Cited

U.S. PATENT DOCUMENTS

| 4,444,887 A | 4/1984 | Hoffmann |
|---|---|---|
| 4,683,195 A | 7/1987 | Mullis et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,658,570 A | 8/1997 | Newman et al. |
| 5,658,727 A | 8/1997 | Barbas et al. |
| 5,693,761 A | 12/1997 | Queen et al. |
| 5,693,762 A | 12/1997 | Queen et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,821,047 A | 10/1998 | Garrard et al. |
| 5,892,019 A | 4/1999 | Schlom et al. |
| 5,939,598 A | 8/1999 | Kucherlapati et al. |
| 5,969,108 A | 10/1999 | McCafferty et al. |

(Continued)

FOREIGN PATENT DOCUMENTS

| WO | WO-02/96948 A2 | 12/2002 |
|---|---|---|
| WO | WO-2007/024715 A2 | 3/2007 |

(Continued)

OTHER PUBLICATIONS

Paul, William E., Fundamental Immunology, 3rd Edition, Raven Press, New York, Chap. 8, pp. 292-295 (1993) (Year: 1993).*

(Continued)

*Primary Examiner* — Gary B Nickol
*Assistant Examiner* — Lakia J Jackson-Tongue
(74) *Attorney, Agent, or Firm* — Sterne, Kessler, Goldstein & Fox P.L.L.C.

(57) ABSTRACT

This disclosure relates to an anti-*Pseudomonas* Psl binding molecule and uses thereof, in particular in prevention and treatment of *Pseudomonas* infection. Furthermore, the disclosure provides compositions and methods for preventing and treating *Pseudomonas* infection.

21 Claims, 48 Drawing Sheets
Specification includes a Sequence Listing.

(56) References Cited

U.S. PATENT DOCUMENTS

| | | | |
|---|---|---|---|
| 6,150,584 | A | 11/2000 | Kucherlapati et al. |
| 6,180,370 | B1 | 1/2001 | Queen et al. |
| 6,420,140 | B1 | 7/2002 | Hori et al. |
| 6,458,592 | B1 | 10/2002 | Jakobovits et al. |
| 7,083,784 | B2 | 8/2006 | Dall'Acqua et al. |
| 7,112,324 | B1 | 9/2006 | Dorken et al. |
| 7,658,921 | B2 | 2/2010 | Dall'Acqua et al. |
| 8,642,039 | B2 | 2/2014 | Yarranton |
| 9,403,901 | B2 | 8/2016 | Digiandomenico et al. |
| 9,527,905 | B2 | 12/2016 | Sellman et al. |
| 9,580,509 | B2 | 2/2017 | Dimasi et al. |
| 9,845,348 | B2 | 12/2017 | Sellman et al. |
| 9,879,070 | B2 | 1/2018 | Sellman et al. |
| 10,370,436 | B2 | 8/2019 | Digiandomenico et al. |
| 10,597,493 | B2 | 3/2020 | Miyazaki et al. |
| 2002/0123057 | A1 | 9/2002 | Zauderer et al. |
| 2002/0146753 | A1 | 10/2002 | Ditzel et al. |
| 2003/0232387 | A1 | 12/2003 | Lu |
| 2008/0095775 | A1 | 4/2008 | Lewis et al. |
| 2008/0131423 | A1 | 6/2008 | Mori et al. |
| 2009/0191186 | A1 | 7/2009 | Bebbington et al. |
| 2009/0215992 | A1 | 8/2009 | Wu et al. |
| 2010/0150939 | A1 | 6/2010 | Blanchetot et al. |
| 2010/0166768 | A1 | 7/2010 | Sleeman et al. |
| 2010/0172862 | A1 | 7/2010 | Correia et al. |
| 2010/0272736 | A1 | 10/2010 | Baer et al. |
| 2011/0150896 | A1 | 6/2011 | Numata et al. |
| 2014/0227285 | A1 | 8/2014 | Digiandomenico et al. |
| 2014/0302038 | A1 | 10/2014 | Dimasi et al. |
| 2015/0023966 | A1 | 1/2015 | Digiandomenico et al. |
| 2015/0284450 | A1 | 10/2015 | Digiandomenico et al. |
| 2016/0115250 | A1 | 4/2016 | Digiandomenico et al. |
| 2016/0297872 | A1 | 10/2016 | DiGiandomenico et al. |
| 2017/0114151 | A1 | 4/2017 | Dimasi et al. |
| 2017/0129943 | A1 | 5/2017 | Sellman et al. |
| 2017/0183397 | A1 | 6/2017 | Digiandomenico et al. |
| 2018/0355026 | A1 | 12/2018 | Jafri et al. |
| 2019/0153076 | A1 | 5/2019 | Weiner et al. |
| 2019/0309095 | A1 | 10/2019 | Digiandomenico et al. |

FOREIGN PATENT DOCUMENTS

| | | | |
|---|---|---|---|
| WO | WO-2008/024188 | A2 | 2/2008 |
| WO | WO-2009/092011 | A1 | 7/2009 |
| WO | WO-2010/107778 | A1 | 9/2010 |
| WO | WO-2010/108153 | A2 | 9/2010 |
| WO | WO-2011/005481 | A1 | 1/2011 |
| WO | WO-2012/170807 | A2 | 12/2012 |
| WO | WO-2013/070565 | A1 | 5/2013 |
| WO | WO-2013/070615 | A1 | 5/2013 |
| WO | WO-2014/074470 | A1 | 5/2014 |
| WO | WO-2014/186358 | A2 | 11/2014 |

OTHER PUBLICATIONS

Rudikoff et al. (Proc. Natl. Acad. Sci. USA, 79(6):1979-1983, Mar. 1982) (Year: 1982).*
Colman P. M. (Research in Immunology, 145:33-36, 1994) (Year: 1994).*
Bendig M. M. (Methods: A Companion to Methods in Enzymology, 1995; 8:83-93) (Year: 1995).*
MacCallum et al. (J. Mol. Biol., 262, 732-745, 1996) (Year: 1996).*
Casset et al. (Biochemical and Biophysical Research Communications, 307:198-205, 2003 (Year: 2003).*
Hoppner, Horm Re. 2002, 58 Suppl. 3:7-15 (Year: 2002).*
Lodish et al., Mol. Cell Biol., 3rd ed. Scientific American Books, NY, 1995 (Year: 1995).*
Bailat et al., "Similarities and disparities between core-specific and 0-side-chain-specific antilipopolysaccharide monoclonal antibodies in models of endotoxemia and bacteremia in mice," Infect Immun., vol. 65, No. 2, pp. 811-814 (Feb. 1997).
Birkenmeier et al., "Polymyxin B-Conjugated a2-Macroglobulin as an Adjunctive Therapy to Sepsis: Modes of Action and Impact on Lethality," J. Pharmacal. Exp. Ther., vol. 318, No. 2, pp. 762-771 (May 2006).
Borlee et al., "Pseudomonas aeruginosa uses a cyclic-di-GMP-regulated adhesion to reinforce the biofilm extracellular matrix", Molecular Microbiology, vol. 75, No. 4, pp. 827-842 (2010).
Bucklin et al., "Differences in therapeutic efficacy among cell wall-active antibiotics in a mouse model of gram-negative sepsis," J. Infect Dis, vol. 172, No. 6, pp. 1519-1527 (Dec. 1995).
Byrd et al., "Genetic and biochemical analyses of the Pseudomonas aeruginosa Psi exopolysaccharide reveal overlapping roles for polysaccharide synthesis enzymes in Psi and LPS production", Mol. Microbiol, vol. 73, No. 4, pp. 622-638 (Aug. 2009).
Byrd et al., "The Pseudomonas aeruginosa Exopolysaccharide Psi Facilitates Surface Adherence and NF-KB Activation in A549 Cell," MBIO, vol. 1, Issue 3, e00140-10, pp. 1-4 (Jun. 29, 2010).
CDC, https://www.cdc.gov/hai/organisms/pseudomonas.html, accessed on Apr. 16, 2018.
Chang et al., "Synergistic effect of 4-hydroperoxycyclophosphamide and etoposide on a human promyelocytic leukemia cell line (HL-60) demonstrated by computer analysis", Cancer Research, vol. 45, No. 6, pp. 2434-2439 (1985).
Choi et al.,"A Tn7-based broad-range bacterial cloning and expression system," Nature Methods, vol. 2, No. 6, pp. 443-448 (Jun. 2005).
Craven et al., "Nosocomial pneumonia in mechanically ventilated adult patients: epidemiology and prevention in 1996", Semin Respir Infect, vol. 11, No. 1, pp. 32-53 (Mar. 1996).
Dall'Acqua, W. F., et al., "Properties of human IgG1s engineered for enhanced binding to the neonatal Fc receptor (FcRn)," J Biol Chem., vol. 281, Issue 33, pp. 23514-23524 (Aug. 18, 2006).
Digiandomenico, A. et al., "Intranasal immunization with heterologously expressed polysaccharide protects against multiple Pseudomonas aeruginosa infections," Proc Natl Acad Sci USA, vol. 104, No. 11, pp. 4624-4629 (Mar. 2007).
Digiandomenico, A., et al., "Identification of broadly protective human antibodies to Pseudomonas aeruginosa exopolysaccharide Psi by phenotypic screening," Journal of Experimental Medicine, vol. 209, No. 7, pp. 1273-1287 (2012).
Digiandomenico, A., et al., "Oral Vaccination of BALB/c Mice with *Salmonella enterica* Serovar Typhimurium Expressing Pseudomonas aeruginosa 0 Antigen Promotes Increased Survival in an Acute Fatal Pneumonia Model", Infect Immun., vol. 72, No. 12, p. 7012-7021 (Dec. 2004).
Dimasi, N. et al., "The design and characterization of oligospecific antibodies for simultaneous targeting of multiple disease mediators," J. Mol. Biol., vol. 393, No. 3, pp. 672-692 (Aug. 20, 2009).
Dixon, R.A. et al., "Polymyxin B and polymyxin B nonapeptide alter cytoplasmic membrane permeability in *Escherichia coli*", J. Antimicrob. Chemother, vol. 18, No. 5, pp. 557-563 (1986).
Drabick, J. J., et al., "Covalent Polymyxin B Conjugate with Human Immunoglobulin G as an Antiendotoxin Reagent", Antimicrobial Agents and Chemotherapy, vol. 42, No. 3, pp. 583-588 (Mar. 1998).
Drenkard, E., "Antimicrobial resistance of Pseudomonas aeruginosa biofilms", Microbes Infect, vol. 5, No. 13, pp. 1213-1219 (2003).
Dunn, D.L. et al., "Anticore endotoxin F(ab')2 equine immunoglobulin fragments protect against lethal effects of gram-negative bacterial sepsis.," Surgery, vol. 96, No. 2, pp. 440-446 (Aug. 1984).
Extended European Search Report in European Patent Application No. 12796646.3, dated Feb. 2, 2015.
Francois et al., "Safety and pharmacokinetics of an anti-PcrV PEGylated monoclonal antibody fragment in mechanically ventilated patients colonized with Pseudomonas aeruginosa: a randomized, double-blind, placebo-controlled trial," Critical Care Medicine, vol. 40, No. 8, pp. 1-7 (2012).
Frank et al., "Generation and Characterization of a Protective Monoclonal Antibody to Pseudomonas aeruginosa PcrV," The Journal of Infectious Diseases, vol. 186, No. 1, pp. 64-73 (Jul. 1, 2002).
Galanos et al., "Galactosamine-induced sensitization to the lethal effects of endotoxin," Proc Natl Acad Sci USA, vol. 76, No. 11, pp. 5939-5943 (Nov. 1979).

(56) References Cited

OTHER PUBLICATIONS

Greenspan et al., Defining epitopes: It's not as easy as it seems, Nat. Biotech., 17(10): 936-7 (Oct. 1999).
Guidet et al., "Endotoxemia and Bacteremia in Patients With Sepsis Syndrome in the Intensive Care Unit", Chest, vol. 106, No. 4, pp. 1194-1201 (Oct. 1994).
Hancock et al., "Antibiotic resistance in Pseudomonas aeruginosa: mechanisms and impact on treatment", Drug Resist Updates, vol. 3, No. 4, pp. 247-255 (Aug. 2000).
Hoang et al., "A broad-host-range Flp-FRT recombination system for site-specific excision of chromosomally-located DNA sequences: application for isolation of unmarked Pseudomonas aeruginosa mutants," Gene, vol. 212, No. 1, pp. 77-86 (May 28, 1998).
Huiqing et al., "Epitope Mapping of Monoclonal Antibodies using Synthetic Oligosaccharides Uncovers Novel Aspects of Immune Recognition of the Psl Exopolysaccharide of Pseudomonas aeruginosa," Chemistry—A European Journal, vol. 19, No. 51, pp. 17425-17431 (Dec. 16, 2013).
Jackson et al., "Identification of psl, a Locus Encoding a Potential Exopolysaccharide That Is Essential for Pseudomonas aeruginosa PAO1 Biofilm Formation", J. Bacteriol, vol. 186, No. 14, pp. 4466-4475 (Jul. 2004).
Ladner, Mapping the epitopes of antibodies, Biotechnol. Genet. Eng. Rev., 24:1-30 (2007).
Liu et al., "Three new major somatic antigens of Pseudomonas aeruginosa," J. Clin. Microbiol, vol. 28, No. 5, pp. 922-925 (May 1990).
Liu et al., "Survey of Heat-Stable, Major Somatic Antigens of Pseudomonas aeruginosa," Int. J. of Syst. And Evol. Microbiology, vol. 33, No. 2, pp. 256-264 (Apr. 1983).
Lyczak et al., "Establishment of Pseudomonas aeruginosa infection: lessons from a versatile opportunist", Microbes and Infect., vol. 2, No. 9, pp. 1051-1060 (Jul. 2000).
Ma et al., "Assembly and Development of the Pseudomonas aeruginosa Biofilm Matrix," PLOS Pathogens, vol. 5, Issue 3, 31000354, pp. 1-11 (Mar. 2009).
Ma et al., "Pseudomonas aeruginosa Psl Is a Galactose- and Mannose-Rich Exopolysaccharide", Journal of Bacteriology, vol. 189, No. 22, pp. 8353-8356 (Nov. 2007).
Mabry et al., "Therapeutic bispecific antibodies: The selection of stable single-chain fragments to overcome engineering obstacles", !drugs, vol. 13, No. 8, pp. 543-549 (2010).
Medimmune, LLC, International Preliminary Report on Patentability in International Patent Application No. PCT/US2012/041538, dated Dec. 10, 2013.
Medimmune, LLC, International Search Report and Written Opinion for International Patent Application No. PCT/US2012/41538, dated Jan. 25, 2013.
Miyazaki et al., "Role of exotoxin A in inducing severe Pseudomonas aeruginosa infections in mice," J Med Microbiol, vol. 43, No. 3, pp. 169-175 (1995).
Moriyama et al., "Protective effects of affinity-purified antibody and truncated vaccines against pseudomona aeruginosa v-antigen in neotropenic mile." Microbiol. Immunol. 53(11): 587-94 (2009).
Morrison et al., "Binding of polymyxin B to the lipid A portion of bacterial lipopolysaccharides," vol. 13, No. 10, pp. 813-818 (Oct. 1976).
Pier, "Pseudomonas aeruginosa: a key problem in cystic fibrosis", ASM News, vol. 64, No. 6, pp. 339-347 (1998).
Preston et al., "Rapid and sensitive method for evaluating Pseudomonas aeruginosa virulence factors during corneal infections in mice," Infection and Immunity, vol. 63, No. 9, pp. 3497-3501 (Sep. 1995).
Russian Patent Application No. 2018102606/10, Office Action, dated May 20, 2019.
Sawa et al., "Active and passive immunization with the Pseudomonas V antigen protects against type III intoxication and lung injury", Nature Medicine, vol. 5, No. 4, pp. 392-398 (Apr. 1999).
Schweizer, "Allelic exchange in Pseudomonas aeruginosa using novel ColE1-type vectors and a family of cassettes containing a portable oriT and the counter-selectable Bacillus subtilis sacB marker," Molecular Microbiology, vol. 6, No. 9, pp. 1195-1204 (May 1992).
Secher et al., "Anti-Pseudomonas aeruginosa serotype 011 LPS immunoglobulin M monoclonal antibody panobacumab (KBPA101) confers protection in a murine model of acute lung infection," J. Antimicrob. Chemother, vol. 66, No. 5, pp. 1100-1109 (2011).
Supplementary European Search Report in European Patent Application No. 12796646.3, dated Jan. 20, 2015.
Cao, Y. et al., "Bispecific Antibodies as Novel Bioconjugates," Bioconjugate Chemistry, 9(6):635-644, The American Chemical Society, United States (1998).
Digiandomenico, A., et al., "A multifunctional bispecific antibody protects against Pseudomonas aeruginosa," Science Translational Medicine, 6(262):262ra155, 12 pages, American Association for the Advancement of Science, United States (2014).
Digiandomenico, A., et al., "Controlling Pseudomonas Aeruginosa Infections Using a Novel Multifunction Antibody Deign," American Journal of Respiratory and Critical Care Medicine, 189(1): A5239, Abstract (2014).
Greenbaum, J.A., et al., "Towards a consensus on datasets and evaluation metrics for developing B-cell epitope prediction tools," Journal of Molecular Recognition, 20(2):75-82, John Wiley and Sons, United States (2007).
International Preliminary Report on Patentability for International Patent Application No. PCT/US2012/063639, dated May 13, 2014, 5 pages.
International Preliminary Report on Patentability for International Patent Application No. PCT/US2012/041538, dated Dec. 10, 2013, 7 pages.
International Preliminary Report on Patentability for International Patent Application No. PCT/US2012/063722, dated May 13, 2014, 7 pages.
International Search Report and Written Opinion for International Patent Application No. PCT/US2012/063639, dated Jan. 22, 2013, 7 pages.
International Search Report and Written Opinion for International Patent Application No. PCT/US2012/041538, dated Jan. 25, 2013, 11 pages.
International Search Report and Written Opinion for International Patent Application No. PCT/US2012/063722, dated Mar. 25, 2013, 11 pages.
Mikkelsen, Helga et al., "Key two-component regulatory systems that control biofilm formation in Pseudomonas aeruginosa", Environmental Microbiology, 13(7): 1666-1681, Society for Applied Microbiology and Blackwell Publishing Ltd., United States (2011).
Supplementary European Search Report for EP Application No. EP 12 84 7479, Munich, Germany, dated Feb. 2, 2016, 19 pages.
Thaden, J.T., et al., "Pseudomonas auruginosa Bacteremic Pateints Exhibit Nonprotective Antibody Titers Against Therapeutic Antibody Targets PcrV and Psl exopolysaccharide," J. Infectious Diseases, 213(4):640-648, Oxford University Press, England (2015).

\* cited by examiner

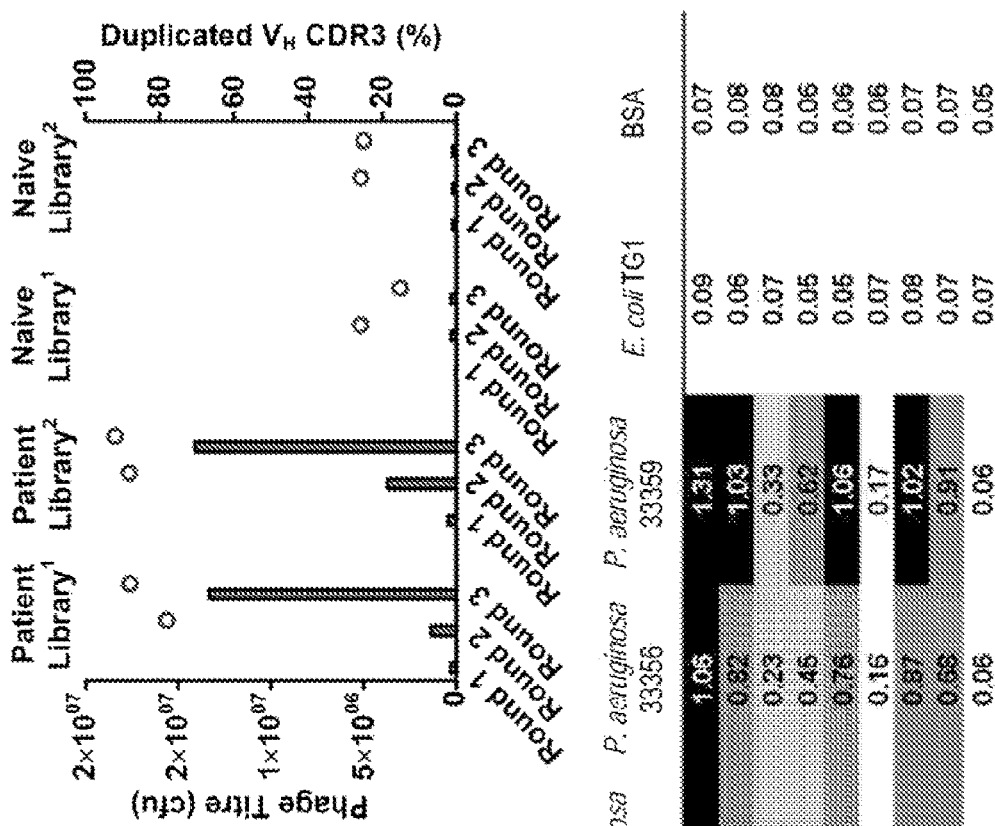

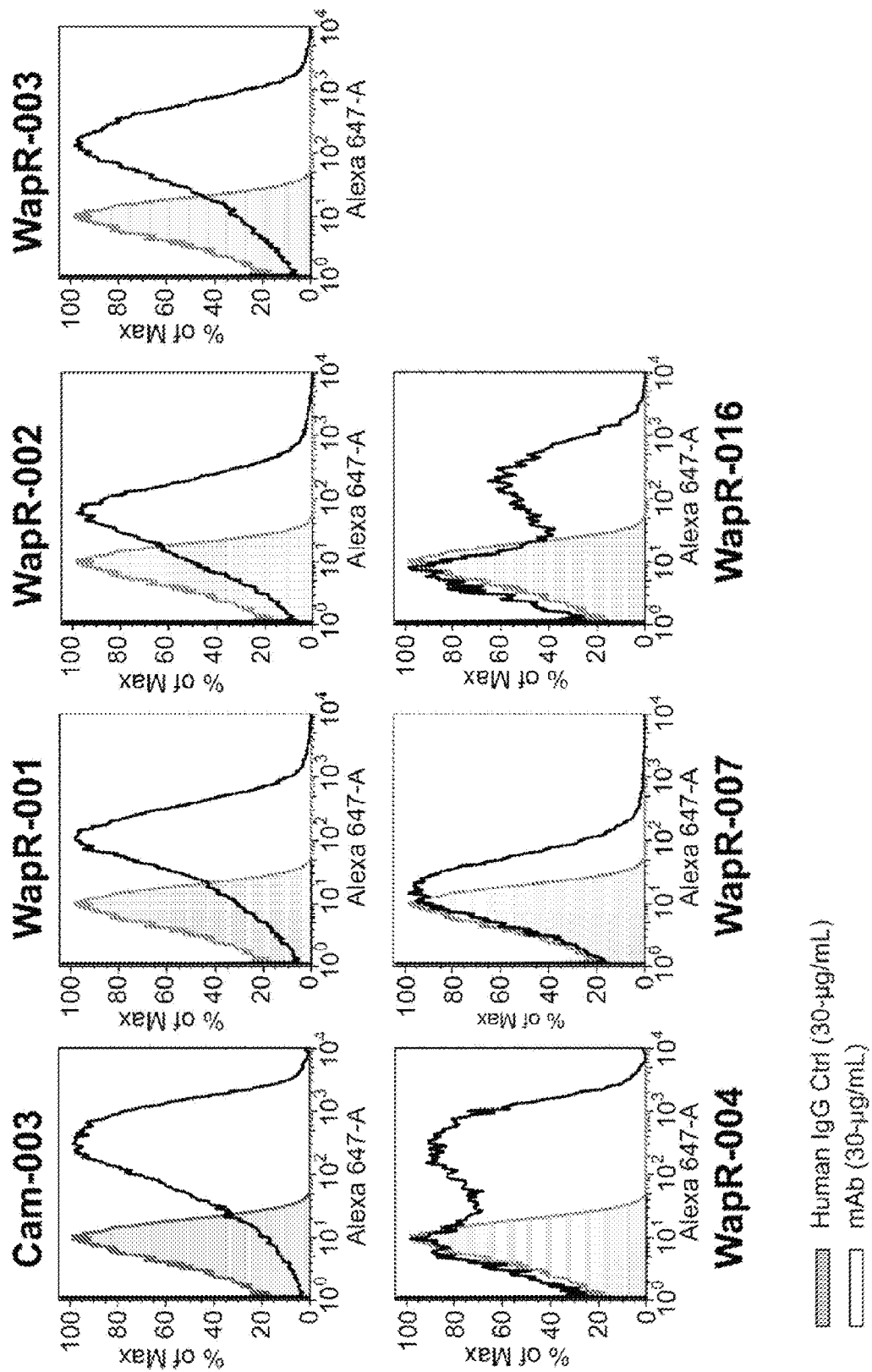

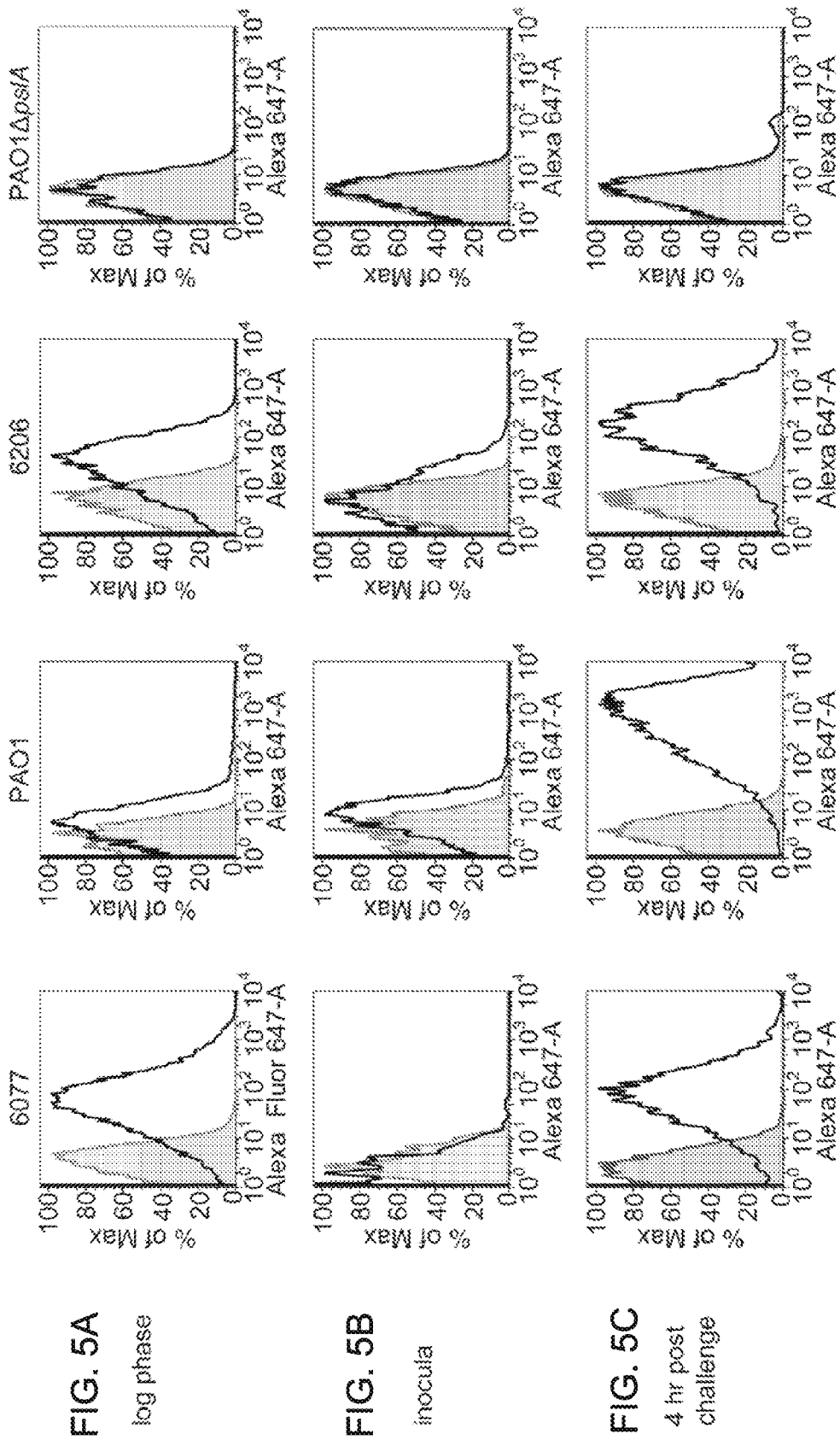
FIG. 5A log phase
FIG. 5B inocula
FIG. 5C 4 hr post challenge

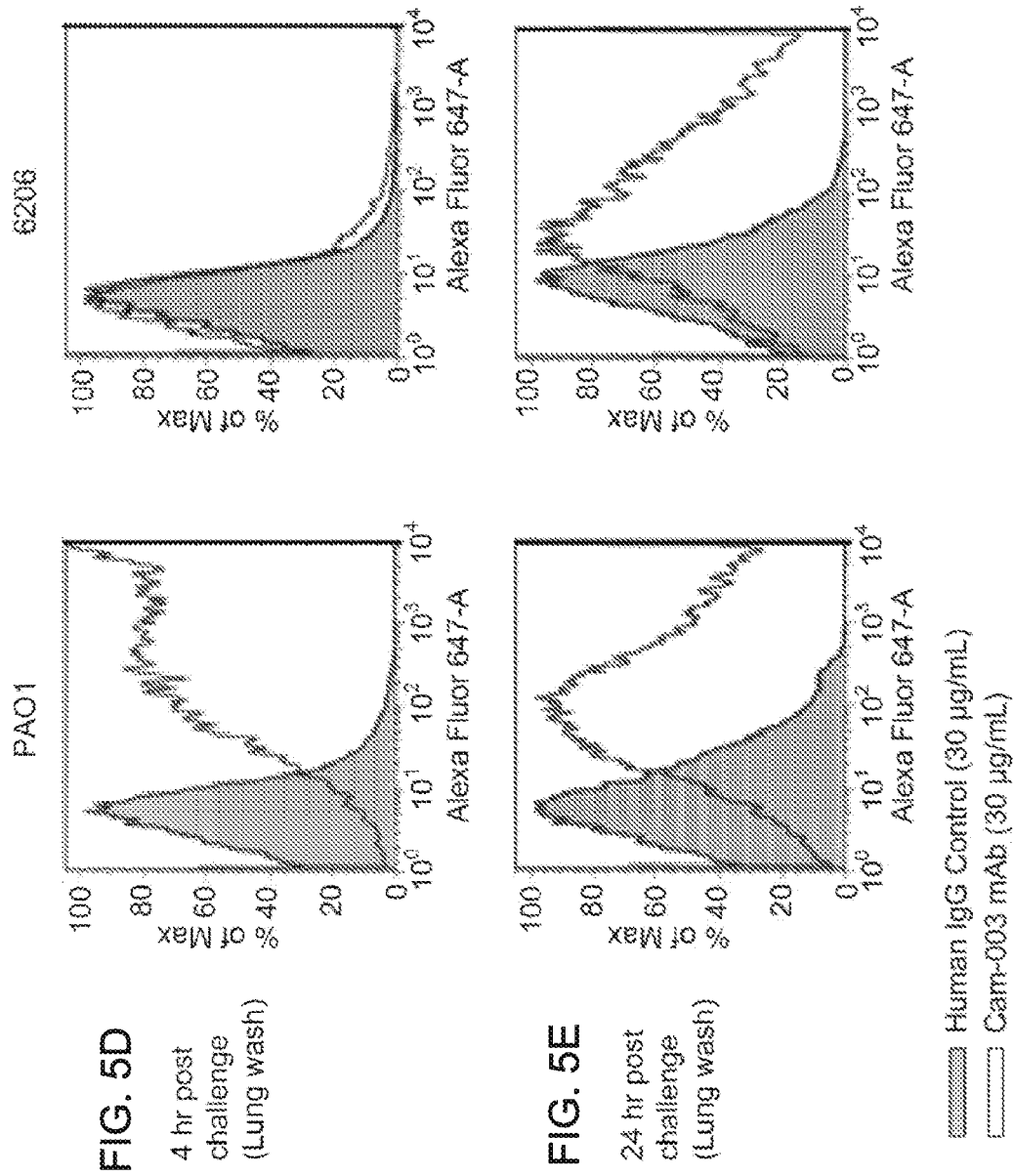

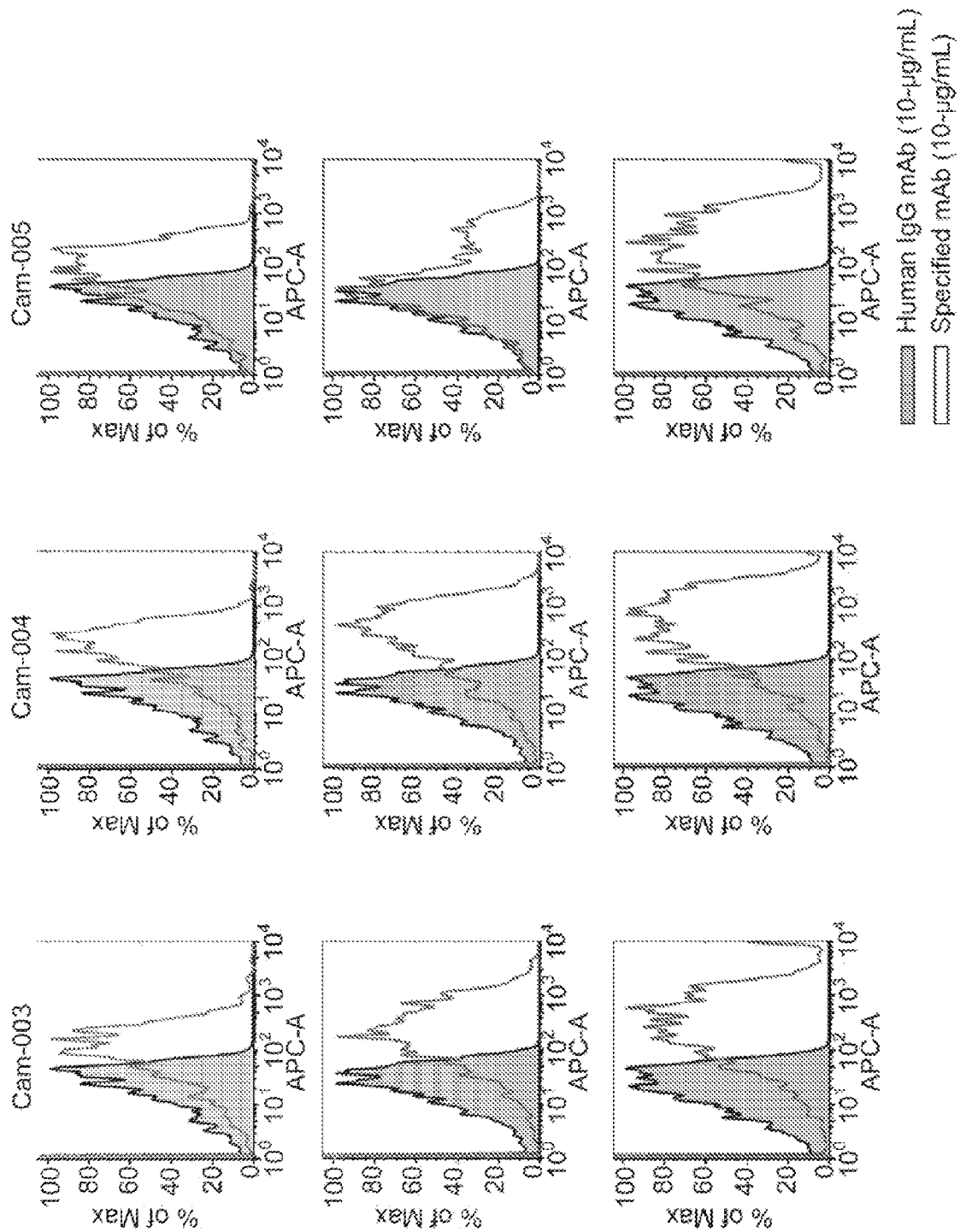

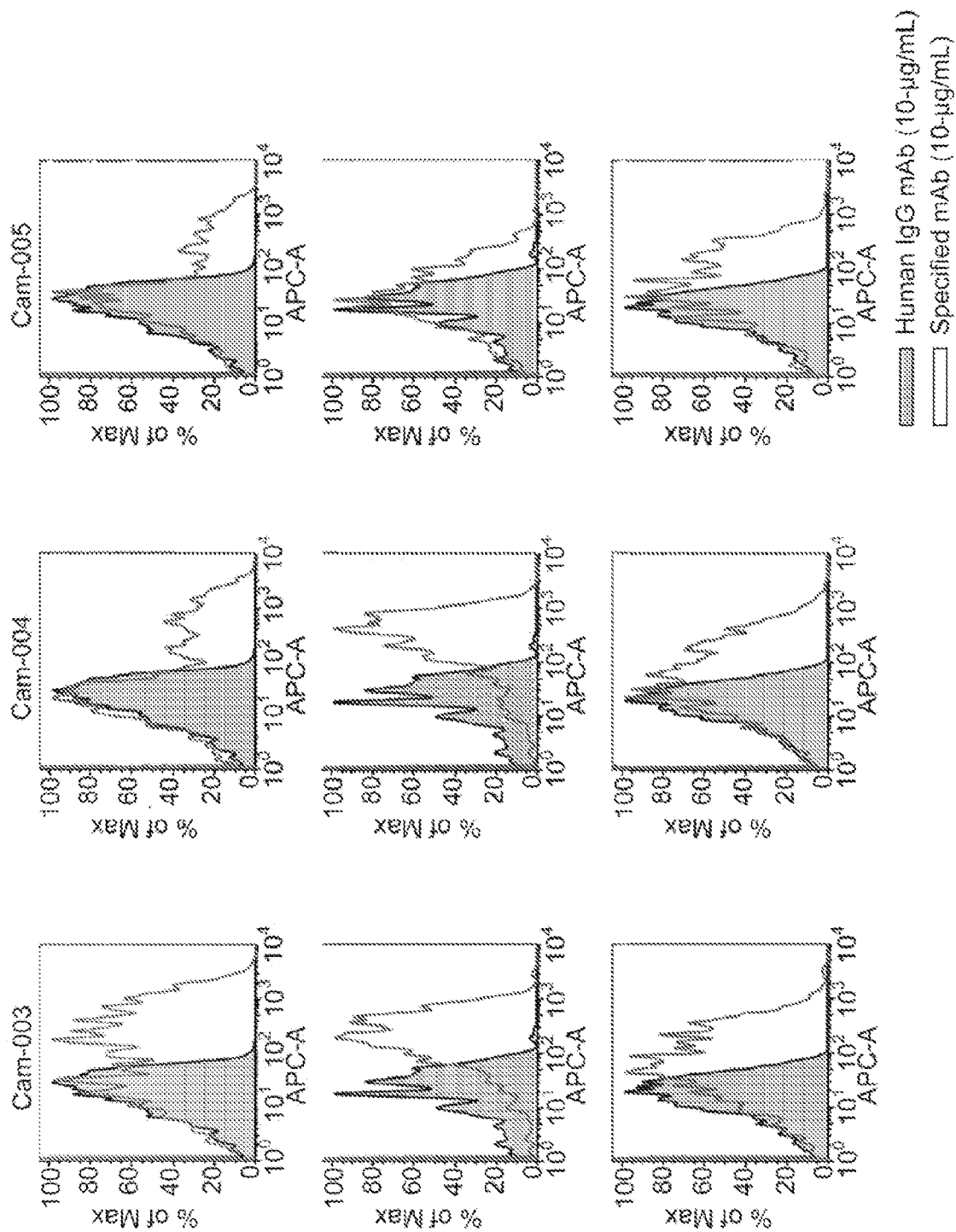
FIG. 5I 2410 (O6)
FIG. 5J 2764 (O11)
FIG. 5K 2757 (O11)

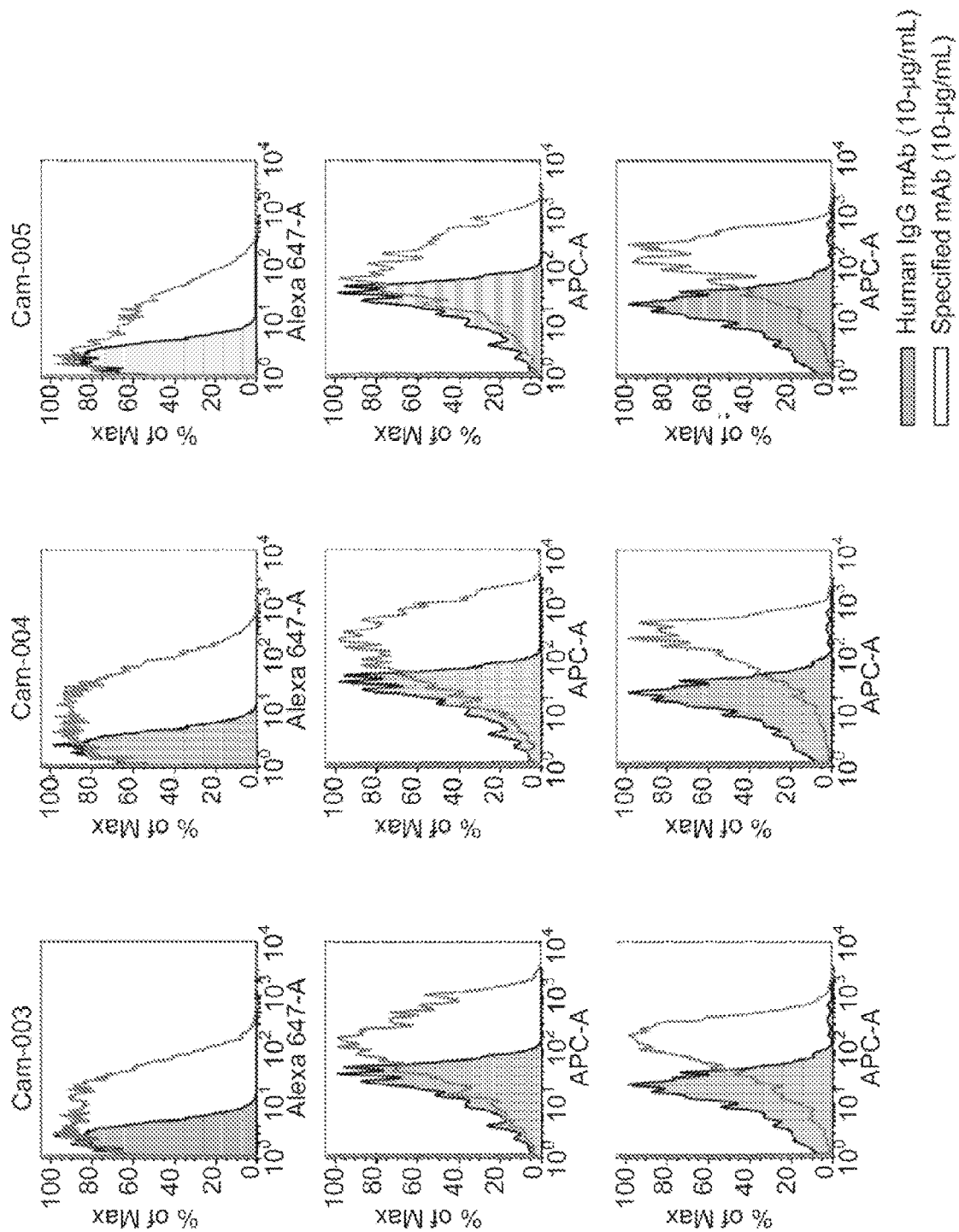
FIG. 5L 33356 (O9)
FIG. 5M 33348 (O1)
FIG. 5N 3039 (NT)

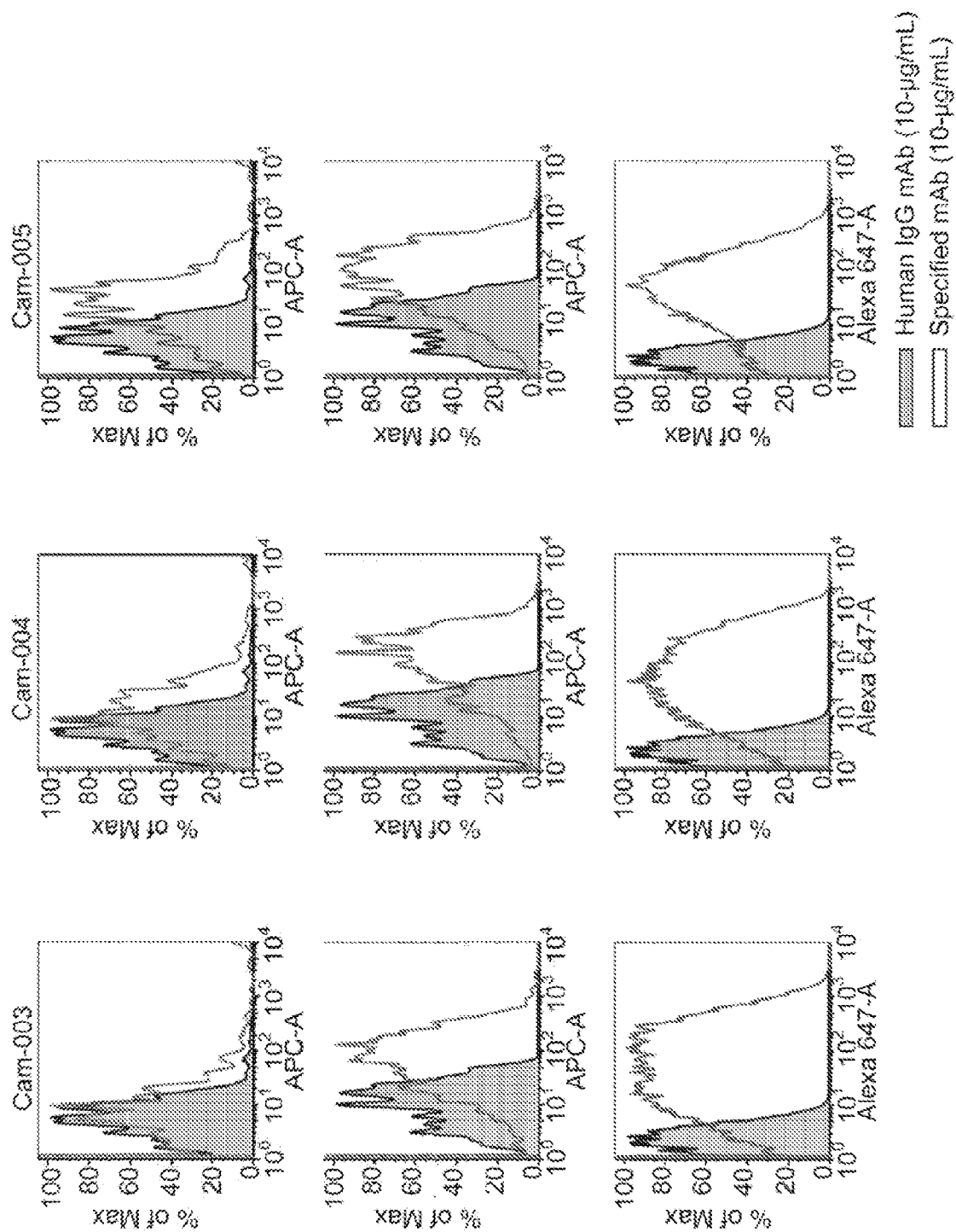

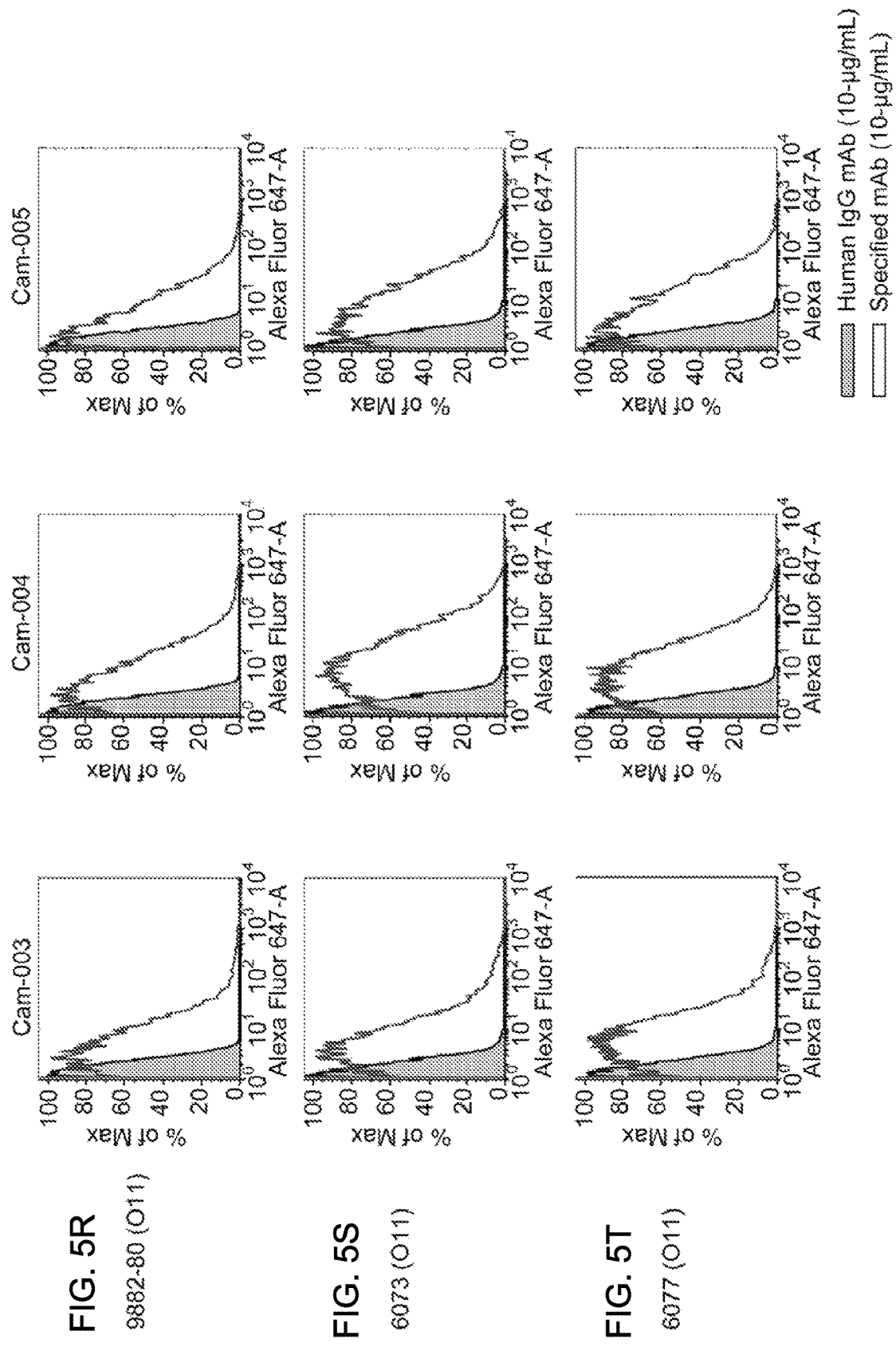
FIG. 5R 9882-80 (O11)
FIG. 5S 6073 (O11)
FIG. 5T 6077 (O11)

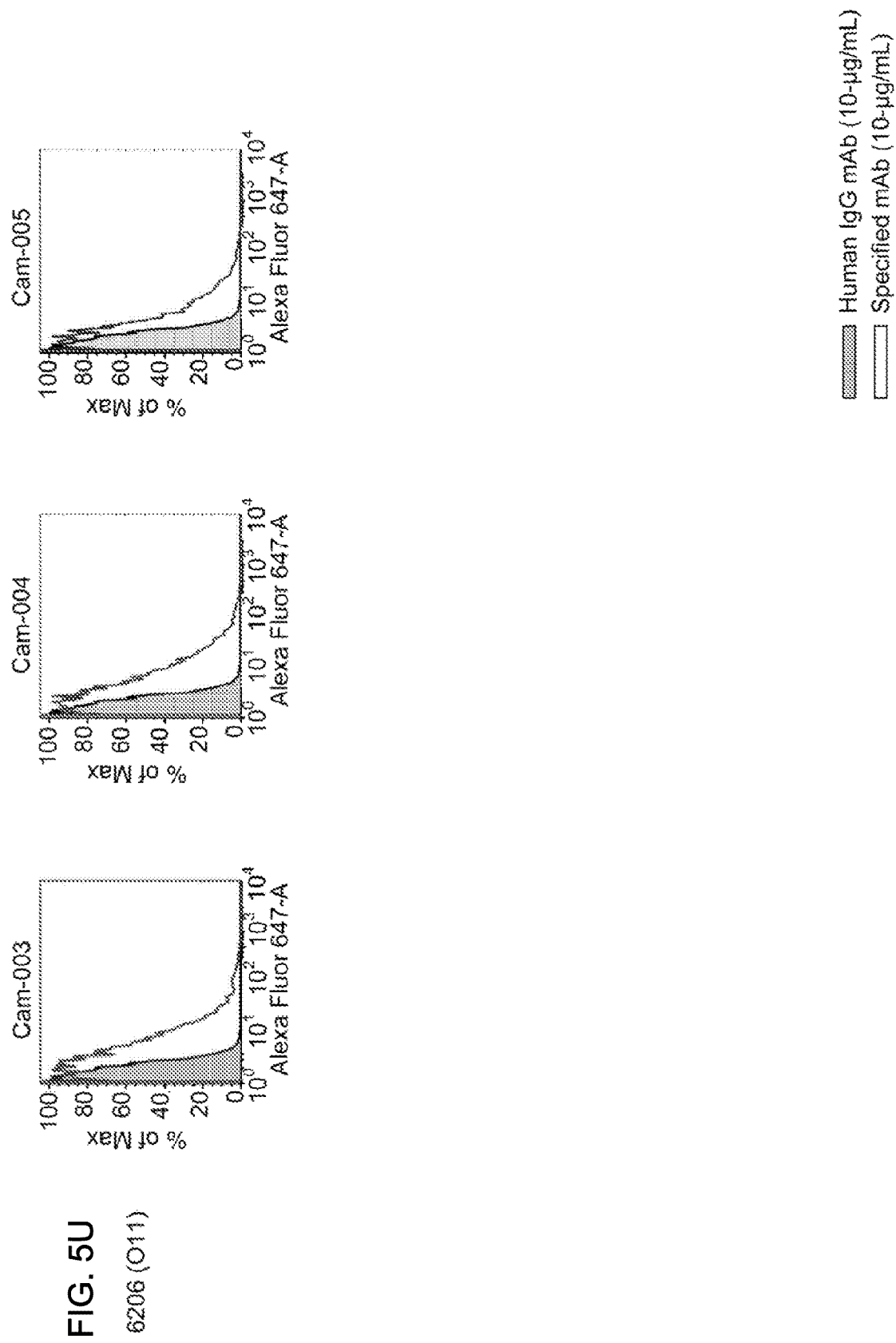

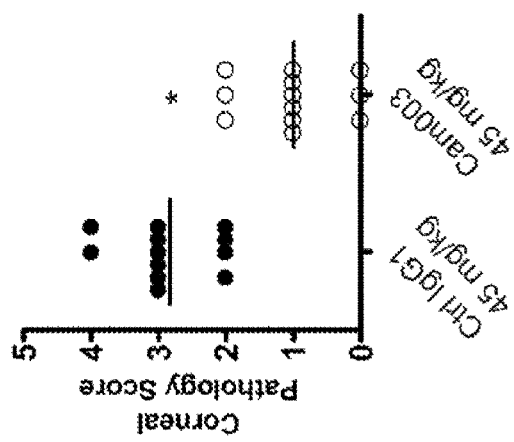

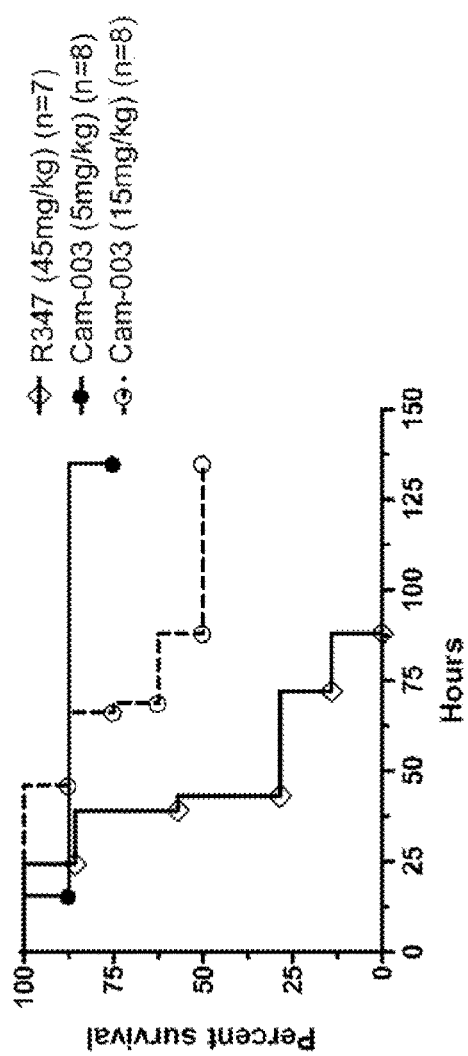
FIG. 8E
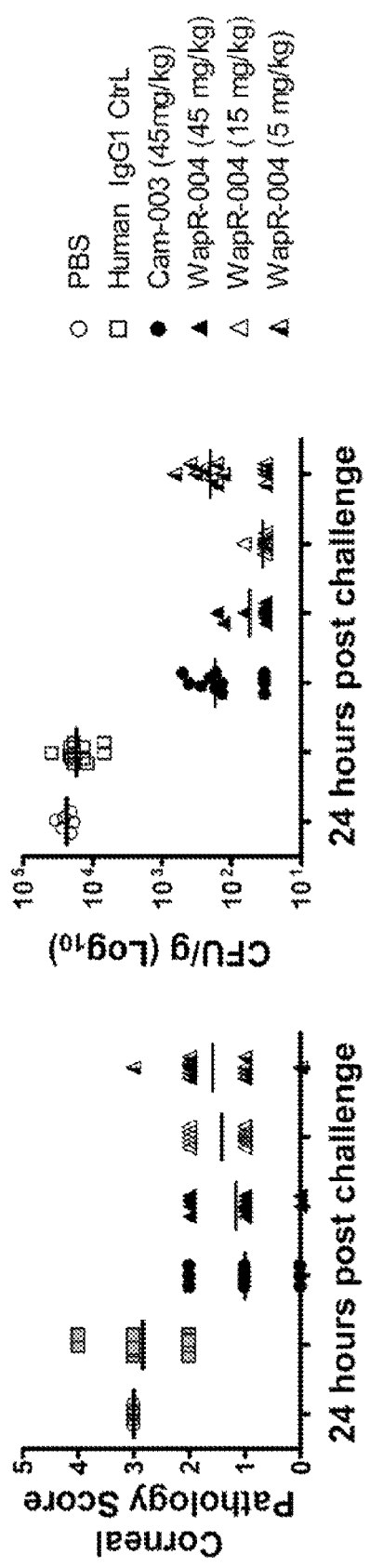
FIG. 8F
FIG. 8G

Fig. 10A

| Epitope | mAb | $K_D$(nM) | Cell attachment max. inhibition (µg/ml) | OPK EC50 (µg/ml) |
|---|---|---|---|---|
| Class 1 | WapR-004 | 118.00 | 0.3 | 0.0027 |
| | Cam-003 | 144.00 | 1.0 | 0.0220 |
| | Cam-004 | 2100.00 | >30.0 | 0.2771 |
| | Cam-005 | 8400.00 | NA | NA |
| Class 2 | WapR-001 | 0.84 | 30.0 | 0.3100 |
| | WapR-003 | 12.20 | 30.0 | 0.2778 |
| | WapR-002 | 12.60 | ND | 0.3960 |
| Class 3 | WapR-016 | 75.00 | ND | 0.2417 |

Fig. 10B

| scFv-Fc | $k_{off}$ | $k_{on}$ | $K_D$ (nM) | OPK EC50 |
|---|---|---|---|---|
| W4 RAD | 1.30E-02 | 5.39E+04 | 241 | 0.0068 |
| W4-M1 | 8.18E-02 | 1.69E+05 | 483 | 0.0475 |
| W4-M7 | 1.28E-02 | 6.49E+04 | 196 | 0.0060 |
| W4-M8 | 1.90E-02 | 1.54E+05 | 124 | 0.0056 |
| W4-M9 | 1.66E-02 | 1.98E+05 | 84 | 0.0167 |
| W4-M11 | 8.50E-03 | 1.25E+05 | 68 | 0.0045 |
| W4-M12 | 9.10E-03 | 1.26E+05 | 72 | 0.0085 |
| W4-M17 | 1.91E-01 | 9.60E+04 | 1990 | 1.3935 |

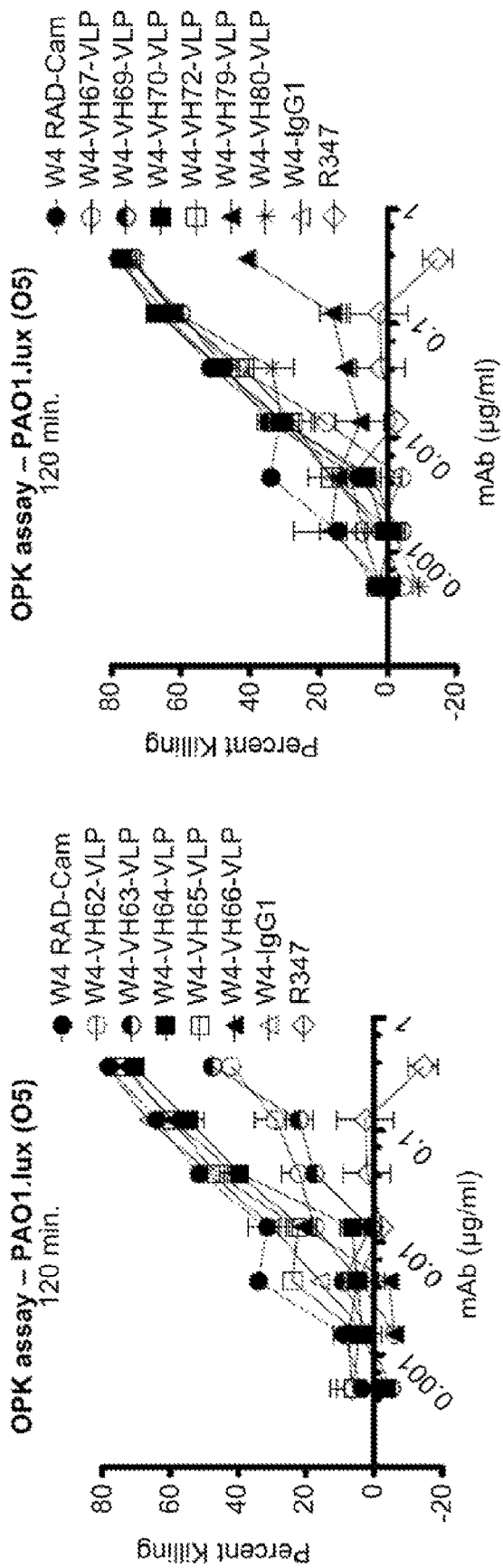

| Construct | PMB/mAb | % Conjugated PMB |
|---|---|---|
| A7-SM-PMB | 1.5 / 2 (75%) | 98.9 |
| CAM-003-SM-PMB | 1.5 / 2 (75%) | 95.5 |
| A7-DM-PMB | 3.4 / 4 (85%) | 99.5 |
| CAM-003-DM-PMB | 3.3 / 4 (82%) | 98.8 |
| A7-TM-PMB | 5.0 / 6 (83%) | 99.0 |
| CAM-003-TM-PMB | 5.1 / 6 (85%) | 99.0 |

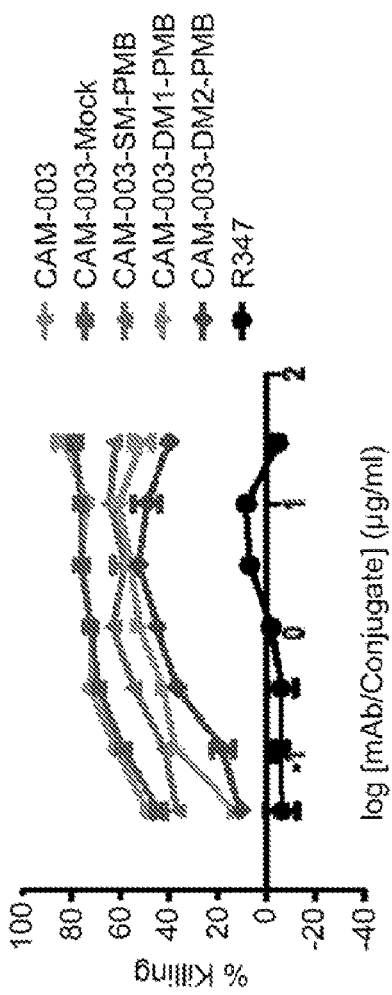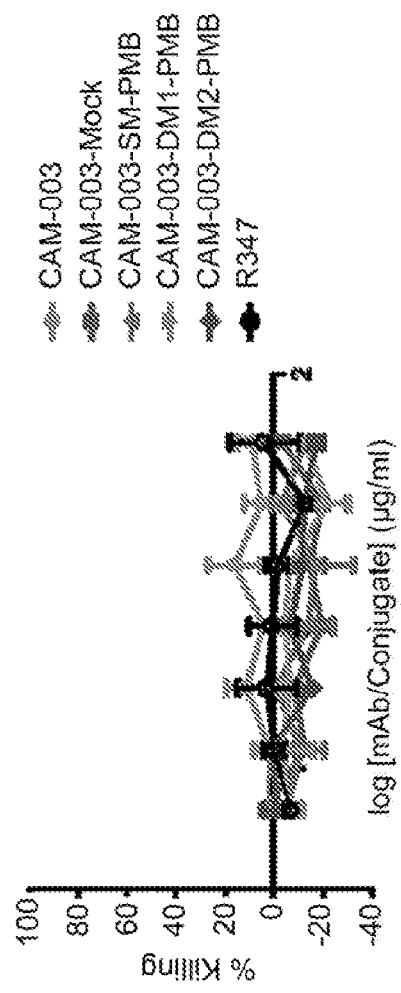
FIG. 15A
FIG. 15B

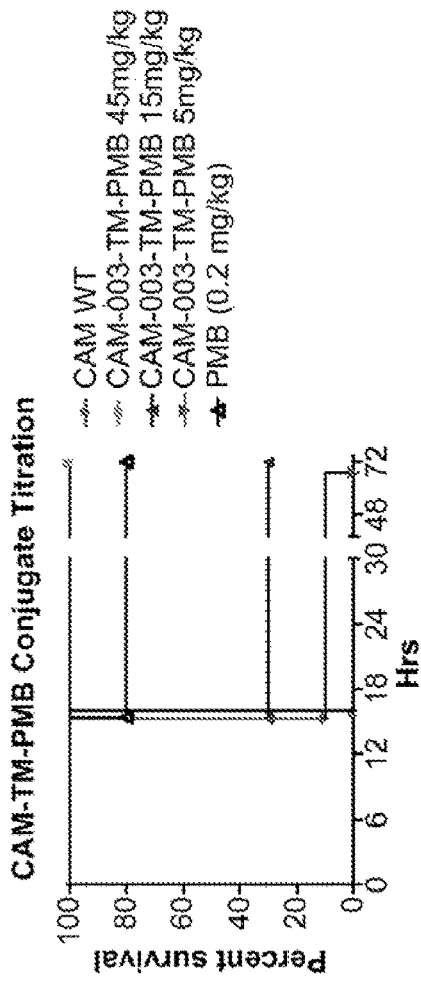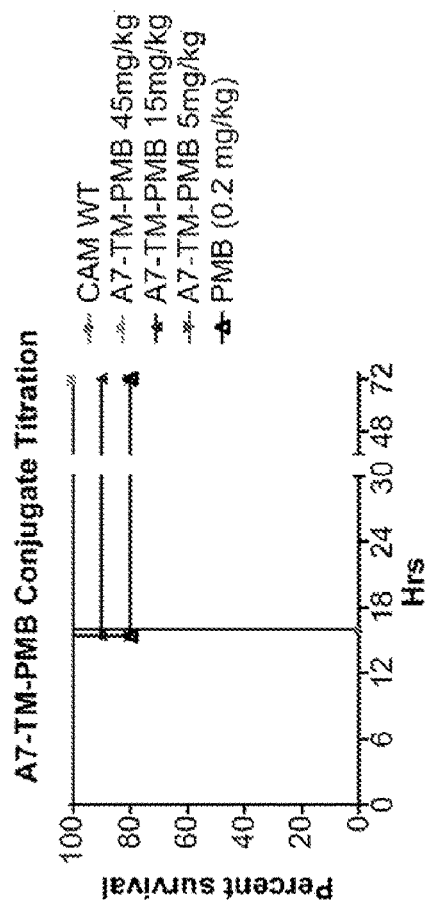

SEQUENCE LISTING

```
<160> NUMBER OF SEQ ID NOS: 215

<210> SEQ ID NO 1
<211> LENGTH: 118
<212> TYPE: PRT
<213> ORGANISM: Artificial
<220> FEATURE:
<223> OTHER INFORMATION: Cam-003 VH

<400> SEQUENCE: 1

Gln Val Arg Leu Gln Gln Ser Gly Pro Gly Leu Val Lys Pro Ser Glu
1               5                   10                  15

Thr Leu Ser Leu Thr Cys Thr Val Ser Gly Gly Ser Thr Ser Pro Tyr
            20                  25                  30
```

```
Phe Trp Ser Trp Leu Arg Gln Pro Gly Lys Gly Leu Glu Trp Ile
            35                  40                  45

Gly Tyr Ile His Ser Asn Gly Thr Asn Tyr Asn Pro Ser Leu Lys
    50                  55                  60

Ser Arg Leu Thr Ile Ser Gly Asp Thr Ser Lys Asn Gln Phe Ser Leu
65                  70                  75                  80

Asn Leu Ser Phe Val Thr Ala Ala Asp Thr Ala Leu Tyr Tyr Cys Ala
                85                  90                  95

Arg Thr Asp Tyr Asp Val Tyr Gly Pro Ala Phe Asp Ile Trp Gly Gln
                100                 105                 110

Gly Thr Met Val Thr Val
            115

<210> SEQ ID NO 2
<211> LENGTH: 108
<212> TYPE: PRT
<213> ORGANISM: Artificial
<220> FEATURE:
<223> OTHER INFORMATION: Cam-003, Cam-004, and Cam-005 VL

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
                100                 105

<210> SEQ ID NO 3
<211> LENGTH: 118
<212> TYPE: PRT
<213> ORGANISM: Artificial
<220> FEATURE:
<223> OTHER INFORMATION: Cam-004 VH

<400> SEQUENCE: 3

Gln Val Gln Leu Gln Gln Ser Gly Pro Gly Arg Val Lys Pro Ser Glu
1               5                   10                  15

Thr Leu Ser Leu Thr Cys Thr Val Ser Gly Tyr Ser Val Ser Ser Gly
                20                  25                  30

Tyr Tyr Trp Gly Trp Ile Arg Gln Ser Pro Gly Thr Gly Leu Glu Trp
            35                  40                  45

Ile Gly Ser Ile Ser His Ser Gly Ser Thr Tyr Tyr Asn Pro Ser Leu
    50                  55                  60

Lys Ser Arg Val Thr Ile Ser Gly Asp Ala Ser Lys Asn Gln Phe Phe
65                  70                  75                  80

Leu Arg Leu Thr Ser Val Thr Ala Ala Asp Thr Ala Val Tyr Tyr Cys
                85                  90                  95
```

```
Ala Arg Ser Glu Ala Thr Ala Asn Phe Asp Ser Trp Gly Arg Gly Thr
                100                 105                 110

Leu Val Thr Val Ser Ser
            115

<210> SEQ ID NO 4
<211> LENGTH: 119
<212> TYPE: PRT
<213> ORGANISM: Artificial
<220> FEATURE:
<223> OTHER INFORMATION: Cam-005 VH

<400> SEQUENCE: 4

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Gly Tyr Tyr Trp Thr Trp Ile Arg Gln Pro Pro Gly Lys Gly Leu Glu
        35                  40                  45

Trp Ile Gly Ser Ile Tyr Ser Gly Ser Thr Tyr Tyr Ser Pro Ser
    50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Asn Trp Gly Thr Val Ser Ala Phe Asp Ile Trp Gly
            100                 105                 110

Arg Gly Thr Leu Val Thr Val
            115

<210> SEQ ID NO 5
<211> LENGTH: 119
<212> TYPE: PRT
<213> ORGANISM: Artificial
<220> FEATURE:
<223> OTHER INFORMATION: WapR-001 VH

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Arg Tyr
            20                  25                  30

Pro Met His Trp Val Arg Gln Ala Pro Gly Lys Gly Leu Glu Tyr Val
        35                  40                  45

Ser Asp Ile Gly Thr Asn Gly Gly Ser Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Ala Glu Asp Thr Ala Val Tyr His Cys
                85                  90                  95

Val Ala Gly Ile Ala Ala Ala Tyr Gly Phe Asp Val Trp Gly Gln Gly
            100                 105                 110

Thr Met Val Thr Val Ser Ser
            115

<210> SEQ ID NO 6
<211> LENGTH: 110
<212> TYPE: PRT
<213> ORGANISM: Artificial
```

<220> FEATURE:
<223> OTHER INFORMATION: WapR-001 VL

<400> SEQUENCE: 6

```
Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Ile Ala Thr Tyr
            20                  25                  30

Asn Tyr Val Ser Trp Tyr Gln Gln His Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Glu Leu Thr Val Leu
            100                 105                 110
```

<210> SEQ ID NO 7
<211> LENGTH: 118
<212> TYPE: PRT
<213> ORGANISM: Artificial
<220> FEATURE:
<223> OTHER INFORMATION: WapR-002 VH

<400> SEQUENCE: 7

```
Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Pro Met His Trp Val Arg Gln Ala Pro Gly Lys Gly Leu Asp Tyr Val
        35                  40                  45

Ser Asp Ile Ser Pro Asn Gly Gly Ser Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Ala Glu Asp Thr Ala Val Tyr Tyr Cys
                85                  90                  95

Val Met Gly Leu Val Pro Tyr Gly Phe Asp Ile Trp Gly Gln Gly Thr
            100                 105                 110

Leu Val Thr Val Ser Ser
        115
```

<210> SEQ ID NO 8
<211> LENGTH: 110
<212> TYPE: PRT
<213> ORGANISM: Artificial
<220> FEATURE:
<223> OTHER INFORMATION: WapR-002 VL

<400> SEQUENCE: 8

```
Gln Thr Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Glu Val Ser Asn Arg Pro Ser Gly Val Ser Asn His Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                    85                  90                  95

Ser Thr Tyr Val Phe Gly Thr Gly Thr Lys Val Thr Val Leu
            100                 105                 110

<210> SEQ ID NO 9
<211> LENGTH: 118
<212> TYPE: PRT
<213> ORGANISM: Artificial
<220> FEATURE:
<223> OTHER INFORMATION: WapR-003 VH

<400> SEQUENCE: 9

Gln Met Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Pro Met His Trp Val Arg Gln Ala Pro Gly Lys Gly Leu Asp Tyr Val
        35                  40                  45

Ser Asp Ile Ser Pro Asn Gly Gly Ala Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Ala Glu Asp Thr Ala Val Tyr Tyr Cys
                85                  90                  95

Val Met Gly Leu Val Pro Tyr Gly Phe Asp Asn Trp Gly Gln Gly Thr
            100                 105                 110

Met Val Thr Val Ser Ser
        115

<210> SEQ ID NO 10
<211> LENGTH: 110
<212> TYPE: PRT
<213> ORGANISM: Artificial
<220> FEATURE:
<223> OTHER INFORMATION: WapR-003 VL

<400> SEQUENCE: 10

Gln Thr Val Val Thr Gln Pro Ala Ser Val Ser Ala Ser Pro Gly Gln
1               5                   10                  15

Ser Ile Thr Ile Ser Cys Ala Gly Thr Ser Gly Asp Val Gly Asn Tyr
            20                  25                  30

Asn Phe Val Ser Trp Tyr Gln Gln His Pro Gly Lys Ala Pro Lys Leu
        35                  40                  45

Leu Ile Tyr Glu Gly Ser Gln Arg Pro Ser Gly Val Ser Asn Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Lys Leu Thr Val Leu
            100                 105                 110

<210> SEQ ID NO 11
```

```
<211> LENGTH: 119
<212> TYPE: PRT
<213> ORGANISM: Artificial
<220> FEATURE:
<223> OTHER INFORMATION: WapR-004 VH

<400> SEQUENCE: 11

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser
            115

<210> SEQ ID NO 12
<211> LENGTH: 107
<212> TYPE: PRT
<213> ORGANISM: Artificial
<220> FEATURE:
<223> OTHER INFORMATION: WapR-004 & WarR-004RAD VL

<400> SEQUENCE: 12

Glu Ile Val Leu Thr Gln Ser Pro Ser Ser Leu Ser Thr Ser Val Gly
1               5                   10                  15

Asp Arg Val Thr Ile Thr Cys Arg Ala Ser Gln Ser Ile Arg Ser His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Leu
                85                  90                  95

Thr Phe Gly Gly Gly Thr Lys Leu Glu Ile Lys
            100                 105

<210> SEQ ID NO 13
<211> LENGTH: 116
<212> TYPE: PRT
<213> ORGANISM: Artificial
<220> FEATURE:
<223> OTHER INFORMATION: WapR-007 VH

<400> SEQUENCE: 13

Glu Val Gln Leu Val Gln Ser Gly Ala Asp Val Lys Lys Pro Gly Ala
1               5                   10                  15

Ser Val Arg Val Thr Cys Lys Ala Ser Gly Tyr Thr Phe Thr Gly His
            20                  25                  30
```

```
Asn Ile His Trp Val Arg Gln Ala Pro Gly Gln Gly Leu Glu Trp Met
             35                  40                  45

Gly Trp Ile Asn Pro Asp Ser Gly Ala Thr Ser Tyr Ala Gln Lys Phe
 50                      55                  60

Gln Gly Arg Val Thr Met Thr Arg Asp Thr Ser Ile Thr Thr Ala Tyr
 65                  70                  75                  80

Met Asp Leu Ser Arg Leu Arg Ser Asp Thr Ala Val Tyr Tyr Cys
                 85                  90                  95

Ala Thr Asp Thr Leu Leu Ser Asn His Trp Gly Gln Gly Thr Leu Val
                    100                 105                 110

Thr Val Ser Ser
            115

<210> SEQ ID NO 14
<211> LENGTH: 108
<212> TYPE: PRT
<213> ORGANISM: Artificial
<220> FEATURE:
<223> OTHER INFORMATION: WapR-007 VL

<400> SEQUENCE: 14

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Thr
                 20                  25                  30

Asn Trp Phe Gln Gln Lys Pro Gly Gln Ala Pro Leu Leu Val Val Tyr
             35                  40                  45

Ala Lys Asn Lys Arg Pro Pro Gly Ile Pro Asp Arg Phe Ser Gly Ser
 50                      55                  60

Ser Ser Gly Asn Thr Ala Ser Leu Thr Ile Thr Gly Ala Gln Ala Glu
 65                  70                  75                  80

Asp Glu Ala Asp Tyr Tyr Cys His Ser Arg Asp Ser Ser Gly Asn His
                 85                  90                  95

Val Val Phe Gly Gly Gly Thr Lys Leu Thr Val Leu
                100                 105

<210> SEQ ID NO 15
<211> LENGTH: 123
<212> TYPE: PRT
<213> ORGANISM: Artificial
<220> FEATURE:
<223> OTHER INFORMATION: WapR-016 VH

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Tyr
                 20                  25                  30

Ala Thr Ser Trp Val Arg Gln Ala Pro Gly Lys Gly Leu Glu Trp Val
             35                  40                  45

Ala Gly Ile Ser Gly Ser Gly Asp Thr Thr Asp Tyr Val Asp Ser Val
 50                      55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Asp Asp Thr Ala Val Tyr Tyr Cys
                 85                  90                  95

Ala Ser Arg Gly Gly Leu Gly Gly Tyr Tyr Arg Gly Gly Phe Asp Phe
                100                 105                 110
```

Trp Gly Gln Gly Thr Met Val Thr Val Ser Ser
        115                 120

<210> SEQ ID NO 16
<211> LENGTH: 108
<212> TYPE: PRT
<213> ORGANISM: Artificial
<220> FEATURE:
<223> OTHER INFORMATION: WapR-016 VL

<400> SEQUENCE: 16

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Cys Ser Ser Tyr Ser Ser Gly Thr
                85                  90                  95

Val Val Phe Gly Gly Gly Thr Glu Leu Thr Val Leu
            100                 105

<210> SEQ ID NO 17
<211> LENGTH: 5
<212> TYPE: PRT
<213> ORGANISM: Artificial
<220> FEATURE:
<223> OTHER INFORMATION: Cam-003 VHCDR1

<400> SEQUENCE: 17

Pro Tyr Phe Trp Ser
1               5

<210> SEQ ID NO 18
<211> LENGTH: 16
<212> TYPE: PRT
<213> ORGANISM: Artificial
<220> FEATURE:
<223> OTHER INFORMATION: Cam-003 VHCDR2

<400> SEQUENCE: 18

Tyr Ile His Ser Asn Gly Gly Thr Asn Tyr Asn Pro Ser Leu Lys Ser
1               5                   10                  15

<210> SEQ ID NO 19
<211> LENGTH: 12
<212> TYPE: PRT
<213> ORGANISM: Artificial
<220> FEATURE:
<223> OTHER INFORMATION: Cam-003 VHCDR3

<400> SEQUENCE: 19

Thr Asp Tyr Asp Val Tyr Gly Pro Ala Phe Asp Ile
1               5                   10

<210> SEQ ID NO 20
<211> LENGTH: 11
<212> TYPE: PRT
<213> ORGANISM: Artificial

```
<220> FEATURE:
<223> OTHER INFORMATION: Cam-003, Cam-004, and Cam-005 VLCDR1

<400> SEQUENCE: 20

Gln Gly Asp Ser Leu Arg Ser Tyr Tyr Ala Ser
1               5                   10

<210> SEQ ID NO 21
<211> LENGTH: 7
<212> TYPE: PRT
<213> ORGANISM: Artificial
<220> FEATURE:
<223> OTHER INFORMATION: Cam-003, Cam-004, and Cam-005 VLCDR2

<400> SEQUENCE: 21

Gly Lys Asn Asn Arg Pro Ser
1               5

<210> SEQ ID NO 22
<211> LENGTH: 11
<212> TYPE: PRT
<213> ORGANISM: Artificial
<220> FEATURE:
<223> OTHER INFORMATION: Cam-003, Cam-004, and Cam-005 VLCDR3

<400> SEQUENCE: 22

Asn Ser Arg Asp Ser Ser Gly Asn His Val Val
1               5                   10

<210> SEQ ID NO 23
<211> LENGTH: 6
<212> TYPE: PRT
<213> ORGANISM: Artificial
<220> FEATURE:
<223> OTHER INFORMATION: Cam-004 VHCDR1

<400> SEQUENCE: 23

Ser Gly Tyr Tyr Trp Gly
1               5

<210> SEQ ID NO 24
<211> LENGTH: 16
<212> TYPE: PRT
<213> ORGANISM: Artificial
<220> FEATURE:
<223> OTHER INFORMATION: Cam-004 VHCDR2

<400> SEQUENCE: 24

Ser Ile Ser His Ser Gly Ser Thr Tyr Tyr Asn Pro Ser Leu Lys Ser
1               5                   10                  15

<210> SEQ ID NO 25
<211> LENGTH: 9
<212> TYPE: PRT
<213> ORGANISM: Artificial
<220> FEATURE:
<223> OTHER INFORMATION: Cam-004 VHCDR3

<400> SEQUENCE: 25

Ser Glu Ala Thr Ala Asn Phe Asp Ser
1               5

<210> SEQ ID NO 26
<211> LENGTH: 7
<212> TYPE: PRT
<213> ORGANISM: Artificial
<220> FEATURE:
```

```
<223> OTHER INFORMATION: Cam-005 VHCDR1

<400> SEQUENCE: 26

Ser Ser Gly Tyr Tyr Trp Thr
1               5

<210> SEQ ID NO 27
<211> LENGTH: 16
<212> TYPE: PRT
<213> ORGANISM: Artificial
<220> FEATURE:
<223> OTHER INFORMATION: Cam-005 VHCDR2

<400> SEQUENCE: 27

Ser Ile Tyr Ser Ser Gly Ser Thr Tyr Tyr Ser Pro Ser Leu Lys Ser
1               5                   10                  15

<210> SEQ ID NO 28
<211> LENGTH: 11
<212> TYPE: PRT
<213> ORGANISM: Artificial
<220> FEATURE:
<223> OTHER INFORMATION: Cam-005 VHCDR3

<400> SEQUENCE: 28

Leu Asn Trp Gly Thr Val Ser Ala Phe Asp Ile
1               5                   10

<210> SEQ ID NO 29
<211> LENGTH: 5
<212> TYPE: PRT
<213> ORGANISM: Artificial
<220> FEATURE:
<223> OTHER INFORMATION: WapR-001 VHCDR1

<400> SEQUENCE: 29

Arg Tyr Pro Met His
1               5

<210> SEQ ID NO 30
<211> LENGTH: 17
<212> TYPE: PRT
<213> ORGANISM: Artificial
<220> FEATURE:
<223> OTHER INFORMATION: WapR-001 VHCDR2

<400> SEQUENCE: 30

Asp Ile Gly Thr Asn Gly Gly Ser Thr Asn Tyr Ala Asp Ser Val Lys
1               5                   10                  15

Gly

<210> SEQ ID NO 31
<211> LENGTH: 10
<212> TYPE: PRT
<213> ORGANISM: Artificial
<220> FEATURE:
<223> OTHER INFORMATION: WapR-001 VHCDR3

<400> SEQUENCE: 31

Gly Ile Ala Ala Ala Tyr Gly Phe Asp Val
1               5                   10

<210> SEQ ID NO 32
<211> LENGTH: 14
<212> TYPE: PRT
<213> ORGANISM: Artificial
```

-continued

<220> FEATURE:
<223> OTHER INFORMATION: WapR-001 VLCDR1

<400> SEQUENCE: 32

Thr Gly Thr Ser Ser Asp Ile Ala Thr Tyr Asn Tyr Val Ser
1               5                   10

<210> SEQ ID NO 33
<211> LENGTH: 7
<212> TYPE: PRT
<213> ORGANISM: Artificial
<220> FEATURE:
<223> OTHER INFORMATION: WapR-001 VLCDR2

<400> SEQUENCE: 33

Glu Gly Thr Lys Arg Pro Ser
1               5

<210> SEQ ID NO 34
<211> LENGTH: 10
<212> TYPE: PRT
<213> ORGANISM: Artificial
<220> FEATURE:
<223> OTHER INFORMATION: WapR-001 VLCDR3

<400> SEQUENCE: 34

Ser Ser Tyr Ala Arg Ser Tyr Thr Tyr Val
1               5                   10

<210> SEQ ID NO 35
<211> LENGTH: 5
<212> TYPE: PRT
<213> ORGANISM: Artificial
<220> FEATURE:
<223> OTHER INFORMATION: WapR-002 VHCDR1

<400> SEQUENCE: 35

Ser Tyr Pro Met His
1               5

<210> SEQ ID NO 36
<211> LENGTH: 17
<212> TYPE: PRT
<213> ORGANISM: Artificial
<220> FEATURE:
<223> OTHER INFORMATION: WapR-002 VHCDR2

<400> SEQUENCE: 36

Asp Ile Ser Pro Asn Gly Gly Ser Thr Asn Tyr Ala Asp Ser Val Lys
1               5                   10                  15

Gly

<210> SEQ ID NO 37
<211> LENGTH: 9
<212> TYPE: PRT
<213> ORGANISM: Artificial
<220> FEATURE:
<223> OTHER INFORMATION: WapR-002 VHCDR3

<400> SEQUENCE: 37

Gly Leu Val Pro Tyr Gly Phe Asp Ile
1               5

<210> SEQ ID NO 38
<211> LENGTH: 14
<212> TYPE: PRT

```
<213> ORGANISM: Artificial
<220> FEATURE:
<223> OTHER INFORMATION: WapR-002 VLCDR1

<400> SEQUENCE: 38

Thr Gly Thr Ser Ser Asp Val Gly Gly Tyr Asn Tyr Val Ser
1               5                   10

<210> SEQ ID NO 39
<211> LENGTH: 7
<212> TYPE: PRT
<213> ORGANISM: Artificial
<220> FEATURE:
<223> OTHER INFORMATION: WapR-002 VLCDR2

<400> SEQUENCE: 39

Glu Val Ser Asn Arg Pro Ser
1               5

<210> SEQ ID NO 40
<211> LENGTH: 10
<212> TYPE: PRT
<213> ORGANISM: Artificial
<220> FEATURE:
<223> OTHER INFORMATION: WapR-002 VLCDR3

<400> SEQUENCE: 40

Ser Ser Tyr Thr Thr Ser Ser Thr Tyr Val
1               5                   10

<210> SEQ ID NO 41
<211> LENGTH: 5
<212> TYPE: PRT
<213> ORGANISM: Artificial
<220> FEATURE:
<223> OTHER INFORMATION: WapR-003 VHCDR1

<400> SEQUENCE: 41

Ser Tyr Pro Met His
1               5

<210> SEQ ID NO 42
<211> LENGTH: 17
<212> TYPE: PRT
<213> ORGANISM: Artificial
<220> FEATURE:
<223> OTHER INFORMATION: WapR-003 VHCDR2

<400> SEQUENCE: 42

Asp Ile Ser Pro Asn Gly Gly Ala Thr Asn Tyr Ala Asp Ser Val Lys
1               5                   10                  15

Gly

<210> SEQ ID NO 43
<211> LENGTH: 9
<212> TYPE: PRT
<213> ORGANISM: Artificial
<220> FEATURE:
<223> OTHER INFORMATION: WapR-003 VHCDR3

<400> SEQUENCE: 43

Gly Leu Val Pro Tyr Gly Phe Asp Asn
1               5

<210> SEQ ID NO 44
<211> LENGTH: 14
```

```
<212> TYPE: PRT
<213> ORGANISM: Artificial
<220> FEATURE:
<223> OTHER INFORMATION: WapR-003 VLCDR1

<400> SEQUENCE: 44

Ala Gly Thr Ser Gly Asp Val Gly Asn Tyr Asn Phe Val Ser
1               5                   10

<210> SEQ ID NO 45
<211> LENGTH: 7
<212> TYPE: PRT
<213> ORGANISM: Artificial
<220> FEATURE:
<223> OTHER INFORMATION: WapR-003 VLCDR2

<400> SEQUENCE: 45

Glu Gly Ser Gln Arg Pro Ser
1               5

<210> SEQ ID NO 46
<211> LENGTH: 10
<212> TYPE: PRT
<213> ORGANISM: Artificial
<220> FEATURE:
<223> OTHER INFORMATION: WapR-003 VLCDR3

<400> SEQUENCE: 46

Ser Ser Tyr Ala Arg Ser Tyr Thr Tyr Val
1               5                   10

<210> SEQ ID NO 47
<211> LENGTH: 5
<212> TYPE: PRT
<213> ORGANISM: Artificial
<220> FEATURE:
<223> OTHER INFORMATION: WapR-004 & WapR-004RAD VHCDR1

<400> SEQUENCE: 47

Pro Tyr Tyr Trp Thr
1               5

<210> SEQ ID NO 48
<211> LENGTH: 16
<212> TYPE: PRT
<213> ORGANISM: Artificial
<220> FEATURE:
<223> OTHER INFORMATION: WapR-004 & WapR-004RAD VHCDR2

<400> SEQUENCE: 48

Tyr Ile His Ser Ser Gly Tyr Thr Asp Tyr Asn Pro Ser Leu Lys Ser
1               5                   10                  15

<210> SEQ ID NO 49
<211> LENGTH: 11
<212> TYPE: PRT
<213> ORGANISM: Artificial
<220> FEATURE:
<223> OTHER INFORMATION: WapR-004 VHCDR3

<400> SEQUENCE: 49

Gly Asp Trp Asp Leu Leu His Ala Leu Asp Ile
1               5                   10

<210> SEQ ID NO 50
<211> LENGTH: 11
<212> TYPE: PRT
```

```
<213> ORGANISM: Artificial
<220> FEATURE:
<223> OTHER INFORMATION: WapR-004 & WapR-004RAD VLCDR1

<400> SEQUENCE: 50

Arg Ala Ser Gln Ser Ile Arg Ser His Leu Asn
1               5                   10

<210> SEQ ID NO 51
<211> LENGTH: 7
<212> TYPE: PRT
<213> ORGANISM: Artificial
<220> FEATURE:
<223> OTHER INFORMATION: WapR-004 & WapR-004RAD VLCDR2

<400> SEQUENCE: 51

Gly Ala Ser Asn Leu Gln Ser
1               5

<210> SEQ ID NO 52
<211> LENGTH: 6
<212> TYPE: PRT
<213> ORGANISM: Artificial
<220> FEATURE:
<223> OTHER INFORMATION: WapR-004 & WapR-004RAD VLCDR3

<400> SEQUENCE: 52

Tyr Ser Phe Pro Leu Thr
1               5

<210> SEQ ID NO 53
<211> LENGTH: 5
<212> TYPE: PRT
<213> ORGANISM: Artificial
<220> FEATURE:
<223> OTHER INFORMATION: WapR-007 VHCDR1

<400> SEQUENCE: 53

Gly His Asn Ile His
1               5

<210> SEQ ID NO 54
<211> LENGTH: 17
<212> TYPE: PRT
<213> ORGANISM: Artificial
<220> FEATURE:
<223> OTHER INFORMATION: WapR-007 VHCDR2

<400> SEQUENCE: 54

Trp Ile Asn Pro Asp Ser Gly Ala Thr Ser Tyr Ala Gln Lys Phe Gln
1               5                   10                  15

Gly

<210> SEQ ID NO 55
<211> LENGTH: 7
<212> TYPE: PRT
<213> ORGANISM: Artificial
<220> FEATURE:
<223> OTHER INFORMATION: WapR-007 VHCDR3

<400> SEQUENCE: 55

Asp Thr Leu Leu Ser Asn His
1               5

<210> SEQ ID NO 56
<211> LENGTH: 11
```

```
<212> TYPE: PRT
<213> ORGANISM: Artificial
<220> FEATURE:
<223> OTHER INFORMATION: WapR-007 VLCDR1

<400> SEQUENCE: 56

Gln Gly Asp Ser Leu Arg Ser Tyr Tyr Thr Asn
1               5                   10

<210> SEQ ID NO 57
<211> LENGTH: 7
<212> TYPE: PRT
<213> ORGANISM: Artificial
<220> FEATURE:
<223> OTHER INFORMATION: WapR-007 VLCDR2

<400> SEQUENCE: 57

Ala Lys Asn Lys Arg Pro Pro
1               5

<210> SEQ ID NO 58
<211> LENGTH: 11
<212> TYPE: PRT
<213> ORGANISM: Artificial
<220> FEATURE:
<223> OTHER INFORMATION: WapR-007 VLCDR3

<400> SEQUENCE: 58

His Ser Arg Asp Ser Ser Gly Asn His Val Val
1               5                   10

<210> SEQ ID NO 59
<211> LENGTH: 5
<212> TYPE: PRT
<213> ORGANISM: Artificial
<220> FEATURE:
<223> OTHER INFORMATION: WapR-016 VHCDR1

<400> SEQUENCE: 59

Ser Tyr Ala Thr Ser
1               5

<210> SEQ ID NO 60
<211> LENGTH: 17
<212> TYPE: PRT
<213> ORGANISM: Artificial
<220> FEATURE:
<223> OTHER INFORMATION: WapR-016 VHCDR2

<400> SEQUENCE: 60

Gly Ile Ser Gly Ser Gly Asp Thr Thr Asp Tyr Val Asp Ser Val Lys
1               5                   10                  15

Gly

<210> SEQ ID NO 61
<211> LENGTH: 14
<212> TYPE: PRT
<213> ORGANISM: Artificial
<220> FEATURE:
<223> OTHER INFORMATION: WapR-016 VHCDR3

<400> SEQUENCE: 61

Arg Gly Gly Leu Gly Gly Tyr Tyr Arg Gly Gly Phe Asp Phe
1               5                   10

<210> SEQ ID NO 62
```

```
<211> LENGTH: 14
<212> TYPE: PRT
<213> ORGANISM: Artificial
<220> FEATURE:
<223> OTHER INFORMATION: WapR-016 VLCDR1

<400> SEQUENCE: 62

Thr Gly Thr Ser Ser Asp Val Gly Gly Tyr Asn Tyr Val Ser
1               5                   10

<210> SEQ ID NO 63
<211> LENGTH: 7
<212> TYPE: PRT
<213> ORGANISM: Artificial
<220> FEATURE:
<223> OTHER INFORMATION: WapR-016 VLCDR2

<400> SEQUENCE: 63

Glu Val Ser Asn Arg Pro Ser
1               5

<210> SEQ ID NO 64
<211> LENGTH: 9
<212> TYPE: PRT
<213> ORGANISM: Artificial
<220> FEATURE:
<223> OTHER INFORMATION: WapR-016 VLCDR3

<400> SEQUENCE: 64

Ser Ser Tyr Ser Ser Gly Thr Val Val
1               5

<210> SEQ ID NO 65
<211> LENGTH: 753
<212> TYPE: DNA
<213> ORGANISM: Artificial
<220> FEATURE:
<223> OTHER INFORMATION: Cam-003 scFv

<400> SEQUENCE: 65
cagccggcca tggcccaggt acagctgcag cagtcaggcc caggactggt gaagccttcg      60
gagaccctgt ccctcacctg cactgtctct ggtggctcca ccagtcctta cttctggagc     120
tggctccggc agccccccag gaagggactg gagtggattg gttatatcca ttccaatggg     180
ggcaccaact acaacccctc cctcaagagt cgactcacca tatcaggaga cacgtccaag     240
aaccaattct ccctgaatct gagttttgtg accgctgcgg acacggccct ctattactgt     300
gcgagaacgg actacgatgt ctacggcccc gcttttgata tctggggcca ggggacaatg     360
gtcaccgtct cgagtggtgg aggcggttca ggcggaggtg gcagcggcgg tggcggatcg     420
tctgagctga ctcaggaccc tgctgtgtct gtggccttgg acagacagt caggatcaca     480 tgccaaggag acagcctcag aagctattat gcaagctggt accagcagaa gccaggacag     540
gcccctgtac ttgtcatcta tggtaaaaac aaccggccct cagggatccc agaccgattc     600
tctggctcca gctcaggaaa cacagcttcc ttgaccatca ctggggctca ggcggaagat     660
gaggctgact attactgtaa ctcccgggac agcagtggta accatgtggt attcggcgga     720
gggaccaagc tgaccgtcct aggtgcggcc gca                                  753

<210> SEQ ID NO 66
<211> LENGTH: 747
<212> TYPE: DNA
<213> ORGANISM: Artificial
<220> FEATURE:
```

<223> OTHER INFORMATION: Cam-004 scFv

<400> SEQUENCE: 66

```
cagccggcca tggcccaggt acagctgcag cagtcaggcc caggacgggt gaagccttcg    60
gagacgctgt ccctcacctg cactgtctct ggttactccg tcagtagtgg ttactactgg   120
ggctggatcc ggcagtcccc agggacgggg ctggagtgga ttgggagtat ctctcatagt   180
gggagcacct actacaaccc gtccctcaag agtcgagtca ccatatcagg agacgcatcc   240
aagaaccagt ttttcctgag gctgacttct gtgaccgccg cggacacggc cgtttattac   300
tgtgcgagat ctgaggctac cgccaacttt gattcttggg caggggcac cctggtcacc    360
gtctcttcag gtggaggcgg ttcaggcgga ggtggcagcg gcggtggcgg atcgtctgag   420
ctgactcagg accctgccgt gtctgtggcc ttgggacaga cagtcaggat cacatgccaa   480
ggagacagcc tcagaagcta ttatgcaagc tggtaccagc agaagccagg acaggcccct   540
gtacttgtca tctatggtaa aacaaccgg ccctcaggga tcccagaccg attctctggc   600
tccagctcag gaaacacagc ttccttgacc atcactgggg ctcaggcgga agatgaggct   660
gactattact gtaactcccg ggacagcagt ggtaaccatg tggtattcgg cggagggacc   720
aagctgaccg tcctaggtgc ggccgca                                        747
```

<210> SEQ ID NO 67
<211> LENGTH: 756
<212> TYPE: DNA
<213> ORGANISM: Artificial
<220> FEATURE:
<223> OTHER INFORMATION: Cam-005 scFv

<400> SEQUENCE: 67

```
cagccggcca tggcccaggt acagctgcag cagtcaggcc caggactggt gaagccttcg    60
gagaccctgt ccctcacctg cactgtctct ggtggctccg tcagcagtag tggttattac   120
tggacctgga tccgccagcc cccagggaag gggctggagt ggattgggag tatctattct   180
agtgggagca catattacag cccgtccctc aagagtcgag tcaccatatc cggagacacg   240
tccaagaacc agttctccct caagctgagc tctgtgaccg ccgcagacac agccgtgtat   300
tactgtgcga gacttaactg gggcactgtg tctgcctttg atatctgggg cagaggcacc   360
ctggtcaccg tctcgagtgg tggaggcggt tcaggcggag gtggcagcgg cggtggcgga   420
tcgtctgagc tgactcagga ccctgctgtg tctgtggcct tgggacagac agtcaggatc   480
acatgccaag agacagcct cagaagctat tatgcaagct ggtaccagca gaagccagga    540
caggcccctg tacttgtcat ctatggtaaa acaaccggc cctcagggat cccagaccga    600
ttctctggct ccagctcagg aaacacagct tccttgacca tcactggggc tcaggcggaa   660
gatgaggctg actattactg taactcccgg gacagcagtg gtaaccatgt ggtattcggc   720
ggagggacca agctgaccgt cctaggtgcg gccgca                              756
```

<210> SEQ ID NO 68
<211> LENGTH: 769
<212> TYPE: DNA
<213> ORGANISM: Artificial
<220> FEATURE:
<223> OTHER INFORMATION: WapR-001 scFv

<400> SEQUENCE: 68

```
tctatgcggc ccagccggcc atggccgagg tgcagctgtt ggagtctggg ggaggtttgg    60
tccagcctgg ggggtccctg agactctcct gttcagcctc tgggttcacc ttcagtcgt    120
```

| | |
|---|---|
| atcctatgca ttgggtccgc caggctccag ggaagggact ggaatatgtt tcagatattg | 180 |
| gtactaatgg gggtagtaca aactacgcag actccgtgaa gggcagattc accatctcca | 240 |
| gagacaattc caagaacacg gtgtatcttc aaatgagcag tctgagagct gaggacacgg | 300 |
| ctgtgtatca ttgtgtggcg ggtatagcag ccgcctatgg ttttgatgtc tggggccaag | 360 |
| ggacaatggt caccgtctcg agtggaggcg gcggttcagg cggaggtggc tctggcggtg | 420 |
| gcggaagtgc acaggcaggg ctgactcagc ctgcctccgt gtctgggtct cctggacagt | 480 |
| cgatcaccat ctcctgcact ggaaccagca gtgacattgc tacttataac tatgtctcct | 540 |
| ggtaccaaca gcacccaggc aaagccccca aactcatgat ttatgagggc actaagcggc | 600 |
| cctcaggggt ttctaatcgc ttctctggct ccaagtctgg caacacggcc tccctgacaa | 660 |
| tctctgggct ccaggctgag gacgaggctg attattactg ttcctcatat gcacgtagtt | 720 |
| acacttatgt cttcggaact gggaccgagc tgaccgtcct agcggccgc | 769 |

<210> SEQ ID NO 69
<211> LENGTH: 764
<212> TYPE: DNA
<213> ORGANISM: Artificial
<220> FEATURE:
<223> OTHER INFORMATION: WapR-002 scFv

<400> SEQUENCE: 69

| | |
|---|---|
| ctatgcggcc cagccggcca tggcccaggt gcagctggtg cagtctgggg gaggcttggt | 60 |
| ccagcctggg gggtccctga gactctcctg ttcagcctct ggattcacct tcagtagcta | 120 |
| tcctatgcac tgggtccgcc aggctccagg aagggactg gattatgttt cagacatcag | 180 |
| tccaaatggg ggttccacaa actacgcaga ctccgtgaag gcagattca ccatctccag | 240 |
| agacaattcc aagaacacac tgtttcttca aatgagcagt ctgagagctg aggacacggc | 300 |
| tgtgtattat tgtgtgatgg ggttagtacc ctatggtttt gatatctggg gccaaggcac | 360 |
| cctggtcacc gtctcgagtg gaggcggcgg ttcaggcgga ggtggctctg gcggtggcgg | 420 |
| aagtgcacag actgtggtga cccagcctgc ctccgtgtct gggtctcctg acagtcgat | 480 |
| caccatctcc tgcactggaa ccagcagtga cgttggtggt tataactatg tctcctggta | 540 |
| ccaacagcac ccaggcaaag cccccaaact catgatttat gaggtcagta atcggccctc | 600 |
| aggggtttct aatcacttct ctggctccaa gtctggcaac acggcctccc tgaccatctc | 660 |
| tgggctccag gctgaggacg aggctgatta ttactgcagc tcatatacaa ccagcagcac | 720 |
| ttatgtcttc ggaactggga ccaaggtcac cgtcctagcg gccg | 764 |

<210> SEQ ID NO 70
<211> LENGTH: 761
<212> TYPE: DNA
<213> ORGANISM: Artificial
<220> FEATURE:
<223> OTHER INFORMATION: WapR-003 scFv

<400> SEQUENCE: 70

| | |
|---|---|
| cggcccagcc ggccatggcc cagatgcagc tggtgcagtc gggggaggc ttggtccagc | 60 |
| ctgggggtc cctgagactc tcctgttcag cctctggatt caccttcagt agctatccta | 120 |
| tgcactgggt ccgccaggct ccagggaagg gactggatta tgtttcagac atcagtccaa | 180 |
| atgggggtgc cacaaactac gcagactccg tgaaggcag attcaccatc tccagagaca | 240 |
| attccaagaa cacggtgtat cttcaaatga gcagtctgag agctgaagac acggctgtct | 300 |

| | |
|---|---|
| attattgtgt gatggggtta gtgccctatg gttttgataa ctggggccag gggacaatgg | 360 |
| tcaccgtctc gagtggaggc ggcggttcag gcggaggtgg ctctggcggt ggcggaagtg | 420 |
| cacagactgt ggtgacccag cctgcctccg tgtctgcatc tcctggacag tcgatcacca | 480 |
| tctcctgcgc tggaaccagc ggtgatgttg gaattataa ttttgtctcc tggtaccaac | 540 |
| aacacccagg caaagccccc aaactcctga tttatgaggg cagtcagcgg ccctcagggg | 600 |
| tttctaatcg cttctctggc tccaggtctg caacacggc ctccctgaca atctctgggc | 660 |
| tccaggctga ggacgaggct gattattact gttcctcata tgcacgtagt tacacttatg | 720 |
| tcttcggaac tgggaccaag ctgaccgtcc tagcggccgc a | 761 |

<210> SEQ ID NO 71
<211> LENGTH: 761
<212> TYPE: DNA
<213> ORGANISM: Artificial
<220> FEATURE:
<223> OTHER INFORMATION: WapR-004 scFv

<400> SEQUENCE: 71

| | |
|---|---|
| tatgcggccc agccggccat ggccgaggtg cagctgttgg agtcgggccc aggactggtg | 60 |
| aagccttcgg agaccctgtc cctcacctgc aatgtcgctg gtggctccat cagtccttac | 120 |
| tactggacct ggatccggca gccccaggg aagggcctgg agttgattgg ttatatccac | 180 |
| tccagtgggt acaccgacta caaccctcc ctcaagagtc gagtcaccat atcaggagac | 240 |
| acgtccaaga agcagttctc cctgcacgtg agctctgtga ccgctgcgga cacggccgtg | 300 |
| tacttctgtg cgagaggcga ttgggacctg cttcatgctc ttgatatctg ggccaagggg | 360 |
| accctggtca ccgtctcgag tggaggcggc ggttcaggcg aggtggctc tggcggtggc | 420 |
| ggaagtgcac tcgaaattgt gttgacacag tctccatcct ccctgtctac atctgtagga | 480 |
| gacagagtca ccatcacttg ccgggcaagt cagagcatta ggagccattt aaattggtat | 540 |
| cagcagaaac cagggaaagc ccctaaactc ctgatctatg gtgcatccaa tttgcaaagt | 600 |
| ggggtcccat caaggttcag tggcagtgga tctgggacag atttcactct caccattagt | 660 |
| agtctgcaac ctgaagattt tgcaacttac tactgtcaac agagttacag tttcccctc | 720 |
| actttcggcg gagggaccaa gctggagatc aaagcggccg c | 761 |

<210> SEQ ID NO 72
<211> LENGTH: 747
<212> TYPE: DNA
<213> ORGANISM: Artificial
<220> FEATURE:
<223> OTHER INFORMATION: WapR-007 scFv

<400> SEQUENCE: 72

| | |
|---|---|
| gcggcccagc cggccatggc cgaagtgcag ctggtgcagt ctggggctga cgtaaagaag | 60 |
| cctggggcct cagtgagggt cacctgcaag gcttctggat acaccttcac cggccacaac | 120 |
| atacactggg tgcgacaggc ccctggacaa gggcttgaat ggatgggatg gatcaaccct | 180 |
| gacagtggtg ccacaagcta tgcacagaag tttcagggca gggtcaccat gaccagggac | 240 |
| acgtccatca ccacagccta catggacctg agcaggctga gatctgacga cacggccgta | 300 |
| tattactgtg cgaccgatac attactgtct aatcactggg gccaaggaac cctggtcacc | 360 |
| gtctcgagtg gtgaggcggc ttcaggcgga ggtggcagcg gcggtggcgg atcgtctgag | 420 |
| ctgactcagg accctgctgt gtctgtggcc ttggacagca gtcaggat cacttgccaa | 480 |
| ggagacagtc tcagaagcta ttacacaaac tggttccagc agaagccagg acaggcccct | 540 |

```
ctacttgtcg tctatgctaa aaataagcgg cccccaggga tcccagaccg attctctggc    600
tccagctcag gaaacacagc ttccttgacc atcactgggg ctcaggcgga agatgaggct    660
gactattact gtcattcccg ggacagcagt ggtaaccatg tggtattcgg cggagggacc    720
aagctgaccg tcctaggtgc ggccgca                                        747
```

<210> SEQ ID NO 73
<211> LENGTH: 771
<212> TYPE: DNA
<213> ORGANISM: Artificial
<220> FEATURE:
<223> OTHER INFORMATION: WapR-016 scFv

<400> SEQUENCE: 73

```
cagccggcca tggccgaggt gcagctggtg gagtctgggg gaggcttggt acagcctggg     60
gggtccctga gactctcctg tgcagcctct ggatacacct ttagcagcta tgccacgagc    120
tgggtccgcc aggctccagg aaggggctg gagtgggtcg caggtattag tggtagtggt    180
gataccacag actacgtaga ctccgtgaag gccggttca ccgtctccag agacaattcc    240
aagaacaccc tatatctgca aatgaacagc ctgagagccg acgacacggc cgtgtattac    300
tgtgcgtcga gaggaggttt aggggttat taccggggcg ctttgactt ctggggccag    360 gggacaatgg tcaccgtctc gagtggaggc ggcggttcag gcggaggtgg ctctggcggt    420
ggcggaagtg cacagtctgt gctgacgcag cctgcctccg tgtctgggtc tcctggacag    480
tcgatcacca tctcctgcac tggaaccagc agtgacgttg gtggttataa ctatgtctcc    540
tggtaccaac agcacccagg caaagccccc aaactcatga tttatgaggt cagtaatcgg    600
ccctcagggg tttctaatcg cttctctggc tccaagtctg gcaacacggc ctccctgacc    660
atctctgggc tccaggctga ggacgaggct gattattact gcagctcata taagcagc     720 ggcactgtgg tattcggcgg agggaccgag ctgaccgtcc tagcggccgc a             771
```

<210> SEQ ID NO 74
<211> LENGTH: 119
<212> TYPE: PRT
<213> ORGANISM: Artificial
<220> FEATURE:
<223> OTHER INFORMATION: WapR-004RAD VH

<400> SEQUENCE: 74

```
Glu Val Gln Leu Leu Glu Ser Gly Pro Gly Leu Val Lys Pro Ser Glu
1               5                  10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser
        115
```

```
<210> SEQ ID NO 75
<211> LENGTH: 11
<212> TYPE: PRT
<213> ORGANISM: Artificial
<220> FEATURE:
<223> OTHER INFORMATION: WapR-004RAD VHCDR3

<400> SEQUENCE: 75

Ala Asp Trp Asp Leu Leu His Ala Leu Asp Ile
1               5                   10

<210> SEQ ID NO 76
<211> LENGTH: 351
<212> TYPE: DNA
<213> ORGANISM: Artificial
<220> FEATURE:
<223> OTHER INFORMATION: WapR-004RAD VH

<400> SEQUENCE: 76
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag agccgattgg     300
gacctgcttc atgctcttga tatctggggc caagggaccc tggtcaccgt c              351

<210> SEQ ID NO 77
<211> LENGTH: 321
<212> TYPE: DNA
<213> ORGANISM: Artificial
<220> FEATURE:
<223> OTHER INFORMATION: WapR-004RAD VL

<400> SEQUENCE: 77
gaaattgtgt tgacacagtc tccatcctcc ctgtctacat ctgtaggaga cagagtcacc      60
atcacttgcc gggcaagtca gagcattagg agccatttaa attggtatca gcagaaacca     120
gggaaagccc ctaaactcct gatctatggt gcatccaatt tgcaaagtgg ggtcccatca     180
aggttcagtg gcagtggatc tgggacagat ttcactctca ccattagtag tctgcaacct     240
gaagattttg caacttacta ctgtcaacag agttacagtt ccccccctca c ttcggcgga    300 gggaccaagc tggagatcaa a                                               321

<210> SEQ ID NO 78
<211> LENGTH: 243
<212> TYPE: PRT
<213> ORGANISM: Artificial
<220> FEATURE:
<223> OTHER INFORMATION: W4-M1 scFv-Fc

<400> SEQUENCE: 78

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60
```

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
210                 215                 220

Gln Gln Ser Tyr Ser Thr Pro Gln Thr Phe Gly Gln Gly Thr Lys Leu
225                 230                 235                 240

Glu Ile Lys

<210> SEQ ID NO 79
<211> LENGTH: 245
<212> TYPE: PRT
<213> ORGANISM: Artificial
<220> FEATURE:
<223> OTHER INFORMATION: W4-M5 scFv-Fc

<400> SEQUENCE: 79

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Ser Gly Ser Ala Gln Ser Val Val Thr Gln Pro Ala Ser
130                 135                 140

Val Ser Gly Ser Leu Gly Gln Ser Ile Thr Ile Ser Cys Thr Gly Thr
145                 150                 155                 160

Ser Ser Asp Ala Gly Ser Tyr Asn Phe Val Ser Trp Tyr Gln Gln His
                165                 170                 175

Pro Gly Lys Ala Pro Lys Leu Ile Ile Tyr Asp Val Asn Asn Arg Pro

```
                    180                 185                 190
Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
            210                 215                 220

Cys Asn Ser Tyr Gly Gly Ser Ser Thr Trp Leu Phe Gly Gly Gly Thr
225                 230                 235                 240

Lys Leu Thr Val Leu
                245

<210> SEQ ID NO 80
<211> LENGTH: 245
<212> TYPE: PRT
<213> ORGANISM: Artificial
<220> FEATURE:
<223> OTHER INFORMATION: W4-M6 scFv-Fc

<400> SEQUENCE: 80

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Leu Ser Tyr Glu Leu Met Gln Pro Pro
        130                 135                 140

Ser Val Ser Gly Thr Pro Gly Gln Arg Val Thr Ile Ser Cys Ser Gly
145                 150                 155                 160

Ser Ser Ser Asn Ile Gly Ser Asn Thr Val Asn Trp Tyr Gln Gln Leu
                165                 170                 175

Pro Gly Thr Ala Pro Lys Leu Leu Ile Tyr Ser Asn Asn Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Gln Ser Glu Asp Glu Ala Asp Tyr Tyr
    210                 215                 220

Cys Ala Ala Trp Asp Asp Ser Leu Asn Val Val Phe Gly Gly Gly Thr
225                 230                 235                 240

Lys Val Thr Val Leu
                245

<210> SEQ ID NO 81
<211> LENGTH: 245
<212> TYPE: PRT
<213> ORGANISM: Artificial
<220> FEATURE:
<223> OTHER INFORMATION: W4-M7 scFv-Fc
```

<400> SEQUENCE: 81

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Ser Gly Ser Ala Gln Thr Val Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245
```

<210> SEQ ID NO 82
<211> LENGTH: 245
<212> TYPE: PRT
<213> ORGANISM: Artificial
<220> FEATURE:
<223> OTHER INFORMATION: W4-M8 scFv-Fc

<400> SEQUENCE: 82

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95
```

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Val Thr Gln Pro Pro Ser
            130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 83
<211> LENGTH: 245
<212> TYPE: PRT
<213> ORGANISM: Artificial
<220> FEATURE:
<223> OTHER INFORMATION: W4-M9 scFv-Fc

<400> SEQUENCE: 83

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Ser Gly Ser Ala Gln Ser Val Leu Thr Gln Pro Ala Ser
            130                 135                 140

Val Ser Gly Ser Pro Gly Gln Ser Ile Thr Ile Ser Cys Thr Gly Thr
145                 150                 155                 160

Thr Ser Asp Val Gly Ala Phe Gly Phe Val Ser Trp Tyr Gln Gln Lys
                165                 170                 175

Pro Gly Glu Val Pro Lys Leu Met Ile Tyr Asp Val Ser Asp Arg Pro
            180                 185                 190

Ser Gly Val Ser Asp Arg Phe Ser Gly Ser Lys Ser Gly Ser Thr Ala
            195                 200                 205

```
Ser Leu Thr Ile Ser Gly Leu Gln Ala Glu Asp Glu Ala Asp Tyr Tyr
    210                 215                 220

Cys Gly Ser Tyr Thr Ser Thr Thr Trp Val Phe Gly Gly Gly Thr
225                 230                 235                 240

Lys Leu Thr Val Leu
                245

<210> SEQ ID NO 84
<211> LENGTH: 246
<212> TYPE: PRT
<213> ORGANISM: Artificial
<220> FEATURE:
<223> OTHER INFORMATION: W4-M11 scFv-Fc

<400> SEQUENCE: 84

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Ser Tyr Glu Leu Met Gln Pro Ala
130                 135                 140

Ser Val Ser Gly Ser Leu Gly Gln Ser Ile Thr Ile Ser Cys Thr Gly
145                 150                 155                 160

Thr Ser Ser Asp Val Gly Ser Tyr Asn Phe Val Ser Trp Tyr Gln Gln
                165                 170                 175

His Pro Gly Lys Ala Pro Lys Leu Met Ile Tyr Glu Gly Thr Lys Arg
            180                 185                 190

Pro Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ser Ser Tyr Ala Arg Ser Tyr Thr Tyr Val Phe Gly Thr Gly
225                 230                 235                 240

Thr Lys Val Thr Val Leu
                245

<210> SEQ ID NO 85
<211> LENGTH: 245
<212> TYPE: PRT
<213> ORGANISM: Artificial
<220> FEATURE:
<223> OTHER INFORMATION: W4-M12 scFv-Fc

<400> SEQUENCE: 85

Glu Val Gln Leu Leu Glu Ser Gly Pro Gly Leu Val Lys Pro Ser Glu
1               5                   10                  15
```

Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Gln Thr Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Gly Asp Ile Gly Ala Tyr Asn Phe Val Ser Trp Tyr Gln Gln His
            165                 170                 175

Pro Gly Lys Ala Pro Lys Leu Ile Ile Tyr Asp Val Asn Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
    210                 215                 220

Cys Ser Ser Tyr Thr Ser Ser Asn Thr Tyr Leu Phe Gly Thr Gly Thr
225                 230                 235                 240

Lys Val Thr Val Leu
            245

<210> SEQ ID NO 86
<211> LENGTH: 245
<212> TYPE: PRT
<213> ORGANISM: Artificial
<220> FEATURE:
<223> OTHER INFORMATION: W4-M14 scFv-Fc

<400> SEQUENCE: 86

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Ser Gly Ser Ala Gln Ser Val Leu Thr Gln Pro Pro Ser
130             135                 140

Ala Phe Gly Thr Pro Gly Gln Ser Leu Thr Ile Ser Cys Ser Gly Ser
145             150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

Lys Val Thr Val Leu
                245

<210> SEQ ID NO 87
<211> LENGTH: 245
<212> TYPE: PRT
<213> ORGANISM: Artificial
<220> FEATURE:
<223> OTHER INFORMATION: W4-M15 scFv-Fc

<400> SEQUENCE: 87

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Gln Ser Val Leu Thr Gln Pro Pro Ser
130             135                 140

Ala Phe Gly Thr Pro Gly Gln Ser Leu Thr Ile Ser Cys Ser Gly Ser
145             150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

```
Lys Val Thr Val Leu
            245

<210> SEQ ID NO 88
<211> LENGTH: 245
<212> TYPE: PRT
<213> ORGANISM: Artificial
<220> FEATURE:
<223> OTHER INFORMATION: W4-M16 scFv-Fc

<400> SEQUENCE: 88

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Ser Gly
        115                 120                 125

Ser Gly Gly Gly Gly Ser Ala Gln Ser Val Leu Thr Gln Pro Pro Ser
    130                 135                 140

Ala Phe Gly Thr Pro Gly Gln Ser Leu Thr Ile Ser Cys Ser Gly Ser
145                 150                 155                 160

Asn Ser Asn Ile Gly Arg Asn Thr Val Thr Trp Tyr Gln His Leu Pro
                165                 170                 175

Gly Thr Ala Pro Lys Leu Leu Ile Tyr Ser Ser Asn Gln Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Gln Ser Glu Asp Glu Ala His Tyr Tyr Cys
    210                 215                 220

Ala Ala Trp Asp Asp Ser Leu His Gly Met Ile Phe Gly Gly Gly Thr
225                 230                 235                 240

Lys Val Thr Val Leu
            245

<210> SEQ ID NO 89
<211> LENGTH: 245
<212> TYPE: PRT
<213> ORGANISM: Artificial
<220> FEATURE:
<223> OTHER INFORMATION: W4-M17 scFv-Fc

<400> SEQUENCE: 89

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
```

```
            35                  40                  45
Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                    85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Gln Thr Val Val Thr Gln Pro Pro Ser
    130                 135                 140

Ala Phe Gly Thr Pro Gly Gln Ser Leu Thr Ile Ser Cys Ser Gly Ser
145                 150                 155                 160

Ser Ser Asn Ile Gly Gly Asn Thr Val Asn Trp Tyr Gln Gln Leu Pro
                165                 170                 175

Gly Thr Ala Pro Arg Leu Leu Ile Tyr Ser Asn Ser Gln Arg Pro Ser
                180                 185                 190

Gly Val Pro Asp Arg Phe Ser Gly Ser Lys Ser Gly Thr Ser Ala Ser
                195                 200                 205

Leu Ala Ile Ser Gly Leu Gln Ser Glu Asp Glu Ala Asp Tyr Tyr Cys
                210                 215                 220

Ala Ala Trp Asp Asp Ser Leu Asn Gly Val Val Phe Gly Gly Gly Thr
225                 230                 235                 240

Lys Leu Thr Val Leu
                245

<210> SEQ ID NO 90
<211> LENGTH: 245
<212> TYPE: PRT
<213> ORGANISM: Artificial
<220> FEATURE:
<223> OTHER INFORMATION: W4-M19 scFv-Fc

<400> SEQUENCE: 90

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
            50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                    85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Gln Ser Val Leu Thr Gln Pro Ala Ser
    130                 135                 140

Val Ser Gly Ser Pro Gly Gln Ser Ile Thr Ile Ser Cys Thr Gly Thr
```

```
                145                 150                 155                 160
Ser Ser Asp Val Gly Ala Tyr Asn Tyr Val Ser Trp Phe Gln Gln His
                165                 170                 175

Pro Gly Lys Val Pro Lys Leu Ile Ile Trp Glu Val Ile Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Ser Ser Tyr Thr Ser Ser Asn Thr Tyr Val Phe Gly Thr Gly Thr
225                 230                 235                 240

Lys Leu Thr Val Leu
                245

<210> SEQ ID NO 91
<211> LENGTH: 245
<212> TYPE: PRT
<213> ORGANISM: Artificial
<220> FEATURE:
<223> OTHER INFORMATION: W4-M20 scFv-Fc

<400> SEQUENCE: 91

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Ser Gly Ser Ala Gln Ser Ala Leu Thr Gln Pro Pro Ser
        130                 135                 140

Val Ser Ala Ala Pro Gly Gln Lys Val Thr Ile Ser Cys Ser Gly Ser
145                 150                 155                 160

Ser Ser Asn Ile Gly Asn Asn Tyr Val Ser Trp Tyr Leu Gln Leu Pro
                165                 170                 175

Gly Thr Ala Pro Lys Leu Leu Ile Tyr Asp Asn Asn Gly Arg Pro Ser
                180                 185                 190

Gly Ile Pro Asp Arg Phe Ser Gly Ser Lys Ser Gly Thr Ser Ala Thr
                195                 200                 205

Leu Gly Ile Thr Gly Leu Gln Thr Gly Asp Glu Ala Asp Tyr Tyr Cys
            210                 215                 220

Ala Thr Trp Asp Ser Ser Leu Ser Ala Gly Val Phe Gly Gly Gly Thr
225                 230                 235                 240

Lys Val Thr Val Leu
                245
```

<210> SEQ ID NO 92
<211> LENGTH: 244
<212> TYPE: PRT
<213> ORGANISM: Artificial
<220> FEATURE:
<223> OTHER INFORMATION: W4-M4 scFv-Fc

<400> SEQUENCE: 92

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Ser Gly Ser Ala Leu Ser Tyr Glu Leu Met Gln Asp Pro
    130                 135                 140

Ala Val Ser Val Ala Leu Gly Gln Thr Val Arg Ile Thr Cys Arg Gly
145                 150                 155                 160

Asp Ser Leu Ser Ser Phe Tyr Thr Ser Trp Tyr Gln Gln Lys Pro Gly
                165                 170                 175

Gln Ala Pro Leu Leu Val Ile Tyr Gly Lys Asn Asn Arg Pro Ser Gly
            180                 185                 190

Ile Pro Asp Arg Phe Ser Gly Ser Ser Gly Asn Thr Ala Ser Leu
        195                 200                 205

Thr Ile Thr Gly Ala Gln Ala Glu Asp Glu Ala Asp Tyr Tyr Cys Asn
    210                 215                 220

Ser Arg Asp Ser Ser Asp Asn Tyr Val Leu Phe Gly Gly Gly Thr Lys
225                 230                 235                 240

Leu Thr Val Leu
```

<210> SEQ ID NO 93
<211> LENGTH: 245
<212> TYPE: PRT
<213> ORGANISM: Artificial
<220> FEATURE:
<223> OTHER INFORMATION: W4-M10 scFv-Fc

<400> SEQUENCE: 93

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

```
                    65                  70                  75                  80
His Val Ser Ser Val Thr Ala Ala Asp Thr Ala Val Tyr Phe Cys Ala
                    85                  90                  95

Arg Gly Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Gln Ser Val Thr Gln Pro Ala Ser
130                 135                 140

Val Ser Gly Ser Pro Gly Gln Ser Val Thr Ile Ser Cys Thr Gly Thr
145                 150                 155                 160

Ser Ser Asp Val Gly Ser Tyr Lys Gly Val Ser Trp Tyr Gln Gln Pro
                165                 170                 175

Pro Gly Thr Ala Pro Lys Leu Leu Ile Tyr Asn Asp Asn Gln Arg Pro
            180                 185                 190

Ser Gly Ile Pro Gly Arg Phe Ser Gly Ser Asn Ser Gly Asn Thr Ala
                195                 200                 205

Ile Leu Thr Ile Ser Gly Thr Gln Ala Met Asp Glu Ala Asp Tyr Tyr
        210                 215                 220

Cys Gln Ala Trp Asp Ser Ser Asn His Val Val Phe Gly Gly Gly Thr
225                 230                 235                 240

Lys Leu Thr Val Leu
            245

<210> SEQ ID NO 94
<211> LENGTH: 243
<212> TYPE: PRT
<213> ORGANISM: Artificial
<220> FEATURE:
<223> OTHER INFORMATION: W4-HC1-LCP

<400> SEQUENCE: 94

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
```

```
                  180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 95
<211> LENGTH: 245
<212> TYPE: PRT
<213> ORGANISM: Artificial
<220> FEATURE:
<223> OTHER INFORMATION: W4-HC1-LC7 scFv-Fc

<400> SEQUENCE: 95

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Ser Gly Ser Ala Gln Thr Val Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 96
<211> LENGTH: 245
<212> TYPE: PRT
<213> ORGANISM: Artificial
<220> FEATURE:
<223> OTHER INFORMATION: W4-HC2-LC7 scFv-Fc
```

-continued

```
<400> SEQUENCE: 96

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Ser Gly Ser Ala Gln Thr Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 97
<211> LENGTH: 243
<212> TYPE: PRT
<213> ORGANISM: Artificial
<220> FEATURE:
<223> OTHER INFORMATION: W4-HC3-LCP scFv-Fc

<400> SEQUENCE: 97

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Phe Asp Ile Trp Gly Gln Gly
```

```
                100             105                 110
Thr Met Val Thr Val Ser Ser Gly Gly Gly Ser Gly Gly Gly
        115                 120                 125

Ser Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 98
<211> LENGTH: 243
<212> TYPE: PRT
<213> ORGANISM: Artificial
<220> FEATURE:
<223> OTHER INFORMATION: W4-HC4-LCP scFv-Fc

<400> SEQUENCE: 98

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Gly Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
        210                 215                 220
```

Gln Gln Ser Tyr Ser Phe Pro Leu Thr Phe Gly Gly Thr Lys Leu
225                 230                 235                 240

Glu Ile Lys

<210> SEQ ID NO 99
<211> LENGTH: 243
<212> TYPE: PRT
<213> ORGANISM: Artificial
<220> FEATURE:
<223> OTHER INFORMATION: W4-HC5-LCP scFv-Fc

<400> SEQUENCE: 99

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Pro Asp Ile Trp Gly Gln Gly
            100                 105                 110

Thr Leu Val Thr Val Ser Gly Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 100
<211> LENGTH: 245
<212> TYPE: PRT
<213> ORGANISM: Artificial
<220> FEATURE:
<223> OTHER INFORMATION: W4-HC5-LC7 scFv-Fc

<400> SEQUENCE: 100

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
            35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Pro Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Ser Gly Ser Ala Gln Thr Val Val Thr Gln Pro Ala Ser
130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 101
<211> LENGTH: 243
<212> TYPE: PRT
<213> ORGANISM: Artificial
<220> FEATURE:
<223> OTHER INFORMATION: W4-HC7-LCP scFv-Fc

<400> SEQUENCE: 101

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
            35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Leu Asp Val Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

```
Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 102
<211> LENGTH: 245
<212> TYPE: PRT
<213> ORGANISM: Artificial
<220> FEATURE:
<223> OTHER INFORMATION: W4-VH1-VL8 scFv-Fc

<400> SEQUENCE: 102

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Ala Gln Ser Val Val Thr Gln Pro Pro Ser
    130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245
```

```
<210> SEQ ID NO 103
<211> LENGTH: 243
<212> TYPE: PRT
<213> ORGANISM: Artificial
<220> FEATURE:
<223> OTHER INFORMATION: W4-VH2-VLP scFv-Fc

<400> SEQUENCE: 103

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 104
<211> LENGTH: 245
<212> TYPE: PRT
<213> ORGANISM: Artificial
<220> FEATURE:
<223> OTHER INFORMATION: W4-VH2-VL8 scFv-Fc

<400> SEQUENCE: 104

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
```

```
                65                  70                  75                  80
His Val Ser Ser Val Thr Ala Ala Asp Thr Ala Val Tyr Phe Cys Ala
                    85                  90                  95

Arg Ala Asp Trp Asp Leu Leu His Ala Leu Asp Ile Trp Gly Gln Gly
                100                 105                 110

Thr Thr Val Thr Val Ser Ser Gly Gly Gly Ser Gly Gly Gly Gly
                115                 120                 125

Ser Gly Gly Gly Gly Ser Ala Gln Ser Val Thr Gln Pro Pro Ser
            130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                    165                 170                 175

Pro Gly Lys Ala Pro Lys Leu Met Ile Tyr Glu Gly Thr Lys Arg Pro
                    180                 185                 190

Ser Gly Val Ser Asn Arg Phe Ser Gly Ser Lys Ser Gly Asn Thr Ala
                    195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 105
<211> LENGTH: 245
<212> TYPE: PRT
<213> ORGANISM: Artificial
<220> FEATURE:
<223> OTHER INFORMATION: W4-VH3-VL7 scFv-Fc

<400> SEQUENCE: 105

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                    85                  90                  95

Arg Ala Asp Trp Asp Leu Leu His Ala Phe Asp Ile Trp Gly Gln Gly
                100                 105                 110

Thr Met Val Thr Val Ser Ser Gly Gly Gly Gly Ser Gly Gly Gly Gly
                115                 120                 125

Ser Gly Gly Ser Gly Ser Ala Gln Thr Val Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                    165                 170                 175

Pro Gly Lys Ala Pro Lys Leu Met Ile Tyr Asp Val Ser Asn Arg Pro
```

```
                  180                 185                 190
Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 106
<211> LENGTH: 245
<212> TYPE: PRT
<213> ORGANISM: Artificial
<220> FEATURE:
<223> OTHER INFORMATION: W4-VH3-VL8 scFv-Fc

<400> SEQUENCE: 106

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Ala Gln Ser Val Val Thr Gln Pro Pro Ser
    130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 107
<211> LENGTH: 245
<212> TYPE: PRT
<213> ORGANISM: Artificial
<220> FEATURE:
<223> OTHER INFORMATION: W4-VH5-VL8 scFv-Fc
```

<400> SEQUENCE: 107

```
Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Thr Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
Arg Ala Asp Trp Asp Leu Leu His Ala Pro Asp Ile Trp Gly Gln Gly
            100                 105                 110
Thr Leu Val Thr Val Ser Gly Gly Gly Gly Ser Gly Gly Gly Gly
        115                 120                 125
Ser Gly Gly Gly Gly Ser Ala Gln Ser Val Val Thr Gln Pro Pro Ser
    130                 135                 140
Val Ser Ala Ala Pro Gly Gln Lys Val Thr Ile Ser Cys Thr Gly Thr
145                 150                 155                 160
Ser Ser Asp Val Gly Ser Tyr Asn Phe Val Ser Trp Tyr Gln Gln His
                165                 170                 175
Pro Gly Lys Ala Pro Lys Leu Met Ile Tyr Glu Gly Thr Lys Arg Pro
            180                 185                 190
Ser Gly Val Ser Asn Arg Phe Ser Gly Ser Lys Ser Gly Asn Thr Ala
        195                 200                 205
Ser Leu Thr Ile Ser Gly Leu Gln Ala Glu Asp Glu Ala Asp Tyr Tyr
    210                 215                 220
Cys Thr Ser Tyr Thr Ser Asp Ser Thr Leu Val Phe Gly Gly Gly Thr
225                 230                 235                 240
Lys Val Thr Val Leu
                245
```

<210> SEQ ID NO 108
<211> LENGTH: 245
<212> TYPE: PRT
<213> ORGANISM: Artificial
<220> FEATURE:
<223> OTHER INFORMATION: W4-VH6-VL7 scFv-Fc

<400> SEQUENCE: 108

```
Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Thr Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
```

```
Arg Ala Asp Trp Asp Leu Leu His Ala Leu Asp Met Trp Gly Gln Gly
            100                 105                 110

Thr Leu Val Thr Val Ser Ser Gly Gly Gly Ser Gly Gly Gly Gly
        115                 120                 125

Ser Gly Gly Ser Gly Ser Ala Gln Thr Val Val Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
            245

<210> SEQ ID NO 109
<211> LENGTH: 245
<212> TYPE: PRT
<213> ORGANISM: Artificial
<220> FEATURE:
<223> OTHER INFORMATION: W4-VH6-VL8 scFv-Fc

<400> SEQUENCE: 109

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Met Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Gln Ser Val Val Thr Gln Pro Pro Ser
    130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
            180                 185                 190

Ser Gly Val Ser Asn Arg Phe Ser Gly Ser Lys Ser Gly Asn Thr Ala
        195                 200                 205
```

-continued

Ser Leu Thr Ile Ser Gly Leu Gln Ala Glu Asp Ala Asp Tyr Tyr
    210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 110
<211> LENGTH: 243
<212> TYPE: PRT
<213> ORGANISM: Artificial
<220> FEATURE:
<223> OTHER INFORMATION: W4-VH6-VLP scFv-Fc

<400> SEQUENCE: 110

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Met Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 111
<211> LENGTH: 243
<212> TYPE: PRT
<213> ORGANISM: Artificial
<220> FEATURE:
<223> OTHER INFORMATION: W4-VH7-VLP scFv-Fc

<400> SEQUENCE: 111

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 112
<211> LENGTH: 245
<212> TYPE: PRT
<213> ORGANISM: Artificial
<220> FEATURE:
<223> OTHER INFORMATION: W4-VH7-VL7 scFv-Fc

<400> SEQUENCE: 112

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
            100                 105                 110

Thr Leu Val Thr Val Ser Ser Gly Gly Gly Gly Ser Gly Gly Gly Gly
        115                 120                 125

Ser Gly Gly Ser Gly Ser Ala Gln Thr Val Val Thr Gln Pro Ala Ser

```
                  130                 135                 140
Val Ser Gly Ser Pro Gly Gln Ser Ile Thr Ile Ser Cys Thr Gly Thr
145                 150                 155                 160

Ser Ser Asp Ile Gly Gly Tyr Asn Tyr Val Ser Trp Tyr Arg Gln His
                165                 170                 175

Pro Gly Lys Ala Pro Lys Leu Met Ile Tyr Asp Val Ser Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Thr Ser Tyr Thr Ser Asp Ser Thr Leu Val Phe Gly Gly Gly Thr
225                 230                 235                 240

Lys Val Thr Val Leu
                245

<210> SEQ ID NO 113
<211> LENGTH: 245
<212> TYPE: PRT
<213> ORGANISM: Artificial
<220> FEATURE:
<223> OTHER INFORMATION: W4-VH7-VL8 scFv-Fc

<400> SEQUENCE: 113

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
                35                  40                  45

Gly Tyr Ile His Ser Ser Gly Tyr Thr Asp Tyr Asn Pro Ser Leu Lys
                50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Val Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Ala Gln Ser Val Val Thr Gln Pro Pro Ser
                130                 135                 140

Val Ser Ala Ala Pro Gly Gln Lys Val Thr Ile Ser Cys Thr Gly Thr
145                 150                 155                 160

Ser Ser Asp Val Gly Ser Tyr Asn Phe Val Ser Trp Tyr Gln Gln His
                165                 170                 175

Pro Gly Lys Ala Pro Lys Leu Met Ile Tyr Glu Gly Thr Lys Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Thr Ser Tyr Thr Ser Asp Ser Thr Leu Val Phe Gly Gly Gly Thr
225                 230                 235                 240

Lys Val Thr Val Leu
```

<210> SEQ ID NO 114
<211> LENGTH: 243
<212> TYPE: PRT
<213> ORGANISM: Artificial
<220> FEATURE:
<223> OTHER INFORMATION: W4-VH9-VLP scFv-Fc

<400> SEQUENCE: 114

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Val Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 115
<211> LENGTH: 243
<212> TYPE: PRT
<213> ORGANISM: Artificial
<220> FEATURE:
<223> OTHER INFORMATION: W4-VH10-VLP scFv-Fc

<400> SEQUENCE: 115

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys

```
                    50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                    85                  90                  95

Arg Ala Asp Trp Asp Leu Phe His Ala Leu Asp Ile Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
                210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 116
<211> LENGTH: 243
<212> TYPE: PRT
<213> ORGANISM: Artificial
<220> FEATURE:
<223> OTHER INFORMATION: W4-VH11-VLP scFv-Fc

<400> SEQUENCE: 116

Glu Val Gln Leu Leu Glu Ser Gly Pro Gly Leu Val Lys Pro Ser Glu
 1               5                  10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
                35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                85                  90                  95

Arg Ala Asp Trp Asp Leu Pro His Ala Leu Asp Ile Trp Gly Gln Gly
                100                 105                 110

Thr Leu Val Thr Val Ser Ser Gly Gly Gly Gly Ser Gly Gly Gly Gly
                115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175
```

```
Gly Lys Ala Pro Lys Leu Leu Ile Tyr Gly Ala Ser Asn Leu Gln Ser
            180                 185                 190

Gly Val Pro Ser Arg Phe Ser Gly Ser Gly Thr Asp Phe Thr
            195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 117
<211> LENGTH: 243
<212> TYPE: PRT
<213> ORGANISM: Artificial
<220> FEATURE:
<223> OTHER INFORMATION: W4-VH12-VLP scFv-Fc

<400> SEQUENCE: 117

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu Arg Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 118
<211> LENGTH: 243
<212> TYPE: PRT
<213> ORGANISM: Artificial
<220> FEATURE:
<223> OTHER INFORMATION: W4-VH15-VLP scFv-Fc
```

<400> SEQUENCE: 118

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Gly Asn Trp Asp Leu Leu His Ala Leu Asp Ile Trp Gly Gln Gly
            100                 105                 110

Thr Leu Val Thr Val Ser Gly Gly Gly Gly Ser Gly Gly Gly Gly
        115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys
```

<210> SEQ ID NO 119
<211> LENGTH: 243
<212> TYPE: PRT
<213> ORGANISM: Artificial
<220> FEATURE:
<223> OTHER INFORMATION: W4-VH16-VLP scFv-Fc

<400> SEQUENCE: 119

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asn Leu Leu His Ala Leu Asp Ile Trp Gly Gln Gly
```

```
                  100                 105                 110
Thr Leu Val Thr Val Ser Ser Gly Gly Gly Ser Gly Gly Gly
            115                 120                 125
Ser Gly Gly Gly Ser Ala Leu Glu Ile Val Leu Thr Gln Ser Pro
            130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
                180                 185                 190
Gly Val Pro Ser Arg Phe Ser Gly Ser Gly Ser Gly Thr Asp Phe Thr
                195                 200                 205
Leu Thr Ile Ser Ser Leu Gln Pro Glu Asp Phe Ala Thr Tyr Tyr Cys
                210                 215                 220
Gln Gln Ser Tyr Ser Phe Pro Leu Thr Phe Gly Gly Gly Thr Lys Leu
225                 230                 235                 240
Glu Ile Lys

<210> SEQ ID NO 120
<211> LENGTH: 243
<212> TYPE: PRT
<213> ORGANISM: Artificial
<220> FEATURE:
<223> OTHER INFORMATION: W4-VH20-VLP scFv-Fc

<400> SEQUENCE: 120

Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
                20                  25                  30
Tyr Trp Thr Trp Ile Arg Gln Pro Pro Gly Lys Gly Leu Glu Leu Ile
            35                  40                  45
Gly Tyr Ile His Ser Ser Gly Tyr Thr Asp Tyr Asn Pro Ser Leu Lys
        50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
Arg Ala Asp Trp Asp Leu Leu His Thr Leu Asp Ile Trp Gly Gln Gly
                100                 105                 110
Thr Leu Val Thr Val Ser Ser Gly Gly Gly Ser Gly Gly Gly Gly
            115                 120                 125
Ser Gly Gly Gly Gly Ser Ala Leu Glu Ile Val Leu Thr Gln Ser Pro
            130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
                180                 185                 190
Gly Val Pro Ser Arg Phe Ser Gly Ser Gly Ser Gly Thr Asp Phe Thr
                195                 200                 205
Leu Thr Ile Ser Ser Leu Gln Pro Glu Asp Phe Ala Thr Tyr Tyr Cys
                210                 215                 220
```

Gln Gln Ser Tyr Ser Phe Pro Leu Thr Phe Gly Gly Thr Lys Leu
225                 230                 235                 240

Glu Ile Lys

<210> SEQ ID NO 121
<211> LENGTH: 243
<212> TYPE: PRT
<213> ORGANISM: Artificial
<220> FEATURE:
<223> OTHER INFORMATION: W4-VH31-VLP scFv-Fc

<400> SEQUENCE: 121

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Glu Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 122
<211> LENGTH: 243
<212> TYPE: PRT
<213> ORGANISM: Artificial
<220> FEATURE:
<223> OTHER INFORMATION: W4-VH37-VLP scFv-Fc

<400> SEQUENCE: 122

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

-continued

Tyr Trp Thr Trp Ile Arg Gln Pro Gly Lys Gly Leu Glu Leu Ile
         35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Asp Leu Leu His Ala Phe Asp Met Trp Gly Gln Gly
                100                 105                 110

Thr Met Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 123
<211> LENGTH: 243
<212> TYPE: PRT
<213> ORGANISM: Artificial
<220> FEATURE:
<223> OTHER INFORMATION: W4-VH41-VLP scFv-Fc

<400> SEQUENCE: 123

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
         35                  40                  45

Gly Tyr Ile His Ser Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                 85                  90                  95

Arg Ala Asp Trp Ala Leu Leu His Ala Leu Asp Ile Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg

Ala Ser Gln Ser Ile Arg Ser His Leu Asn Trp Tyr Gln Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 124
<211> LENGTH: 243
<212> TYPE: PRT
<213> ORGANISM: Artificial
<220> FEATURE:
<223> OTHER INFORMATION: W4-VH42-VLP scFv-Fc

<400> SEQUENCE: 124

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Ser Arg Val Thr Ile Ser Gly Asp Thr Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Arg Asp Leu Leu His Ala Leu Asp Ile Trp Gly Gln Gly
            100                 105                 110

Thr Met Val Thr Val Ser Ser Gly Gly Gly Ser Gly Gly Gly
            115                 120                 125

Ser Gly Gly Gly Ser Ala Leu Glu Ile Val Leu Thr Gln Ser Pro
        130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 125
<211> LENGTH: 243

<212> TYPE: PRT
<213> ORGANISM: Artificial
<220> FEATURE:
<223> OTHER INFORMATION: W4-VH35-VLP scFv-Fc

<400> SEQUENCE: 125

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Thr
                85                  90                  95

Arg Ala Asp Trp Asp Leu Leu His Ala Leu Asp Ile Trp Gly Gln Gly
            100                 105                 110

Thr Leu Val Thr Val Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 126
<211> LENGTH: 243
<212> TYPE: PRT
<213> ORGANISM: Artificial
<220> FEATURE:
<223> OTHER INFORMATION: W4-VH36-VLP scFv-Fc

<400> SEQUENCE: 126

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Val
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 127
<211> LENGTH: 243
<212> TYPE: PRT
<213> ORGANISM: Artificial
<220> FEATURE:
<223> OTHER INFORMATION: W4-VH52-VLP scFv-Fc

<400> SEQUENCE: 127

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Pro Ser Leu Lys
        50                  55                  60

Gly Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Thr Lys Leu
225                 230                 235                 240

Glu Ile Lys

<210> SEQ ID NO 128
<211> LENGTH: 243
<212> TYPE: PRT
<213> ORGANISM: Artificial
<220> FEATURE:
<223> OTHER INFORMATION: W4-VH53-VLP scFv-Fc

<400> SEQUENCE: 128

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Pro Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Thr Lys Leu
225                 230                 235                 240

Glu Ile Lys

<210> SEQ ID NO 129
<211> LENGTH: 243
<212> TYPE: PRT
<213> ORGANISM: Artificial
<220> FEATURE:
<223> OTHER INFORMATION: W4-VH54-VLP scFv-Fc

<400> SEQUENCE: 129

Glu Val Gln Leu Leu Glu Ser Gly Pro Gly Leu Val Lys Pro Ser Glu
1               5                   10                  15

```
Thr Leu Ser Leu Thr Cys Asn Val Ala Gly Gly Ser Ile Ser Pro Tyr
            20                  25                  30

Tyr Trp Thr Trp Ile Arg Gln Pro Gly Lys Gly Leu Glu Leu Ile
        35                  40                  45

Gly Tyr Ile His Ser Asn Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 130
<211> LENGTH: 243
<212> TYPE: PRT
<213> ORGANISM: Artificial
<220> FEATURE:
<223> OTHER INFORMATION: W4-VH55-VLP scFv-Fc

<400> SEQUENCE: 130

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Thr His Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125
```

-continued

```
Ser Gly Gly Gly Ser Ala Leu Glu Ile Val Leu Thr Gln Ser Pro
    130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Tyr Cys
    210                 215                 220
Gln Gln Ser Tyr Ser Phe Pro Leu Thr Phe Gly Gly Gly Thr Lys Leu
225                 230                 235                 240
Glu Ile Lys

<210> SEQ ID NO 131
<211> LENGTH: 243
<212> TYPE: PRT
<213> ORGANISM: Artificial
<220> FEATURE:
<223> OTHER INFORMATION: W4-VH56-VLP scFv-Fc

<400> SEQUENCE: 131

Glu Val Gln Leu Leu Glu Ser Gly Pro Gly Leu Val Lys Pro Ser Glu
1               5                   10                  15
Thr Leu Ser Leu Thr Cys Asn Val Ala Gly Gly Ser Ile Ser Pro Tyr
            20                  25                  30
Tyr Trp Thr Trp Ile Arg Gln Pro Pro Gly Lys Gly Leu Glu Leu Ile
        35                  40                  45
Gly Tyr Ile His Ser Ser Gly Tyr Ala Asp Tyr Asn Pro Ser Leu Lys
    50                  55                  60
Ser Arg Val Thr Ile Ser Gly Asp Thr Ser Lys Lys Gln Phe Ser Leu
65                  70                  75                  80
His Val Ser Ser Val Thr Ala Ala Asp Thr Ala Val Tyr Phe Cys Ala
                85                  90                  95
Arg Ala Asp Trp Asp Leu Leu His Ala Leu Asp Ile Trp Gly Gln Gly
            100                 105                 110
Thr Leu Val Thr Val Ser Ser Gly Gly Gly Ser Gly Gly Gly Gly
        115                 120                 125
Ser Gly Gly Gly Ser Ala Leu Glu Ile Val Leu Thr Gln Ser Pro
    130                 135                 140
Ser Ser Leu Ser Thr Ser Val Gly Asp Arg Val Thr Ile Thr Cys Arg
145                 150                 155                 160
Ala Ser Gln Ser Ile Arg Ser His Leu Asn Trp Tyr Gln Gln Lys Pro
                165                 170                 175
Gly Lys Ala Pro Lys Leu Leu Ile Tyr Gly Ala Ser Asn Leu Gln Ser
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Tyr Cys
    210                 215                 220
Gln Gln Ser Tyr Ser Phe Pro Leu Thr Phe Gly Gly Gly Thr Lys Leu
225                 230                 235                 240
Glu Ile Lys
```

<210> SEQ ID NO 132
<211> LENGTH: 243
<212> TYPE: PRT
<213> ORGANISM: Artificial
<220> FEATURE:
<223> OTHER INFORMATION: W4-VH57-VLP scFv-Fc

<400> SEQUENCE: 132

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Gly Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 133
<211> LENGTH: 243
<212> TYPE: PRT
<213> ORGANISM: Artificial
<220> FEATURE:
<223> OTHER INFORMATION: W4-VH58-VLP scFv-Fc

<400> SEQUENCE: 133

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Arg Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 134
<211> LENGTH: 243
<212> TYPE: PRT
<213> ORGANISM: Artificial
<220> FEATURE:
<223> OTHER INFORMATION: W4-VH60-VLP scFv-Fc

<400> SEQUENCE: 134

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Ser Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 135
<211> LENGTH: 243
<212> TYPE: PRT
<213> ORGANISM: Artificial
<220> FEATURE:
<223> OTHER INFORMATION: W4-VH61-VLP scFv-Fc

<400> SEQUENCE: 135

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Phe Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 136
<211> LENGTH: 243
<212> TYPE: PRT
<213> ORGANISM: Artificial
<220> FEATURE:
<223> OTHER INFORMATION: W4-VH62-VLP scFv-Fc -continued

```
<400> SEQUENCE: 136

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Arg Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 137
<211> LENGTH: 243
<212> TYPE: PRT
<213> ORGANISM: Artificial
<220> FEATURE:
<223> OTHER INFORMATION: W4-VH63-VLP scFv-Fc

<400> SEQUENCE: 137

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Gly Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110
```

```
Thr Leu Val Thr Val Ser Ser Gly Gly Gly Ser Gly Gly Gly
            115                 120                 125

Ser Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
                210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 138
<211> LENGTH: 243
<212> TYPE: PRT
<213> ORGANISM: Artificial
<220> FEATURE:
<223> OTHER INFORMATION: W4-VH64-VLP scFv-Fc

<400> SEQUENCE: 138

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
                20                  25                  30

Tyr Trp Thr Trp Ile Arg Gln Pro Pro Gly Lys Gly Leu Glu Leu Ile
            35                  40                  45

Gly Tyr Ile Arg Ser Ser Gly Tyr Thr Asp Tyr Asn Pro Ser Leu Lys
        50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
                210                 215                 220
```

```
Gln Gln Ser Tyr Ser Phe Pro Leu Thr Phe Gly Gly Thr Lys Leu
225                 230                 235                 240

Glu Ile Lys
```

<210> SEQ ID NO 139
<211> LENGTH: 243
<212> TYPE: PRT
<213> ORGANISM: Artificial
<220> FEATURE:
<223> OTHER INFORMATION: W4-VH65-VLP scFv-Fc

<400> SEQUENCE: 139

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Asn Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys
```

<210> SEQ ID NO 140
<211> LENGTH: 243
<212> TYPE: PRT
<213> ORGANISM: Artificial
<220> FEATURE:
<223> OTHER INFORMATION: W4-VH66-VLP scFv-Fc

<400> SEQUENCE: 140

```
Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
```

```
                    35                  40                  45
Gly Tyr Ile His Ser Ser Gly Tyr Thr Asp His Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                     85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
                210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 141
<211> LENGTH: 243
<212> TYPE: PRT
<213> ORGANISM: Artificial
<220> FEATURE:
<223> OTHER INFORMATION: W4-VH67-VLP scFv-Fc

<400> SEQUENCE: 141

Glu Val Gln Leu Leu Glu Ser Gly Pro Gly Leu Val Lys Pro Ser Glu
 1                5                  10                  15

Thr Leu Ser Leu Thr Cys Asn Val Ala Gly Gly Ser Ile Ser Pro Tyr
                 20                  25                  30

Tyr Trp Thr Trp Ile Arg Gln Pro Pro Gly Lys Gly Leu Glu Leu Ile
                 35                  40                  45

Gly Tyr Ile His Phe Ser Gly Tyr Thr Asp Tyr Asn Pro Ser Leu Lys
 50                  55                  60

Ser Arg Val Thr Ile Ser Gly Asp Thr Ser Lys Lys Gln Phe Ser Leu
 65                  70                  75                  80

His Val Ser Ser Val Thr Ala Ala Asp Thr Ala Val Tyr Phe Cys Ala
                     85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Gly Ser Gly Gly Gly Gly
                115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160
```

Ala Ser Gln Ser Ile Arg Ser His Leu Asn Trp Tyr Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 142
<211> LENGTH: 243
<212> TYPE: PRT
<213> ORGANISM: Artificial
<220> FEATURE:
<223> OTHER INFORMATION: W4-VH69-VLP scFv-Fc

<400> SEQUENCE: 142

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Tyr Thr Asp Tyr Asn Ser Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Gly Gly Gly Gly Ser Gly Gly Gly Gly
            115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Lys Pro
            165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 143
<211> LENGTH: 243
<212> TYPE: PRT

<213> ORGANISM: Artificial
<220> FEATURE:
<223> OTHER INFORMATION: W4-VH70-VLP scFv-Fc

<400> SEQUENCE: 143

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Arg
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Glu Ile Val Leu Thr Gln Ser Pro
    130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 144
<211> LENGTH: 243
<212> TYPE: PRT
<213> ORGANISM: Artificial
<220> FEATURE:
<223> OTHER INFORMATION: W4-VH72-VLP scFv-Fc

<400> SEQUENCE: 144

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly His Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala

```
                    85                  90                  95
Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Thr Lys Leu
225                 230                 235                 240

Glu Ile Lys

<210> SEQ ID NO 145
<211> LENGTH: 243
<212> TYPE: PRT
<213> ORGANISM: Artificial
<220> FEATURE:
<223> OTHER INFORMATION: W4-VH79-VLP scFv-Fc

<400> SEQUENCE: 145

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Tyr His Pro Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
                100                 105                 110

Thr Leu Val Thr Val Ser Ser Gly Gly Gly Ser Gly Gly Gly Gly
            115                 120                 125

Ser Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
                180                 185                 190

Gly Val Pro Ser Arg Phe Ser Gly Ser Gly Ser Gly Thr Asp Phe Thr
                195                 200                 205
```

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 146
<211> LENGTH: 243
<212> TYPE: PRT
<213> ORGANISM: Artificial
<220> FEATURE:
<223> OTHER INFORMATION: W4-VH80-VLP scFv-Fc

<400> SEQUENCE: 146

Glu Val Gln Leu Leu Glu Ser Gly Pro Gly Leu Val Lys Pro Ser Glu
1               5                   10                  15

Thr Leu Ser Leu Thr Cys Asn Val Ala Gly Gly Ser Ile Ser Pro Tyr
            20                  25                  30

Tyr Trp Thr Trp Ile Arg Gln Pro Pro Gly Lys Gly Leu Glu Leu Ile
            35                  40                  45

Gly Tyr Ile His Ser Ser Gly Phe Thr Ser Tyr Asn Pro Ser Leu Lys
50                  55                  60

Ser Arg Val Thr Ile Ser Gly Asp Thr Ser Lys Lys Gln Phe Ser Leu
65                  70                  75                  80

His Val Ser Ser Val Thr Ala Ala Asp Thr Ala Val Tyr Phe Cys Ala
                85                  90                  95

Arg Ala Asp Trp Asp Leu Leu His Ala Leu Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Leu Glu Ile Val Leu Thr Gln Ser Pro
130                 135                 140

Ser Ser Leu Ser Thr Ser Val Gly Asp Arg Val Thr Ile Thr Cys Arg
145                 150                 155                 160

Ala Ser Gln Ser Ile Arg Ser His Leu Asn Trp Tyr Gln Gln Lys Pro
                165                 170                 175

Gly Lys Ala Pro Lys Leu Leu Ile Tyr Gly Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
            210                 215                 220

Gln Gln Ser Tyr Ser Phe Pro Leu Thr Phe Gly Gly Gly Thr Lys Leu
225                 230                 235                 240

Glu Ile Lys

<210> SEQ ID NO 147
<211> LENGTH: 729
<212> TYPE: DNA
<213> ORGANISM: Artificial
<220> FEATURE:
<223> OTHER INFORMATION: W4-M1 scFv-Fc

<400> SEQUENCE: 147
gaggtgcagc tgttggagtc gggcccagga ctggtgaagc cttcggagac cctgtccctc      60
acctgcaatg tcgctggtgg ctccatcagt ccttactact ggacctggat ccggcagccc     120

```
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgctg    420
actcagtctc catcctccct gtctgcatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc atcagcagtc tgcaacctga ggattttgca    660
acttattatt gtcaacagag ttacagtacc cctcagacgt tcggccaagg gaccaagctg    720
gagatcaaa                                                            729

<210> SEQ ID NO 148
<211> LENGTH: 735
<212> TYPE: DNA
<213> ORGANISM: Artificial
<220> FEATURE:
<223> OTHER INFORMATION: W4-M5 scFv-Fc

<400> SEQUENCE: 148
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcacagtc tgtcgtgacg    420
cagcctgcct ccgtgtctgg gtctcttgga cagtcgatca ccatctcctg cactggaacc    480
agcagtgatg ctgggagtta aactttgtc tcctggtacc aacaacaccc aggcaaagcc    540
cccaaactca tcatttatga tgtcaataat cggccctcag gggtttctaa tcgcttctct    600
ggctccaagt ctggcaacac ggcctccctg accatctctg gctccaggc tgaggacgag    660 gctgattatt attgcaactc atacggaggc agcagcactt ggctgttcgg cggagggacc    720
aagctgaccg tccta                                                     735

<210> SEQ ID NO 149
<211> LENGTH: 735
<212> TYPE: DNA
<213> ORGANISM: Artificial
<220> FEATURE:
<223> OTHER INFORMATION: W4-M6 scFv-Fc

<400> SEQUENCE: 149
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
```

```
gacctgcttc atgctcttga tatctggggc aagggaccc tggtcaccgt ctcgagtgga    360
ggcggcggtt caggcggagg tggctctggc ggtggcggaa gtgcactctc ctatgagctg    420
atgcagccac cctcagtgtc tgggaccccc gggcagaggg tcaccatctc ttgttctgga    480
agcagctcca acatcggaag taatactgta aactggtacc agcagctccc aggaacggcc    540
cccaaactcc tcatctatag taataatcag cggccctcag gggtccctga ccgattctct    600
ggctccaagt ctggcacctc agcctccctg gccatcagtg gctccagtc tgaggatgag    660 gctgattatt actgtgcagc atgggatgac agcctgaatg tggtattcgg cggagggacc    720
aaggtcaccg tccta                                                    735

<210> SEQ ID NO 150
<211> LENGTH: 735
<212> TYPE: DNA
<213> ORGANISM: Artificial
<220> FEATURE:
<223> OTHER INFORMATION: W4-M7 scFv-Fc

<400> SEQUENCE: 150
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc aagggaccc tggtcaccgt ctcgagtgga    360
ggcggcggtt caggcggagg tggctctggc ggtagcggaa gtgcacagac tgtggtgacc    420
cagcctgcct ccgtgtctgg gtctcctgga cagtcgatca ccatctcctg cactggaacc    480
agcagtgaca ttggtggtta taactatgtc tcctggtacc acagcaccc aggcaaagcc    540 cccaaactca tgatttatga tgtcagtaat cggccctcag gggtttctaa tcgcttctct    600
ggctccaagt ctggcaacac ggcctccctg accatctctg gctccaggc tgaggacgag    660 gctgattatt actgcacctc atatacaagc gacagcactc tggttttcgg cggaggcacc    720
aaggtgaccg tcctc                                                    735

<210> SEQ ID NO 151
<211> LENGTH: 735
<212> TYPE: DNA
<213> ORGANISM: Artificial
<220> FEATURE:
<223> OTHER INFORMATION: W4-M8 scFv-Fc

<400> SEQUENCE: 151
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc aagggaccc tggtcaccgt ctcgagtgga    360
ggcggcggtt caggcggagg tggctctggc ggtggcggaa gtgcacagtc tgtcgtgacg    420
cagccgccct cagtgtctgc ggccccagga cagaaggtca ccatctcctg cactggaacc    480
agcagtgatg ttgggagtta aactttgtc tcctggtacc aacagcaccc aggcaaagcc    540
```

```
cccaaaactca tgatttatga gggcactaag cggccctcag gggtttctaa tcgcttctct    600
ggctccaagt ctggcaacac ggcctccctg accatctctg gctccaggc tgaggacgag     660 gctgattatt actgcacctc atatacaagc gacagcactc tggttttcgg cggaggcacc    720
aaggtgaccg tcctc                                                     735
```

<210> SEQ ID NO 152
<211> LENGTH: 735
<212> TYPE: PRT
<213> ORGANISM: Artificial
<220> FEATURE:
<223> OTHER INFORMATION: W4-M9 scFv-Fc
<400> SEQUENCE: 152

```
Gly Ala Gly Gly Thr Gly Cys Ala Gly Cys Thr Gly Thr Thr Gly Gly
 1               5                  10                  15

Ala Gly Thr Cys Gly Gly Cys Cys Cys Ala Gly Gly Ala Cys Thr
            20                  25                  30

Gly Gly Thr Gly Ala Ala Gly Cys Thr Thr Cys Gly Gly Ala Gly
        35                  40                  45

Ala Cys Cys Cys Thr Gly Thr Cys Cys Thr Cys Ala Cys Cys Thr
50                  55                  60

Gly Cys Ala Ala Thr Gly Thr Cys Gly Cys Thr Gly Thr Gly Gly
65                  70                  75                  80

Cys Thr Cys Cys Ala Thr Cys Ala Gly Thr Cys Thr Thr Ala Cys
                85                  90                  95

Thr Ala Cys Thr Gly Gly Ala Cys Thr Gly Gly Ala Thr Cys Cys
                100                 105                 110

Gly Gly Cys Ala Gly Cys Cys Cys Cys Ala Gly Gly Ala Ala Ala
                115                 120                 125

Gly Gly Gly Cys Cys Thr Gly Gly Ala Gly Thr Thr Gly Ala Thr Thr
130                 135                 140

Gly Gly Thr Thr Ala Thr Ala Thr Cys Cys Ala Cys Thr Cys Cys Ala
145                 150                 155                 160

Gly Thr Gly Gly Thr Ala Cys Ala Cys Cys Gly Ala Cys Thr Ala
                165                 170                 175

Cys Ala Ala Cys Cys Cys Thr Cys Cys Cys Thr Cys Ala Ala Gly
                180                 185                 190

Ala Gly Thr Cys Gly Ala Gly Thr Cys Ala Cys Cys Ala Thr Ala Thr
            195                 200                 205

Cys Ala Gly Gly Ala Gly Ala Cys Ala Cys Gly Thr Cys Cys Ala Ala
        210                 215                 220

Gly Ala Ala Gly Cys Ala Gly Thr Thr Cys Thr Cys Cys Cys Thr Gly
225                 230                 235                 240

Cys Ala Cys Gly Thr Gly Ala Gly Cys Thr Cys Thr Gly Thr Gly Ala
            245                 250                 255

Cys Cys Gly Cys Thr Gly Cys Gly Gly Ala Cys Ala Cys Gly Gly Cys
                260                 265                 270

Cys Gly Thr Gly Thr Ala Cys Thr Thr Cys Thr Gly Thr Gly Cys Gly
            275                 280                 285

Ala Gly Ala Gly Gly Cys Gly Ala Thr Thr Gly Gly Ala Cys Cys
        290                 295                 300

Thr Gly Cys Thr Thr Cys Ala Thr Gly Cys Thr Cys Thr Gly Ala
305                 310                 315                 320
```

```
Thr Ala Thr Cys Thr Gly Gly Gly Cys Ala Gly Gly
                    325                 330             335
Ala Cys Cys Cys Thr Gly Thr Cys Ala Cys Gly Thr Cys Thr
                340             345             350
Cys Gly Ala Gly Thr Gly Ala Gly Cys Gly Gly Cys Gly Gly
                355             360             365
Thr Thr Cys Ala Gly Gly Cys Gly Ala Gly Thr Gly Gly Cys
    370             375             380
Thr Cys Thr Gly Gly Gly Gly Thr Ala Cys Gly Gly Ala Ala
385             390             395             400
Gly Thr Gly Cys Ala Cys Ala Gly Thr Cys Thr Gly Cys Thr
            405             410             415
Gly Ala Cys Thr Cys Ala Gly Cys Thr Gly Cys Thr Cys Cys
            420             425             430
Gly Thr Gly Thr Cys Gly Gly Gly Thr Cys Ala Cys Thr Gly
            435             440             445
Gly Ala Cys Ala Gly Thr Cys Gly Ala Thr Cys Ala Cys Ala
    450             455             460
Ala Thr Cys Cys Thr Gly Cys Ala Cys Thr Gly Gly Cys Ala Cys Cys
465             470             475             480
Ala Cys Cys Ala Gly Cys Gly Ala Cys Gly Thr Thr Gly Thr Gly
            485             490             495
Cys Thr Thr Thr Thr Gly Gly Cys Thr Thr Thr Gly Thr Cys Thr Cys
            500             505             510
Cys Thr Gly Gly Thr Ala Cys Ala Ala Cys Ala Gly Ala Ala Gly
            515             520             525
Cys Cys Ala Gly Gly Cys Gly Ala Ala Gly Thr Cys Cys Cys Ala
        530             535             540
Ala Ala Cys Thr Cys Ala Thr Gly Ala Thr Thr Thr Ala Thr Gly Ala
545             550             555             560
Thr Gly Thr Cys Ala Gly Thr Gly Ala Thr Cys Gly Gly Cys Cys Cys
        565             570             575
Thr Cys Ala Gly Gly Gly Gly Thr Thr Thr Cys Thr Gly Ala Thr Cys
            580             585             590
Gly Cys Thr Thr Cys Thr Cys Thr Gly Gly Cys Thr Cys Cys Ala Ala
            595             600             605
Gly Thr Cys Thr Gly Gly Cys Ala Gly Cys Ala Cys Gly Gly Cys Cys
        610             615             620
Thr Cys Cys Cys Thr Gly Ala Cys Cys Ala Thr Cys Thr Cys Thr Gly
625             630             635             640
Gly Gly Cys Thr Cys Cys Ala Gly Gly Cys Thr Gly Ala Gly Gly Ala
                645             650             655
Cys Gly Ala Gly Gly Cys Thr Gly Ala Thr Thr Ala Thr Thr Ala Cys
        660             665             670
Thr Gly Cys Gly Gly Cys Thr Cys Ala Thr Ala Thr Ala Cys Ala Ala
        675             680             685
Gly Cys Ala Cys Cys Ala Gly Cys Ala Cys Thr Thr Gly Gly Gly Thr
        690             695             700
Gly Thr Thr Cys Gly Gly Cys Gly Gly Ala Gly Gly Ala Cys Cys
705             710             715             720
Ala Ala Gly Cys Thr Gly Ala Cys Cys Gly Thr Cys Cys Thr Ala
            725             730             735
```

<210> SEQ ID NO 153
<211> LENGTH: 738
<212> TYPE: DNA
<213> ORGANISM: Artificial
<220> FEATURE:
<223> OTHER INFORMATION: W4-M11 scFv-Fc

<400> SEQUENCE: 153

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacg ccaagaagca gttctccctg       240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtggcggaa gtgcactctc ctatgagctg     420
atgcagcctg cctccgtgtc tgggtctctt ggacagtcga tcaccatctc ctgcactgga     480
accagcagtg atgttgggag ttataacttt gtctcctggt accaacagca cccaggcaaa     540 gccccccaaac tcatgattta tgagggcact aagcggccct caggggtccc tgaccgattc     600
tctggctcca agtctggcaa cacggcctcc ctgacaatct ctgggctcca ggctgaggac     660
gaggctgatt attactgttc ctcatatgca cgtagttaca cttatgtctt cggaactggc     720
accaaggtga ccgtcctc                                                    738
```

<210> SEQ ID NO 154
<211> LENGTH: 735
<212> TYPE: DNA
<213> ORGANISM: Artificial
<220> FEATURE:
<223> OTHER INFORMATION: W4-M12 scFv-Fc

<400> SEQUENCE: 154

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtggcggaa gtgcacagac tgtggtgacc     420
cagcctgcct cagtgtctgg gtctcctgga cagtcgatca ccatctcctg cactgggacc     480
agcggtgaca ttggtgctta taactttgtc tcctggtacc aacaacccc aggcaaagcc      540 cccaaactca tcatttatga tgtcaataat cggccctcag gggtttctaa tcgcttctct     600
ggctccaagt ctggcaacac ggcctccctg accatctctg gctccaggc tgaggacgag      660 gctgattatt actgcagctc atatacaagc agcaacactt atctcttcgg aactgggacc     720
aaggtcaccg tccta                                                       735
```

<210> SEQ ID NO 155
<211> LENGTH: 735
<212> TYPE: DNA
<213> ORGANISM: Artificial
<220> FEATURE:
<223> OTHER INFORMATION: W4-M14 scFv-Fc

<400> SEQUENCE: 155

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtagcggaa gtgcacagtc tgtgttgacg     420
cagccaccct cagcgtttgg gacccccgga cagagtctca ccatctcttg ttctggaagc     480
aactccaaca tcggacgtaa tactgttact tggtaccagc atctcccagg aacggccccc     540
aaactcctca tctatagttc taatcagcgg ccctcggggg tccctgaccg attctctggc     600
tccaagtctg gcacctcagc ctccctggcc atcagtgggc tccagtctga ggatgaggct     660
cattattact gtgcagcatg ggatgacagc ctgcatggca tgatatttgg cggagggacc     720
aaggtcaccg tccta                                                      735
```

<210> SEQ ID NO 156
<211> LENGTH: 735
<212> TYPE: DNA
<213> ORGANISM: Artificial
<220> FEATURE:
<223> OTHER INFORMATION: W4-M15 scFv-Fc

<400> SEQUENCE: 156

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca agagtcgagt caccatatca ggagacacgt ccaagaagca gttctccctg     240
cacgtgagct ctgtgaccgc tgcggacacg gccgtgtact tctgtgcgag aggcgattgg     300
gacctgcttc atgctcttga tatctggggc caagggaccc tggtcaccgt ctcgagtgga     360
ggcggcggtt caggcggagg tggctctggc ggtggcggaa gtgcacagtc tgtgctgacg     420
cagccaccct cagcgtttgg gacccccgga cagagtctca ccatctcttg ttctggaagc     480
aactccaaca tcggacgtaa tactgttact tggtaccagc atctcccagg aacggccccc     540
aaactcctca tctatagttc taatcagcgg ccctcggggg tccctgaccg attctctggc     600
tccaagtctg gcacctcagc ctccctggcc atcagtgggc tccagtctga ggatgaggct     660
cattattact gtgcagcatg ggatgacagc ctgcatggca tgatatttgg cggagggacc     720
aaggtcaccg tccta                                                      735
```

<210> SEQ ID NO 157
<211> LENGTH: 735
<212> TYPE: DNA
<213> ORGANISM: Artificial
<220> FEATURE:
<223> OTHER INFORMATION: W4-M16 scFv-Fc

<400> SEQUENCE: 157

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
```

```
ccctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggaag tggctctggc ggtggcggaa gtgcacagtc tgtgttgacg    420
cagccaccct cagcgtttgg accccggga cagagtctca ccatctcttg ttctggaagc    480
aactccaaca tcggacgtaa tactgttact tggtaccagc atctcccagg aacggccccc    540
aaactcctca tctatagttc taatcagcgg ccctcggggg tccctgaccg attctctggc    600
tccaagtctg gcacctcagc ctccctggcc atcagtgggc tccagtctga ggatgaggct    660
cattattact gtgcagcatg ggatgacagc ctgcatggca tgatatttgg cggagggacc    720
aaggtcaccg tccta                                                    735
```

<210> SEQ ID NO 158
<211> LENGTH: 735
<212> TYPE: DNA
<213> ORGANISM: Artificial
<220> FEATURE:
<223> OTHER INFORMATION: W4-M17 scFv-Fc

<400> SEQUENCE: 158

```
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcacagac tgtggtgacc    420
cagccaccct cagcgtttgg accccggga cagagtctca ccatctcttg ttctggaagc    480
agctccaaca tcggaggtaa tactgtaaac tggtaccagc agctcccagg aacggccccc    540
agactcctca tctatagtaa tagtcagcgg ccctcagggg tccctgaccg attctctggc    600
tccaagtctg gcacctcagc ctccctggcc atcagtgggc tccagtctga ggatgaggct    660
gactattact gtgcagcatg ggatgacagc ctgaatggtg tggtattcgg cggagggacc    720
aagctgaccg tccta                                                    735
```

<210> SEQ ID NO 159
<211> LENGTH: 735
<212> TYPE: DNA
<213> ORGANISM: Artificial
<220> FEATURE:
<223> OTHER INFORMATION: W4-M19 scFv-Fc

<400> SEQUENCE: 159

```
gaggtgcagc tgttggagtc gggcccagga ctggtgaagc cttcggagac cctgtccctc    60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
```

```
ggcggcggtt caggcggagg tggctctggc ggtggcggaa gtgcacagtc tgtgctgact    420
cagcctgcct ccgtgtctgg gtctcctgga cagtcgatca ccatctcctg cactggaacc    480
agcagtgacg ttggtgctta taactatgtc tcctggttcc aacaacaccc aggcaaagtc    540
cccaaactca taatttggga ggtcattaat cggccctcag gggtttctaa tcgcttctct    600
ggctccaagt ctggcaacac ggcctccctg accatctctg gctccaggc tgaggacgag     660 gctgattatt actgttcctc atatacaagc agcaacactt atgtcttcgg aactgggacc    720
aagctgaccg tccta                                                    735

<210> SEQ ID NO 160
<211> LENGTH: 735
<212> TYPE: DNA
<213> ORGANISM: Artificial
<220> FEATURE:
<223> OTHER INFORMATION: W4-M20 scFv-Fc

<400> SEQUENCE: 160
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcacagtc tgccctgact    420
cagccgccct cagtgtctgc ggccccagga cagaaggtca ccatctcctg ctctggaagc    480
agctccaaca ttgggaacaa ttatgtctcc tggtatctgc agctcccagg aacagccccc    540
aaactcctca tttatgacaa taatgggcga ccctcaggga ttcctgaccg attctctggc    600
tccaagtctg gcacgtcagc caccctgggc atcaccggac tccagactgg gacgaggcc     660 gattattact gcgcaacatg ggatagcagc ctgagtgctg gggtgttcgg cggagggacc    720
aaggtcaccg tccta                                                    735

<210> SEQ ID NO 161
<211> LENGTH: 732
<212> TYPE: DNA
<213> ORGANISM: Artificial
<220> FEATURE:
<223> OTHER INFORMATION: W4-M4 scFv-Fc

<400> SEQUENCE: 161
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag aggcgattgg    300
gacctgcttc atgctcttga tatctggggc caagggaccc tggtcaccgt ctcgagtgga    360
ggcggcggtt caggcggagg tggctctggc ggtagcggaa gtgcactctc ctatgagctg    420
atgcaggacc ctgctgtgtc tgtggccttg gacagacag tcaggatcac atgccgggga     480
gacagcctca gcagctttta tacaagctgg taccagcaga agccaggaca ggcccctcta    540
cttgtcatct atggtaaaaa caaccggccc tcagggatcc agaccggtt ctctggctcc     600
```

| | |
|---|---|
| agctcaggaa acacagcttc cttgaccatc actggggctc aggcggaaga tgaggctgac | 660 |
| tattactgta actcccggga cagcagtgat aactatgtgt tattcggcgg agggaccaag | 720 |
| ctgaccgtcc ta | 732 |

<210> SEQ ID NO 162
<211> LENGTH: 735
<212> TYPE: DNA
<213> ORGANISM: Artificial
<220> FEATURE:
<223> OTHER INFORMATION: W4-M10 scFv-Fc

<400> SEQUENCE: 162

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag aggcgattgg | 300 |
| gacctgcttc atgctcttga tatctggggc caagggaccc tggtcaccgt ctcgagtgga | 360 |
| ggcggcggtt caggcggagg tggctctggc ggtggcggaa gtgcacagtc tgtcgtgacg | 420 |
| cagcctgcct ccgtgtctgg gtctcctgga cagtcggtca ccatctcctg cactggaacc | 480 |
| agcagtgacg ttggtagtta aagggtgtc tcctggtacc agcagccccc aggcacagcc | 540 |
| cccaaactcc tcatctataa tgacaatcag cggccctcag ggatccctgg gcgattctct | 600 |
| ggctccaact ctggaaacac agccattctg accatcagcg ggactcaggc tatggatgag | 660 |
| gctgactatt actgtcaggc gtgggacagc agtaatcatg tggttttcgg cggagggacc | 720 |
| aagctgaccg tccta | 735 |

<210> SEQ ID NO 163
<211> LENGTH: 729
<212> TYPE: DNA
<213> ORGANISM: Artificial
<220> FEATURE:
<223> OTHER INFORMATION: W4-HC1-LCP scFv-Fc

<400> SEQUENCE: 163

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 164
<211> LENGTH: 735
<212> TYPE: DNA
<213> ORGANISM: Artificial
<220> FEATURE:
<223> OTHER INFORMATION: W4-HC1-LC7

<400> SEQUENCE: 164

| | | |
|---|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca tggtcaccgt ctcgagtgga | 360 |
| ggcggcggtt caggcggagg tggctctggc ggtagcggaa gtgcacagac tgtggtgacc | 420 |
| cagcctgcct ccgtgtctgg gtctcctgga cagtcgatca ccatctcctg cactggaacc | 480 |
| agcagtgaca ttggtggtta aactatgtc tcctggtacc acagcaccc aggcaaagcc | 540 |
| cccaaactca tgatttatga tgtcagtaat cggccctcag gggtttctaa tcgcttctct | 600 |
| ggctccaagt ctggcaacac ggcctccctg accatctctg gctccaggc tgaggacgag | 660 |
| gctgattatt actgcaccct catatacaagc gacagcactc tggttttcgg cggaggcacc | 720 |
| aaggtgaccg tcctc | 735 |

<210> SEQ ID NO 165
<211> LENGTH: 735
<212> TYPE: DNA
<213> ORGANISM: Artificial
<220> FEATURE:
<223> OTHER INFORMATION: W4-HC2-LC7 scFv-Fc

<400> SEQUENCE: 165

| | | |
|---|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca cggtcaccgt ctcgagtgga | 360 |
| ggcggcggtt caggcggagg tggctctggc ggtagcggaa gtgcacagac tgtggtgacc | 420 |
| cagcctgcct ccgtgtctgg gtctcctgga cagtcgatca ccatctcctg cactggaacc | 480 |
| agcagtgaca ttggtggtta aactatgtc tcctggtacc acagcaccc aggcaaagcc | 540 |
| cccaaactca tgatttatga tgtcagtaat cggccctcag gggtttctaa tcgcttctct | 600 |
| ggctccaagt ctggcaacac ggcctccctg accatctctg gctccaggc tgaggacgag | 660 |
| gctgattatt actgcaccct catatacaagc gacagcactc tggttttcgg cggaggcacc | 720 |
| aaggtgaccg tcctc | 735 |

<210> SEQ ID NO 166
<211> LENGTH: 729
<212> TYPE: DNA
<213> ORGANISM: Artificial
<220> FEATURE:
<223> OTHER INFORMATION: W4-HC3-LCP scFv-Fc

<400> SEQUENCE: 166

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgcttttga tatctggggc caagggacca tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729
```

<210> SEQ ID NO 167
<211> LENGTH: 729
<212> TYPE: DNA
<213> ORGANISM: Artificial
<220> FEATURE:
<223> OTHER INFORMATION: W4-HC4-LCP scFv-Fc

<400> SEQUENCE: 167

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttgg tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729
```

<210> SEQ ID NO 168
<211> LENGTH: 729
<212> TYPE: DNA
<213> ORGANISM: Artificial
<220> FEATURE:
<223> OTHER INFORMATION: W4-HC5-LCP scFv-Fc

<400> SEQUENCE: 168

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
```

```
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcctga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcacttt cggcggaggg gaccaagctg    720
gagatcaaa                                                             729

<210> SEQ ID NO 169
<211> LENGTH: 735
<212> TYPE: DNA
<213> ORGANISM: Artificial
<220> FEATURE:
<223> OTHER INFORMATION: W4-HC5-LC7 scFv-Fc

<400> SEQUENCE: 169
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcctga tatctggggc caagggaccc tggtcaccgt ctcgagtgga    360
ggcggcggtt caggcggagg tggctctggc ggtagcggaa gtgcagacgac tgtggtgacc    420 cagcctgcct ccgtgtctgg gtctcctgga cagtcgatca ccatctcctg cactggaacc    480
agcagtgaca ttggtggtta taactatgtc tcctggtacc aacagcaccc aggcaaagcc    540
cccaaactca tgatttatga tgtcagtaat cggccctcag gggtttctaa tcgcttctct    600
ggctccaagt ctggcaacac ggcctccctg accatctctg gctccaggc tgaggacgag    660 gctgattatt actgcacctc atatacaagc gacagcactc tggttttcgg cggaggcacc    720
aaggtgaccg tcctc                                                      735

<210> SEQ ID NO 170
<211> LENGTH: 729
<212> TYPE: DNA
<213> ORGANISM: Artificial
<220> FEATURE:
<223> OTHER INFORMATION: W4-HC7-LCP scFv-Fc

<400> SEQUENCE: 170
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc caagggaccc tggtcaccgt ctcgagtgga    360
```

```
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 171
<211> LENGTH: 735
<212> TYPE: DNA
<213> ORGANISM: Artificial
<220> FEATURE:
<223> OTHER INFORMATION: W4-VH1-VL8 scFv-Fc

<400> SEQUENCE: 171

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggacca tggtcaccgt ctcgagtgga    360
ggcggcggtt caggcggagg tggctctggc ggtggcggaa gtgcacagtc tgtcgtgacg    420
cagccgccct cagtgtctgc ggccccagga cagaaggtca ccatctcctg cactggaacc    480
agcagtgatg ttgggagtta aactttgtc tcctggtacc aacagcaccc aggcaaagcc    540
cccaaactca tgatttatga gggcactaag cggccctcag gggtttctaa tcgcttctct    600
ggctccaagt ctggcaacac ggcctccctg accatctctg gctccaggc tgaggacgag    660 gctgattatt actgcacctc atatacaagc gacagcactc tggttttcgg cggaggcacc    720
aaggtgaccg tcctc                                                     735
```

<210> SEQ ID NO 172
<211> LENGTH: 729
<212> TYPE: DNA
<213> ORGANISM: Artificial
<220> FEATURE:
<223> OTHER INFORMATION: W4-VH2-VLP scFv-Fc

<400> SEQUENCE: 172

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180 ccctcccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggacca cggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
```

| | |
|---|---|
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 173
<211> LENGTH: 735
<212> TYPE: DNA
<213> ORGANISM: Artificial
<220> FEATURE:
<223> OTHER INFORMATION: W4-VH2-VL8 scFv-Fc

<400> SEQUENCE: 173

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacg ccaagaagca gttctccctg | 240 |
| cacgtgagct ctgtgaccgc tgcggacacg gccgtgtact tctgtgcgag agccgattgg | 300 |
| gacctgcttc atgctcttga tatctggggc caagggacca cggtcaccgt ctcgagtgga | 360 |
| ggcggcggtt caggcggagg tggctctggc ggtggcggaa gtgcacagtc tgtcgtgacg | 420 |
| cagccgccct cagtgtctgc ggccccagga cagaaggtca ccatctcctg cactggaacc | 480 |
| agcagtgatg ttgggagtta aactttgtc tcctggtacc aacagcaccc aggcaaagcc | 540 |
| cccaaactca tgatttatga gggcactaag cggccctcag gggtttctaa tcgcttctct | 600 |
| ggctccaagt ctggcaacac ggcctccctg accatctctg ggctccaggc tgaggacgag | 660 |
| gctgattatt actgcacctc atatacaagc gacagcactc tggttttcgg cggaggcacc | 720 |
| aaggtgaccg tcctc | 735 |

<210> SEQ ID NO 174
<211> LENGTH: 735
<212> TYPE: DNA
<213> ORGANISM: Artificial
<220> FEATURE:
<223> OTHER INFORMATION: W4-VH3-VL7 scFv-Fc

<400> SEQUENCE: 174

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctttga tatctggggc caagggacca tggtcaccgt ctcgagtgga | 360 |
| ggcggcggtt caggcggagg tggctctggc ggtagcggaa gtgcacagac tgtggtgacc | 420 |
| cagcctgcct ccgtgtctgg gtctcctgga cagtcgatca ccatctcctg cactggaacc | 480 |
| agcagtgaca ttgtggtta taactatgtc tcctggtacc gacagcaccc aggcaaagcc | 540 |
| cccaaactca tgatttatga tgtcagtaat cggccctcag gggtttctaa tcgcttctct | 600 |
| ggctccaagt ctggcaacac ggcctccctg accatctctg ggctccaggc tgaggacgag | 660 |
| gctgattatt actgcacctc atatacaagc gacagcactc tggttttcgg cggaggcacc | 720 |
| aaggtgaccg tcctc | 735 |

<210> SEQ ID NO 175
<211> LENGTH: 735
<212> TYPE: DNA
<213> ORGANISM: Artificial
<220> FEATURE:
<223> OTHER INFORMATION: W4-VH3-VL8 scFv-Fc

<400> SEQUENCE: 175

| | | | | | |
|---|---|---|---|---|---|
| gaggtgcagc | tgttggagtc | gggcccagga | ctggtgaagc | cttcggagac | cctgtccctc | 60 |
| acctgcaatg | tcgctggtgg | ctccatcagt | ccttactact | ggacctggat | ccggcagccc | 120 |
| ccagggaagg | gcctggagtt | gattggttat | atccactcca | gtgggtacac | cgactacaac | 180 |
| ccctccctca | agagtcgagt | caccatatca | ggagacacgt | ccaagaagca | gttctccctg | 240 |
| cacgtgagct | ctgtgaccgc | tgcggacacg | gccgtgtact | tctgtgcgag | agccgattgg | 300 |
| gacctgcttc | atgcttttga | tatctggggc | caagggacca | tggtcaccgt | ctcgagtgga | 360 |
| ggcggcggtt | caggcggagg | tggctctggc | ggtggcggaa | gtgcacagtc | tgtcgtgacg | 420 |
| cagccgccct | cagtgtctgc | ggccccagga | cagaaggtca | ccatctcctg | cactggaacc | 480 |
| agcagtgatg | ttgggagtta | taactttgtc | tcctggtacc | aacagcaccc | aggcaaagcc | 540 |
| cccaaactca | tgatttatga | gggcactaag | cggccctcag | gggtttctaa | tcgcttctct | 600 |
| ggctccaagt | ctggcaacac | ggcctccctg | accatctctg | gctccaggc | tgaggacgag | 660 |
| gctgattatt | actgcacctc | atatacaagc | gacagcactc | tggttttcgg | cggaggcacc | 720 |
| aaggtgaccg | tcctc | | | | | 735 |

<210> SEQ ID NO 176
<211> LENGTH: 735
<212> TYPE: DNA
<213> ORGANISM: Artificial
<220> FEATURE:
<223> OTHER INFORMATION: W4-VH5-VL8 scFv-Fc

<400> SEQUENCE: 176

| | | | | | |
|---|---|---|---|---|---|
| gaggtgcagc | tgttggagtc | gggcccagga | ctggtgaagc | cttcggagac | cctgtccctc | 60 |
| acctgcaatg | tcgctggtgg | ctccatcagt | ccttactact | ggacctggat | ccggcagccc | 120 |
| ccagggaagg | gcctggagtt | gattggttat | atccactcca | gtgggtacac | cgactacaac | 180 |
| ccctccctca | agagtcgagt | caccatatca | ggagacacgt | ccaagaagca | gttctccctg | 240 |
| cacgtgagct | ctgtgaccgc | tgcggacacg | gccgtgtact | tctgtgcgag | agccgattgg | 300 |
| gacctgcttc | atgctcctga | tatctggggc | caagggaccc | tggtcaccgt | ctcgagtgga | 360 |
| ggcggcggtt | caggcggagg | tggctctggc | ggtggcggaa | gtgcacagtc | tgtcgtgacg | 420 |
| cagccgccct | cagtgtctgc | ggccccagga | cagaaggtca | ccatctcctg | cactggaacc | 480 |
| agcagtgatg | ttgggagtta | taactttgtc | tcctggtacc | aacagcaccc | aggcaaagcc | 540 |
| cccaaactca | tgatttatga | gggcactaag | cggccctcag | gggtttctaa | tcgcttctct | 600 |
| ggctccaagt | ctggcaacac | ggcctccctg | accatctctg | gctccaggc | tgaggacgag | 660 |
| gctgattatt | actgcacctc | atatacaagc | gacagcactc | tggttttcgg | cggaggcacc | 720 |
| aaggtgaccg | tcctc | | | | | 735 |

<210> SEQ ID NO 177
<211> LENGTH: 735
<212> TYPE: DNA
<213> ORGANISM: Artificial
<220> FEATURE:

<223> OTHER INFORMATION: W4-VH6-VL7 scFv-Fc

<400> SEQUENCE: 177

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatgtggggc caagggaccc tggtcaccgt ctcgagtgga     360
ggcggcggtt caggcggagg tggctctggc ggtagcggaa gtgcacagac tgtggtgacc     420
cagcctgcct ccgtgtctgg gtctcctgga cagtcgatca ccatctcctg cactggaacc     480
agcagtgaca ttggtggtta taactatgtc tcctggtacc gacagcaccc aggcaaagcc     540
cccaaactca tgatttatga tgtcagtaat cggccctcag gggtttctaa tcgcttctct     600
ggctccaagt ctggcaacac ggcctccctg accatctctg gctccaggc tgaggacgag      660
gctgattatt actgcaccct atatacaagc gacagcactc tggttttcgg cggaggcacc     720
aaggtgaccg tcctc                                                      735
```

<210> SEQ ID NO 178
<211> LENGTH: 735
<212> TYPE: DNA
<213> ORGANISM: Artificial
<220> FEATURE:
<223> OTHER INFORMATION: W4-VH6-VL8 scFv-Fc

<400> SEQUENCE: 178

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatgtggggc caagggaccc tggtcaccgt ctcgagtgga     360
ggcggcggtt caggcggagg tggctctggc ggtggcggaa gtgcacagtc tgtcgtgacg     420
cagccgccct cagtgtctgc ggcccaggga cagaaggtca ccatctcctg cactggaacc     480
agcagtgatg ttgggagtta aactttgtc tcctggtacc aacagcaccc aggcaaagcc      540
cccaaactca tgatttatga gggcactaag cggccctcag gggtttctaa tcgcttctct     600
ggctccaagt ctggcaacac ggcctccctg accatctctg gctccaggc tgaggacgag      660
gctgattatt actgcaccct atatacaagc gacagcactc tggttttcgg cggaggcacc     720
aaggtgaccg tcctc                                                      735
```

<210> SEQ ID NO 179
<211> LENGTH: 729
<212> TYPE: DNA
<213> ORGANISM: Artificial
<220> FEATURE:
<223> OTHER INFORMATION: W4-VH6-VLP scFv-Fc

<400> SEQUENCE: 179

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
```

```
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatgtggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                           729

<210> SEQ ID NO 180
<211> LENGTH: 729
<212> TYPE: DNA
<213> ORGANISM: Artificial
<220> FEATURE:
<223> OTHER INFORMATION: W4-VH7-VLP scFv-Fc

<400> SEQUENCE: 180
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                           729

<210> SEQ ID NO 181
<211> LENGTH: 735
<212> TYPE: DNA
<213> ORGANISM: Artificial
<220> FEATURE:
<223> OTHER INFORMATION: W4-VH7-VL7 scFv-Fc

<400> SEQUENCE: 181
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
```

```
gacctgcttc atgctcttga tgtctggggc caagggaccc tggtcaccgt ctcgagtgga    360
ggcggcggtt caggcggagg tggctctggc ggtagcggaa gtgcacagac tgtggtgacc    420
cagcctgcct ccgtgtctgg gtctcctgga cagtcgatca ccatctcctg cactggaacc    480
agcagtgaca ttgtggggtta taactatgtc tcctggtacc gacagcaccc aggcaaagcc    540
cccaaactca tgatttatga tgtcagtaat cggccctcag gggtttctaa tcgcttctct    600
ggctccaagt ctggcaacac ggcctccctg accatctctg gctccaggc tgaggacgag    660
gctgattatt actgcacctc atatacaagc gacagcactc tggttttcgg cggaggcacc    720
aaggtgaccg tcctc                                                    735

<210> SEQ ID NO 182
<211> LENGTH: 735
<212> TYPE: DNA
<213> ORGANISM: Artificial
<220> FEATURE:
<223> OTHER INFORMATION: W4-VH7-VL8 scFc-Fv

<400> SEQUENCE: 182
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tgtctggggc caagggaccc tggtcaccgt ctcgagtgga    360
ggcggcggtt caggcggagg tggctctggc ggtggcggaa gtgcacagtc tgtcgtgacg    420
cagccgccct cagtgtctgc ggccccagga cagaaggtca ccatctcctg cactggaacc    480
agcagtgatg ttgggagtta aactttgtc tcctggtacc aacagcaccc aggcaaagcc    540
cccaaactca tgatttatga gggcactaag cggccctcag gggtttctaa tcgcttctct    600
ggctccaagt ctggcaacac ggcctccctg accatctctg gctccaggc tgaggacgag    660
gctgattatt actgcacctc atatacaagc gacagcactc tggttttcgg cggaggcacc    720
aaggtgaccg tcctc                                                    735

<210> SEQ ID NO 183
<211> LENGTH: 729
<212> TYPE: DNA
<213> ORGANISM: Artificial
<220> FEATURE:
<223> OTHER INFORMATION: W4-VH9-VLP scFv-Fc

<400> SEQUENCE: 183
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgttcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
```

```
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcactt tcggcggagg gaccaagctg     720
gagatcaaa                                                            729
```

<210> SEQ ID NO 184
<211> LENGTH: 729
<212> TYPE: DNA
<213> ORGANISM: Artificial
<220> FEATURE:
<223> OTHER INFORMATION: W4-VH10-VLP scFv-Fc

<400> SEQUENCE: 184

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgtttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcactt tcggcggagg gaccaagctg     720
gagatcaaa                                                            729
```

<210> SEQ ID NO 185
<211> LENGTH: 729
<212> TYPE: DNA
<213> ORGANISM: Artificial
<220> FEATURE:
<223> OTHER INFORMATION: W4-VH11-VLP scFv-Fc

<400> SEQUENCE: 185

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca gagtcgagt caccatatca ggagacacgt ccaagaagca gttctccctg    240
cacgtgagct ctgtgaccgc tgcggacacg gccgtgtact tctgtgcgag agccgattgg    300
gacctgcctc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc ccctcactt tcggcggagg gaccaagctg     720
```

```
gagatcaaa                                                                  729

<210> SEQ ID NO 186
<211> LENGTH: 729
<212> TYPE: DNA
<213> ORGANISM: Artificial
<220> FEATURE:
<223> OTHER INFORMATION: W4-VH12-VLP scFv-Fc

<400> SEQUENCE: 186
gaggtgcagc tgttggagtc gggcccagga ctggtgaagc cttcggagac cctgtccctc   60
acctgcaatg tcgctggtgg ctccatcagt ccttactact ggacctggat ccggcagccc  120
ccagggaagg gcctggagtt gattggttat atccactcca gtgggtacac cgactacaac  180
ccctcccctca agagtcgagt caccatatca ggagacacgt ccaagaagca gttctccctg  240
cacgtgagct ctgtgaccgc tgcggacacg gccgtgtact tctgtgcgag agccgattgg  300
gacctgcttc gtgctcttga tatctggggc caagggaccc tggtcaccgt ctcgagtgga  360
ggcggcggtt caggcggagg tggctctggc ggtggcggaa gtgcactcga aattgtgttg  420
acacagtctc catcctccct gtctacatct gtaggagaca gagtcaccat cacttgccgg  480
gcaagtcaga gcattaggag ccatttaaat tggtatcagc agaaaccagg gaaagcccct  540
aaactcctga tctatggtgc atccaatttg caaagtgggg tcccatcaag gttcagtggc  600
agtggatctg ggacagattt cactctcacc attagtagtc tgcaacctga agattttgca  660
acttactact gtcaacagag ttacagtttc cccctcactt tcggcggagg gaccaagctg  720
gagatcaaa                                                                  729

<210> SEQ ID NO 187
<211> LENGTH: 729
<212> TYPE: DNA
<213> ORGANISM: Artificial
<220> FEATURE:
<223> OTHER INFORMATION: W4-VH15-VLP scFv-Fc

<400> SEQUENCE: 187
gaggtgcagc tgttggagtc gggcccagga ctggtgaagc cttcggagac cctgtccctc   60
acctgcaatg tcgctggtgg ctccatcagt ccttactact ggacctggat ccggcagccc  120
ccagggaagg gcctggagtt gattggttat atccactcca gtgggtacac cgactacaac  180
ccctcccctca agagtcgagt caccatatca ggagacacgt ccaagaagca gttctccctg  240
cacgtgagct ctgtgaccgc tgcggacacg gccgtgtact tctgtgcgag aggcaattgg  300
gacctgcttc atgctcttga tatctggggc caagggaccc tggtcaccgt ctcgagtgga  360
ggcggcggtt caggcggagg tggctctggc ggtggcggaa gtgcactcga aattgtgttg  420
acacagtctc catcctccct gtctacatct gtaggagaca gagtcaccat cacttgccgg  480
gcaagtcaga gcattaggag ccatttaaat tggtatcagc agaaaccagg gaaagcccct  540
aaactcctga tctatggtgc atccaatttg caaagtgggg tcccatcaag gttcagtggc  600
agtggatctg ggacagattt cactctcacc attagtagtc tgcaacctga agattttgca  660
acttactact gtcaacagag ttacagtttc cccctcactt tcggcggagg gaccaagctg  720
gagatcaaa                                                                  729

<210> SEQ ID NO 188
<211> LENGTH: 729
<212> TYPE: DNA
<213> ORGANISM: Artificial
```

```
<220> FEATURE:
<223> OTHER INFORMATION: W4-VH16-VLP scFv-Fc

<400> SEQUENCE: 188
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca gagtcgagt caccatatca ggagacacgt ccaagaagca gttctccctg   240
cacgtgagct ctgtgaccgc tgcggacacg gccgtgtact tctgtgcgag agccgattgg   300
aacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg gacagattt cactctcacc attagtagtc tgcaacctga gattttgca   660 acttactact gtcaacagag ttacagtttc cccctcactt tcggcggagg gaccaagctg   720
gagatcaaa                                                              729

<210> SEQ ID NO 189
<211> LENGTH: 729
<212> TYPE: DNA
<213> ORGANISM: Artificial
<220> FEATURE:
<223> OTHER INFORMATION: W4-VH20-VLP scFv-Fc

<400> SEQUENCE: 189
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca gagtcgagt caccatatca ggagacacgt ccaagaagca gttctccctg   240
cacgtgagct ctgtgaccgc tgcggacacg gccgtgtact tctgtgcgag agccgattgg   300
gacctgcttc atactcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg gacagattt cactctcacc attagtagtc tgcaacctga gattttgca   660 acttactact gtcaacagag ttacagtttc cccctcactt tcggcggagg gaccaagctg   720
gagatcaaa                                                              729

<210> SEQ ID NO 190
<211> LENGTH: 729
<212> TYPE: DNA
<213> ORGANISM: Artificial
<220> FEATURE:
<223> OTHER INFORMATION: W4-VH31-VLP scFv-Fc

<400> SEQUENCE: 190
gaggtgcagc tgttggagtc gggcccagga ctggtgaagc cttcggagac cctgtccctc    60
```

| | |
|---|---|
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gagctgcttc atgctcttga tatctggggc caagggaccc tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 191
<211> LENGTH: 729
<212> TYPE: DNA
<213> ORGANISM: Artificial
<220> FEATURE:
<223> OTHER INFORMATION: W4-VH37-VLP scFv-Fc

<400> SEQUENCE: 191

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |
| gacctgcttc atgctttga tatgtgggc caagggacca tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg gaaagcccct | 540 |
| aaactcctga tctatggtgc atccaatttg caaagtgggg tcccatcaag gttcagtggc | 600 |
| agtggatctg ggacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 192
<211> LENGTH: 729
<212> TYPE: DNA
<213> ORGANISM: Artificial
<220> FEATURE:
<223> OTHER INFORMATION: W4-VH41-VLP scFv-Fc

<400> SEQUENCE: 192

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca agagtcgagt caccatatca ggagacacgt ccaagaagca gttctccctg | 240 |
| cacgtgagct ctgtgaccgc tgcggacacg gccgtgtact tctgtgcgag agccgattgg | 300 |

| | |
|---|---|
| gccctgcttc atgctcttga tatctggggc caagggaccc tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg aaagccccct | 540 |
| aaactcctga tctatggtgc atccaatttg caaagtgggg tcccatcaag gttcagtggc | 600 |
| agtggatctg gacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 193
<211> LENGTH: 729
<212> TYPE: DNA
<213> ORGANISM: Artificial
<220> FEATURE:
<223> OTHER INFORMATION: W4-VH42-VLP scFv-Fc

<400> SEQUENCE: 193

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacgt ccaagaagca gttctccctg | 240 |
| cacgtgagct ctgtgaccgc tgcggacacg gccgtgtact tctgtgcgag agccgatcgg | 300 |
| gacctgcttc atgctcttga tatctggggc caagggacca tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |
| gcaagtcaga gcattaggag ccatttaaat tggtatcagc agaaaccagg aaagccccct | 540 |
| aaactcctga tctatggtgc atccaatttg caaagtgggg tcccatcaag gttcagtggc | 600 |
| agtggatctg gacagattt cactctcacc attagtagtc tgcaacctga agattttgca | 660 |
| acttactact gtcaacagag ttacagtttc cccctcactt tcggcggagg gaccaagctg | 720 |
| gagatcaaa | 729 |

<210> SEQ ID NO 194
<211> LENGTH: 729
<212> TYPE: DNA
<213> ORGANISM: Artificial
<220> FEATURE:
<223> OTHER INFORMATION: W4-VH35-VLP scFv-Fc

<400> SEQUENCE: 194

| | |
|---|---|
| gaggtgcagc tgttggagtc gggcccagga ctggtgaagc cttcggagac cctgtccctc | 60 |
| acctgcaatg tcgctggtgg ctccatcagt ccttactact ggacctggat ccggcagccc | 120 |
| ccagggaagg gcctggagtt gattggttat atccactcca gtgggtacac cgactacaac | 180 |
| ccctccctca gagtcgagt caccatatca ggagacacgt ccaagaagca gttctccctg | 240 |
| cacgtgagct ctgtgaccgc tgcggacacg gccgtgtact tctgtacgag agccgattgg | 300 |
| gacctgcttc atgctcttga tatctggggc caagggaccc tggtcaccgt ctcgagtgga | 360 |
| ggcggcggtt caggcggagg tggctctggc ggtggcggaa gtgcactcga aattgtgttg | 420 |
| acacagtctc catcctccct gtctacatct gtaggagaca gagtcaccat cacttgccgg | 480 |

```
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                           729
```

```
<210> SEQ ID NO 195
<211> LENGTH: 729
<212> TYPE: DNA
<213> ORGANISM: Artificial
<220> FEATURE:
<223> OTHER INFORMATION: W4-VH36-VLP scFv-Fc

<400> SEQUENCE: 195
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgtgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                           729
```

```
<210> SEQ ID NO 196
<211> LENGTH: 729
<212> TYPE: DNA
<213> ORGANISM: Artificial
<220> FEATURE:
<223> OTHER INFORMATION: W4-VH52-VLP scFv-Fc

<400> SEQUENCE: 196
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agggtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
```

```
gagatcaaa                                                            729

<210> SEQ ID NO 197
<211> LENGTH: 729
<212> TYPE: DNA
<213> ORGANISM: Artificial
<220> FEATURE:
<223> OTHER INFORMATION: W4-VH53-VLP scFv-Fc

<400> SEQUENCE: 197
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccacccca gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729

<210> SEQ ID NO 198
<211> LENGTH: 729
<212> TYPE: DNA
<213> ORGANISM: Artificial
<220> FEATURE:
<223> OTHER INFORMATION: W4-VH54-VLP scFv-Fc

<400> SEQUENCE: 198
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca atgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729

<210> SEQ ID NO 199
<211> LENGTH: 729
<212> TYPE: DNA
```

<213> ORGANISM: Artificial
<220> FEATURE:
<223> OTHER INFORMATION: W4-VH55-VLP scFv-Fc

<400> SEQUENCE: 199

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat acccactcca gtgggtacac cgactacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg gacagattt cactctcacc attagtagtc tgcaacctga agattttgca      660
acttactact gtcaacagag ttacagtttc cccctcactt tcggcggagg gaccaagctg     720
gagatcaaa                                                             729
```

<210> SEQ ID NO 200
<211> LENGTH: 729
<212> TYPE: DNA
<213> ORGANISM: Artificial
<220> FEATURE:
<223> OTHER INFORMATION: W4-VH56-VLP scFv-Fc

<400> SEQUENCE: 200

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacgc cgactacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg gacagattt cactctcacc attagtagtc tgcaacctga agattttgca      660
acttactact gtcaacagag ttacagtttc cccctcactt tcggcggagg gaccaagctg     720
gagatcaaa                                                             729
```

<210> SEQ ID NO 201
<211> LENGTH: 729
<212> TYPE: DNA
<213> ORGANISM: Artificial
<220> FEATURE:
<223> OTHER INFORMATION: W4-VH57-VLP scFv-Fc

<400> SEQUENCE: 201

```
gaggtgcagc tgttggagtc gggcccagga ctggtgaagc cttcggagac cctgtccctc      60
```

```
acctgcaatg tcgctggtgg ctccatcagt ccttactact ggacctggat ccggcagccc    120
ccagggaagg gcctggagtt gattggttat atccactccg gtgggtacac cgactacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg gacagatttc actctcacc attagtagtc tgcaacctga gattttgca     660 acttactact gtcaacagag ttacagtttc ccctcactt tcggcggagg gaccaagctg     720
gagatcaaa                                                            729

<210> SEQ ID NO 202
<211> LENGTH: 729
<212> TYPE: DNA
<213> ORGANISM: Artificial
<220> FEATURE:
<223> OTHER INFORMATION: W4-VH58-VLP scFv-Fc

<400> SEQUENCE: 202
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
ccctccctca agcgtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg gacagatttc actctcacc attagtagtc tgcaacctga gattttgca     660 acttactact gtcaacagag ttacagtttc ccctcactt tcggcggagg gaccaagctg     720
gagatcaaa                                                            729

<210> SEQ ID NO 203
<211> LENGTH: 729
<212> TYPE: DNA
<213> ORGANISM: Artificial
<220> FEATURE:
<223> OTHER INFORMATION: W4-VH60-VLP scFv-Fc

<400> SEQUENCE: 203
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacagc    180
ccctccctca agagtcgagt caccatatca ggagacacgt ccaagaagca gttctccctg    240
```

```
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagccccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 204
<211> LENGTH: 729
<212> TYPE: DNA
<213> ORGANISM: Artificial
<220> FEATURE:
<223> OTHER INFORMATION: W4-VH61-VLP scFv-Fc

<400> SEQUENCE: 204

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggtacac cgactacaac    180
cccttcctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg aaagccccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

<210> SEQ ID NO 205
<211> LENGTH: 729
<212> TYPE: DNA
<213> ORGANISM: Artificial
<220> FEATURE:
<223> OTHER INFORMATION: W4-VH62-VLP scFv-Fc

<400> SEQUENCE: 205

```
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtcggtacac cgactacaac    180
cccctcctca gagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
```

```
gcaagtcaga gcattaggag ccatttaaat tggtatcagc agaaaccagg gaaagcccct        540
aaactcctga tctatggtgc atccaatttg caaagtgggg tcccatcaag gttcagtggc        600
agtggatctg ggacagattt cactctcacc attagtagtc tgcaacctga agattttgca        660
acttactact gtcaacagag ttacagtttc cccctcactt tcggcggagg gaccaagctg        720
gagatcaaa                                                                729
```

<210> SEQ ID NO 206
<211> LENGTH: 729
<212> TYPE: DNA
<213> ORGANISM: Artificial
<220> FEATURE:
<223> OTHER INFORMATION: W4-VH63-VLP scFv-Fc

<400> SEQUENCE: 206

```
gaggtgcagc tgttggagtc gggcccagga ctggtgaagc cttcggagac cctgtccctc        60
acctgcaatg tcgctggtgg ctccatcagt ccttactact ggacctggat ccggcagccc       120
ccagggaagg gcctggagtt gattggttat atccactcca gtgggtacac cggctacaac       180
ccctccctca agagtcgagt caccatatca ggagacacgt ccaagaagca gttctccctg       240
cacgtgagct ctgtgaccgc tgcggacacg gccgtgtact tctgtgcgag agccgattgg       300
gacctgcttc atgctcttga tatctggggc caagggaccc tggtcaccgt ctcgagtgga       360
ggcggcggtt caggcggagg tggctctggc ggtggcggaa gtgcactcga aattgtgttg       420
acacagtctc catcctccct gtctacatct gtaggagaca gagtcaccat cacttgccgg       480
gcaagtcaga gcattaggag ccatttaaat tggtatcagc agaaaccagg gaaagcccct       540
aaactcctga tctatggtgc atccaatttg caaagtgggg tcccatcaag gttcagtggc       600
agtggatctg ggacagattt cactctcacc attagtagtc tgcaacctga agattttgca       660
acttactact gtcaacagag ttacagtttc cccctcactt tcggcggagg gaccaagctg       720
gagatcaaa                                                               729
```

<210> SEQ ID NO 207
<211> LENGTH: 729
<212> TYPE: DNA
<213> ORGANISM: Artificial
<220> FEATURE:
<223> OTHER INFORMATION: W4-VH64-VLP scFv-Fc

<400> SEQUENCE: 207

```
gaggtgcagc tgttggagtc gggcccagga ctggtgaagc cttcggagac cctgtccctc        60
acctgcaatg tcgctggtgg ctccatcagt ccttactact ggacctggat ccggcagccc       120
ccagggaagg gcctggagtt gattggttat atccgctcca gtgggtacac cgactacaac       180
ccctccctca agagtcgagt caccatatca ggagacacgt ccaagaagca gttctccctg       240
cacgtgagct ctgtgaccgc tgcggacacg gccgtgtact tctgtgcgag agccgattgg       300
gacctgcttc atgctcttga tatctggggc caagggaccc tggtcaccgt ctcgagtgga       360
ggcggcggtt caggcggagg tggctctggc ggtggcggaa gtgcactcga aattgtgttg       420
acacagtctc catcctccct gtctacatct gtaggagaca gagtcaccat cacttgccgg       480
gcaagtcaga gcattaggag ccatttaaat tggtatcagc agaaaccagg gaaagcccct       540
aaactcctga tctatggtgc atccaatttg caaagtgggg tcccatcaag gttcagtggc       600
agtggatctg ggacagattt cactctcacc attagtagtc tgcaacctga agattttgca       660
```

```
acttactact gtcaacagag ttacagtttc ccctcactt tcggcggagg gaccaagctg      720
gagatcaaa                                                             729
```

<210> SEQ ID NO 208
<211> LENGTH: 729
<212> TYPE: DNA
<213> ORGANISM: Artificial
<220> FEATURE:
<223> OTHER INFORMATION: W4-VH65-VLP scFv-Fc

<400> SEQUENCE: 208

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgactacaac     180
ccctccctca gaatcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc ccctcactt tcggcggagg gaccaagctg      720
gagatcaaa                                                             729
```

<210> SEQ ID NO 209
<211> LENGTH: 729
<212> TYPE: DNA
<213> ORGANISM: Artificial
<220> FEATURE:
<223> OTHER INFORMATION: W4-VH66-VLP scFv-Fc

<400> SEQUENCE: 209

```
gaggtgcagc tgttggagtc gggcccagga ctggtgaagc cttcggagac cctgtccctc      60
acctgcaatg tcgctggtgg ctccatcagt ccttactact ggacctggat ccggcagccc     120
ccagggaagg gcctggagtt gattggttat atccactcca gtgggtacac cgaccacaac     180
ccctccctca gagtcgagt caccatatca ggagacacgt ccaagaagca gttctccctg      240
cacgtgagct ctgtgaccgc tgcggacacg gccgtgtact tctgtgcgag agccgattgg     300
gacctgcttc atgctcttga tatctggggc caagggaccc tggtcaccgt ctcgagtgga     360
ggcggcggtt caggcggagg tggctctggc ggtggcggaa gtgcactcga aattgtgttg     420
acacagtctc catcctccct gtctacatct gtaggagaca gagtcaccat cacttgccgg     480
gcaagtcaga gcattaggag ccatttaaat tggtatcagc agaaaccagg gaaagcccct     540
aaactcctga tctatggtgc atccaatttg caaagtgggg tcccatcaag gttcagtggc     600
agtggatctg ggacagattt cactctcacc attagtagtc tgcaacctga agattttgca     660
acttactact gtcaacagag ttacagtttc ccctcactt tcggcggagg gaccaagctg      720
gagatcaaa                                                             729
```

<210> SEQ ID NO 210
<211> LENGTH: 729

<212> TYPE: DNA
<213> ORGANISM: Artificial
<220> FEATURE:
<223> OTHER INFORMATION: W4-VH67-VLP scFv-Fc

<400> SEQUENCE: 210

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccacttca gtgggtacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729
```

<210> SEQ ID NO 211
<211> LENGTH: 729
<212> TYPE: DNA
<213> ORGANISM: Artificial
<220> FEATURE:
<223> OTHER INFORMATION: W4-VH69-VLP scFv-Fc

<400> SEQUENCE: 211

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
tcctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc cccctcactt tcggcggagg gaccaagctg   720
gagatcaaa                                                            729
```

<210> SEQ ID NO 212
<211> LENGTH: 729
<212> TYPE: DNA
<213> ORGANISM: Artificial
<220> FEATURE:
<223> OTHER INFORMATION: W4-VH70-VLP scFv-Fc

<400> SEQUENCE: 212

```
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggtacac cgactacaac   180
ccctccctca ggagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc ccctcactt tcggcggagg gaccaagctg   720
gagatcaaa                                                          729

<210> SEQ ID NO 213
<211> LENGTH: 729
<212> TYPE: DNA
<213> ORGANISM: Artificial
<220> FEATURE:
<223> OTHER INFORMATION: W4-VH72-VLP scFv-Fc

<400> SEQUENCE: 213
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat atccactcca gtgggcacac cgactacaac   180
ccctccctca agagtcgagt caccatatca ggagacacgt ccaagaagca gttctccctg   240
cacgtgagct ctgtgaccgc tgcggacacg gccgtgtact tctgtgcgag agccgattgg   300
gacctgcttc atgctcttga tatctggggc caagggaccc tggtcaccgt ctcgagtgga   360
ggcggcggtt caggcggagg tggctctggc ggtggcggaa gtgcactcga aattgtgttg   420
acacagtctc catcctccct gtctacatct gtaggagaca gagtcaccat cacttgccgg   480
gcaagtcaga gcattaggag ccatttaaat tggtatcagc agaaaccagg gaaagcccct   540
aaactcctga tctatggtgc atccaatttg caaagtgggg tcccatcaag gttcagtggc   600
agtggatctg ggacagattt cactctcacc attagtagtc tgcaacctga agattttgca   660
acttactact gtcaacagag ttacagtttc ccctcactt tcggcggagg gaccaagctg   720
gagatcaaa                                                          729

<210> SEQ ID NO 214
<211> LENGTH: 729
<212> TYPE: DNA
<213> ORGANISM: Artificial
<220> FEATURE:
<223> OTHER INFORMATION: W4-VH79-VLP scFv-Fc

<400> SEQUENCE: 214
gaggtgcagc tgttggagtc gggcccagga ctggtgaagc cttcggagac cctgtccctc    60
acctgcaatg tcgctggtgg ctccatcagt ccttactact ggacctggat ccggcagccc   120
ccagggaagg gcctggagtt gattggttat taccacccca gtgggtacac cgactacaac   180
ccctccctca agagtcgagt caccatatca ggagacacgt ccaagaagca gttctccctg   240
```

```
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729

<210> SEQ ID NO 215
<211> LENGTH: 729
<212> TYPE: DNA
<213> ORGANISM: Artificial
<220> FEATURE:
<223> OTHER INFORMATION: W4-VH80-VLP scFv-Fc

<400> SEQUENCE: 215
gaggtgcagc tgttggagtc gggcccagga ctggtgaagc cttcggagac cctgtccctc     60
acctgcaatg tcgctggtgg ctccatcagt ccttactact ggacctggat ccggcagccc    120
ccagggaagg gcctggagtt gattggttat atccactcca gtgggttcac cagctacaac    180
ccctccctca agagtcgagt caccatatca ggagacacgt ccaagaagca gttctccctg    240
cacgtgagct ctgtgaccgc tgcggacacg gccgtgtact tctgtgcgag agccgattgg    300
gacctgcttc atgctcttga tatctggggc caagggaccc tggtcaccgt ctcgagtgga    360
ggcggcggtt caggcggagg tggctctggc ggtggcggaa gtgcactcga aattgtgttg    420
acacagtctc catcctccct gtctacatct gtaggagaca gagtcaccat cacttgccgg    480
gcaagtcaga gcattaggag ccatttaaat tggtatcagc agaaaccagg gaaagcccct    540
aaactcctga tctatggtgc atccaatttg caaagtgggg tcccatcaag gttcagtggc    600
agtggatctg ggacagattt cactctcacc attagtagtc tgcaacctga agattttgca    660
acttactact gtcaacagag ttacagtttc cccctcactt tcggcggagg gaccaagctg    720
gagatcaaa                                                            729
```

ANTI-*PSEUDOMONAS* PSL BINDING MOLECULES AND USES THEREOF

CROSS-REFERENCE

This application is a Divisional of U.S. patent application Ser. No. 15/192,072, filed Jun. 24, 2016, which is a Divisional of U.S. patent application Ser. No. 14/125,073, filed Apr. 22, 2014, now U.S. Pat. No. 9,403,901, issued on Aug. 2, 2016, which is a National Phase Application of PCT/US2012/041538, filed Jun. 8, 2012, which claims the priority benefit of U.S. Provisional Patent Application Nos. 61/613,317, filed Mar. 20, 2012, 61/530,461, filed Sep. 2, 2011 and 61/495,460, filed Jun. 10, 2011, the disclosures of which are incorporated herein by reference in their entirety.

BACKGROUND

Field of the Disclosure

This disclosure relates to an anti-*Pseudomonas* Psl binding molecules and uses thereof, in particular in prevention and treatment of *Pseudomonas* infection. Furthermore, the disclosure provides compositions and methods for preventing and treating *Pseudomonas* infection.

Background of the Disclosure

*Pseudomonas aeruginosa* (*P. aeruginosa*) is a gram-negative opportunistic pathogen that causes both acute and chronic infections in compromised individuals (Ma et al., *Journal of Bacteriology* 189(22):8353-8356 (2007)). This is partly due to the high innate resistance of the bacterium to clinically used antibiotics, and partly due to the formation of highly antibiotic-resistant biofilms (Drenkard E., *Microbes Infect* 5:1213-1219 (2003); Hancokc & Speert, *Drug Resist Update* 3:247-255 (2000)).

*P. aeruginosa* is a common cause of hospital-acquired infections in the Western world. It is a frequent causative agent of bacteremia in burn victims and immune compromised individuals (Lyczak et al., *Microbes Infect* 2:1051-1060 (2000)). It is also the most common cause of nosocomial gram-negative pneumonia (Craven et al., *Semin Respir Infect* 11:32-53 (1996)), especially in mechanically ventilated patients, and is the most prevalent pathogen in the lungs of individuals with cystic fibrosis (Pier et al., *ASM News* 6:339-347 (1998)). Serious *P. aeruginosa* infections can become systemic, resulting in sepsis. Sepsis is characterized by severe systemic inflammation, often resulting in multiple organ failure and death.

*Pseudomonas* Psl exopolysaccharide is reported to be anchored to the surface of *P. aeruginosa* and is thought to be important in facilitating colonization of host tissues and in establishing/maintaining biofilm formation (Jackson, K. D., et al., *J Bacteriol* 186, 4466-4475 (2004)). Its structure comprises mannose-rich repeating pentasaccharide (Byrd, M. S., et al., *Mol Microbiol* 73, 622-638 (2009))

Due to increasing multidrug resistance, there remains a need in the art for the development of novel strategies for the identification of new *Pseudomonas*-specific prophylactic and therapeutic agents.

BRIEF SUMMARY

One embodiment is directed to an isolated binding molecule, e.g., an antibody or antigen-binding fragment thereof which specifically binds to *Pseudomonas* Psl, wherein the binding molecule (a) can inhibit attachment of *Pseudomonas aeruginosa* to epithelial cells, (b) can promote OPK of *P. aeruginosa*, or (c) can inhibit attachment of *P. aeruginosa* to epithelial cells and can promote OPK of *P. aeruginosa*.

Also disclosed is an isolated binding molecule e.g., an antibody or antigen-binding fragment thereof which specifically binds to the same *Pseudomonas* Psl epitope as an antibody or antigen-binding fragment thereof comprising the heavy chain variable region (VH) and light chain variable region (VL) region of WapR-004, Cam-003, Cam-004, or Cam-005.

Also disclosed is an isolated binding molecule e.g., an antibody or antigen-binding fragment thereof as which specifically binds to *Pseudomonas* Psl, and competitively inhibits *Pseudomonas* Psl binding by an antibody or antigen-binding fragment thereof comprising the VH and VL of WapR-004, Cam-003, Cam-004, or Cam-005.

Some embodiments include the present disclosure includes the binding molecule e.g., an antibody or antigen-binding fragment thereof as described above, wherein the VH and VL of WapR-004 comprise SEQ ID NO:11 and SEQ ID NO:12, respectively, the VH and VL of Cam-003 comprise SEQ ID NO:1 and SEQ ID NO:2, respectively, the VH and VL of Cam-004 comprise SEQ ID NO:3 and SEQ ID NO:2, respectively, and the VH and VL of Cam-005 comprise SEQ ID NO:4 and SEQ ID NO:2, respectively.

Also disclosed is an isolated binding molecule e.g., an antibody or antigen-binding fragment thereof which specifically binds to the same *Pseudomonas* Psl epitope as an antibody or antigen-binding fragment thereof comprising the VH and VL regions of WapR-001, WapR-002, or WapR-003.

Further disclosed is an isolated binding molecule e.g., an antibody or antigen-binding fragment thereof which specifically binds to *Pseudomonas* Psl, and competitively inhibits *Pseudomonas* Psl binding by an antibody or antigen-binding fragment thereof comprising the VH and VL of WapR-001, WapR-002, or WapR-003.

Some embodiments include the binding molecule e.g., an antibody or antigen-binding fragment thereof as described above, wherein the VH and VL of WapR-001 comprise SEQ ID NO: 5 and SEQ ID NO: 6, respectively, the VH and VL of WapR-002 comprise SEQ ID NO: 7 and SEQ ID NO: 8, respectively, and the VH and VL of WapR-003 comprise SEQ ID NO: 9 and SEQ ID NO: 10, respectively.

Further provided is an isolated binding molecule e.g., an antibody or antigen-binding fragment thereof which specifically binds to the same *Pseudomonas* Psl epitope as an antibody or antigen-binding fragment thereof comprising the VH and VL regions of WapR-016.

Also provided is an isolated binding molecule e.g., an antibody or antigen-binding fragment thereof which specifically binds to *Pseudomonas* Psl, and competitively inhibits *Pseudomonas* Psl binding by an antibody or antigen-binding fragment thereof comprising the VH and VL of WapR-016.

Some embodiments include the binding molecule e.g., an antibody or fragment thereof as described above, where the VH and VL of WapR-016 comprise SEQ ID NO: SEQ ID NO: 15 and SEQ ID NO:16, respectively.

Also provided is an isolated binding molecule e.g., an antibody or antigen-binding fragment thereof which specifically binds to *Pseudomonas* Psl comprising an antibody VH, where the VH comprises an amino acid sequence at least 90% identical or identical to SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, or SEQ ID NO: 15.

Some embodiments include an isolated binding molecule e.g., an antibody or antigen-binding fragment thereof which specifically binds to *Pseudomonas* Psl comprising an antibody VL, where the VL comprises an amino acid sequence at least 90% identical or identical to SEQ ID NO: 2, SEQ ID NO: 4, SEQ ID NO: 6, SEQ ID NO: 8, SEQ ID NO: 10, SEQ ID NO: 12, SEQ ID NO: 14, and SEQ ID NO: 16.

Also provided is an isolated antibody or antigen-binding fragment thereof which specifically binds to *Pseudomonas* psl, comprising VH and VL amino acid sequences at least 90% identical or identical to: (a) SEQ ID NO: 1 and SEQ ID NO: 2, respectively, (b) SEQ ID NO: 3 and SEQ ID NO: 2, respectively, (c) SEQ ID NO: 4 and SEQ ID NO: 2, respectively, (d) SEQ ID NO: 5 and SEQ ID NO: 6, respectively, (e) SEQ ID NO: 7 and SEQ ID NO: 8, respectively, (f) SEQ ID NO: 9 and SEQ ID NO: 10, respectively, (g) SEQ ID NO: 11 and SEQ ID NO: 12, respectively, (h) SEQ ID NO: 13 and SEQ ID NO: 14, respectively; or (i) SEQ ID NO: 15 and SEQ ID NO: 16, respectively. In specific embodiments, the above-described antibody or antigen-binding fragment thereof comprises a VH with the amino acid sequence SEQ ID NO: 1 and a VL with the amino acid sequence of SEQ ID NO: 2. In other embodiments, the above-described antibody or antigen-binding fragment thereof comprises a VH with the amino acid sequence SEQ ID NO: 11 and a VL with the amino acid sequence of SEQ ID NO: 12.

Also disclosed is an isolated binding molecule e.g., an antibody or antigen-binding fragment thereof which specifically binds to *Pseudomonas* Psl comprising an antibody VH, where the VH comprises a VH complementarity determining region-1 (VHCDR1) amino acid sequence identical to, or identical except for four, three, two, or one amino acid substitutions to: SEQ ID NO: 17, SEQ ID NO: 23, SEQ ID NO: 26, SEQ ID NO: 29, SEQ ID NO: 35, SEQ ID NO: 41, SEQ ID NO: 47, SEQ ID NO: 53, or SEQ ID NO: 59.

Also provided is an isolated binding molecule e.g., an antibody or antigen-binding fragment thereof which specifically binds to *Pseudomonas* Psl comprising an antibody VH, where the VH comprises a VH complementarity determining region-2 (VHCDR2) amino acid sequence identical to, or identical except for four, three, two, or one amino acid substitutions to: SEQ ID NO: 18, SEQ ID NO: 24, SEQ ID NO: 27, SEQ ID NO: 30, SEQ ID NO: 36, SEQ ID NO: 42, SEQ ID NO: 48, SEQ ID NO: 54, or SEQ ID NO: 60.

Further provided is an isolated binding molecule e.g., an antibody or antigen-binding fragment thereof which specifically binds to *Pseudomonas* Psl comprising an antibody VH, where the VH comprises a VH complementarity determining region-3 (VHCDR3) amino acid sequence identical to, or identical except for four, three, two, or one amino acid substitutions to: SEQ ID NO: 19, SEQ ID NO: 25, SEQ ID NO: 28, SEQ ID NO: 31, SEQ ID NO: 37, SEQ ID NO: 43, SEQ ID NO: 49, SEQ ID NO: 55, or SEQ ID NO: 61.

Also disclosed is an isolated binding molecule e.g., an antibody or antigen-binding fragment thereof which specifically binds to *Pseudomonas* psl comprising an antibody VL, where the VL comprises a VL complementarity determining region-1 (VLCDR1) amino acid sequence identical to, or identical except for four, three, two, or one amino acid substitutions to: SEQ ID NO: 20, SEQ ID NO: 32, SEQ ID NO: 38, SEQ ID NO: 44, SEQ ID NO: 50, SEQ ID NO: 56, or SEQ ID NO: 62.

Further provided is an isolated binding molecule e.g., an antibody or antigen-binding fragment thereof which specifically binds to *Pseudomonas* Psl comprising an antibody VL, where the VL comprises a VL complementarity determining region-2 (VLCDR2) amino acid sequence identical to, or identical except for four, three, two, or one amino acid substitutions to: SEQ ID NO: 21, SEQ ID NO: 33, SEQ ID NO: 39, SEQ ID NO: 45, SEQ ID NO: 51, SEQ ID NO: 57, or SEQ ID NO: 63.

Some embodiments include an isolated binding molecule e.g., an antibody or antigen-binding fragment thereof which specifically binds to *Pseudomonas* Psl comprising an antibody VL, where the VL comprises a VL complementarity determining region-3 (VLCDR3) amino acid sequence identical to, or identical except for four, three, two, or one amino acid substitutions to: SEQ ID NO: 22, SEQ ID NO: 34, SEQ ID NO: 40, SEQ ID NO: 46, SEQ ID NO: 52, SEQ ID NO: 58, or SEQ ID NO: 64.

Also provided is an isolated binding molecule e.g., an antibody or antigen-binding fragment thereof which specifically binds to *Pseudomonas* Psl comprising an antibody VH, where the VH comprises VHCDR1, VHCDR2, and VHCDR3 amino acid sequences identical to, or identical except for four, three, two, or one amino acid substitutions in one or more of the VHCDRs to: SEQ ID NOs: 17, 18, and 19, SEQ ID NOs: 23, 24, and 25, SEQ ID NOs: 26, 27, and 28, SEQ ID NOs: 29, 30, and 31, SEQ ID NOs: 35, 36, and 37, SEQ ID NOs: 41, 42, and 43, SEQ ID NOs: 47, 48, and 49, SEQ ID NOs: 53, 54, and 55, or SEQ ID NOs: 59, 60, and 61, respectively.

Some embodiments include an isolated binding molecule e.g., an antibody or antigen-binding fragment thereof which specifically binds to *Pseudomonas* Psl comprising an antibody VL, where the VL comprises VLCDR1, VLCDR2, and VLCDR3 amino acid sequences identical to, or identical except for four, three, two, or one amino acid substitutions in one or more of the VHCDRs to: SEQ ID NOs: 20, 21, and 22, SEQ ID NOs: 32, 33, and 34, SEQ ID NOs: 38, 39, and 40, SEQ ID NOs: 44, 45, and 46, SEQ ID NOs: 50, 51, and 52, SEQ ID NOs: 56, 57, and 58, or SEQ ID NOs: 62, 63, and 64, respectively.

Also disclosed is an isolated binding molecule e.g., an antibody or antigen-binding fragment thereof which specifically binds to *Pseudomonas* Psl comprising an antibody VL, where the VL comprises VLCDR1, VLCDR2, and VLCDR3 amino acid sequences identical to, or identical except for four, three, two, or one amino acid substitutions in one or more of the VHCDRs to: SEQ ID NOs: 20, 21, and 22, SEQ ID NOs: 32, 33, and 34, SEQ ID NOs: 38, 39, and 40, SEQ ID NOs: 44, 45, and 46, SEQ ID NOs: 50, 51, and 52, SEQ ID NOs: 56, 57, and 58, or SEQ ID NOs: 62, 63, and 64, respectively.

Some embodiments include the isolated binding molecule e.g., an antibody or fragment thereof as described above, which (a) can inhibit attachment of *Pseudomonas aeruginosa* to epithelial cells, (b) can promote OPK of *P. aeruginosa*, or (c) can inhibit attachment of *P. aeruginosa* to epithelial cells and can promote OPK of *P. aeruginosa*.

Other embodiments include the isolated binding molecule e.g., an antibody or fragment thereof as described above, where maximum inhibition of *P. aeruginosa* attachment to epithelial cells is achieved at an antibody concentration of about 50 µg/ml or less, 5.0 µg/ml or less, or about 0.5 µg/ml or less, or at an antibody concentration ranging from about 30 µg/ml to about 0.3 µg/ml, or at an antibody concentration of about 1 µg/ml, or at an antibody concentration of about 0.3 µg/ml.

Certain embodiments include the isolated binding molecule e.g., an antibody or fragment thereof as described above, where the OPK EC50 is less than about 0.5 µg/ml, less than about 0.05 µg/ml, or less than about 0.005 µg/ml, or where the OPK EC50 ranges from about 0.001 µg/ml to about 0.5 µg/ml, or where the OPK EC50 is less than about 0.2 µg/ml, or wherein the OPK EC50 is less than about 0.02 µg/ml.

Also included is the isolated binding molecule e.g., an antibody or fragment thereof as described above, which specifically binds to *P. aeruginosa* Psl with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M, or wherein $K_D$ is in a range of about $1 \times 10^{-10}$ to about $1 \times 10^{-6}$ M. In one embodiment, an isolated antibody as described herein specifically binds to *Pseudomonas* Psl, with an affinity characterized by a $K_D$ of about $1.18 \times 10^{-7}$ M, as determined by the OCTET® binding assay. In another embodiment, an isolated antibody as described herein specifically binds to *Pseudomonas* Psl, with an affinity characterized by a $K_D$ of about $1.44 \times 10^{-7}$ M, as determined by the OCTET® binding assay.

In various embodiments, the above-described binding molecules are humanized.

In various embodiments, the above-described binding molecules are chimeric.

In various embodiments, the above-described binding molecules are fully human.

In certain embodiments, the above-described binding molecules are Fab fragments, Fab' fragments, F(ab)$_2$ fragments, or scFv fragments.

In certain embodiments, the above-described binding molecules comprise light chain constant regions consisting of a human kappa constant region or a human lambda constant region.

In certain embodiments, the above-described binding molecules comprise a heavy chain constant region or fragment thereof. In further embodiments, the heavy chain constant region or fragment thereof is a human IgG1.

In certain embodiments, the above-described binding molecules are monoclonal antibodies.

In some embodiments, the above described binding molecules e.g., an antibodies or fragments thereof are conjugated to an agent selected from the group consisting of antimicrobial agent, a therapeutic agent, a prodrug, a peptide, a protein, an enzyme, a lipid, a biological response modifier, pharmaceutical agent, a lymphokine, a heterologous antibody or fragment thereof, a detectable label, polyethylene glycol (PEG), and a combination of two or more of any said agents. In further embodiments, detectable label is selected from the group consisting of an enzyme, a fluorescent label, a chemiluminescent label, a bioluminescent label, a radioactive label, or a combination of two or more of any said detectable labels.

Additional embodiments include compositions comprising the above-described binding molecules e.g., antibodies or fragments thereof, and a carrier.

Certain embodiments include an isolated polynucleotide comprising a nucleic acid which encodes the above-described VH. In some embodiments, the polynucleotide further comprises a nucleic acid which encodes the above-described VL, where a binding molecule or antigen-binding fragment thereof expressed by the polynucleotide specifically binds *Pseudomonas* Psl. In some embodiments the polynucleotide as described herein encodes an scFv molecule including VH and VL, comprising the nucleotide sequence SEQ ID NO: 65, SEQ ID NO: 66, SEQ ID NO: 67, SEQ ID NO: 68, SEQ ID NO: 69 or SEQ ID NO: 70. In other embodiments, the disclosure includes an isolated polynucleotide comprising a nucleic acid which encodes the above-described VL. In further embodiments, the polynucleotide further comprises a nucleic acid which encodes the above-described VH, where a binding molecule or antigen-binding fragment thereof expressed by the polynucleotide specifically binds *Pseudomonas* Psl.

Certain embodiments provide vectors comprising the above-described polynucleotides. In further embodiments, the polynucleotides are operably associated with a promoter. In additional embodiments, the disclosure provides host cells comprising such vectors. In further embodiments, the disclosure provides vectors where the polynucleotide is operably associated with a promoter, where vectors can express a binding molecule e.g., an antibody or fragment thereof as described above which specifically binds *Pseudomonas* Psl in a suitable host cell.

Some embodiments provides a method of producing a binding molecule e.g., an antibody or fragment thereof as described above which specifically binds *Pseudomonas* Psl, comprising culturing a host cell containing a vector comprising the above-described polynucleotides, and recovering said antibody, or fragment thereof. Further embodiments provide an isolated binding molecule or fragment thereof produced by the above-described method.

In some embodiments, the *Pseudomonas* species is *Pseudomonas aeruginosa*.

In further embodiments, the above-described binding molecules or fragments thereof, antibodies or fragments thereof, or compositions, bind to two or more, three or more, four or more, or five or more different *P. aeruginosa* serotypes, or to at least 80%, at least 85%, at least 90% or at least 95% of *P. aeruginosa* strains isolated from infected patients. In further embodiments, the *P. aeruginosa* strains are isolated from one or more of lung, sputum, eye, pus, feces, urine, sinus, a wound, skin, blood, bone, or knee fluid. *P. aeruginosa* serotypes are categorized according to an International Antigen Typing System (IATS) originally described in Liu, P. V. et al. *Int. J. Syst. Bacteriol.* 33:256-264 (1983), as supplemented, e.g., by Liu P. V., Wang S., *J. Clin. Microbiol.* 28:922-925 (1990).

Some embodiments are directed to a method of preventing or treating a *Pseudomonas* infection in a subject in need thereof, comprising administering to the subject an effective amount of the binding molecule or fragment thereof, the antibody or fragment thereof, the composition, the polynucleotide, the vector, or the host cell described herein. In further embodiments, the *Pseudomonas* infection is a *P. aeruginosa* infection. In some embodiments, the subject is a human. In certain embodiments, the infection is an ocular infection, a lung infection, a burn infection, a wound infection, a skin infection, a blood infection, a bone infection, or a combination of two or more of said infections. In further embodiments, the subject suffers from acute pneumonia, burn injury, corneal infection, cystic fibrosis, or a combination thereof.

Some embodiments are directed to a method of blocking or preventing attachment of *P. aeruginosa* to epithelial cells comprising contacting a mixture of epithelial cells and *P. aeruginosa* with the binding molecule or fragment thereof, the antibody or fragment thereof, the composition, the polynucleotide, the vector, or the host cell described herein.

Also disclosed is a method of promoting OPK of *P. aeruginosa* comprising contacting a mixture of phagocytic cells and *P. aeruginosa* with the binding molecule or fragment thereof, the antibody or fragment thereof, the composition, the polynucleotide, the vector, or the host cell described herein. In further embodiments, the phagocytic cells are differentiated HL-60 cells or human polymorphonuclear leukocytes (PMNs).

BRIEF DESCRIPTION OF THE DRAWINGS/FIGURES

FIGS. 1A-1F show phenotypic whole cell screening with human antibody phage libraries identified P. aeruginosa functionally active specific antibodies. (FIG. 1A) Overview of complete antibody selection strategy. (FIG. 1B) Flow diagram describing the process to isolate antibody variable region genes from patients recently exposed to P. aeruginosa. (FIG. 1C) Characteristics of the scFv phage display libraries, indicating the size and diversity of the cloned antibody repertoire. (FIG. 1D) Comparison of the phage display selection efficiency using either the patient antibody library or a naïve antibody library, when selected on P. aeruginosa 3064 Δ WapR ($^1$) or P. aeruginosa PAO1 MexAB OprM Δ WapR ($^2$) in suspension. Bars indicate the output titers (in CFU) at each round of selection, and circles indicate the proportion of duplicated VH CDR3 sequences, an indication of clonal enrichment. (FIG. 1E) ELISA screen of scFv from phage display to test binding to multiple strains of P. aeruginosa. ELISA data (absorbance at 450 nm) are shown for eight individual phage-scFvs from selections and one irrelevant phage-scFv. (FIG. 1F) FACS binding of P. aeruginosa specific antibodies with representative strains from unique P. aeruginosa serotypes. For each antibody tested a human IgG negative control antibody is shown as a shaded peak.

FIGS. 2A-2D show evaluation of specific mAbs promoting OPK of P. aeruginosa (FIG. 2A) Opsonophagocytosis assay with luminescent P. aeruginosa serogroup O5 strain (PAO1.lux), with dilutions of purified monoclonal antibodies derived from phage panning. (FIG. 2B) Opsonophagocytosis assay with luminescent P. aeruginosa serogroup O11 strain (9882-80.lux), with dilutions of purified WapR-004 and Cam-003 monoclonal antibodies derived from phage panning. In both FIG. 2A and FIG. 2B, R347, an isotype matched human monoclonal antibody that does not bind P. aeruginosa antigens, was used as a negative control. (FIGS. 2A-2B) Results are representative data from three independent experiments performed for each antibody. (FIGS. 2C-2D): Evaluation of Cam-003 promoting opsonophagocytic killing (OPK) of P. aeruginosa (FIG. 2C) Opsonophagocytosis assay with representative non-mucoid strains from clinically relevant O-antigen serotypes (6294 (O6 ExoU$^-$), 6077 (O11 ExoU$^+$), 9882-80.lux (O11 ExoU$^-$), 33356 (O9 ExoU$^-$), 2410.lux (O6) and 6206.lux (O11 ExoU$^+$)). (FIG. 2D) Opsonophagocytosis assay with representative mucoid strains that were engineered to be luminescent (A004.lux, A010.lux and A015.lux). The lines represent the mean percent killing and error bars represent the standard deviation. Percent killing was calculated relative to results obtained in assays run in the absence of antibody. (FIGS. 2C-2D) An R347 control was used within individual assays for each strain. For simplicity, the R347 control was not included in the figures. Results are representative data from three independent experiments performed for each strain.

FIGS. 3A-3K show identification of the P. aeruginosa Psl exopolysaccharide target of antibodies derived from phenotypic screening. Reactivity of antibodies was determined by indirect ELISA on plates coated with indicated P. aeruginosa strains: (FIG. 3A) wild type PAO1, PAO1ΔwbpL, PAO1ΔrmlC and PAO1ΔgalU. (FIG. 3B) PAO1ΔpslA. The Genway antibody is specific to a P. aeruginosa outer membrane protein and was used as a positive control. (FIG. 3C) FACS binding analysis of Cam-003 to PAO1 and PAO1ΔpslA. Cam-003 is indicated by a solid black line and clear peak; an isotype matched non-P. aeruginosa-specific human IgG1 antibody was used as a negative control and is indicated by a gray line and shaded peak. (FIG. 3D) LPS purified from PAO1 and PAO1ΔpslA was resolved by SDS-PAGE and immunoblotted with antisera derived from mice vaccinated with PAO1ΔwapRΔalgD, a mutant strain deficient in O-antigen transport to the outer membrane and alginate production. (FIG. 3E) Cam-003 ELISA binding data with isogenic mutants of PAO1. Lane 1: PAO1ΔwbpLΔalgD; Lane 2: PAO1ΔwbpLΔalgDΔpslA; Lane 3: PAO1ΔwbpLΔalgDΔpelA; Lane 4: PAO1ΔwbpLΔalgDΔpslA+pUCP; Lane 5: PAO1ΔwbpLΔalgDΔpslA+pPW145. pPW145 is a pUCP expression vector containing pslA.
* Indicates P<0.005 using the Mann-Whitney U-test when comparing Cam-003 vs. R347 binding. (FIG. 3F and FIG. 3G) Opsonophagocytosis assays indicating that Cam-003 only mediates killing of strains capable of producing Psl (wild type PAO1 and PAO1ΔpslA complemented in trans with the pslA gene). (FIG. 3H and FIG. 3I) ELISA data indicating reactivity of anti-Psl antibodies WapR-001, WapR-004, and WapR-016 with PAO1 ΔwbpLΔalgD and PAO1 ΔwbpLΔalgDΔpslA. (FIG. 3J) Reactivity of antibodies was determined by indirect ELISA on plates coated with indicated P. aeruginosa strains: wild type PAO1, PAO1ΔwbpL, PAO1ΔwbpLΔalgD, PAO1ΔrmlC and PAO1ΔgalU. R347 was used as a negative control in all experiments. (FIGS. 3A-3C and FIGS. 3F-3I). Each panel is a representative data set from three independent experiments.

(FIG. 3K) Anti-Psl antibody capture of enriched Psl isolated from whole P. aeruginosa cells as measured on a FORTEBIO® OCTET® 384 instrument. R347 was used as a negative control. Results are representative data from three independent experiments.

FIG. 4: Anti-Psl mAbs inhibit cell attachment of luminescent P. aeruginosa strain PAO1.lux to A549 cells. Log-phase PAO1.lux were added to a confluent monolayer of A549 cells at an MOI of 10 followed by analysis of RLU after repeated washing to remove unbound P. aeruginosa. Results are representative of three independent experiments performed in duplicate for each antibody concentration.

FIGS. 5A-5U show in vivo passaged P. aeruginosa strains maintain/increase expression of Psl. The Cam-003 antibody is shown by a solid black line and a clear peak; the human IgG negative control antibody is shown as a gray line and a shaded peak. (FIG. 5A) For the positive control, Cam-003 was assayed for binding to strains grown to log phase from an overnight culture (~5×10$^8$/ml). (FIG. 5B) The inocula for each strain were prepared to 5×10$^8$ CFU/ml from an overnight TSA plate grown to lawn and tested for reactivity to Cam-003 by flow cytometry. (FIG. 5C) Four hours post intraperitoneal challenge, bacteria was harvested from mice by peritoneal lavage and assayed for the presence of Psl with Cam-003 by flow cytometry. (FIG. 5D) Four hours and (FIG. 5E) twenty four hours post intranasal challenge, bacteria were harvested from mice by bronchoalveolar lavage (BAL) and assayed for the presence of Psl with Cam-003 by flow cytometry. Each flow cytometry panel is a representative data set from five independent experiments (FIGS. 5F-5U) The binding of P. aeruginosa specific antibodies (Cam-003, Cam-004 and Cam-005) to representative strains from unique *P. aeruginosa* serotypes (FIG. 5F) PAO1 (O5), (FIG. 5G) 2135 (O1), (FIG. 5H) 2531 (O1), (FIG. 5I) 2410 (O6), (FIG. 5J) 2764 (O11), (FIG. 5K) 2757 (O11), (FIG. 5L) 33356 (O9), (FIG. 5M) 33348 (O1), (FIG. 5N) 3039 (NT), (FIG. 5O) 3061 (NT), (FIG. 5P) 3064 (NT), (FIG. 5Q) 19660 (NT), (FIG. 5R) 9882-80 (O11), (FIG. 5S) 6073 (O11), (FIG. 5T) 6077 (O11) and (FIG. 5U) 6206 (O11). Cam-003, Cam-004, and Cam-005 antibodies are shown by as gray line and a clear peak; the human IgG negative control antibody is shown as a solid black line and a shaded peak.

FIGS. 6A-6G show survival rates for animals treated with anti-Psl monoclonal antibodies Cam-003 or WapR-004 in a *P. aeruginosa* acute pneumonia model. (FIGS. 6A-6D) Animals were treated with Cam-003 at 45, 15, and 5 mg/kg and R347 at 45 mg/kg or PBS 24 hours prior to intranasal infection with (FIG. 6A) PAO1 ($1.6 \times 10^7$ CFU), (FIG. 6B) 33356 ($3 \times 10^7$ CFU), (FIG. 6C) 6294 ($7 \times 10^6$ CFU), (FIG. 6D) 6077 ($1 \times 10^6$ CFU). (FIGS. 6E-6F) Animals were treated with WapR-004 at 5 and 1 mg/kg as indicated followed by infection with 6077 at (FIG. 6E) ($8 \times 10^5$ CFU), or (FIG. 6F) ($6 \times 10^5$ CFU). Animals were carefully monitored for survival up to 72 hours (FIGS. 6A-6D) or for 120 hours (FIGS. 6E-6F). (FIG. 6G) Animals were treated with Cam-003 at 15 mg/kg or 5 mg/kg, or R347 at 15 mg/kg 24 hours prior to intranasal infection with PAO1 ($4.4 \times 10^7$ CFU), and Cam-003 at 15 mg/kg 24 hours prior to intranasal infection with PAO1$\Delta$pslA ($3 \times 10^7$ CFU). In all experiments, PBS and R347 served as negative controls. Results are represented as Kaplan-Meier survival curves; differences in survival were calculated by the Log-rank test for Cam-003 vs. R347. (FIG. 6A) Cam-003 (45 mg/kg–P<0.0001; 15 mg/kg–P=0.0003; 5 mg/kg–P=0.0033). (FIG. 6B) Cam-003 (45 mg/kg–P=0.0012; 15 mg/kg–P=0.0012; 5 mg/kg–P=0.0373). (FIG. 6C) Cam-003 (45 mg/kg–P=0.0007; 15 mg/kg–P=0.0019; 5 mg/kg–P=0.0212). (FIG. 6D) Cam-003 (45 mg/kg–P<0.0001; 15 mg/kg–P<0.0001; 5 mg/kg–P=0.0001). Results are representative of at least two independent experiments. (FIG. 6E) [Cam-003 (5 mg/kg) vs. R347 (5 mg/kg): P=0.02; Cam-003 (1 mg/kg) vs. R347 (5 mg/kg): P=0.4848; WapR-004 (5 mg/kg) vs. R347 (5 mg/kg): P<0.0001; WapR-004 (1 mg/kg) vs. R347 (5 mg/kg): P=0.0886; WapR-004 (5 mg/kg) vs. Cam-003 (5 mg/kg): P=0.0017; WapR-004 (1 mg/kg) vs. Cam-003 (1 mg/kg): P=0.2468; R347 (5 mg/kg) vs. PBS: P=0.6676] (FIG. 6F) [Cam-003 (5 mg/kg) vs. R347 (5 mg/kg): P=0.0004; Cam-003 (1 mg/kg) vs. R347 (5 mg/kg): P<0.0001; WapR-004 (5 mg/kg) vs. R347 (5 mg/kg): P<0.0001; WapR-004 (1 mg/kg) vs. R347 (5 mg/kg): P<0.0001; WapR-004 (5 mg/kg) vs. Cam-003 (5 mg/kg): P=0.0002; WapR-004 (1 mg/kg) vs. Cam-003 (1 mg/kg): P=0.2628; R347 (5 mg/kg) vs. PBS: P=0.6676. (FIG. 6G) Cam-003 (15 mg/kg–P=0.0028; 5 mg/kg–P=0.0028)]. Results are representative of five independent experiments.

FIGS. 7A-7F show anti-Psl monoclonal antibodies, Cam-003 and WapR-004, reduce organ burden after induction of acute pneumonia. Mice were treated with Cam-003 antibody 24 hours prior to infection with (FIG. 7A) PAO1 ($1.1 \times 10^7$ CFU), (FIG. 7B) 33356 ($1 \times 10^7$ CFU), (FIG. 7C) 6294 ($6.25 \times 10^6$ CFU) (FIG. 7D) 6077 ($1 \times 10^6$ CFU), and WapR-004 antibody 24 hours prior to infection with (FIG. 7E) 6294 (~$1 \times 10^7$ CFU), and (FIG. 7F) 6206 (~$1 \times 10^6$ CFU). 24 hours post-infection, animals were euthanized followed by harvesting or organs for identification of viable CFU. Differences in viable CFU were determined by the Mann-Whitney U-test for Cam-003 or WapR-004 vs. R347. (FIG. 7A) Lung: Cam-003 (45 mg/kg–P=0.0015; 15 mg/kg–P=0.0021; 5 mg/kg–P=0.0015); Spleen: Cam-003 (45 mg/kg–P=0.0120; 15 mg/kg–P=0.0367); Kidneys: Cam-003 (45 mg/kg–P=0.0092; 15 mg/kg–P=0.0056); (FIG. 7B) Lung: Cam-003 (45 mg/kg–P=0.0010; 15 mg/kg–P<0.0001; 5 mg/kg–P=0.0045); (FIG. 7C) Lung: Cam-003 (45 mg/kg–P=0.0003; 15 mg/kg–P=0.0039; 5 mg/kg–P=0.0068); Spleen: Cam-003 (45 mg/kg–P=0.0057; 15 mg/kg–P=0.0230; 5 mg/kg–P=0.0012); (FIG. 7D) Lung: Cam-003 (45 mg/kg–P=0.0005; 15 mg/kg–P=0.0003; 5 mg/kg–P=0.0007); Spleen: Cam-003 (45 mg/kg–P=0.0015; 15 mg/kg–P=0.0089; 5 mg/kg–P=0.0089); Kidneys: Cam-003 (45 mg/kg–P=0.0191; 15 mg/kg–P=0.0355; 5 mg/kg–P=0.0021). (FIG. 7E) Lung: WapR-004 (15 mg/kg–P=0.0011; 5 mg/kg–P=0.0004; 1 mg/kg–P=0.0002); Spleen: WapR-004 (15 mg/kg–P<0.0001; 5 mg/kg–P=0.0014; 1 mg/kg–P<0.0001); (FIG. 7F) Lung: WapR-004 (15 mg/kg–P<0.0001; 5 mg/kg–P=0.0006; 1 mg/kg–P=0.0079); Spleen: WapR-004 (15 mg/kg–P=0.0059; 5 mg/kg–P=0.0261; 1 mg/kg–P=0.0047); Kidney: WapR-004 (15 mg/kg–P=0.0208; 5 mg/kg–P=0.0268.

FIGS. 8A-8G show anti-Psl monoclonal antibodies Cam-003 and WapR-004 are active in a *P. aeruginosa* keratitis model and thermal injury model. Mice were treated with a control IgG1 antibody or Cam-003 at 45 mg/kg (FIGS. 8A-8B) or 15 mg/kg (FIGS. 8C-8D) or PBS or a control IgG1 antibody or Cam-003 at 45 mg/kg or WapR-004 at 45 mg/kg or 15 mg/kg or 5 mg/kg (FIGS. 8F-8G) 24 hours prior to infection with 6077 (O11-cytotoxic-$2 \times 10^6$ CFU). Immediately before infection, three 1 mm scratches were made on the left cornea of each animal followed by topical application of *P. aeruginosa* in a 5 µl inoculum. 24 hours after infection, the corneal pathology scores were calculated followed by removal of the eye for determination of viable CFU. Differences in pathology scores and viable CFU were determined by the Mann-Whitney U-test. (FIG. 8A) P=0.0001, (FIG. 8B) P<0.0001, (FIG. 8C) P=0.0003, (FIG. 8D) P=0.0015. (FIG. 8F) and (FIG. 8G) Cam-003 (45 mg/kg) vs. WapR-004 (45 mg/kg): P=0.018; Cam-003 (45 mg/kg) vs. WapR-004 (15 mg/kg): P=0.0025; WapR-004 (45 mg/kg) vs. WapR-004 (15 mg/kg): P=0.1331; WapR-004 (5 mg/kg) vs. Ctrl: P<0.0001. Results are representative of five independent experiments. (FIG. 8E) Survival analysis from Cam-003 and R347 treated CF-1 mice in a *P. aeruginosa* thermal injury model after 6077 infection ($2 \times 10^5$ CFU) (log-rank: R347 vs. Cam-003 15 mg/kg, P=0.0094; R347 vs. Cam-003 5 mg/kg, P=0.0017). Results are representative of at least three independent experiments. (n) refers to number of animals in each group.

FIGS. 9A-9E show a Cam-003 Fc mutant antibody, Cam-003-TM, has diminished OPK and in vivo efficacy but maintains anti-cell attachment activity. (FIG. 9A) PAO1.lux OPK assay with Cam-003 and Cam-003-TM, which harbors mutations in the Fc domain that prevents Fc interactions with Fcγ receptors (Oganesyan, V., et al., *Acta Crystallogr D Biol Crystallogr* 64, 700-704 (2008)). R347 was used as a negative control. Results are representative data from three independent experiments. (FIG. 9B) PAO1 cell attachment assay with Cam-003 and Cam-003-TM. Results are representative data from two independent experiments. (FIG. 9C-9E) Acute pneumonia model comparing efficacy of Cam-003 vs. Cam-003-TM. *P. aeruginosa* strain 6077 acute pneumonia model using BALB/c mice inoculated with (FIG. 9C) $1.22 \times 10^6$ (FIG. 9D) $2.35 \times 10^5$ or (FIG. 9E) $1.07 \times 10^6$ comparing efficacy of Cam-003 versus Cam-003-TM. Mice were treated with antibody 24 hours before challenge. (FIG. 9C-9E) Ten animals were used in each group. Results are representative data from two independent experiments.

FIGS. 10A-10B. FIG. 10A: Epitope mapping and identification of the relative binding affinity for anti-Psl monoclonal antibodies. Epitope mapping was performed by competition ELISA and confirmed using an OCTET® flow system with Psl derived from the supernatant of an overnight culture of *P. aeruginosa* strain PAO1. Relative binding affinities were measured on a FORTEBIO® OCTET® 384 instrument. Also shown are antibody concentrations where cell attachment was maximally inhibited and OPK EC50 values for each antibody. FIG. 10B. Relative binding affinities of various WapR-004 mutants as measured on a FORTEBIO® OCTET® 384 instrument. Also shown are OPK EC50 values for the various mutants.

FIG. 11A-11M show evaluation of WapR-004 (W4) mutants clones in the *P. aeruginosa* OPK assay (FIG. 11A-11M) Opsonophagocytosis assay with luminescent *P. aeruginosa* serogroup 05 strain (PAO1.lux), with dilutions of different W4 mutant clones in scFv-Fc format. In some instances, W4 IgG1 was included in the assay and is indicated as W4-IgG1. W4-RAD-Cam and W4-RAD-GB represent the same WapR-004RAD sequence described herein. "W4-RAD" is a shorthand name for WapR-004RAD, and W4-RAD-Cam and W4-RAD-GB designations in FIG. 11D through FIG. 11M represent two different preparations of WapR-004RAD. In all experiments, R347, a human IgG1 monoclonal antibody that does not bind *P. aeruginosa* antigens, was used as a negative control.

FIG. 12: Method of site-directed conjugation of Polymyxin B (PMB) to mAbs in which a heterobifunctional SM-PEG$_{12}$ linker (Pierce) was conjugated to a primary amine on PMB under conditions determined to favor conjugation of a single linker. Conjugation efficiency and levels free PMB-linker in the samples were determined by UPLC and mass spectrometry.

FIGS. 13A-13B show PMB-mAb site-directed conjugates. Using the developed site-directed conjugation method, PMB was conjugated to CAM-003 and A7 (hIgG1 control) mAb variants with either one (SM, ND10), two (DM, ND10/19) or three (TM, ND4/10/19) cysteine engineered into the Fc region. FIG. 13A: Cam-003 and A7 Fc region mutated residues. FIG. 13B: The average number of PMB in PMB-mAb conjugates (single mutant (SM)>double mutant 1 (DM1)>double mutant 2 (DM2)).

FIGS. 14A-14B show evaluation of PMB-mAb conjugates binding to wild-type *P. aeruginosa* PAO1 cells by FACS analysis. FIG. 14A: Cam-003 (Cam-003-SM-PMB, Cam-003-DM1-PMB, Cam-003-DM2-PMB, mock-conjugated wild-type Cam-003 (Cam-003-Mock-PMB)). FIG. 14B: A7 control conjugates (A7-SM-PMB, A7-DM1-PMB, A7-DM2-PMB, mock-conjugated wild-type A7 (A7-Mock-PMB)). R347 was used as a negative control in all experiments.

FIGS. 15A-15B show OPK activity of PMB-mAb conjugates against FIG. 15A: *P. aeruginosa* PAO1 wild-type strain and FIG. 15B: against the ΔpslA *P. aeruginosa* strain which does not express the Psl target.

FIG. 16A: PMB-Cam-003 conjugates and mock-conjugated wild-type Cam-003 and FIG. 16B: PMB-A7 conjugates and mock-conjugated wild-type A7.

Figure 17:
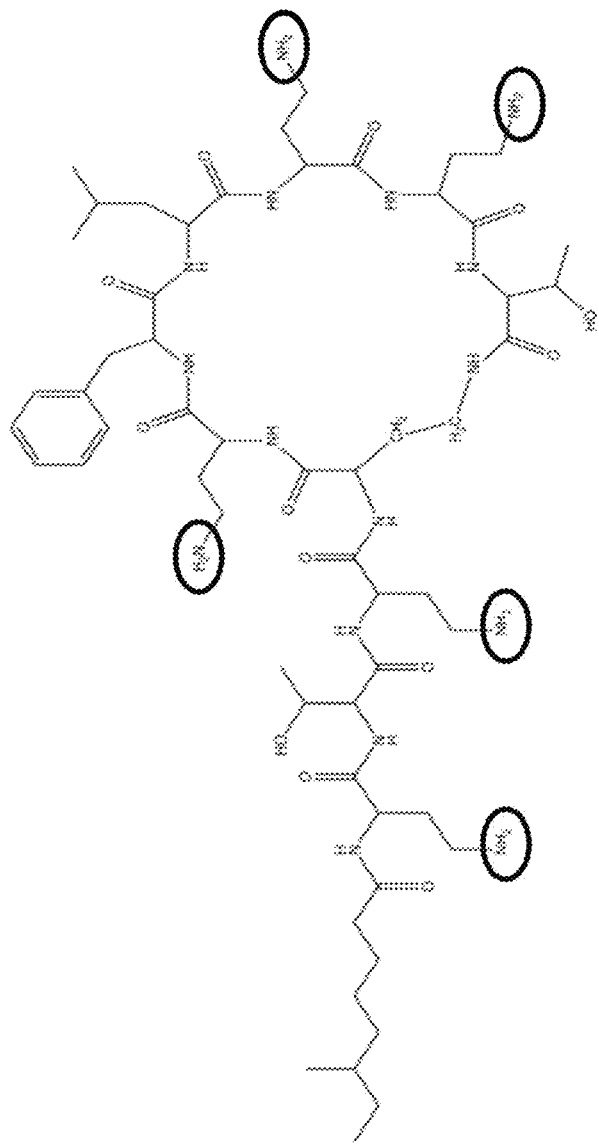

FIG. 17: Structure showing polymyxin, a cyclic antibacterial lipopeptide that neutralize the proinflammatory effects of LPS and can be used for the treatment of Gram-negative MDR infections (colistin/polymyxin E). Polymyxins have 5 positively charged diamonbutyric acids (circled) that mediate interactions with negatively-charged Lipid A in LPS and neutralize its proinflammatory activity.

Figure 18B:
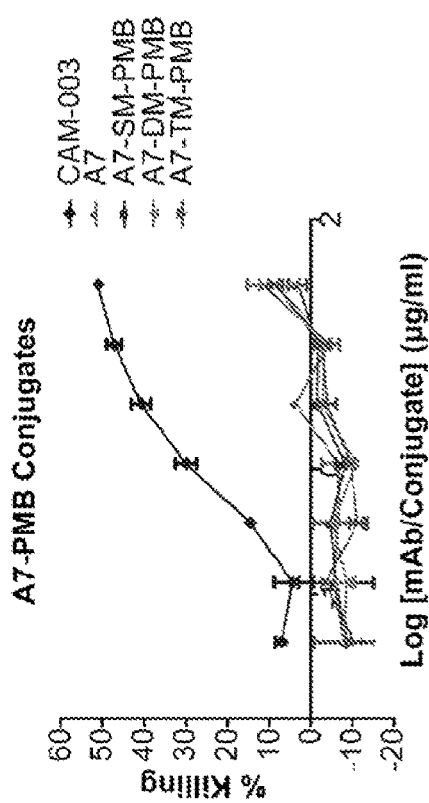
Figure 18A:
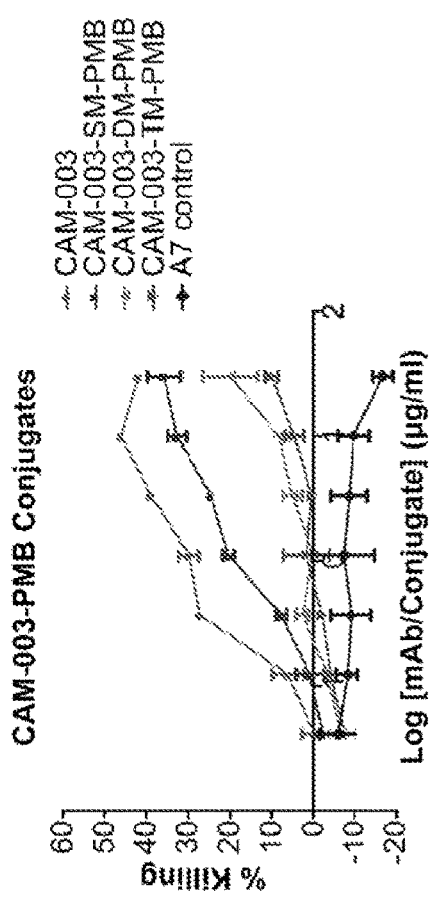

FIGS. 18A-18B show OPK activity by human HL-60 neutrophil cell line in the presence of rabbit complement was evaluated using *P. aeruginosa* strain PAO1 expressing bacterial luciferase. FIG. 18A: % killing by CAM-003-PMB Conjugates. FIG. 18B: % killing by A7-PMB Conjugates.

FIGS. 19A-19B. FIG. 19A: Percent Survival of C57Bl/6 mice dosed with 45 mg/kg CAM-TM-PMB Conjugates. FIG. 19B: Percent Survival of C57Bl/6 mice dosed with 45 mg/kg A7-TM-PMB Conjugates.

Figure 20A:
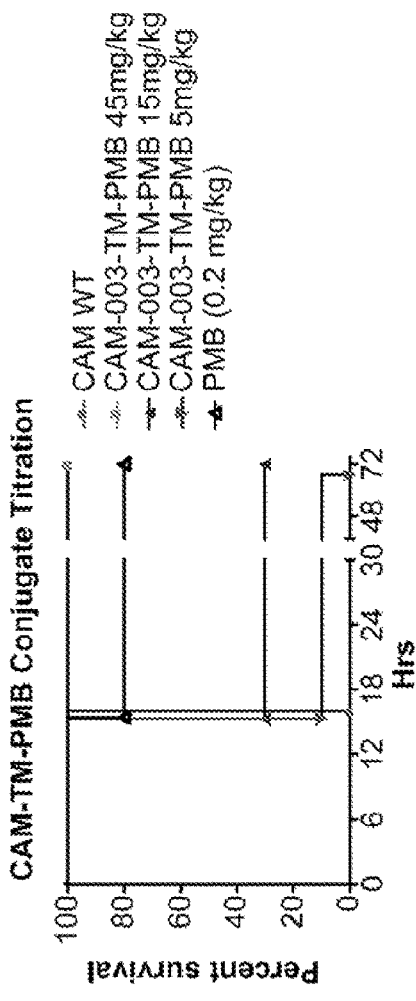
Figure 20B:
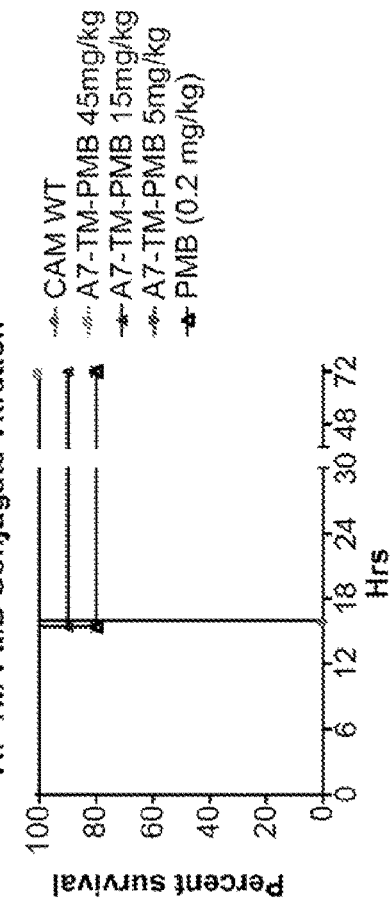

FIGS. 20A-20B. FIG. 20A: Percent Survival of C57Bl/6 mice dosed with 45 mg/kg, 15 mg/kg and 5 mg/kg CAM-TM-PMB Conjugates. FIG. 20B: Percent Survival of C57Bl/6 mice dosed with 45 mg/kg, 15 mg/kg and 5 mg/kg A7-TM-PMB Conjugates.

Figure 21B:
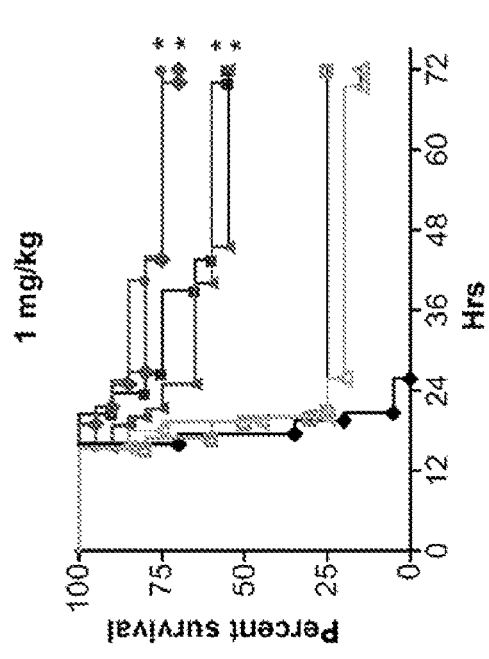
Figure 21A:
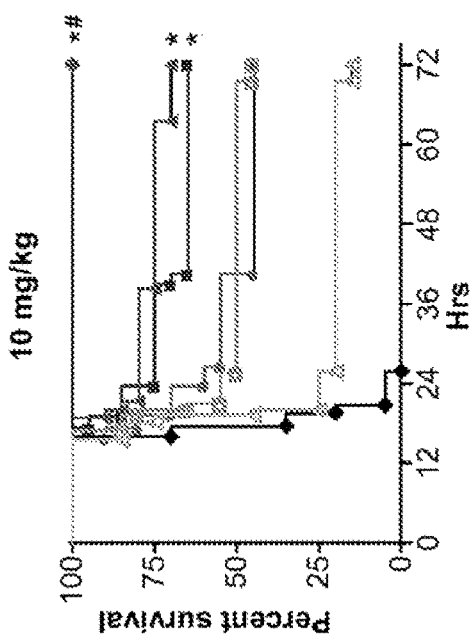
Figure 21C:
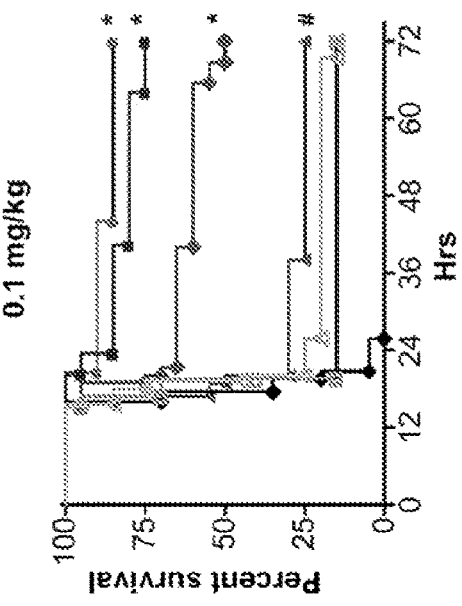

FIGS. 21A-21C show percent survival of C57Bl/6 mice dosed with mAb or PMB-mAb conjugates i.p FIG. 21A: 10 mg/kg. FIG. 21B: 1 mg/kg. FIG. 21C: 0.1 mg/kg.

DETAILED DESCRIPTION

I. Definitions

It is to be noted that the term "a" or "an" entity refers to one or more of that entity; for example, "a binding molecule which specifically binds to *Pseudomonas* Psl," is understood to represent one or more binding molecules which specifically bind to *Pseudomonas* Psl. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

Other polypeptides disclosed herein are fragments, derivatives, analogs, or variants of the foregoing polypeptides, and any combination thereof. The terms "fragment," "variant," "derivative" and "analog" when referring to a binding molecule such as an antibody which specifically binds to *Pseudomonas* Psl as disclosed herein include any polypeptides which retain at least some of the antigen-binding properties of the corresponding native antibody or polypeptide. Fragments of polypeptides include, for example, proteolytic fragments, as well as deletion fragments, in addition to specific antibody fragments discussed elsewhere herein. Variants of a binding molecule, e.g., an antibody which specifically binds to *Pseudomonas* Psl as disclosed herein include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of a binding molecule, e.g., an antibody which specifically binds to *Pseudomonas* Psl as disclosed herein are polypeptides which have been altered so as to exhibit additional features not found on the native polypeptide. Examples include fusion proteins. Variant polypeptides can also be referred to herein as "polypeptide analogs." As used herein a "derivative" of a binding molecule, e.g., an antibody which specifically binds to *Pseudomonas* Psl refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a binding molecule, e.g., an antibody which specifically binds to *Pseudomonas* Psl contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding an a binding molecule which specifically binds to *Pseudomonas* Psl, e.g., an antibody, or antigen-binding fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein, e.g., a polynucleotide encoding a binding molecule which specifically binds to *Pseudomonas* Psl, e.g., an antibody, or antigen-binding fragment, variant, or derivative thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. A non-limiting example of an antigen binding molecule is an antibody or fragment thereof that retains antigen-specific binding.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. This quaternary binding molecule structure forms the antigen binding site present at the end of each arm of the Y. More specifically, the antigen binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a binding molecule which specifically binds to Pseudomonas Psl, e.g., an antibody, or antigen-binding fragment, variant, or derivative thereof as disclosed herein are according to the Kabat numbering system.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" may be deemed to have a higher specificity for a given epitope than binding molecule "B," or binding molecule "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody can cross-react with the related epitope.

By way of non-limiting example, a binding molecule, e.g., an antibody can be considered to bind a first epitope preferentially if it binds said first epitope with a dissociation constant ($K_D$) that is less than the antibody's $K_D$ for the second epitope. In another non-limiting example, a binding molecule such as an antibody can be considered to bind a first antigen preferentially if it binds the first epitope with an affinity that is at least one order of magnitudeless than the antibody's $K_D$ for the second epitope. In another non-limiting example, a binding molecule can be considered to bind a first epitope preferentially if it binds the first epitope with an affinity that is at least two orders of magnitude less than the antibody's $K_D$ for the second epitope.

In another non-limiting example, a binding molecule, e.g., an antibody or fragment, variant, or derivative thereof can be considered to bind a first epitope preferentially if it binds the first epitope with an off rate (k(off)) that is less than the antibody's k(off) for the second epitope. In another non-limiting example, a binding molecule can be considered to bind a first epitope preferentially if it binds the first epitope with an affinity that is at least one order of magnitude less than the antibody's k(off) for the second epitope. In another non-limiting example, a binding molecule can be considered to bind a first epitope preferentially if it binds the first epitope with an affinity that is at least two orders of magnitude less than the antibody's k(off) for the second epitope.

A binding molecule, e.g., an antibody or fragment, variant, or derivative thereof disclosed herein can be said to bind a target antigen, e.g., a polysaccharide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. A binding molecule as disclosed herein can be said to bind a target antigen, e.g., a polysaccharide with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein can be said to bind a target antigen, e.g., a polysaccharide with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. A binding molecule as disclosed herein can be said to bind a target antigen, e.g., a polysaccharide with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibody fragments including single-chain antibodies can comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. Binding molecules, e.g., antibodies, or antigen-binding fragments thereof disclosed herein can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. a binding molecule, e.g., an antibody comprising a heavy chain portion comprises at least one of: a CH1 domain, a hinge (e.g., upper, middle, and/or lower hinge region) domain, a CH2 domain, a CH3 domain, or a variant or fragment thereof. For example, a binding molecule, e.g., an antibody or fragment, variant, or derivative thereof can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a binding molecule, e.g., an antibody or fragment, variant, or derivative thereof comprises a polypeptide chain comprising a CH3 domain. Further, a binding molecule for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

The heavy chain portions of a binding molecule, e.g., an antibody as disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion comprises at least one of a VL or CL domain.

Binding molecules, e.g., antibodies or antigen-binding fragments, variants, or derivatives thereof disclosed herein can be described or specified in terms of the epitope(s) or portion(s) of an antigen, e.g., a target polysaccharide that they recognize or specifically bind. The portion of a target polysaccharide which specifically interacts with the antigen binding domain of an antibody is an "epitope," or an "antigenic determinant." A target antigen, e.g., a polysaccharide can comprise a single epitope, but typically comprises at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., anti-*Pseudomonas* Psl antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change, infection, or disorder. Beneficial or desired clinical results include, but are not limited to, alleviation of symptoms, diminishment of extent of disease, stabilized (i.e., not worsening) state of disease, clearance or reduction of an infectious agent such as *P. aeruginosa* in a subject, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the infection, condition, or disorder as well as those prone to have the condition or disorder or those in which the condition or disorder is to be prevented, e.g., in burn patients or immunosuppressed patients susceptible to *P. aeruginosa* infection.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-*Pseudomonas* Psl antibody" and "an animal in need of treatment" includes subjects, such as mammalian subjects, that would benefit from administration of an anti-*Pseudomonas* Psl antibody used, e.g., for detection of *Pseudomonas* Psl (e.g., for a diagnostic procedure) and/or from treatment, i.e., palliation or prevention of a disease, with an anti-*Pseudomonas* Psl antibody. As described in more detail herein, the anti-*Pseudomonas* Psl antibody can be used in unconjugated form or can be conjugated, e.g., to a drug, prodrug, or an isotope.

II. Binding Molecules

One embodiment is directed to an isolated binding molecule e.g., an antibody or antigen-binding fragment thereof which specifically binds to *Pseudomonas* Psl, wherein the binding molecule (a) can inhibit attachment of *Pseudomonas aeruginosa* to epithelial cells, (b) can promote, mediate, or enhance opsonophagocytic killing (OPK) of *P. aeruginosa*, or (c) can inhibit attachment of *P. aeruginosa* to epithelial cells and can promote, mediate, or enhance OPK of *P. aeruginosa*. In certain embodiments, the binding molecule or fragment thereof as described above can be antibody or antigen-binding fragment thereof such as Cam-003 or WapR-004.

As used herein, the term "antigen binding domain" includes a site that specifically binds an epitope on an antigen (e.g., an epitope of *Pseudomonas* Psl). The antigen binding domain of an antibody typically includes at least a portion of an immunoglobulin heavy chain variable region and at least a portion of an immunoglobulin light chain variable region. The binding site formed by these variable regions determines the specificity of the antibody.

The disclosure is more specifically directed to an isolated binding molecule, e.g., an antibody or antigen-binding fragment thereof which specifically binds to the same *Pseudomonas* Psl epitope as an antibody or antigen-binding fragment thereof comprising the heavy chain variable region (VH) and light chain variable region (VL) region of WapR-004, Cam-003, Cam-004, or Cam-005.

Further included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR-004, Cam-003, Cam-004, or Cam-005.

One embodiment is directed to an isolated binding molecule, e.g., an antibody or antigen-binding fragment thereof which specifically binds to the same *Pseudomonas* Psl epitope as an antibody or antigen-binding fragment thereof comprising the VH and VL region of WapR-001, WapR-002, or WapR-003.

Also included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR-001, WapR-002, or WapR-003.

Further included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR-016.

Also included is an isolated binding molecule, e.g., an antibody or fragment thereof which specifically binds to *Pseudomonas* Psl and competitively inhibits *Pseudomonas* Psl binding by an antibody or antigen-binding fragment thereof comprising the VH and VL of WapR16.

Methods of making antibodies are well known in the art and described herein. Once antibodies to various fragments of, or to the full-length *Pseudomonas* Psl without the signal sequence, have been produced, determining which amino acids, or epitope, of *Pseudomonas* Psl to which the antibody or antigen binding fragment binds can be determined by epitope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional epitope mapping protocols can be found in Morris, G. *Epitope Mapping Protocols*, New Jersey: Humana Press (1996), which are both incorporated herein by reference in their entireties. Epitope mapping can also be performed by commercially available means (i.e. ProtoPROBE, Inc. (Milwaukee, Wis.)).

In certain aspects, the disclosure is directed to a binding molecule, e.g., an antibody or fragment, variant, or derivative thereof which specifically binds to *Pseudomonas* Psl with an affinity characterized by a dissociation constant ($K_D$) which is less than the $K_D$ for said reference monoclonal antibody.

In certain embodiments an anti-*Pseudomonas* Psl binding molecule, e.g., an antibody or antigen-binding fragment, variant or derivative thereof as disclosed herein binds specifically to at least one epitope of Psl, i.e., binds to such an epitope more readily than it would bind to an unrelated, or random epitope; binds preferentially to at least one epitope of Psl, i.e., binds to such an epitope more readily than it would bind to a related, similar, homologous, or analogous epitope; competitively inhibits binding of a reference antibody which itself binds specifically or preferentially to a certain epitope of Psl; or binds to at least one epitope of Psl with an affinity characterized by a dissociation constant $K_D$ of less than about $5\times10^{-2}$ M, about $10^{-2}$ M, about $5\times10^{-3}$ M, about $10^{-3}$ M, about $5\times10^{4}$ M, about $10^{4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M.

As used in the context of binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments a binding molecule, e.g., an antibody, or antigen-binding fragment, variant, or derivative thereof binds *Pseudomonas* Psl with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof binds *Pseudomonas* Psl with an off rate (k(off)) of less than or equal to $5\times10^{-4}$ sec$^{-1}$, $10^{4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, a binding molecule, e.g., an antibody, or antigen-binding fragment, variant, or derivative thereof as disclosed herein binds *Pseudomonas* Psl with an on rate (k(on)) of greater than or equal to $10^{3}$ M$^{-1}$ sec$^{-1}$, $5\times10^{3}$ M$^{-1}$ sec$^{-1}$, $10^{4}$ M$^{-1}$ sec$^{-1}$ or $5\times10^{4}$ M$^{-1}$ sec$^{-1}$. Alternatively, a binding molecule, e.g., an antibody, or antigen-binding fragment, variant, or derivative thereof as disclosed herein binds *Pseudomonas* Psl with an on rate (k(on)) greater than or equal to $10^{5}$ M$^{-1}$ sec$^{-1}$, $5\times10^{5}$ M$^{-1}$ sec$^{-1}$, $10^{6}$ M$^{-1}$ sec$^{-1}$, or $5\times106$ M$^{-1}$ sec$^{-1}$ or $10^{7}$ M$^{-1}$ sec$^{-1}$.

In various embodiments, an anti-*Pseudomonas* Psl binding molecule, e.g., an antibody, or antigen-binding fragment, variant, or derivative thereof as described herein promotes opsonophagocytic killing of *Pseudomonas*, or inhibits *Pseudomonas* binding to epithelial cells. In certain embodiments described herein, the *Pseudomonas* Psl target is *Pseudomonas aeruginosa* Psl. In other embodiments, certain binding molecules described herein can bind to structurally related polysaccharide molecules regardless of their source. Such Psl-like molecules would be expected to be identical to or have sufficient structural relatedness to *P. aeruginosa* Psl to permit specific recognition by one or more of the binding molecules disclosed. For example, certain binding molecules described herein can bind to Psl-like molecules produced by other bacterial species, for example, Psl-like molecules produced by other *Pseudomonas* species, e.g., *Pseudomonas fluorescens, Pseudomonas putida,* or *Pseudomonas alcaligenes.* Alternatively, certain binding molecules as described herein can bind to Psl-like molecules produced synthetically or by host cells genetically modified to produce Psl-like molecules.

Unless it is specifically noted, as used herein a "fragment thereof" in reference to a binding molecule, e.g., an antibody refers to an antigen-binding fragment, i.e., a portion of the antibody which specifically binds to the antigen.

An anti-*Pseudomonas* Psl binding molecules, e.g., antibodies or antigen-binding fragments, variants, or derivatives thereof can comprise a constant region which mediates one or more effector functions. For example, binding of the C1 component of complement to an antibody constant region can activate the complement system. Activation of complement is important in the opsonization and lysis of pathogens. The activation of complement also stimulates the inflammatory response and can also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments disclosed herein include an anti-*Pseudomonas* Psl binding molecule, e.g., an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain binding molecules described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

Modified forms of anti-*Pseudomonas* Psl binding molecules, e.g., antibodies or antigen-binding fragments, variants, or derivatives thereof can be made from whole precursor or parent antibodies using techniques known in the art. Exemplary techniques are discussed elsewhere herein.

In certain embodiments both the variable and constant regions of anti-*Pseudomonas* Psl binding molecules, e.g., antibodies or antigen-binding fragments are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human anti bodies can likewise be produced by various display technologies, e.g., phage display or other viral display systems, as described in more detail elsewhere herein.

Anti-*Pseudomonas* Psl binding molecules, e.g., antibodies or antigen-binding fragments, variants, or derivatives thereof as disclosed herein can be made or manufactured using techniques that are known in the art. In certain embodiments, binding molecules or fragments thereof are "recombinantly produced," i.e., are produced using recombinant DNA technology. Exemplary techniques for making antibody molecules or fragments thereof are discussed in more detail elsewhere herein.

In certain anti-*Pseudomonas* Psl binding molecules, e.g., antibodies or antigen-binding fragments, variants, or derivatives thereof described herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases it can be that constant region modifications moderate complement binding and thus reduce the serum half-life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as localization, biodistribution and serum half-life, can easily be measured and quantified using well known immunological techniques without undue experimentation.

In certain embodiments, anti-*Pseudomonas* Psl binding molecules, e.g., antibodies or antigen-binding fragments, variants, or derivatives thereof will not elicit a deleterious immune response in the animal to be treated, e.g., in a human. In one embodiment, anti-*Pseudomonas* Psl binding molecules, e.g., antibodies or antigen-binding fragments, variants, or derivatives thereof are modified to reduce their immunogenicity using art-recognized techniques. For example, antibodies can be humanized, de-immunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., *Pseudomonas* Psl-specific antibodies or antigen-binding fragments thereof disclosed herein, which are then tested for function. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Anti-*Pseudomonas* Psl binding molecules, e.g., antibodies or antigen-binding fragments, variants, or derivatives thereof can be generated by any suitable method known in the art. Polyclonal antibodies to an antigen of interest can be produced by various procedures well known in the art. For example, an anti-*Pseudomonas* Psl antibody or antigen-binding fragment thereof can be administered to various host animals including, but not limited to, rabbits, mice, rats, chickens, hamsters, goats, donkeys, etc., to induce the production of sera containing polyclonal antibodies specific for the antigen. Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988)

DNA encoding antibodies or antibody fragments (e.g., antigen binding sites) can also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with scFv, Fab, Fv OE DAB (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding VH and VL regions are amplified from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH or VL regions are usually recombinantly fused to either the phage gene III or gene VIII. Phage expressing an antigen binding domain that binds to an antigen of interest (i.e., *Pseudomonas* Psl) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references and in the examples below, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). In certain embodiments such as therapeutic administration, chimeric, humanized, or human antibodies can be used. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Fully human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. In addition, various companies can be engaged to provide human antibodies produced in transgenic mice directed against a selected antigen using technology similar to that described above.

Fully human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332.)

In another embodiment, DNA encoding desired monoclonal antibodies can be readily isolated and sequenced using conventional procedures (e.g., by using oligonucleotide probes that are capable of binding specifically to genes encoding the heavy and light chains of murine antibodies). Isolated and subcloned hybridoma cells or isolated phage, for example, can serve as a source of such DNA. Once isolated, the DNA can be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which can be synthetic as described herein) can be used to clone constant and variable region sequences for the manufacture antibodies as described in Newman et al., U.S. Pat. No. 5,658,570, filed Jan. 25, 1995, which is incorporated by reference herein. Transformed cells expressing the desired antibody can be grown up in relatively large quantities to provide clinical and commercial supplies of the immunoglobulin.

In one embodiment, an isolated binding molecule, e.g., an antibody comprises at least one heavy or light chain CDR of an antibody molecule. In another embodiment, an isolated binding molecule comprises at least two CDRs from one or more antibody molecules. In another embodiment, an isolated binding molecule comprises at least three CDRs from one or more antibody molecules. In another embodiment, an isolated binding molecule comprises at least four CDRs from one or more antibody molecules. In another embodiment, an isolated binding molecule comprises at least five CDRs from one or more antibody molecules. In another embodiment, an isolated binding molecule of the description comprises at least six CDRs from one or more antibody molecules.

In a specific embodiment, the amino acid sequence of the heavy and/or light chain variable domains can be inspected to identify the sequences of the complementarity determining regions (CDRs) by methods that are well-known in the art, e.g., by comparison to known amino acid sequences of other heavy and light chain variable regions to determine the regions of sequence hypervariability. Using routine recombinant DNA techniques, one or more of the CDRs can be inserted within framework regions, e.g., into human framework regions to humanize a non-human antibody. The framework regions can be naturally occurring or consensus framework regions, and preferably human framework regions (see, e.g., Chothia et al., *J. Mol. Biol.* 278:457-479 (1998) for a listing of human framework regions). The polynucleotide generated by the combination of the framework regions and CDRs encodes an antibody that specifically binds to at least one epitope of a desired antigen, e.g., Psl. One or more amino acid substitutions can be made within the framework regions, and, the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and are within the capabilities of a person of skill of the art.

Also provided are binding molecules that comprise, consist essentially of, or consist of, variants (including derivatives) of antibody molecules (e.g., the VH regions and/or VL regions) described herein, which binding molecules or fragments thereof specifically bind to *Pseudomonas* Psl. Standard techniques known to those of skill in the art can be used to introduce mutations in the nucleotide sequence encoding a binding molecule or fragment thereof which specifically binds to *Pseudomonas* Psl, including, but not limited to, site-directed mutagenesis and PCR-mediated mutagenesis which result in amino acid substitutions. The variants (including derivatives) encode polypeptides comprising less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an *Pseudomonas* Psl).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to bind at least one epitope of *Pseudomonas* Psl) can be determined using techniques described herein or by routinely modifying techniques known in the art.

III. Antibody Polypeptides

The disclosure is further directed to isolated polypeptides which make up binding molecules, e.g., antibodies or antigen-binding fragments thereof, which specifically bind to *Pseudomonas* Psl and polynucleotides encoding such polypeptides. Binding molecules, e.g., antibodies or fragments thereof as disclosed herein, comprise polypeptides, e.g., amino acid sequences encoding, for example, Psl-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

Also disclosed is an isolated binding molecule, e.g., an antibody or antigen-binding fragment thereof which specifically binds to *Pseudomonas* Psl comprising an immunoglobulin heavy chain variable region (VH) amino acid sequence at least 80%, 85%, 90% 95% or 100% identical to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Further disclosed is an isolated binding molecule, e.g., an antibody or antigen-binding fragment thereof which specifically binds to *Pseudomonas* Psl comprising a VH amino acid sequence identical to, or identical except for one, two, three, four, five, or more amino acid substitutions to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Some embodiments include an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are at least 80%, 85%, 90%, 95% or 100% identical to one or more reference heavy chain VHCDR1, VHCDR2 or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Further disclosed is an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2. Thus, according to this embodiment the VH comprises one or more of a VHCDR1, VHCDR2, or VHCDR3 identical to or identical except for four, three, two, or one amino acid substitutions, to one or more of the VHCDR1, VHCDR2, or VHCDR3 amino acid sequences shown in Table 3.

Also disclosed is an isolated binding molecule, e.g., an antibody or antigen-binding fragment thereof which specifically binds to *Pseudomonas* Psl comprising an immunoglobulin light chain variable region (VL) amino acid sequence at least 80%, 85%, 90% 95% or 100% identical to one or more of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Some embodiments disclose an isolated binding molecule, e.g., an antibody or antigen-binding fragment thereof which specifically binds to *Pseudomonas* Psl comprising a VL amino acid sequence identical to, or identical except for one, two, three, four, five, or more amino acid substitutions, to one or more of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Also provided is an isolated binding molecule, e.g., an antibody or antigen-binding fragment thereof which specifically binds to *Pseudomonas* Psl comprising a VL, where one or more of the VLCDR1, VLCDR2 or VLCDR3 regions of the VL are at least 80%, 85%, 90%, 95% or 100% identical to one or more reference light chain VLCDR1, VLCDR2 or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Further provided is an isolated binding molecule, e.g., an antibody or antigen-binding fragment thereof which specifically binds to *Pseudomonas* Psl comprising a VL, where one or more of the VLCDR1, VLCDR2 or VLCDR3 regions of the VL are identical to, or identical except for four, three, two, or one amino acid substitutions, to one or more reference heavy chain VLCDR1, VLCDR2 and/or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2. Thus, according to this embodiment the VL comprises one or more of a VLCDR1, VLCDR2, or VLCDR3 identical to or identical except for four, three, two, or one amino acid substitutions, to one or more of the VLCDR1, VLCDR2, or VLCDR3 amino acid sequences shown in Table 3.

In other embodiments, an isolated antibody or antigen-binding fragment thereof which specifically binds to *Pseudomonas* Psl, comprises, consists essentially of, or consists of VH and VL amino acid sequences at least 80%, 85%, 90% 95% or 100% identical to:
(a) SEQ ID NO: 1 and SEQ ID NO: 2, respectively, (b) SEQ ID NO: 3 and SEQ ID NO: 2, respectively, (c) SEQ ID NO: 4 and SEQ ID NO: 2, respectively, (d) SEQ ID NO: 5 and SEQ ID NO: 6, respectively, (e) SEQ ID NO: 7 and SEQ ID NO: 8, respectively, (f) SEQ ID NO: 9 and SEQ ID NO: 10, respectively, (g) SEQ ID NO: 11 and SEQ ID NO: 12, respectively, (h) SEQ ID NO: 13 and SEQ ID NO: 14, respectively, (i) SEQ ID NO: 15 and SEQ ID NO: 16, respectively; or (j) SEQ ID NO: 74 and SEQ ID NO: 12, respectively. In certain embodiments, the above-described antibody or antigen-binding fragment thereof comprises a VH with the amino acid sequence SEQ ID NO: 11 and a VL with the amino acid sequence of SEQ ID NO: 12. In some embodiments, the above-described antibody or antigen-binding fragment thereof comprises a VH with the amino acid sequence SEQ ID NO: 1 and a VL with the amino acid sequence of SEQ ID NO: 2. In other embodiments, the above-described antibody or antigen-binding fragment thereof comprises a VH with the amino acid sequence SEQ ID NO: 11 and a VL with the amino acid sequence of SEQ ID NO: 12.

In certain embodiments, an isolated binding molecule, e.g., an antibody or antigen-binding fragment thereof as described herein specifically binds to *Pseudomonas* Psl with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In specific embodiments, an isolated binding molecule, e.g., an antibody or antigen-binding fragment thereof as described herein specifically binds to *Pseudomonas* Psl, with an affinity characterized by a dissociation constant ($K_D$) in a range of about $1 \times 10^{-10}$ to about $1 \times 10^{-6}$ M. In one embodiment, an isolated binding molecule, e.g., an antibody or antigen-binding fragment thereof as described herein specifically binds to *Pseudomonas* Psl, with an affinity characterized by a $K_D$ of about $1.18 \times 10^{-7}$ M, as determined by the OCTET® binding assay described herein. In another embodiment, an isolated binding molecule, e.g., an antibody or antigen-binding fragment thereof as described herein specifically binds to *Pseudomonas* Psl, with an affinity characterized by a $K_D$ of about $1.44 \times 10^{-7}$ M, as determined by the OCTET® binding assay described herein.

Some embodiments include the isolated binding molecule e.g., an antibody or fragment thereof as described above, which (a) can inhibit attachment of *Pseudomonas aeruginosa* to epithelial cells, (b) can promote OPK of *P. aerugi-* nosa, or (c) can inhibit attachment of *P. aeruginosa* to epithelial cells and can promote OPK of *P. aeruginosa*.

In some embodiments the isolated binding molecule e.g., an antibody or fragment thereof as described above, where maximum inhibition of *P. aeruginosa* attachment to epithelial cells is achieved at an antibody concentration of about 50 µg/ml or less, 5.0 µg/ml or less, or about 0.5 µg/ml or less, or at an antibody concentration ranging from about 30 µg/ml to about 0.3 µg/ml, or at an antibody concentration of about 1 µg/ml, or at an antibody concentration of about 0.3 µg/ml.

Certain embodiments include the isolated binding molecule e.g., an antibody or fragment thereof as described above, where the OPK EC50 is less than about 0.5 µg/ml, less than about 0.05 µg/ml, or less than about 0.005 µg/ml, or where the OPK EC50 ranges from about 0.001 µg/ml to about 0.5 µg/ml, or where the OPK EC50 ranges from about 0.02 µg/ml to about 0.08 µg/ml, or where the OPK EC50 ranges from about 0.002 µg/ml to about 0.01 µg/ml or where the OPK EC50 is less than about 0.2 µg/ml, or wherein the OPK EC50 is less than about 0.02 µg/ml. In certain embodiments, an anti-*Pseudomonas* Psl binding molecule, e.g., antibody or fragment, variant or derivative thereof described herein specifically binds to the same Psl epitope as monoclonal antibody WapR-004, WapR-004RAD, Cam-003, Cam-004, or Cam-005, or will competitively inhibit such a monoclonal antibody from binding to *Pseudomonas* Psl. WapR-004RAD is identical to WapR-004 except for an amino acid substitution G98A of the VH amino acid sequence of SEQ ID NO:11.

Some embodiments include WapR-004 (W4) mutants comprising an scFv-Fc molecule amino acid sequence identical to, or identical except for one, two, three, four, five, or more amino acid substitutions to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

Other embodiments include WapR-004 (W4) mutants comprising an scFv-Fc molecule amino acid sequence at least 80%, 85%, 90% 95% or 100% identical to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

In some embodiments, an anti-*Pseudomonas* Psl binding molecule, e.g., antibody or fragment, variant or derivative thereof described herein specifically binds to the same epitope as monoclonal antibody WapR-001, WapR-002, or WapR-003, or will competitively inhibit such a monoclonal antibody from binding to *Pseudomonas* Psl.

In certain embodiments, an anti-*Pseudomonas* Psl binding molecule, e.g., antibody or fragment, variant or derivative thereof described herein specifically binds to the same epitope as monoclonal antibody WapR-016, or will competitively inhibit such a monoclonal antibody from binding to *Pseudomonas* Psl.

TABLE 2

Reference VH and VL amino acid sequences*

| Antibody Name | VH | VL |
|---|---|---|
| Cam-003 | QVRLQQSGPGLVKPSET LSLTCTVSGGSTSPYFW SWLRQPPGKGLEWIGYI HSNGGTNYNPSLKSRLT ISGDTSKNQFSLNLSFV TAADTALYYCARTDYDV YGPAFDIWGQGTMVTV SEQ ID NO: 1 | SSELTQDPAVSVALGQT VRITCQGDSLRSYYASW YQQKPGQAPVLVIYGKN NRPSGIPDRFSGSSSGN TASLTITGAQAEDEADY YCNSRDSSGNHVVFGGG TKLTVL SEQ ID NO: 2 |
| Cam-004 | QVQLQQSGPGRVKPSET LSLTCTVSGYSVSSGYY WGWIRQSPGTGLEWIGS ISHSGSTYYNPSLKSRV TISGDASKNQFFLRLTS VTAADTAVYYCARSEAT ANFDSWGRGTLVTVSS SEQ ID NO: 3 | SSELTQDPAVSVALGQT VRITCQGDSLRSYYASW YQQKPGQAPVLVIYGKN NRPSGIPDRFSGSSSGN TASLTITGAQAEDEADY YCNSRDSSGNHVVFGGG TKLTVL SEQ ID NO: 2 |
| Cam-005 | QVQLQQSGPGLVKPSET LSLTCTVSGGSVSSSGY YWTWIRQPPGKGLEWIG SIYSSGSTYYSPSLKSR VTISGDTSKNQFSLKLS SVTAADTAVYYCARLNW GTVSAFDIWGRGTLVTV SEQ ID NO: 4 | SSELTQDPAVSVALGQT VRITCQGDSLRSYYASW YQQKPGQAPVLVIYGKN NRPSGIPDRFSGSSSGN TASLTITGAQAEDEADY YCNSRDSSGNHVVFGGG TKLTVL SEQ ID NO: 2 |
| WapR-001 | EVQLLESGGGLVQPGGS LRLSCSASGFTFSRYPM HWVRQAPGKGLEYVSDI GTNGGSTNYADSVKGRF TISRDNSKNTVLQMSS LRAEDTAVYHCVAGIAA AYGFDVWGQGTMVTVSS SEQ ID NO: 5 | QAGLTQPASVSGSPGQS ITISCTGTSSDIATYNY VSWYQQHPGKAPKLMIY EGTKRPSGVSNRFSGSK SGNTASLTISGLQAEDE ADYYCSSYARSYTYVFG TGTELTVL SEQ ID NO: 6 |
| WapR-002 | QVQLVQSGGGLVQPGGS LRLSCSASGFTFSSYPM HWVRQAPGKGLDYVSDI SPNGGSTNYADSVKGRF TISRDNSKNTLFLQMSS LRAEDTAVYYCVMGLVP YGFDIWGQGTLVTVSS SEQ ID NO: 7 | QTVVTQPASVSGSPGQS ITISCTGTSSDVGGYNY VSWYQQHPGKAPKLMIY EVSNRPSGVSNHFSGSK SGNTASLTISGLQAEDE ADYYCSSYTTSSTYVFG TGTKVTVL SEQ ID NO: 8 |

TABLE 2-continued

Reference VH and VL amino acid sequences*

| Antibody Name | VH | VL |
|---|---|---|
| WapR-003 | QMQLVQSGGGLVQPGGS LRLSCSASGFTFSSYPM HWVRQAPGKGLDYVSDI SPNGGATNYADSVKGRF TISRDNSKNTVYLQMSS LRAEDTAVYYCVMGLVP YGFDNWGQGTMVTVSS SEQ ID NO: 9 | QTVVTQPASVSASPGQS ITISCAGTSGDVGNYNF VSWYQQHPGKAPKLLIY EGSQRPSGVSNRFSGSR SGNTASLTISGLQAEDE ADYCSSYARSYTYVFG TGTKLTVL SEQ ID NO: 10 |
| WapR-004 | EVQLLESGPGLVKPSET LSLTCNVAGGSISPYYW TWIRQPPGKGLELIGYI HSSGYTDYNPSLKSRVT ISGDTSKKQFSLHVSSV TAADTAVYFCARGDWDL LHALDIWGQGTLVTVSS SEQ ID NO: 11 | EIVLTQSPSSLSTSVGD RVTITCRASQSIRSHLN WYQQKPGKAPKLLIYGA SNLQSGVPSRFSGSGSG TDFTLTISSLQPEDFAT YYCQQSYSFPLTFGGGT KLEIK SEQ ID NO: 12 |
| WapR-007 | EVQLVQSGADVKKPGAS VRVTCKASGYTFTGHNI HWVRQAPGQGLEWMGWI NPDSGATSYAQKFQGRV TMTRDTSTTAYMDLSR LRSDDTAVYYCATDTLL SNHWGQGTLVTVSS SEQ ID NO: 13 | SSELTQDPAVSVALGQT VRITCQGDSLRSYYTNW FQQKPGQAPLLVVYAKN KRPPGIPDRFSGSSSGN TASLTITGAQAEDEADY YCHSRDSSGNHVVFGGG TKLTVL SEQ ID NO: 14 |
| WapR-016 | EVQLVESGGGLVQPGGS LRLSCAASGYTFSSYAT SWVRQAPGKGLEWVAGI SGSGDTTDYVDSVKGRF TVSRDNSKNTLYLQMNS LRADDTAVYYCASRGGL GGYYRGGFDFWGQGMV TVSS SEQ ID NO: 15 | QSVLTQPASVSGSPGQS ITISCTGTSSDVGGYNY VSWYQQHPGKAPKLMIY EVSNRPSGVSNRFSGSK SGNTASLTISGLQAEDE ADYCSSYSSGTVVFGGG TELTVL SEQ ID NO: 16 |
| WapR-004RAD | EVQLLESGPGLVKPSET LSLTCNVAGGSISPYYW TWIRQPPGKGLELIGYI HSSGYTDYNPSLKSRVT ISGDTSKKQFSLHVSSV TAADTAVYFCARADWDL LHALDIWGQGTLVTVSS SEQ ID NO: 74 | EIVLTQSPSSLSTSVGD RVTITCRASQSIRSHLN WYQQKPGKAPKLLIYGA SNLQSGVPSRFSGSGSG TDFTLTISSLQPEDFAT YYCQQSYSFPLTFGGGT KLEIK SEQ ID NO: 12 |

*VH and VL CDR1, CDR2, and CDR3 amino acid sequences are underlined

TABLE 3

Reference VH and VL CDR1, CDR2, and CDR3 amino acid sequences

| Antibody Name | VHCDR1 | VHCDR2 | VHCDR3 | VLCDR1 | VLCDR2 | VLCDR3 |
|---|---|---|---|---|---|---|
| Cam-003 | PYFWS SEQ ID NO: 17 | YIHSNGGTNYNPSLKS SEQ ID NO: 18 | TDYDVYGPAFDI SEQ ID NO: 19 | QGDSLRSYYAS SEQ ID NO: 20 | GKNNRPS SEQ ID NO: 21 | NSRDSSGNHVV SEQ ID NO: 22 |
| Cam-004 | SGYYWG SEQ ID NO: 23 | SISHSGSTYYNPSLKS SEQ ID NO: 24 | SEATANFDS SEQ ID NO: 25 | QGDSLRSYYAS SEQ ID NO: 20 | GKNNRPS SEQ ID NO: 21 | NSRDSSGNHVV SEQ ID NO: 22 |
| Cam-005 | SSGYYWT SEQ ID NO: 26 | SIYSSGSTYYSPSLKS SEQ ID NO: 27 | LNWGTVSAFDI SEQ ID NO: 28 | QGDSLRSYYAS SEQ ID NO: 20 | GKNNRPS SEQ ID NO: 21 | NSRDSSGNHVV SEQ ID NO: 22 |
| WapR-001 | RYPMH SEQ ID NO: 29 | DIGTNGGSTNYADSVKG SEQ ID NO: 30 | GIAAAYGFDV SEQ ID NO: 31 | TGTSSDIATYNYVS SEQ ID NO: 32 | EGTKRPS SEQ ID NO: 33 | SSYARSYTYV SEQ ID NO: 34 |
| WapR-002 | SYPMH SEQ ID NO: 35 | DISPNGGSTNYADSVKG SEQ ID NO: 36 | GLVPYGFDI SEQ ID NO: 37 | TGTSSDVGGYNYVS SEQ ID NO: 38 | EVSNRPS SEQ ID NO: 39 | SSYTTSSTYV SEQ ID NO: 40 |
| WapR-003 | SYPMH SEQ ID NO: 41 | DISPNGGATNYADSVKG SEQ ID NO: 42 | GLVPYGFDN SEQ ID NO: 43 | AGTSGDVGNYNFVS SEQ ID NO: 44 | EGSQRPS SEQ ID NO: 45 | SSYARSYTYV SEQ ID NO: 46 |
| WapR-004 | PYYWT SEQ ID NO: 47 | YIHSSGYTDYNPSLKS SEQ ID NO: 48 | GDWDLLHALDI SEQ ID NO: 49 | RASQSIRSHLN SEQ ID NO: 50 | GASNLQS SEQ ID NO: 51 | YSFPLT SEQ ID NO: 52 |
| WapR-007 | GHNIH SEQ ID NO: 53 | WINPDSGATSYAQKFQG SEQ ID NO: 54 | DTLLSNH SEQ ID NO: 55 | QGDSLRSYYTN SEQ ID NO: 56 | AKNKRPP SEQ ID NO: 57 | HSRDSSGNHVV SEQ ID NO: 58 |
| WapR-016 | SYATS SEQ ID NO: 59 | GISGSGDTTDYVDSVKG SEQ ID NO: 60 | RGGLGGYYRGGFDF SEQ ID NO: 61 | TGTSSDVGGYNYVS SEQ ID NO: 62 | EVSNRPS SEQ ID NO: 63 | SSYSSGTVV SEQ ID NO: 64 |
| WapR-004RAD | PYYWT SEQ ID NO: 47 | YIHSSGYTDYNPSLKS SEQ ID NO: 48 | ADWDLLHALDI SEQ ID NO: 75 | RASQSIRSHLN SEQ ID NO: 50 | GASNLQS SEQ ID NO: 51 | YSFPLT SEQ ID NO: 52 |

Any anti-*Pseudomonas* Psl binding molecules, e.g., antibodies or fragments, variants or derivatives thereof described herein can further include additional polypeptides, e.g., a signal peptide to direct secretion of the encoded polypeptide, antibody constant regions as described herein, or other heterologous polypeptides as described herein. Additionally, binding molecules or fragments thereof of the description include polypeptide fragments as described elsewhere. Additionally anti-*Pseudomonas* Psl binding molecules, e.g., antibodies or fragments, variants or derivatives thereof described herein can be fusion polypeptides, Fab fragments, scFvs, or other derivatives, as described herein.

Also, as described in more detail elsewhere herein, the disclosure includes compositions comprising anti-*Pseudomonas* Psl binding molecules, e.g., antibodies or fragments, variants or derivatives thereof described herein.

It will also be understood by one of ordinary skill in the art that anti-*Pseudomonas* Psl binding molecules, e.g., antibodies or fragments, variants or derivatives thereof described herein can be modified such that they vary in amino acid sequence from the naturally occurring binding polypeptide from which they were derived. For example, a polypeptide or amino acid sequence derived from a designated protein can be similar, e.g., have a certain percent identity to the starting sequence, e.g., it can be 60%, 70%, 75%, 80%, 85%, 90%, or 95% identical to the starting sequence.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculated percent sequence identity may be curated either automatically or manually.

Whether any particular polypeptide is at least about 70%, 75%, 80%, 85%, 90% or 95% identical to another polypeptide can also be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence, the parameters are set, of course, such that the percentage of identity is calculated over the full length of the reference polypeptide sequence and that gaps in homology of up to 5% of the total number of amino acids in the reference sequence are allowed.

Furthermore, nucleotide or amino acid substitutions, deletions, or insertions leading to conservative substitutions or changes at "non-essential" amino acid regions can be made. For example, a polypeptide or amino acid sequence derived from a designated protein can be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

An anti-*Pseudomonas* Psl binding molecule, e.g., an antibody or fragment, variant or derivative thereof described herein can comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide, polypeptide, or other moiety means that the polynucleotide, polypeptide, or other moiety is derived from a distinct entity from that of the rest of the entity to which it is being compared. In a non-limiting example, a "heterologous polypeptide" to be fused to a binding molecule, e.g., an antibody or an antigen-binding fragment, variant, or derivative thereof is derived from a non-immunoglobulin polypeptide of the same species, or an immunoglobulin or non-immunoglobulin polypeptide of a different species.

IV. Fusion Proteins and Antibody Conjugates

In some embodiments, the anti-*Pseudomonas* Psl binding molecules, e.g., antibodies or fragments, variants or derivatives thereof can be administered multiple times in conjugated form. In still another embodiment, the anti-*Pseudomonas* Psl binding molecules, e.g., antibodies or fragments, variants or derivatives thereof can be administered in unconjugated form, then in conjugated form, or vice versa.

In specific embodiments, the anti-*Pseudomonas* Psl binding molecules, e.g., antibodies or fragments, variants or derivatives thereof can be conjugated to one or more antimicrobial agents, for example, Polymyxin B (PMB). PMB is a small lipopeptide antibiotic approved for treatment of multidrug-resistant Gram-negative infections. In addition to its bactericidal activity, PMB binds lipopolysaccharide (LPS) and neutralizes its proinflammatory effects. (Dixon, R. A. & Chopra, I. *J Antimicrob Chemother* 18, 557-563 (1986)). LPS is thought to significantly contribute to inflammation and the onset of Gram-negative sepsis. (Guidet, B., et al., *Chest* 106, 1194-1201 (1994)). Therapies that neutralize and/or clear LPS from circulation have the potential to prevent or delay the onset of sepsis and improve clinical outcome. Polymyxin B (PMB) is a lipopeptide antibiotic approved for treatment of multidrug-resistant Gram-negative infections. In addition to its bactericidal activity, PMB binds LPS and neutralizes its proinflammatory effects. Conjugates of PMB to carrier molecules have been shown to neutralize LPS and mediate protection in animal models of endotoxemia and infection. (Drabick, J. J., et al. *Antimicrob Agents Chemother* 42, 583-588 (1998)). Also disclosed is a method for attaching one or more PMB molecules to cysteine residues introduced into the Fc region of monoclonal antibodies (mAb) of the disclosure. For example, the Cam-003-PMB conjugates retained specific, mAb-mediated binding to *P. aeruginosa* and also retained OPK activity. Furthermore, mAb-PMB conjugates bound and neutralized LPS in vitro.

In certain embodiments, an anti-*Pseudomonas* Psl binding molecule, e.g., an antibody or fragment, variant or derivative thereof described herein can comprise a heterologous amino acid sequence or one or more other moieties not normally associated with an antibody (e.g., an antimicrobial agent, a therapeutic agent, a prodrug, a peptide, a protein, an enzyme, a lipid, a biological response modifier, pharmaceutical agent, a lymphokine, a heterologous antibody or fragment thereof, a detectable label, polyethylene glycol (PEG), and a combination of two or more of any said agents). In further embodiments, an anti-*Pseudomonas* Psl binding molecule, e.g., an antibody or fragment, variant or derivative thereof can comprise a detectable label selected from the group consisting of an enzyme, a fluorescent label, a chemiluminescent label, a bioluminescent label, a radioactive label, or a combination of two or more of any said detectable labels.

V. Polynucleotides Encoding Binding Molecules

Also provided herein are nucleic acid molecules encoding the anti-*Pseudomonas* Psl binding molecules, e.g., antibodies or fragments, variants or derivatives thereof described herein.

One embodiment provides an isolated polynucleotide comprising, consisting essentially of, or consisting of a nucleic acid encoding an immunoglobulin heavy chain variable region (VH) amino acid sequence at least 80%, 85%, 90% 95% or 100% identical to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ IS NO: 74 as shown in Table 2.

Another embodiment provides an isolated polynucleotide comprising, consisting essentially of, or consisting of a nucleic acid encoding a VH amino acid sequence identical to, or identical except for one, two, three, four, five, or more amino acid substitutions to one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Further embodiment provides an isolated polynucleotide comprising, consisting essentially of, or consisting of a nucleic acid encoding a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

Another embodiment provides an isolated polynucleotide comprising, consisting essentially of, or consisting of a nucleic acid encoding an isolated binding molecule, e.g., an antibody or antigen-binding fragment thereof which specifically binds to *Pseudomonas* Psl comprising a VH, where one or more of the VHCDR1, VHCDR2 or VHCDR3 regions of the VH are identical to, or identical except for four, three, two, or one amino acid substitutions, to one or more reference heavy chain VHCDR1, VHCDR2 and/or VHCDR3 amino acid sequences of one or more of: SEQ ID NO: 1, SEQ ID NO: 3, SEQ ID NO: 4, SEQ ID NO: 5, SEQ ID NO: 7, SEQ ID NO: 9, SEQ ID NO: 11, SEQ ID NO: 13, SEQ ID NO: 15, or SEQ ID NO: 74 as shown in Table 2.

A further embodiment provides an isolated binding molecule e.g., an antibody or antigen-binding fragment comprising the VH encoded by the polynucleotide specifically or preferentially binds to *Pseudomonas* Psl.

Another embodiment provides an isolated polynucleotide comprising, consisting essentially of, or consisting of a nucleic acid encoding an immunoglobulin light chain variable region (VL) amino acid sequence at least 80%, 85%, 90% 95% or 100% identical to one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

A further embodiment provides an isolated polynucleotide comprising, consisting essentially of, or consisting of a nucleic acid encoding a VL amino acid sequence identical to, or identical except for one, two, three, four, five, or more amino acid substitutions to one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

Another embodiment provides an isolated polynucleotide comprising, consisting essentially of, or consisting of a nucleic acid encoding a VL, where one or more of the VLCDR1, VLCDR2 or VLCDR3 regions of the VL are at least 80%, 85%, 90%, 95% or 100% identical to one or more reference light chain VLCDR1, VLCDR2 or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

A further embodiment provides an isolated polynucleotide comprising, consisting essentially of, or consisting of a nucleic acid encoding an isolated binding molecule, e.g., an antibody or antigen-binding fragment thereof which specifically binds to *Pseudomonas* Psl comprising an VL, where one or more of the VLCDR1, VLCDR2 or VLCDR3 regions of the VL are identical to, or identical except for four, three, two, or one amino acid substitutions, to one or more reference heavy chain VLCDR1, VLCDR2 and/or VLCDR3 amino acid sequences of one or more of: SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16 as shown in Table 2.

In another embodiment, an isolated binding molecule e.g., an antibody or antigen-binding fragment comprising the VL encoded by the polynucleotide specifically or preferentially binds to *Pseudomonas* Psl.

One embodiment provides an isolated polynucleotide comprising, consisting essentially of, or consisting of a nucleic acid which encodes an scFv molecule including a VH and a VL, where the scFv is at least 80%, 85%, 90% 95% or 100% identical to one or more of SEQ ID NO:65, SEQ ID NO:66, SEQ ID NO:67, SEQ ID NO:68, SEQ ID NO:69, or SEQ ID NO:70 as shown in Table 4.

TABLE 4

Reference scFv nucleic acid sequences

| Antibody Name | scFv nucleotide sequences |
|---|---|
| Cam-003 | CAGCCGGCCATGGCCCAGGTACAGCTGCAGCAGTCAGGCCCAGG ACTGGTGAAGCCTTCGGAGACCCTGTCCCTCACCTGCACTGTCT CTGGTGGCTCCACCAGTCCTTACTTCTGGAGCTGGCTCCGGCAG CCCCCAGGGAAGGGACTGGAGTGGATTGGTTATATCCATTCCAA TGGGGGCACCAACTACAACCCCTCCCTCAAGAGTCGACTCACCA TATCAGGAGACAGTCCAAGAACCAATTCTCCCTGAATCTGAGT TTTGTGACCGCTGCGGACACGGCCCTCTATTACTGTGCGAGAAC GGACTACGATGTCTACGGCCCCGCTTTTGATATCTGGGGCCAGG GGACAATGGTCACCGTCTCGAGTGGTGGAGGCGGTTCAGGCGGA GGTGGCAGCGGCGGTGGCGGATCGTCTGAGCTGACTCAGGACCC TGCTGTGTCTGTGGCCTTGGGACAGACAGTCAGGATCACATGCC AAGGAGACAGCCTCAGAAGCTATTATGCAAGCTGGTACCAGCAG AAGCCAGGACAGGCCCCTGTACTTGTCATCTATGGTAAAAACAA CCGGCCCTCAGGGATCCCAGACCGATTCTCTGGCTCCAGCTCA GAAACACAGCTTCCTTGACCATCACTGGGGCTCAGGCGGAAGAT GAGGCTGACTATTACTGTAACTCCCGGGACAGCAGTGGTAACCA TGTGGTATTCGGCGGAGGGACCAAGCTGACCGTCCTAGGTGCGG CCGCA<br>SEQ ID NO: 65 |
| Cam-004 | CAGCCGGCCATGGCCCAGGTACAGCTGCAGCAGTCAGGCCCAGG ACGGGTGAAGCCTTCGGAGACGCTGTCCCTCACCTGCACTGTCT CTGGTTACTCCGTCAGTAGTGGTTACTACTGGGGCTGGATCCGG CAGTCCCCAGGGACGGGGCTGGAGTGGATTGGGAGTATCTCTCA TAGTGGGAGCACCTACTACAACCCGTCCCTCAAGAGTCGAGTCA CCATATCAGGAGACGCATCCAAGAACCAGTTTTTCCTGAGGCTG ACTTCTGTGACCGCCGCGGACACGGCCGTGTTTATTACTGTGCGAG ATCTGAGGCTACCGCCAACTTTGATTCTTGGGGCAGGGGCACCC TGGTCACCGTCTCTTCAGGTGGAGGCGGTTCAGGCGGAGGTGGC AGCGGCGGTGGCGGATCGTCTGAGCTGACTCAGGACCCTGCCGT GTCTGTGGCCTTGGGACAGACAGTCAGGATCACATGCCAAGGAG ACAGCCTCAGAAGCTATTATGCAAGCTGGTACCAGCAGAAGCCA GGACAGGCCCCTGTACTTGTCATCTATGGTAAAAACAACCGGCC CTCAGGGATCCCAGACCGATTCTCTGGCTCCAGCTCAGGAAACA CAGCTTCCTTGACCATCACTGGGGCTCAGGCGGAAGATGAGGCT GACTATTACTGTAACTCCCGGGACAGCAGTGGTAACCATGTGGT ATTCGGCGGAGGGACCAAGCTGACCGTCCTAGGTGCGGCCGCA<br>SEQ ID NO: 66 |
| Cam-005 | CAGCCGGCCATGGCCCAGGTACAGCTGCAGCAGTCAGGCCCAGG ACTGGTGAAGCCTTCGGAGACCCTGTCCCTCACCTGCACTGTCT CTGGTGGCTCCGTCAGCAGTAGTGGTTATTACTGGACCTGGATC CGCCAGCCCCCAGGGAAGGGGCTGGAGTGGATTGGGAGTATCTA TTCTAGTGGGAGCACATATTACAGCCCGTCCCTCAAGAGTCGAG TCACCATATCCGGAGACACGTCCAAGAACCAGTTCTCCCTCAAG CTGAGCTCTGTGACCGCCGCAGACACAGCCGTGTATTACTGTGC GAGACTTAACTGGGGCACTGTGTCTGCCTTTGATATCTGGGGCA GAGGCACCCTGGTCACCGTCTCGAGTGGTGGAGGCGGTTCAGGC GGAGGTGGCAGCGGCGGTGGCGGATCGTCTGAGCTGACTCAGGA CCCTGCTGTGTCTGTGGCCTTGGGACAGACAGTCAGGATCACAT GCCAAGGAGACAGCCTCAGAAGCTATTATGCAAGCTGGTACCAG CAGAAGCCAGGACAGGCCCCTGTACTTGTCATCTATGGTAAAAA CAACCGGCCCTCAGGGATCCCAGACCGATTCTCTGGCTCCAGCT CAGGAAACACAGCTTCCTTGACCATCACTGGGGCTCAGGCGGAA GATGAGGCTGACTATTACTGTAACTCCCGGGACAGCAGTGGTAA CCATGTGGTATTCGGCGGAGGGACCAAGCTGACCGTCCTAGGTG CGGCCGCA<br>SEQ ID NO: 67 |
| WapR-001 | TCTATGCGGCCCAGCCGGCCATGGCCGAGGTGCAGCTGTTGGAG TCTGGGGGAGGTTTGGTCCAGCCTGGGGGGTCCCTGAGACTCTC CTGTTCAGCCTCTGGGTTCACCTTCAGTCGGTATCCTATGCATT GGGTCCGCCAGGCTCCAGGGAAGGGACTGGAATATGTTTCAGAT ATTGGTACTAATGGGGGTAGTACAAACTACGCAGACTCCGTGAA GGGCAGATTCACCATCTCCAGAGACAATTCCAAGAACACGGTGT ATCTTCAAATGAGCAGTCTGAGAGCTGAGGACACGGCTGTGTAT CATTGTGTGGCGGGTATAGCAGCCGCCTATGGTTTTGATGTCTG GGGCCAAGGGACAATGGTCACCGTCTCGAGTGGAGGCGGCGGTT CAGGCGGAGGTGGCTCTGGCGGTGGCGGAAGTGCACAGGCAGGG CTGACTCAGCCTGCCTCCGTGTCTGGGTCTCCTGGACAGTCGAT CACCATCTCCTGCACTGGAACCAGCAGTGACATTGCTACTTATA ACTATGTCTCCTGGTACCAACAGCACCCAGGCAAAGCCCCCAAA CTCATGATTTATGAGGGCACTAAGCGGCCCTCAGGGGTTTCTAA TCGCTTCTCTGGCTCCAAGTCTGGCAACACGGCCTCCCTGACAA TCTCTGGGCTCCAGGCTGAGGACGAGGCTGATTATTACTGTTCC TCATATGCACGTAGTTACACTTATGTCTTCGGAACTGGGACCGA GCTGACCGTCCTAGCGGCCGC<br>SEQ ID NO: 68 |
| WapR-002 | CTATGCGGCCCAGCCGGCCATGGCCCAGGTGCAGCTGGTGCAGT CTGGGGGAGGCTTGGTCAGCCTGGGGGGTCCCTGAGACTCTCC TGTTCAGCTCTGGATTCACCTTCAGTAGCTATCCTATGCACTG GGTCCGCCAGGCTCCAGGGAAGGGACTGGATTATGTTTCAGACA TCAGTCCAAATGGGGGTTCCACAAACTACGCAGACTCCGTGAAG GGCAGATTCACCATCTCCAGAGACAATTCCAAGAACACACTGTT TCTTCAAATGAGCAGTCTGAGAGCTGAGGACACGGCTGTGTATT ATTGTGTGATGGGGTTAGTACCCTATGGTTTTGATATCTGGGGC CAAGGCACCCTGGTCACCGTCTCGAGTGGAGGCGGCGGTTCAGG CGGAGGTGGCTCTGGCGGTGGCGGAAGTGCACAGACTGTTGTGA CCCAGCCTGCCTCCGTGTCTGGGTCTCCTGGACAGTCGATCACC ATCTCCTGCACTGGAACCAGCAGTGACGTTGGTGGTTATAACTA TGTCTCCTGGTACCAACAGCACCCAGGCAAAGCCCCCAAACTCA TGATTTATGAGGTCAGTAATCGGCCCTCAGGGGTTTCTAATCAC TTCTCTGGCTCCAAGTCTGGCAACACGGCCTCCCTGACCATCTC |

TABLE 4-continued

Reference scFv nucleic acid sequences

| Antibody Name | scFv nucleotide sequences |
|---|---|
|  | TGGGCTCCAGGCTGAGGACGAGGCTGATTATTACTGCAGCTCAT<br>ATACAACCAGCAGCACTTATGTCTTCGGAACTGGGACCAAGGTC<br>ACCGTCCTAGCGGCCG<br>SEQ ID NO: 69 |
| WapR-003 | CGGCCCAGCCGGCCATGGCCCAGATGCAGCTGGTGCAGTCGGGG<br>GGAGGCTTGGTCCAGCCTGGGGGGTCCCTGAGACTCTCCTGTTC<br>AGCCTCTGGATTCACCTTCAGTAGCTATCCTATGCACTGGGTCC<br>GCCAGGCTCCAGGGAAGGGACTGGATTATGTTTCAGACATCAGT<br>CCAAATGGGGGTGCCACAAACTACGCAGACTCCGTGAAGGGCAG<br>ATTCACCATCTCCAGAGACAATTCCAAGAACACGGTGTATCTTC<br>AAATGAGCAGTCTGAGAGCTGAAGACACGGCTGTCTATTATTGT<br>GTGATGGGGTTAGTGCCCTATGGTTTTGATAACTGGGGCCAGGG<br>GACAATGGTCACCGTCTCGAGTGGAGGCGGCGGTTCAGGCGGAG<br>GTGGCTCTGGCGGTGGCGGAAGTGCACAGACTGTGGTGACCCAG<br>CCTGCCTCCGTGTCTGCATCTCCTGGACAGTCGATCACCATCTC<br>CTGCGCTGGAACCAGCGGTGATGTTGGGAATTATAATTTTGTCT<br>CCTGGTACCAACAACACCCAGGCAAAGCCCCCAAACTCCTGATT<br>TATGAGGGCAGTCAGCGGCCCTCAGGGGTTTCTAATCGCTTCTC<br>TGGCTCCAGGTCTGGCAACACGGCCTCCCTGACAATCTCTGGGC<br>TCCAGGCTGAGGACGAGGCTGATTATTACTGTTCCTCATATGCA<br>CGTAGTTACACTTATGTCTTCGGAACTGGGACCAAGCTGACCGT<br>CCTAGCGGCCGCA<br>SEQ ID NO: 70 |
| WapR-004 | TATGCGGCCCAGCCGGCCATGGCCGAGGTGCAGCTGTTGGAGTC<br>GGGGCCCAGGACTGGTGAAGCCTTCGGAGACCCTGTCCCTCACCT<br>GCAATGTCGCTGGTGGCTCCATCAGTCCTTACTACTGGACCTGG<br>ATCCGGCAGCCCCCAGGGAAGGGCCTGGAGTTGATTGGTTATAT<br>CCACTCCAGTGGGTACACCGACTACAACCCCTCCCTCAAGAGTC<br>GAGTCACCATATCAGGAGACACGTCCAAGAAGCAGTTCTCCCTG<br>CACGTGAGCTCTGTGACCGCTGCGGACACGGCCGTGTACTTCTG<br>TGCGAGAGGCGATTGGGACCTGCTTCATGCTCTTGATATCTGGG<br>GCCAAGGGACCCTGGTCACCGTCTCGAGTGGAGGCGGCGGTTCA<br>GGCGGAGGTGGCTCTGGCGGTGGCGAAGTGCACTCGAAATTGT<br>GTTGACACAGTCTCCATCCTCCCTGTCTACATCTGTAGGAGACA<br>GAGTCACCATCACTTGCCGGGCAAGTCAGAGCATTAGGAGCCAT<br>TTAAATTGGTATCAGCAGAAACAGGGAAAGCCCCTAAACTCCT<br>GATCTATGGTGCATCCAATTTGCAAAGTGGGGTCCCATCAAGGT<br>TCAGTGGCAGTGGATCTGGGACAGATTTCACTCTCACCATTAGT<br>AGTCTGCAACCTGAAGATTTTGCAACTTACTACTGTCAACAGAG<br>TTACAGTTTCCCCCTCACTTTCGGCGGAGGGACCAAGCTGGAGA<br>TCAAAGCGGCCGC<br>SEQ ID NO: 71 |
| WapR-007 | GCGGCCCAGCCGGCCATGGCCGAAGTGCAGCTGGTGCAGTCTGG<br>GGCTGACGTAAAGAAGCCTGGGGCCTCAGTGAGGGTCACCTGCA<br>AGGCTTCTGGATACACCTTCACCGGCCACAACATACACTGGGTG<br>CGACAGGCCCCTGGACAAGGGCTTGAATGGATGGGATGGATCAA<br>CCCTGACAGTGGTGCCACAAGCTATGCACAGAAGTTTCAGGGCA<br>GGGTCACCATGACCAGGGACACGTCCATCACCACAGCCTACATG<br>GACCTGAGCAGGCTGAGATCTGACGACACGGCCGTATATTACTG<br>TGCGACCGATACATTACTGTCTAATCACTGGGGCCAAGGAACCC<br>TGGTCACCGTCTCGAGTGGTGGAGGCGGTTCAGGCGGAGGTGGC<br>AGCGGCGGTGCGGATCGTCTGAGCTGACTCAGGACCCTGCTGT<br>GTCTGTGGCCTTGGGACAGACAGTCAGGATCACTTGCCAAGGAG<br>ACAGTCTCAGAAGCTATTACACAAACTGGTTCCAGCAGAAGCCA<br>GGACAGGCCCCTCTACTTGTCGTCTATGCTAAAAATAAGCGGCC<br>CCCAGGGATCCCAGACCGATTCTCTGGCTCCAGCTCAGGAAACA<br>CAGCTTCCTTGACCATCACTGGGGCTCAGGCGGAAGATGAGGCT<br>GACTATTACTGTCATTCCCGGGACAGCAGTGGTAACCATGTGGT<br>ATTCGGCGGAGGGACCAAGCTGACCGTCCTAGGTGCGGCCGCA<br>SEQ ID NO: 72 |
| WapR-016 | CAGCCGGCCATGGCCGAGGTGCAGCTGGTGGAGTCTGGGGGAGG<br>CTTGGTACAGCCTGGGGGGTCCCTGAGACTCTCCTGTGCAGCCT<br>CTGGATACACCTTTAGCAGCTATGCCACGAGCTGGGTCCGCCAG<br>GCTCCAGGGAAGGGCTGGAGTGGGTCGCAGGTATTAGTGGTAG<br>TGGTGATACCACAGACTACGTAGACTCCGTGAAGGGCCGGTTCA<br>CCGTCTCCAGAGACAATTCCAAGAACACCCTATATCTGCAAATG<br>AACAGCCTGAGAGCCGACGACACGGCCGTGTATTACTGTGCGTC<br>GAGAGGAGGTTTAGGGGGTTATTACCGGGGCGGCTTTGACTTCT<br>GGGGCCAGGGGACAATGGTCACCGTCTCGAGTGGAGGCGGCGGT<br>TCAGGCGGAGGTGGCTCTGGCGGTGGCGAAGTGCACAGTCTGT |

| Antibody Name | scFv nucleotide sequences |
|---|---|
|  | GCTGACGCAGCCTGCCTCCGTGTCTGGGTCTCCTGGACAGTCGA<br>TCACCATCTCCTGCACTGGAACCAGCAGTGACGTTGGTGGTTAT<br>AACTATGTCTCCTGGTACCAACAGCACCCAGGCAAAGCCCCCAA<br>ACTCATGATTTATGAGGTCAGTAATCGGCCCTCAGGGGTTTCTA<br>ATCGCTTCTCTGGCTCCAAGTCTGGCAACACGGCCTCCCTGACC<br>ATCTCTGGGCTCCAGGCTGAGGACGAGGCTGATTATTACTGCAG<br>CTCATATACAAGCAGCGGCACTGTGGTATTCGGCGGAGGGACCG<br>AGCTGACCGTCCTAGCGGCCGCA<br>SEQ ID NO: 73 |

In some embodiments, an isolated antibody or antigen-binding fragment thereof encoded by one or more of the polynucleotides described above, which specifically binds to *Pseudomonas* Psl, comprises, consists essentially of, or consists of VH and VL amino acid sequences at least 80%, 85%, 90% 95% or 100% identical to:

(a) SEQ ID NO: 1 and SEQ ID NO: 2, respectively, (b) SEQ ID NO: 3 and SEQ ID NO: 2, respectively, (c) SEQ ID NO: 4 and SEQ ID NO: 2, respectively, (d) SEQ ID NO: 5 and SEQ ID NO: 6, respectively, (e) SEQ ID NO: 7 and SEQ ID NO: 8, respectively, (f) SEQ ID NO: 9 and SEQ ID NO: 10, respectively, (g) SEQ ID NO: 11 and SEQ ID NO: 12, respectively, (h) SEQ ID NO: 13 and SEQ ID NO: 14, respectively; (i) SEQ ID NO: 15 and SEQ ID NO: 16, respectively; or (j) SEQ ID NO: 74 and SEQ ID NO: 12, respectively.

In certain embodiments, an isolated binding molecule, e.g., an antibody or antigen-binding fragment thereof encoded by one or more of the polynucleotides described above, specifically binds to *Pseudomonas* Psl with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In specific embodiments, an isolated binding molecule, e.g., an antibody or antigen-binding fragment thereof encoded by one or more of the polynucleotides described above, specifically binds to *Pseudomonas* Psl, with an affinity characterized by a dissociation constant ($K_D$) in a range of about $1 \times 10^{-10}$ to about $1 \times 10^{-6}$ M. In one embodiment, an isolated binding molecule, e.g., an antibody or antigen-binding fragment thereof encoded by one or more of the polynucleotides described above, specifically binds to *Pseudomonas* Psl, with an affinity characterized by a $K_D$ of about $1.18 \times 10^{-7}$ M, as determined by the OCTET® binding assay described herein. In another embodiment, an isolated binding molecule, e.g., an antibody or antigen-binding fragment thereof encoded by one or more of the polynucleotides described above, specifically binds to *Pseudomonas* Psl, with an affinity characterized by a $K_D$ of about $1.44 \times 10^{-7}$ M, as determined by the OCTET® binding assay described herein.

In certain embodiments, an anti-*Pseudomonas* Psl binding molecule, e.g., antibody or fragment, variant or derivative thereof encoded by one or more of the polynucleotides described above, specifically binds to the same Psl epitope as monoclonal antibody WapR-004, WapR-004RAD, Cam-003, Cam-004, or Cam-005, or will competitively inhibit such a monoclonal antibody from binding to *Pseudomonas*

Psl. WapR-004RAD is identical to WapR-004 except for a nucleic acid substitution G293C of the VH nucleic acid sequence encoding the VH amino acid sequence of SEQ ID NO:11 (a substitution of the nucleotide in the VH-encoding portion of SEQ ID NO:71 at position 317). The nucleic acid sequence encoding the WapR-004RAD VH is presented as SEQ ID NO 76.

Some embodiments provide an isolated polynucleotide comprising, consisting essentially of, or consisting of a nucleic acid encoding a W4 mutant scFv-Fc molecule amino acid sequence identical to, or identical except for one, two, three, four, five, or more amino acid substitutions to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

Other embodiments provide an isolated polynucleotide comprising, consisting essentially of, or consisting of a nucleic acid encoding a W4 mutant scFv-Fc molecule amino acid sequence at least 80%, 85%, 90% 95% or 100% identical to one or more of: SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145; or SEQ ID NO: 146.

One embodiment provides an isolated polynucleotide comprising, consisting essentially of, or consisting of a nucleic acid which encodes a W4 mutant scFv-Fc molecule, where the nucleic acid is at least 80%, 85%, 90% 95% or 100% identical to one or more of SEQ ID NO: 147, SEQ ID NO: 148, SEQ ID NO: 149, SEQ ID NO: 150, SEQ ID NO: 151, or SEQ ID NO: 152, SEQ IS NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214; or SEQ ID NO: 215.

In other embodiments, an anti-*Pseudomonas* Psl binding molecule, e.g., antibody or fragment, variant or derivative thereof encoded by one or more of the polynucleotides described above, specifically binds to the same epitope as monoclonal antibody WapR-001, WapR-002, or WapR-003, or will competitively inhibit such a monoclonal antibody from binding to *Pseudomonas* Psl.

In certain embodiments, an anti-*Pseudomonas* Psl binding molecule, e.g., antibody or fragment, variant or derivative thereof encoded by one or more of the polynucleotides described above, specifically binds to the same epitope as monoclonal antibody WapR-016, or will competitively inhibit such a monoclonal antibody from binding to *Pseudomonas* Psl.

The disclosure also includes fragments of the polynucleotides as described elsewhere herein. Additionally polynucleotides which encode fusion polynucleotides, Fab fragments, and other derivatives, as described herein, are also provided.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-*Pseudomonas* Psl binding molecule, e.g., antibody or fragment, variant or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, preferably poly A+RNA, isolated from, any tissue or cells expressing the antibody or such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of an anti-*Pseudomonas* Psl binding molecule, e.g., antibody or fragment, variant or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

A polynucleotide encoding an anti-*Pseudomonas* Psl binding molecule, e.g., antibody or fragment, variant or derivative thereof can be composed of any polyribonucleotide or polydeoxribonucleotide, which can be unmodified RNA or DNA or modified RNA or DNA. For example, a polynucleotide encoding an anti-*Pseudomonas* Psl binding molecule, e.g., antibody or fragment, variant or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an anti-*Pseudomonas* Psl binding molecule, e.g., antibody or fragment, variant or derivative thereof can be composed of triple-stranded regions comprising RNA or DNA or both RNA and DNA. A polynucleotide encoding an anti-*Pseudomonas* Psl binding molecule, e.g., antibody or fragment, variant or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions are made at one or more non-essential amino acid residues.

VI. Expression of Antibody Polypeptides

As is well known, RNA can be isolated from the original hybridoma cells or from other transformed cells by standard techniques, such as guanidinium isothiocyanate extraction and precipitation followed by centrifugation or chromatography. Where desirable, mRNA can be isolated from total RNA by standard techniques such as chromatography on oligo dT cellulose. Suitable techniques are familiar in the art.

In one embodiment, cDNAs that encode the light and the heavy chains of the anti-*Pseudomonas* Psl binding molecule, e.g., antibody or fragment, variant or derivative thereof can be made, either simultaneously or separately, using reverse transcriptase and DNA polymerase in accordance with well-known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present disclosure at any point during the isolation process or subsequent analysis.

Following manipulation of the isolated genetic material to provide an anti-*Pseudomonas* Psl binding molecule, e.g., antibody or fragment, variant or derivative thereof of the disclosure, the polynucleotides encoding anti-*Pseudomonas* Psl binding molecules, are typically inserted in an expression vector for introduction into host cells that can be used to produce the desired quantity of anti-*Pseudomonas* Psl binding molecules.

Recombinant expression of an antibody, or fragment, derivative or analog thereof, e.g., a heavy or light chain of an antibody which binds to a target molecule described herein, e.g., Psl, requires construction of an expression vector containing a polynucleotide that encodes the antibody. Once a polynucleotide encoding an antibody molecule or a heavy or light chain of an antibody, or portion thereof (containing the heavy or light chain variable domain), of the disclosure has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding an antibody molecule of the disclosure, or a heavy or light chain thereof, or a heavy or light chain variable domain, operably linked to a promoter. Such vectors can include the nucleotide sequence encoding the constant region of the antibody molecule (see, e.g., PCT Publication WO 86/05807; PCT Publication WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present disclosure as a vehicle for introducing into and expressing a desired gene in a host cell. As known to those skilled in the art, such vectors can easily be selected from the group consisting of plasmids, phages, viruses and retroviruses. In general, vectors compatible with the instant disclosure will comprise a selection marker, appropriate restriction sites to facilitate cloning of the desired gene and the ability to enter and/or replicate in eukaryotic or prokaryotic cells.

For the purposes of this disclosure, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements can also be needed for optimal synthesis of mRNA. These elements can include signal sequences, splice signals, as well as transcriptional promoters, enhancers, and termination signals.

In some embodiments the cloned variable region genes are inserted into an expression vector along with the heavy and light chain constant region genes (e.g., human) synthetic as discussed above. Of course, any expression vector which is capable of eliciting expression in eukaryotic cells can be used in the present disclosure. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems.

More generally, once the vector or DNA sequence encoding a monomeric subunit of the anti-*Pseudomonas* Psl binding molecule, e.g., antibody or fragment, variant or derivative thereof of the disclosure has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the disclosure includes host cells containing a polynucleotide encoding anti-*Pseudomonas* Psl binding molecule, e.g., antibody or fragment, variant or derivative thereof, or a heavy or light chain thereof, operably linked to a heterologous promoter. In some embodiments for the expression of double-chained antibodies, vectors encoding both the heavy and light chains can be co-expressed in the host cell for expression of the entire immunoglobulin molecule, as detailed below.

Certain embodiments include an isolated polynucleotide comprising a nucleic acid which encodes the above-described VH and VL, wherein a binding molecule or antigen-binding fragment thereof expressed by the polynucleotide specifically binds *Pseudomonas* Psl. In some embodiments the polynucleotide as described encodes an scFv molecule including VH and VL, at least 80%, 85%, 90% 95% or 100% identical to one or more of SEQ ID NO: 65, SEQ ID NO: 66, SEQ ID NO: 67, SEQ ID NO: 68, SEQ ID NO: 69, or SEQ ID NO: 70 as shown in Table 4.

Some embodiments include vectors comprising the above-described polynucleotides. In further embodiments, the polynucleotides are operably associated with a promoter. In additional embodiments, the disclosure provides host cells comprising such vectors. In further embodiments, the disclosure provides vectors where the polynucleotide is operably associated with a promoter, wherein vectors can express a binding molecule which specifically binds *Pseudomonas* Psl in a suitable host cell.

Also provided is a method of producing a binding molecule or fragment thereof which specifically binds *Pseudomonas* Psl, comprising culturing a host cell containing a vector comprising the above-described polynucleotides, and recovering said antibody, or fragment thereof. In further embodiments, the disclosure provides an isolated binding molecule or fragment thereof produced by the above-described method.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells which can, when transformed or transfected with the appropriate nucleotide coding sequences, express an antibody molecule of the disclosure in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Constructs encoding anti-*Pseudomonas* Psl binding molecules, e.g., antibodies or fragments, variants or derivatives thereof, as disclosed herein can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologouspolypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruther et al., *EMBO J.* 2:1791 (1983)), in which the antibody coding sequence can be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once the anti-*Pseudomonas* Psl binding molecule, e.g., antibody or fragment, variant or derivative thereof, as disclosed herein has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Another method for increasing the affinity of antibodies of the disclosure is disclosed in US 2002 0123057 A1.

VII. Identification of Serotype-Indifferent Binding Molecules

The disclosure encompasses a target indifferent whole-cell approach to identify serotype independent therapeutic binding molecules e.g., antibodies or fragments thereof with superior or desired therapeutic activities. The method can be utilized to identify binding molecules which can antagonize, neutralize, clear, or block an undesired activity of an infectious agent, e.g., a bacterial pathogen. As is known in the art, many infectious agents exhibit significant variation in their dominant surface antigens, allowing them to evade immune surveillance. The identification method described herein can identify binding molecules which target antigens which are shared among many different *Pseudomonas* species or other Gram-negative pathogens, thus providing a therapeutic agent which can target multiple pathogens from multiple species. For example, the method was utilized to identify a series of binding molecules which bind to the surface of *P. aeruginosa* in a serotype-independent manner, and when bound to bacterial pathogens, mediate, promote, or enhance opsonophagocytic (OPK) activity against bacterial cells such as bacterial pathogens, e.g. opportunistic *Pseudomonas* species (e.g., *Pseudomonas aeruginosa, Pseudomonas fluorescens, Pseudomonas putida*, and *Pseudomonas alcaligenes*) and/or inhibit the attachment of such bacterial cells to epithelial cells.

Certain embodiments disclose a method of identifying serotype-indifferent binding molecules comprising: (a) preparing naïve and/or convalescent antibody libraries in phage, (b) removing serotype-specific antibodies from the library by depletion panning, (c) screening the library for antibodies that specifically bind to whole cells independent of serotype, and (d) screening of the resulting antibodies for desired functional properties.

Certain embodiments provide a whole-cell phenotypic screening approach as disclosed herein with antibody phage libraries derived from either naive or *P. aeruginosa* infected convalescing patients. Using a panning strategy that initially selected against serotype-specific reactivity, different clones that bound *P. aeruginosa* whole cells were isolated. Selected clones were converted to human IgG1 antibodies and were confirmed to react with *P. aeruginosa* clinical isolates regardless of serotype classification or site of tissue isolation (See Examples). Functional activity screens described herein indicated that the antibodies were effective in preventing *P. aeruginosa* attachment to mammalian cells and mediated opsonophagocytic (OPK) killing in a concentration-dependent and serotype-independent manner.

In further embodiments, the above-described binding molecules or fragments thereof, antibodies or fragments thereof, or compositions, bind to two or more, three or more, four or more, or five or more different *P. aeruginosa* serotypes, or to at least 80%, at least 85%, at least 90% or at least 95% of *P. aeruginosa* strains isolated from infected patients. In further embodiments, the *P. aeruginosa* strains are isolated from one or more of lung, sputum, eye, pus, feces, urine, sinus, a wound, skin, blood, bone, or knee fluid.

VIII. Pharmaceutical Compositions Comprising Anti-*Pseudomonas* Psl Binding Molecules The pharmaceutical compositions used in this disclosure comprise pharmaceutically acceptable carriers well known to those of ordinary skill in the art. Preparations for parenteral administration include sterile aqueous or non-aqueous solutions, suspensions, and emulsions. Certain pharmaceutical compositions as disclosed herein can be orally administered in an acceptable dosage form including, e.g., capsules, tablets, aqueous suspensions or solutions. Certain pharmaceutical compositions also can be administered by nasal aerosol or inhalation. Preservatives and other additives can also be present such as for example, antimicrobials, antioxidants, chelating agents, and inert gases and the like. Suitable formulations for use in the therapeutic methods disclosed herein are described in *Remington's Pharmaceutical Sciences*, Mack Publishing Co., 16th ed. (1980).

The amount of an anti-*Pseudomonas* Psl binding molecule, e.g., antibody or fragment, variant or derivative thereof, that can be combined with the carrier materials to produce a single dosage form will vary depending upon the host treated and the particular mode of administration. Dosage regimens also can be adjusted to provide the optimum desired response (e.g., a therapeutic or prophylactic response). The compositions can also comprise the anti-*Pseudomonas* Psl binding molecules, e.g., antibodies or fragments, variants or derivatives thereof dispersed in a biocompatible carrier material that functions as a suitable delivery or support system for the compounds.

IX. Treatment Methods Using Therapeutic Binding Molecules

Methods of preparing and administering an anti-*Pseudomonas* Psl binding molecule, e.g., an antibody or fragment, variant or derivative thereof, as disclosed herein to a subject in need thereof are well known to or are readily determined by those skilled in the art. The route of administration of the anti-*Pseudomonas* Psl binding molecule, e.g., antibody or fragment, variant or derivative thereof, can be, for example, oral, parenteral, by inhalation or topical. The term parenteral as used herein includes, e.g., intravenous, intraarterial, intraperitoneal, intramuscular, or subcutaneous administration. A suitable form for administration would be a solution for injection, in particular for intravenous or intraarterial injection or drip. However, in other methods compatible with the teachings herein, an anti-*Pseudomonas* Psl binding molecule, e.g., antibody or fragment, variant or derivative thereof, as disclosed herein can be delivered directly to the site of the adverse cellular population e.g., infection thereby increasing the exposure of the diseased tissue to the therapeutic agent. For example, an anti-*Pseudomonas* Psl binding molecule can be directly administered to ocular tissue, burn injury, or lung tissue.

Anti-*Pseudomonas* Psl binding molecules, e.g., antibodies or fragments, variants or derivatives thereof, as disclosed herein can be administered in a pharmaceutically effective amount for the in vivo treatment of *Pseudomonas* infection. In this regard, it will be appreciated that the disclosed binding molecules will be formulated so as to facilitate administration and promote stability of the active agent. For the purposes of the instant application, a pharmaceutically effective amount shall be held to mean an amount sufficient to achieve effective binding to a target and to achieve a benefit, e.g., treat, ameliorate, lessen, clear, or prevent *Pseudomonas* infection.

Some embodiments are directed to a method of preventing or treating a *Pseudomonas* infection in a subject in need thereof, comprising administering to the subject an effective amount of the binding molecule or fragment thereof, the antibody or fragment thereof, the composition, the polynucleotide, the vector, or the host cell described herein. In further embodiments, the *Pseudomonas* infection is a *P. aeruginosa* infection. In some embodiments, the subject is a human. In certain embodiments, the infection is an ocular infection, a lung infection, a burn infection, a wound infection, a skin infection, a blood infection, a bone infection, or a combination of two or more of said infections. In further embodiments, the subject suffers from acute pneumonia, burn injury, corneal infection, cystic fibrosis, or a combination thereof.

Certain embodiments are directed to a method of blocking or preventing attachment of *P. aeruginosa* to epithelial cells comprising contacting a mixture of epithelial cells and *P. aeruginosa* with the binding molecule or fragment thereof, the antibody or fragment thereof, the composition, the polynucleotide, the vector, or the host cell described herein.

Also disclosed is a method of enhancing OPK of *P. aeruginosa* comprising contacting a mixture of phagocytic cells and *P. aeruginosa* with the binding molecule or fragment thereof, the antibody or fragment thereof, the composition, the polynucleotide, the vector, or the host cell described herein. In further embodiments, the phagocytic cells are differentiated HL-60 cells or human polymorphonuclear leukocytes (PMNs).

In keeping with the scope of the disclosure, anti-*Pseudomonas* Psl binding molecules, e.g., antibodies or fragments, variants or derivatives thereof, can be administered to a human or other animal in accordance with the aforementioned methods of treatment in an amount sufficient to produce a therapeutic effect. The anti-*Pseudomonas* Psl binding molecules, e.g., antibodies or fragments, variants or derivatives thereof, disclosed herein can be administered to such human or other animal in a conventional dosage form prepared by combining the antibody of the disclosure with a conventional pharmaceutically acceptable carrier or diluent according to known techniques.

Effective doses of the compositions of the present disclosure, for treatment of *Pseudomonas* infection vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Anti-*Pseudomonas* Psl binding molecules, e.g., antibodies or fragments, variants or derivatives thereof can be administered multiple occasions at various frequencies depending on various factors known to those of skill in the art. Alternatively, anti-*Pseudomonas* Psl binding molecules, e.g., antibodies or fragments, variants or derivatives thereof can be administered as a sustained release formulation, in which case less frequent administration is required. Dosage and frequency vary depending on the half-life of the antibody in the patient.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

X. Immunoassays

Anti-*Pseudomonas* Psl binding molecules, e.g., antibodies or fragments, variants or derivatives thereof can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, John Wiley & Sons, Inc., New York, Vol. 1 (1994), which is incorporated by reference herein in its entirety). Exemplary immunoassays are described briefly below (but are not intended by way of limitation).

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities. Antibody affinity can be measured by a number of methods, including OCTET®, BIACORE®, ELISA, and FACS.

The OCTET® system uses biosensors in a 96-well plate format to report kinetic analysis. Protein binding and dissociation events can be monitored by measuring the binding of one protein in solution to a second protein immobilized on the FortéBio biosensor. In the case of measuring binding of anti-Psl antibodies to Psl, the Psl is immobilized onto OCTET® tips followed by analysis of binding of the antibody, which is in solution. Association and disassociation of antibody to immobilized Psl is then detected by the instrument sensor. The data is then collected and exported to GraphPad Prism for affinity curve fitting.

Surface plasmon resonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt, I., Brostoff, J. and Male D., Immunology, 6$^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

Having now described the disclosure in detail, the same will be more clearly understood by reference to the following examples, which are included herewith for purposes of illustration only and are not intended to be limiting of the disclosure. All patents and publications referred to herein are expressly incorporated by reference in their entireties.

EXAMPLES

Example 1: Construction and Screening of Human Antibody Phage Display Libraries

Figure 1B:
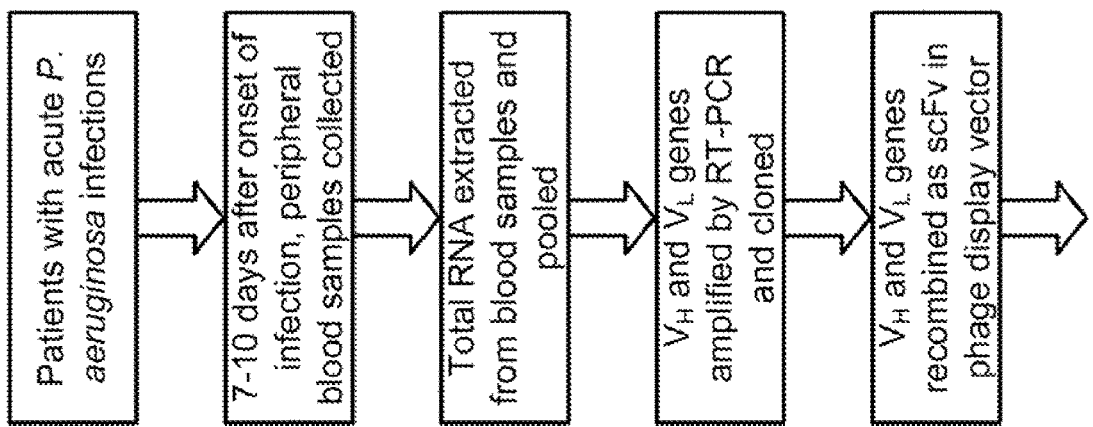
Figure 1A:
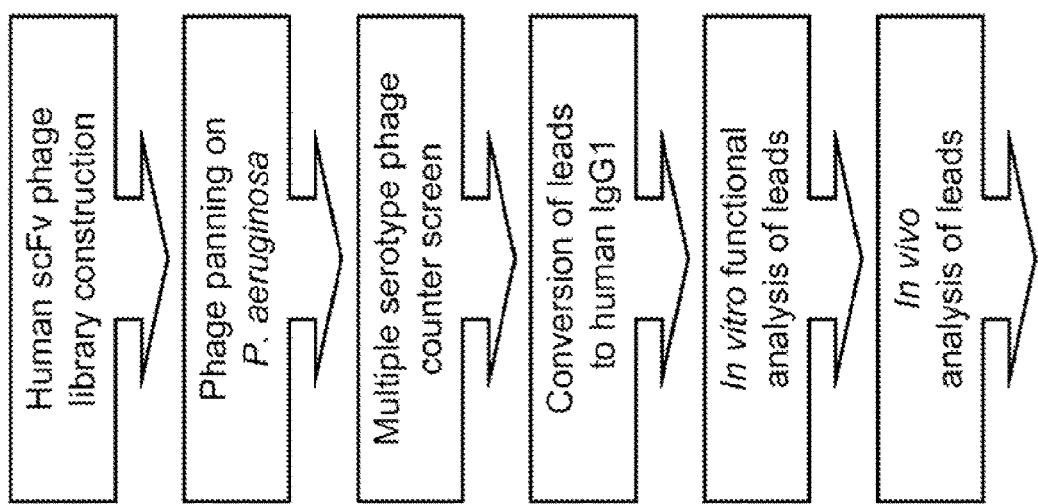

This example describes a target indifferent whole cell panning approach with human antibody phage libraries derived from both naive and *P. aeruginosa* infected convalescing patients to identify novel protective antigens against *Pseudomonas* infection (FIG. 1A). Assays included in the in vitro functional screens included opsonophagocytosis (OPK) killing assays and cell attachment assays using the epithelial cell line A549. The lead candidates, based on superior in vitro activity, were tested in *P. aeruginosa* acute pneumonia, keratitis, and burn infection models.

FIG. 1B shows construction of patient antibody phage display library. Whole blood was pooled from 6 recovering patients 7-10 days post diagnosis followed by RNA extraction and phage library construction as previously described (Vaughan, T. J., et al., *Nat Biotechnol* 14, 309-314 (1996); Wrammert, J., et al., *Nature* 453, 667-671 (2008)). FIG. 1C shows that the final cloned scFv library contained $5.4\times10^8$ transformants and sequencing revealed that 79% of scFv genes were full-length and in frame. The VH CDR3 loops, often important for determining epitope specificity, were 84% diverse at the amino acid level prior to library selection.

In addition to the patient library, a naïve human scFv phage display library containing up to $1\times10^{11}$ binding members (Lloyd, C., et al., *Protein Eng Des Sel* 22, 159-168 (2009)) was used for antibody isolation (Vaughan, T. J., et al., *Nat Biotechnol* 14, 309-314 (1996)). Heat killed *P. aeruginosa* ($1\times10^9$) was immobilized in IMMUNO™ Tubes (Nunc; MAXISORP™) followed for phage display selections as described (Vaughan, T. J., et al., *Nat Biotechnol* 14, 309-314 (1996)) with the exception of triethanolamine (100 nM) being used as the elution buffer. For selection on *P. aeruginosa* in suspension, heat killed cells were blocked followed by addition of blocked phage to cells. After washing, eluted phage was used to infect *E. coli* cells as described (Vaughan, 1996). Rescue of phage from *E. coli* and binding to heat-killed *P. aeruginosa* by ELISA was performed as described (Vaughan, 1996).

Following development and validation of the whole-cell affinity selection methodology, both the new convalescing patient library and a previously constructed naive library (Vaughan, T. J., et al., *Nat Biotechnol* 14, 309-314 (1996)) underwent affinity selection on suspensions of *P. aeruginosa* strain 3064 possessing a complete O-antigen as well as an isogenic wapR mutant strain which lacked surface expression of O-antigen. FIG. 1D shows that output titers from successive patient library selections were found to increase at a greater rate for the patient library than for the naïve library ($1\times10^7$ vs $3\times10^5$ at round 3, respectively). In addition, duplication of VH CDR3 loop sequences in the libraries (a measure of clonal enrichment during selection), was also found to be higher in the patient library, reaching 88-92%, compared to 15-25% in the naïve library at round 3 (FIG. 1D). Individual scFv phage from affinity selections were next screened by ELISA for reactivity to *P. aeruginosa* heterologous serotype strains (FIG. 1E). ELISA plates (Nunc; MAXISORP™) were coated with *P. aeruginosa* strains from overnight cultures as described (DiGiandomenico, A., et al., *Infect Immun* 72, 7012-7021 (2004)). Diluted antibodies were added to blocked plates for 1 hour, washed, and treated with HRP-conjugated anti-human secondary antibodies for 1 hour followed by development and analysis as described (Ulbrandt, N. D., et al., *J Virol* 80, 7799-7806 (2006)). The dominant species of phage obtained from whole cell selections with both libraries yielded serotype specific reactivity (data not shown). Clones exhibiting serotype independent binding in the absence of nonspecific binding to *E. coli* or bovine serum albumin were selected for further evaluation.

For IgG expression, the VH and VL chains of selected antibodies were cloned into human IgG1 expression vectors, co-expressed in HEK293 cells, and purified by protein A affinity chromatography as described (Persic, L., et al., *Gene* 187, 9-18 (1997)). Human IgG1 antibodies made with the variable regions from these selected serotype independent phage were confirmed for *P. aeruginosa* specificity and prioritized for subsequent analysis by whole cell binding to dominant clinically relevant serotypes by FACS analysis (FIG. 1F), since this method is more stringent than ELISA. For the flow cytometry based binding assays mid-log phase *P. aeruginosa* strains were concentrated in PBS to an $OD_{650}$ of 2.0. After incubation of antibody (10 µg/mL) and bacteria (~$1\times10^7$ cells) for 1 hr at 4° C. with shaking, washed cells were incubated with an ALEXA FLUOR 647® goat anti-human IgG antibody (Invitrogen, Carlsbad, Calif.) for 0.5 hr at 4° C. Washed cells were stained with BACLIGHT™ green bacterial stain as recommended (Invitrogen, Carlsbad, Calif.). Samples were run on a LSR II flow cytometer (BD Biosciences) and analyzed using BD FacsDiva (v. 6.1.3) and FlowJo (v. 9.2; TreeStar). Antibodies exhibiting binding by FACS were further prioritized for functional activity testing in an opsonophagocytosis killing (OPK) assay.

Example 2: Evaluation of mAbs Promoting OPK of *P. aeruginosa*

Figures 2A, 2B:
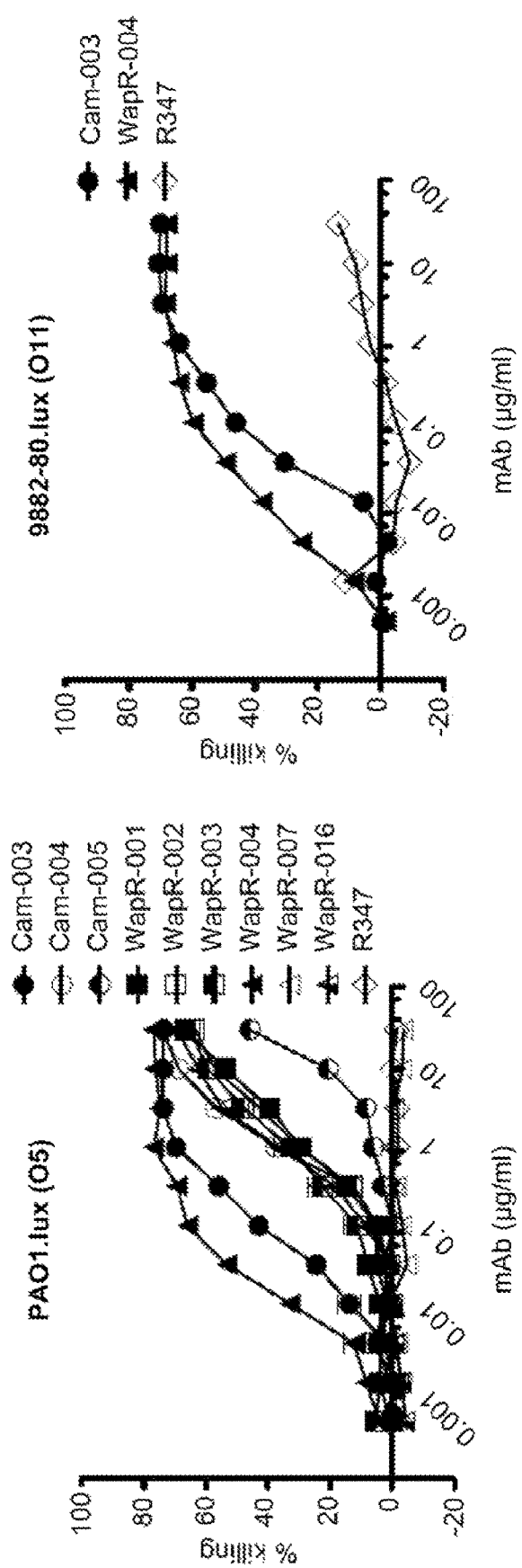

This example describes the evaluation of prioritized human IgG1 antibodies to promote OPK of *P. aeruginosa*. FIG. 2A shows that with the exception of WapR-007 and the negative control antibody R347, all antibodies mediated concentration dependent killing of luminescent *P. aeruginosa* serogroup O5 strain (PAO1.lux). WapR-004 and Cam-003 exhibited superior OPK activity. OPK assays were performed as described in (DiGiandomenico, A., et al., *Infect Immun* 72, 7012-7021 (2004)), with modifications. Briefly, assays were performed in 96-well plates using 0.025 ml of each OPK component; *P. aeruginosa* strains; diluted baby rabbit serum; differentiated HL-60 cells; and monoclonal antibody. In some OPK assays, luminescent *P. aeruginosa* strains, which were constructed as described (Choi, K. H., et al., *Nat Methods* 2, 443-448 (2005)), were used. Luminescent OPK assays were performed as described above but with determination of relative luciferase units (RLUs) using a Perkin Elmer ENVISION Multilabel plate reader (Perkin Elmer).

The ability of the WapR-004 and Cam-003 antibodies to mediate OPK activity against another clinically relevant O-antigen serotype strain, 9882-80.lux, was evaluated. FIG. 2B shows that enhanced WapR-004 and Cam-003 OPK activity extends to strain 9882-80 (O11).

Figures 2C, 2D:
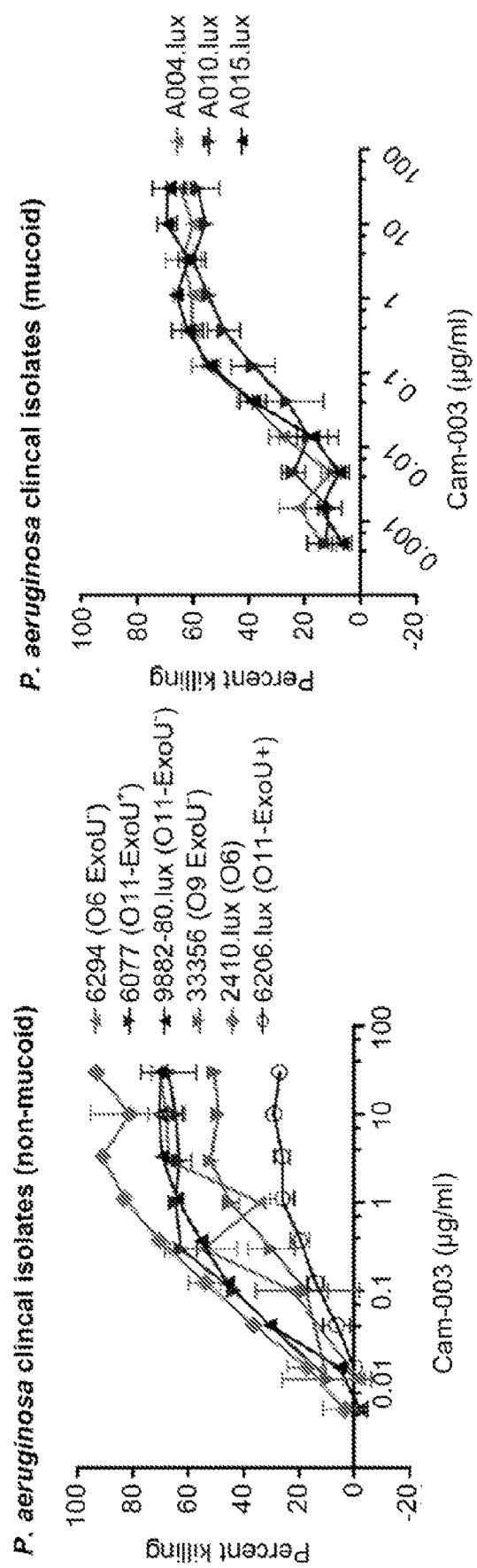

The ability of Cam-003 to mediate OPK activity against representative non-mucoid strains from clinically relevant O-antigen serotypes and against mucoid *P. aeruginosa* strains which were derived from cystic fibrosis patients was evaluated. Cam-003 mediated potent OPK of all non-mucoid clinical isolates tested (FIG. 2C). In addition, Cam-003 mediated potent killing of all mucoid *P. aeruginosa* isolates that were tested (FIG. 2D).

In addition, this example describes the evaluation of WapR-004 (W4) mutants in scFv-Fc format to promote OPK of *P. aeruginosa*. One mutant, Wap-004RAD (W4-RAD), was specifically created through site-directed mutagenesis to remove an RGD motif in VH. Other W4 mutants were prepared as follows. Nested PCR was performed as described (Roux, K. H., *PCR Methods Appl* 4, S185-194 (1995)), to amplify W4 variants (derived from somatic hypermutation) from the scFv library derived from the convalescing *P. aeruginosa* infected patients, for analysis. This is the library from which WapR-004 was derived. W4 variant fragments were subcloned and sequenced using standard procedures known in the art. W4 mutant light chains (LC) were recombined with the WapR-004 heavy chain (HC) to produce W4 mutants in scFv-Fc format. In addition WapR-004 RAD heavy chain (HC) mutants were recombined with parent LCs of M7 and M8 in the scFv-Fc format. Constructs were prepared using standard procedures known in the art. FIG. 11 (A-M) show that with the exception of the negative control antibody R347, all WapR-004 (W4) mutants mediated concentration dependent killing of luminescent *P. aeruginosa* serogroup O5 strain (PAO1.lux).

Figure 3A:
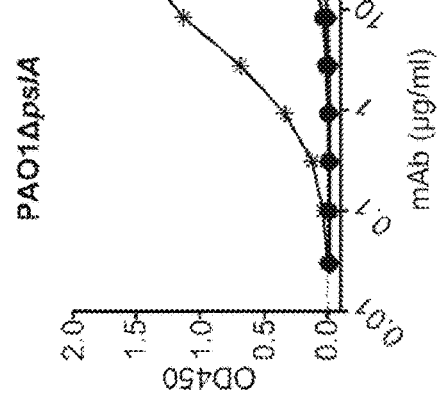
Figure 3B:
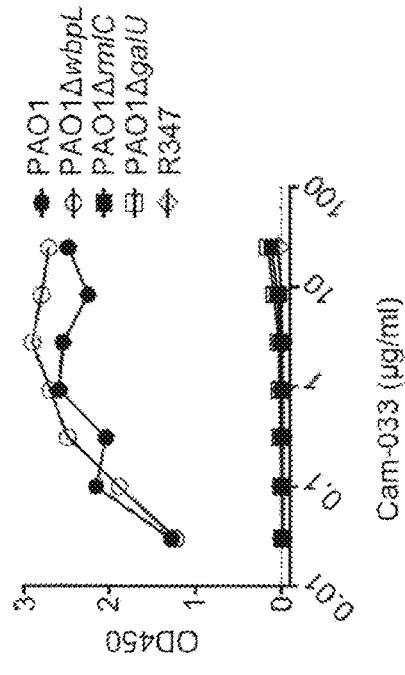
Figure 3D:
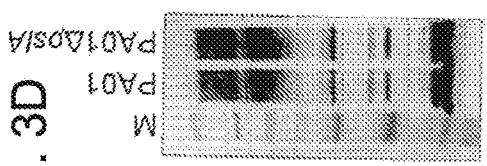
Figure 3E:
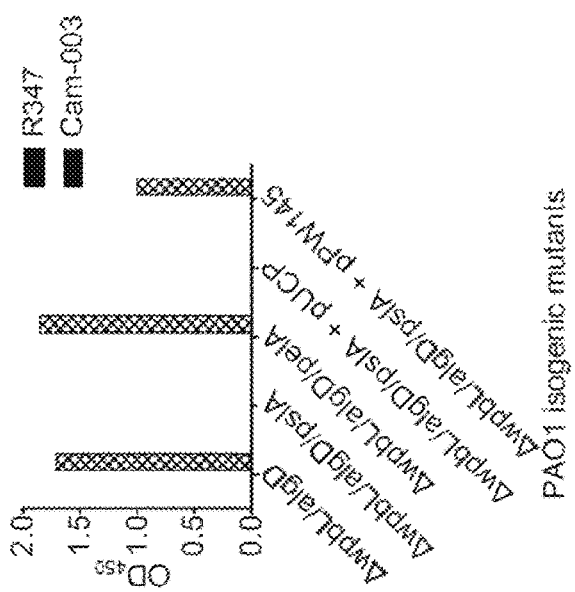
Figure 3C:
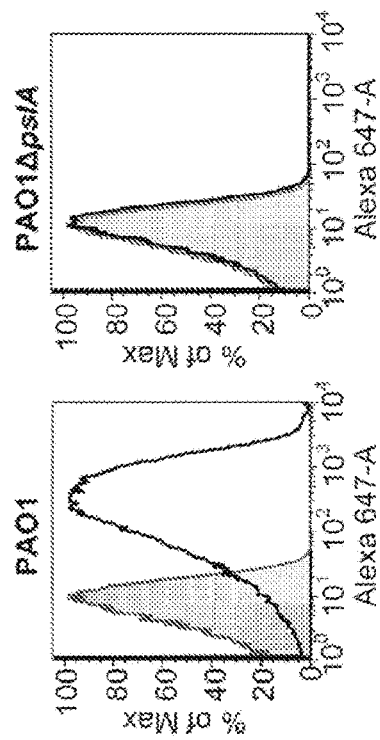
Figure 3F:
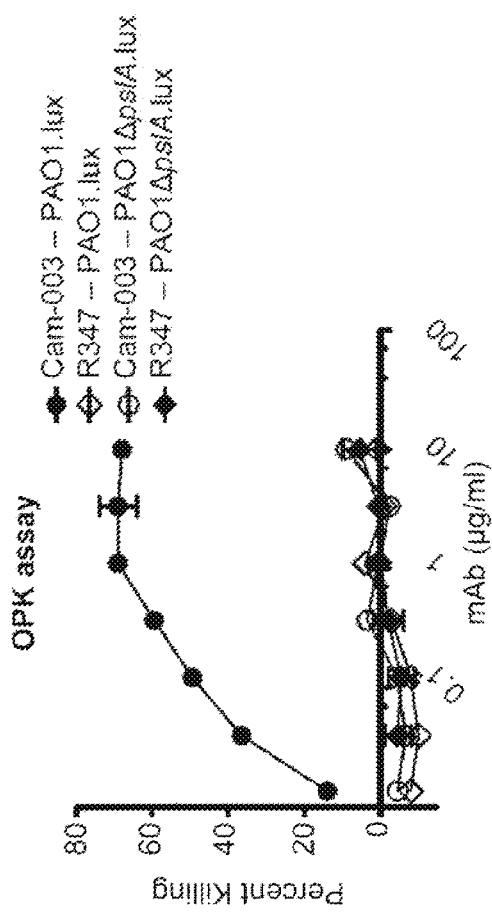
Figure 3G:
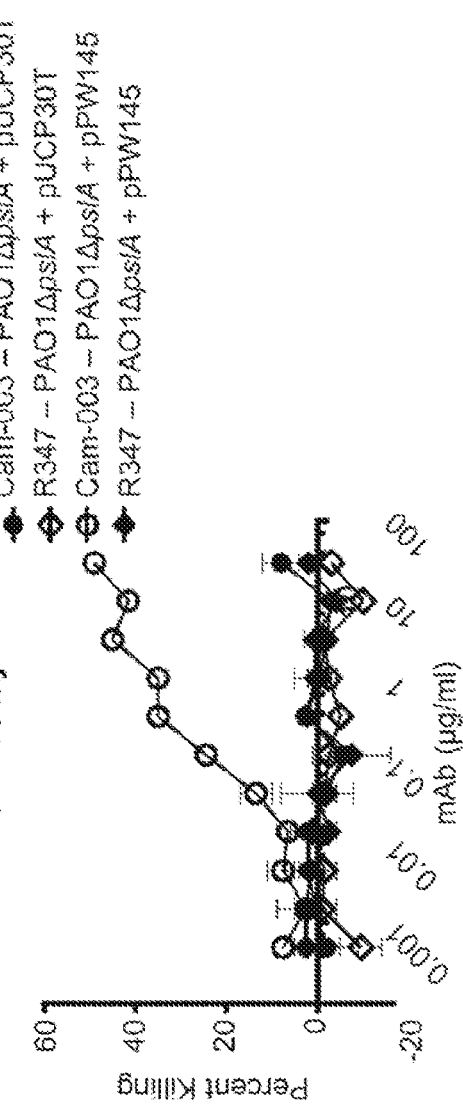
Figure 3I:
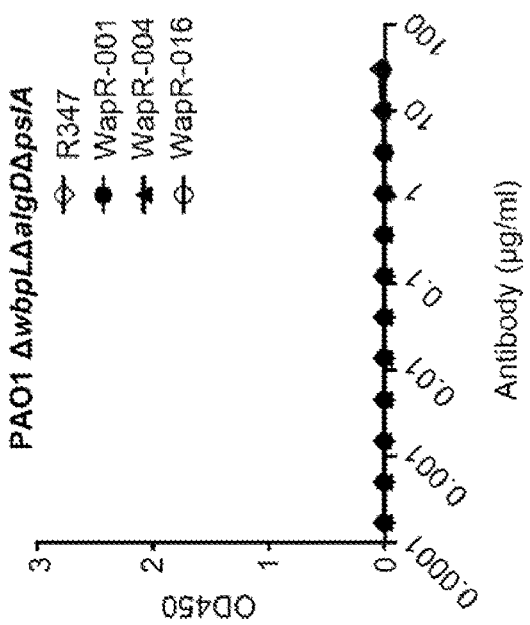
Figure 3H:
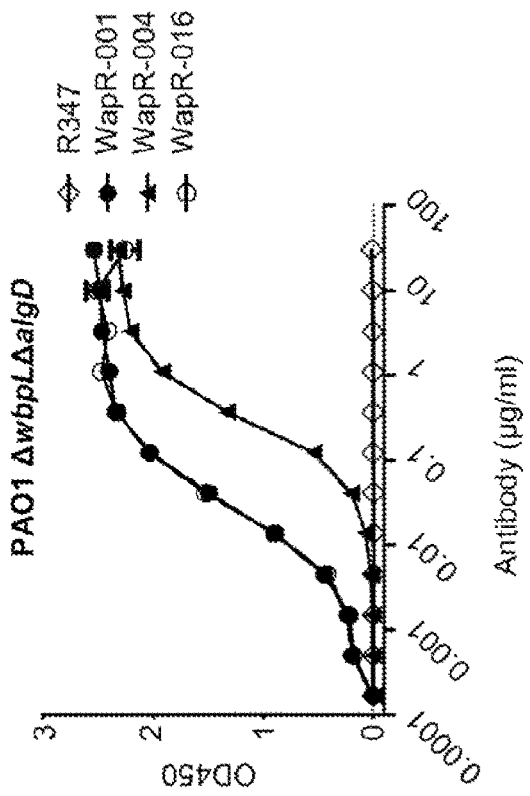
Figure 3J:
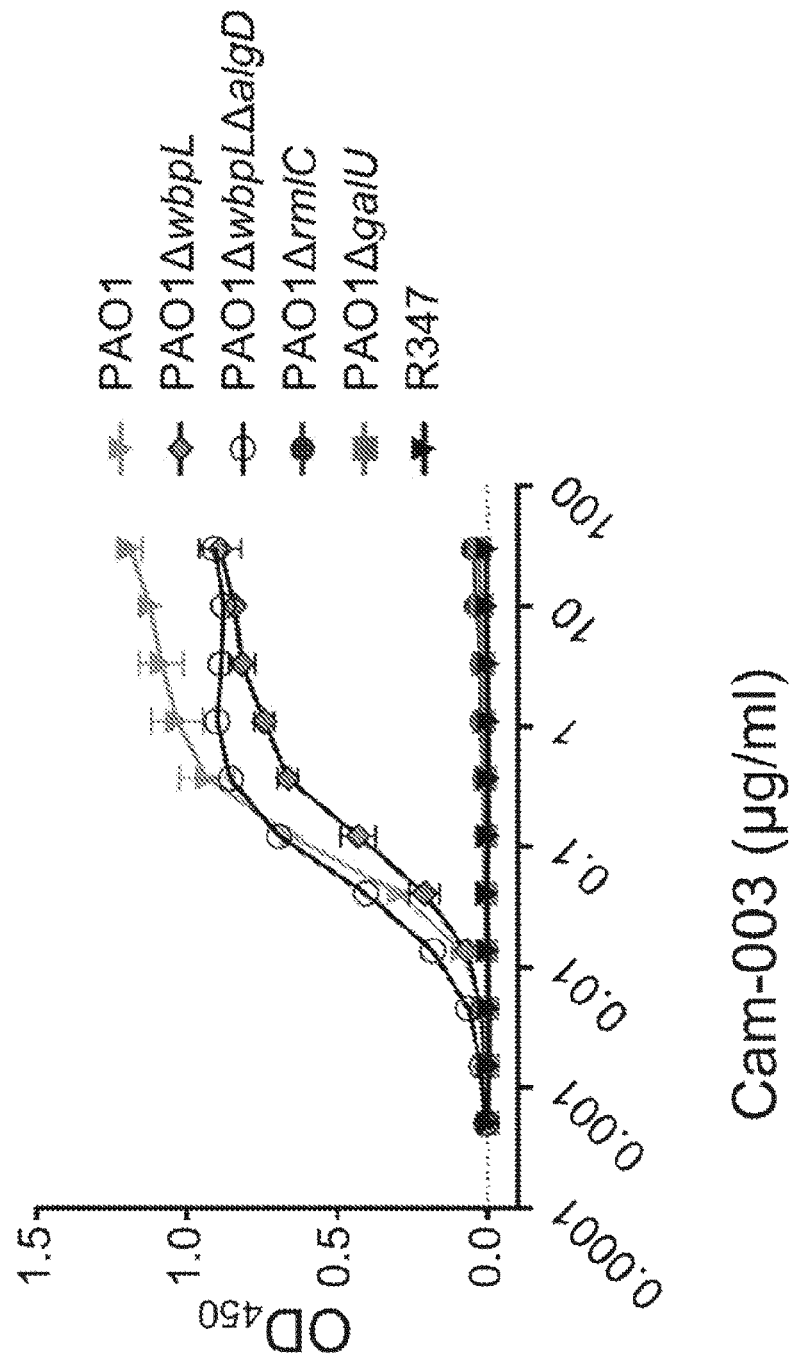

Example 3: Serotype Independent Anti-*P. aeruginosa* Antibodies Target the Psl Exopolysaccharide This example describes identification of the target of anti-*P. aeruginosa* antibodies derived from phenotypic screening. Target analysis was performed to test whether the serotype independent antibodies targeted protein or carbohydrate antigens. No loss of binding was observed in ELISA to PAO1 whole cell extracts exhaustively digested with proteinase K, suggesting that reactivity targeted surface accessible carbohydrate residues (data not shown). Isogenic mutants were constructed in genes responsible for O-antigen, alginate, and LPS core biosynthesis; wbpL (O-antigen-deficient); wbpL/algD (O-antigen and alginate deficient); rmlC (O-antigen-deficient and truncated outer core); and galU (O-antigen-deficient and truncated inner core). *P. aeruginosa* mutants were constructed based on the allele replacement strategy described by Schweizer (Schweizer, H. P., *Mol Microbiol* 6, 1195-1204 (1992); Schweizer, H. D., *Biotechniques* 15, 831-834 (1993)). Vectors were mobilized from *E. coli* strain 517.1 into *P. aeruginosa* strain PAO1; recombinants were isolated as described (Hoang, T. T., et al., *Gene* 212, 77-86 (1998)). Gene deletion was confirmed by PCR. *P. aeruginosa* mutants were complemented with pUCP30T-based constructs harboring wild type genes. Reactivity of antibodies was determined by indirect ELISA on plates coated with above indicated *P. aeruginosa* strains: FIGS. 3A and 3J show that Cam-003 binding to the wbpL or the wbpL/algD double mutant was unaffected, however binding to the rmlC and galU mutants were abolished. While these results were consistent with binding to LPS core, reactivity to LPS purified from PAO1 was not observed. The rmlC and galU genes were recently shown to be required for biosynthesis of the Psl exopolysaccharide, a repeating pentasaccharide polymer consisting of D-mannose, L-rhamnose, and D-glucose. Cam-003 binding to an isogenic pslA knockout PAO1ΔpslA, was tested, as pslA is required for Psl biosynthesis (Byrd, M. S., et al., *Mol Microbiol* 73, 622-638 (2009)). Binding of Cam-003 to PAO1ΔpslA was abolished when tested by ELISA (FIG. 3B) and FACS (FIG. 3C), while the LPS molecule in this mutant was unaffected (FIG. 3D). Binding of Cam-003 was restored in a PAO1ΔwbpL/algD/pslA triple mutant complemented with pslA (FIG. 3E) as was the ability of Cam-003 to mediate opsonic killing to complemented PAO1ΔpslA in contrast to the mutant (FIGS. 3F and 3G). Binding of Cam-003 antibody to a Pel exopolysaccharide mutant was also unaffected further confirming Psl as our antibody target (FIG. 3E). Binding assays confirmed that the remaining antibodies also bound Psl (FIGS. 3H and 3I).

Figure 3K:
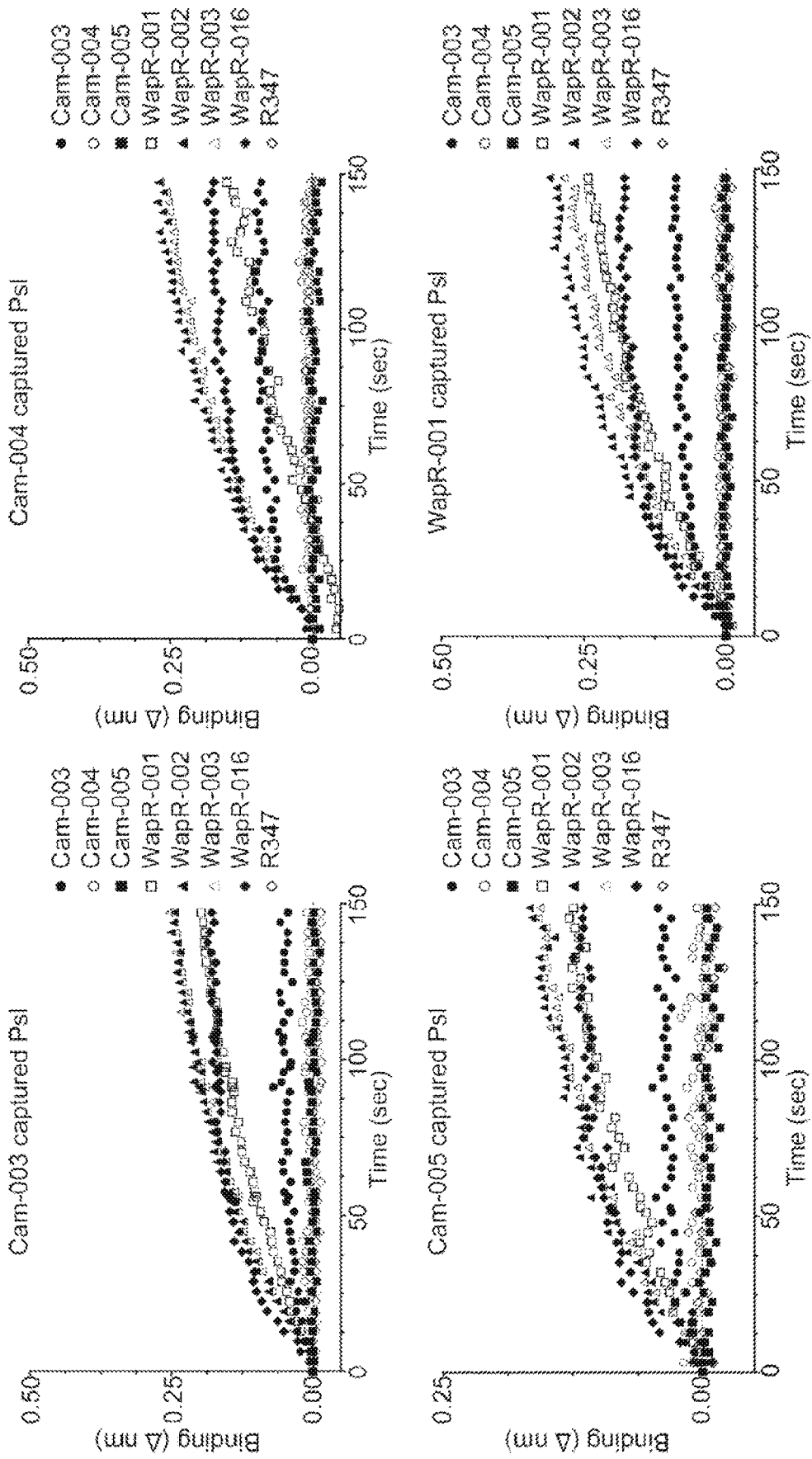
Figure 3K:
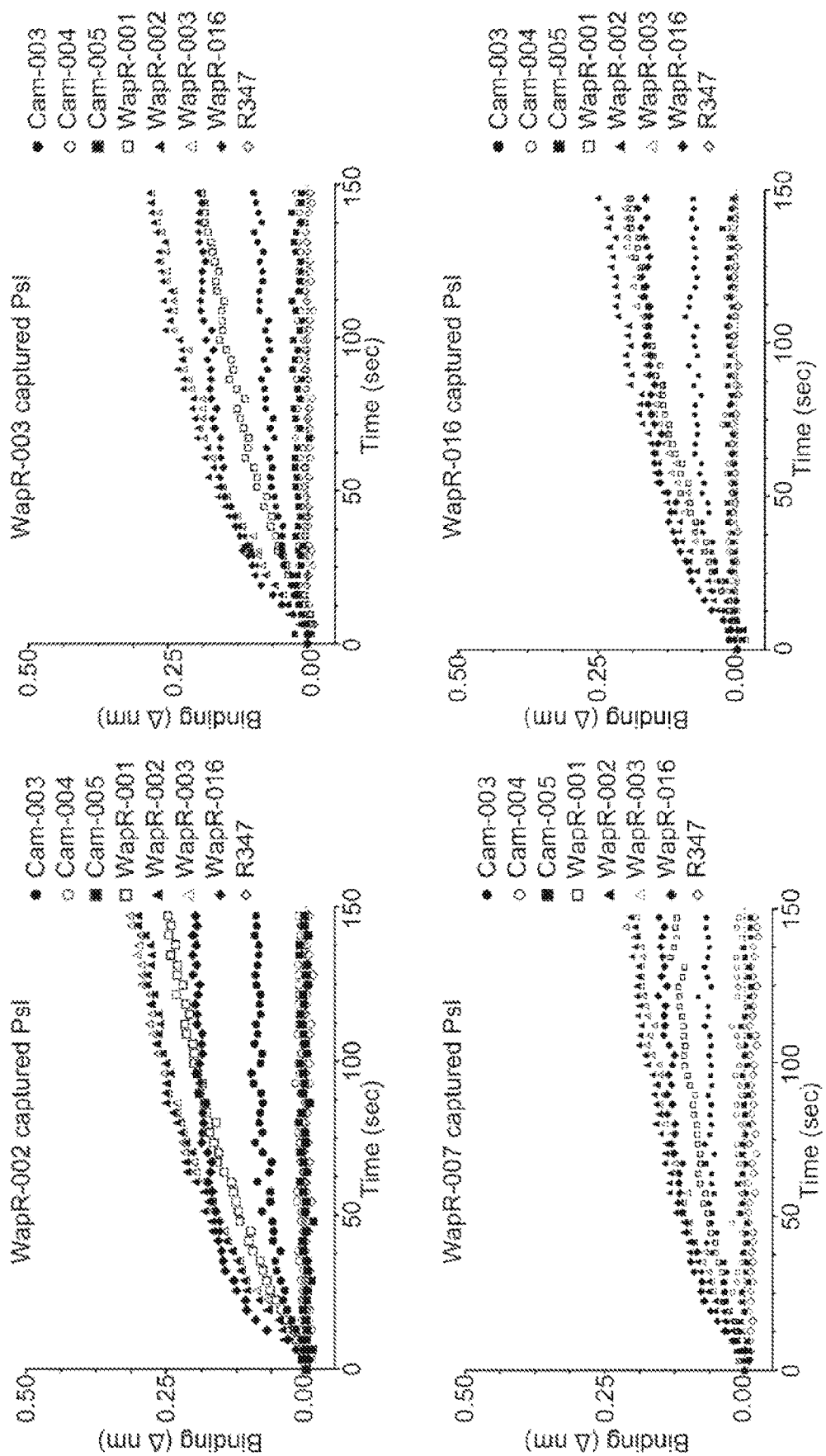
Figure 3K:
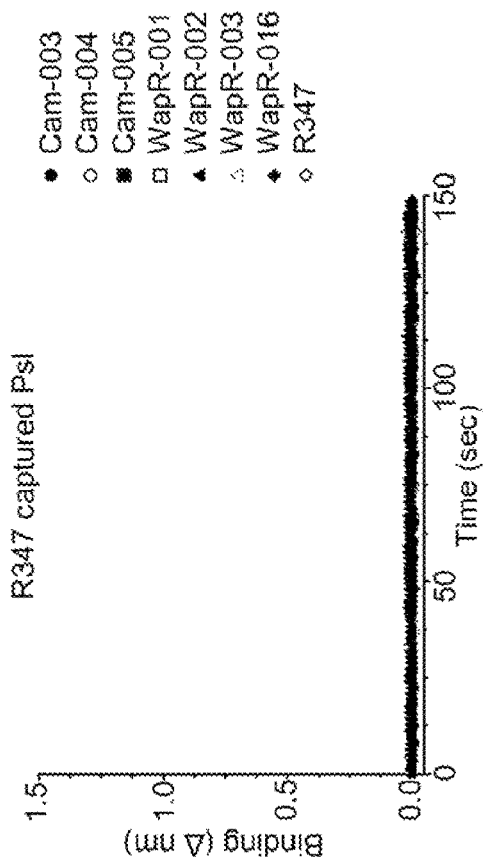

To confirm that all of the antibodies bound to the same antigen, a Psl capture binding assay was performed using a FORTEBIO® OCTET® 384 instrument as described above. The antigen was proteinase K-treated enriched carbohydrate purified from PAO1ΔwbpL/algD/pelA (O-antigen-, alginate- and Pel exopolysaccharide-deficient). Individual antibodies were bound to aminopropylsilane biosensors followed by blocking and the addition of the enriched carbohydrate antigen. After washing to remove unbound antigen, binding of unlabelled mAbs to captured antigen was assessed. All bound antibodies (Cam-003, Cam-004, Cam-005, WapR-001, WapR-002, WapR-003, WapR-007 and WapR-016), with the exception of the control mAb R347, were capable of capturing antigen that reacted with each of Cam-003, WapR-001, WapR-002, WapR-003, and WapR-016 (FIG. 3K). Minimal reactivity to captured Psl was observed with Cam-004, Cam-005 and WapR-007 even though all three of these antibodies captured sufficient Psl to potently react with Cam-003, WapR-001, WapR-002, WapR-003, and WapR-016 (FIG. 3K). These results suggest that all of the mAbs derived by phenotypic screening that bound *P. aeruginosa* independently of serotype, targeted epitopes associated with Psl exopolysaccharide.

Figure 4:
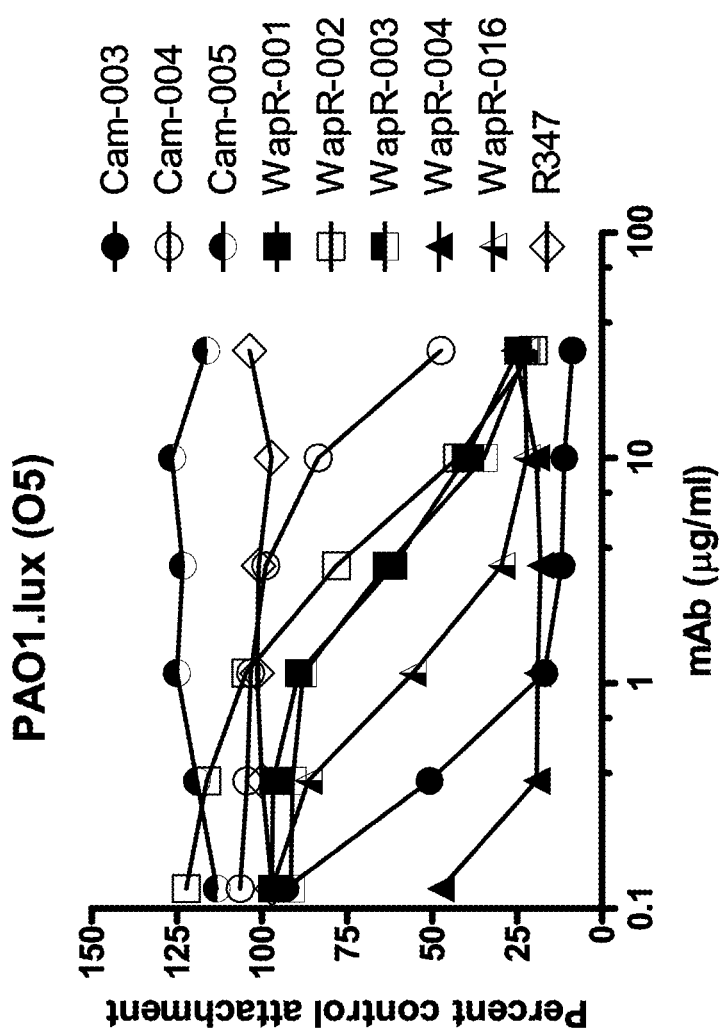

Example 4: Anti-Psl mAbs Block Attachment of *P. aeruginosa* to Cultured Epithelial Cells This example shows that anti-Psl antibodies blocked *P. aeruginosa* association with epithelial cells. Anti-Psl antibodies were added to a confluent monolayer of A549 cells (an adenocarcinoma human alveolar basal epithelial cell line) grown in opaque 96-well plates (Nunc Nunclon Delta). Log-phase luminescent *P. aeruginosa* PAO1 strain (PAO1.lux) was added at an MOI of 10. After incubation of PAO1.lux with A549 cells at 37° C. for 1 hour, the A549 cells were washed, followed by addition of LB+0.5% glucose. Bacteria were quantified following a brief incubation at 37° C. as performed in the OPK assay described in Example 2. Measurements from wells without A549 cells were used to correct for non-specific binding. FIG. 4 shows that with the exception of Cam-005 and WapR-007, all antibodies reduced association of PAO1.lux to A549 cells in a dose-dependent manner. The mAbs which performed best in OPK assays, WapR-004 and Cam-003 (see FIGS. 2A-B, and Example 2), were also most active at inhibiting *P. aeruginosa* cell attachment to A549 lung epithelial cells, providing up to ~80% reduction compared to the negative control. WapR-016 was the third most active antibody, showing similar inhibitory activity as WapR-004 and Cam-003 but at 10-fold higher antibody concentration.

Example 5: In Vivo Passaged *P. aeruginosa* Strains Maintain/Increase Expression of Psl To test if Psl expression in vivo is maintained, mice were injected intraperitoneally with *P. aeruginosa* isolates followed by harvesting of bacteria by peritoneal lavage four hours post-infection. The presence of Psl was analyzed with a control antibody and Cam-003 by flow cytometry as conditions for antibody binding are more stringent and allow for quantification of cells that are positive or negative for Psl expression. For ex vivo binding, bacterial inocula (0.1 ml) was prepared from an overnight TSA plate and delivered intraperitoneally to BALB/c mice. At 4 hr. following challenge, bacteria were harvested, RBCs lysed, sonicated and resuspended in PBS supplemented with 0.1% Tween-20 and 1% BSA. Samples were stained and analyzed as previously described in Example 1. FIG. 5 shows that bacteria harvested after peritoneal lavage with three wild type *P. aeruginosa* strains showed strong Cam-003 staining, which was comparable to log phase cultured bacteria (compare FIGS. 5A and 5C). In vivo passaged wild type bacteria exhibited enhanced staining when compared to the inoculum (compare FIGS. 5B and 5C). Within the inocula, Psl was not detected for strain 6077 and was minimally detected for strains PAO1 (O5) and 6206 (O11-cytotoxic). The binding of Cam-003 to bacteria increased in relation to the inocula indicating that Psl expression is maintained or increased in vivo. Wild type strains 6077, PAO1, and 6206 express Psl after in vivo passage, however strain PAO1 harboring a deletion of pslA (PAO1ΔpslA) is unable to react with Cam-003. These results further emphasize Psl as the target of the monoclonal antibodies.

The level of Psl expression/accessibility on the surface of *P. aeruginosa* strains PAO1 and 6206 in the acute pneumonia model was also assessed. Bacteria prepared from overnight-incubated, confluent plates, as described above, were intranasally administered to BALB/c mice. At 4 and 24 hours post-infection, bacteria were recovered from the lungs by bronchoalveolar lavage. Samples were stained and analyzed as previously described in Example 1. Strong Cam-003 staining was observed for PAO1 at 4 hours post-infection, but was minimal for 6206 at this time point (FIG. 5D). However, for both strain PAO1 and 6206, strong Cam-003 staining was observed at 24 hours post-infection (FIG. 5E).

The binding of *P. aeruginosa* specific antibodies (Cam-003, Cam-004 and Cam-005) to representative strains from unique *P. aeruginosa* serotypes (PAO1 (O5) (FIG. 5F), 2135 (O1) (FIG. 5G), 2531 (O1) (FIG. 5H), 2410 (O6) (FIG. 5I), 2764 (O11) (FIG. 5J), 2757 (O11) (FIG. 5K), 33356 (O9) (FIG. 5L), 33348 (O1) (FIG. 5M), 3039 (NT) (FIG. 5N), 3061 (NT) (FIG. 5O), 3064 (NT) (FIG. 5P), 19660 (NT) (FIG. 5Q), 9882-80 (O11) (FIG. 5R), 6073 (O11) (FIG. 5S), 6077 (O11) (FIG. 5T) and 6206 (O11) (FIG. 5U), was evaluated by flow cytometry as generally described above.

Example 6: Survival Rates for Animals Treated with Anti-Psl Monoclonal Antibodies Cam-003 and WapR-004 in a *P. aeruginosa* Acute Pneumonia Model Antibodies or PBS were administered 24 hours before infection in each model. *P. aeruginosa* acute pneumonia, keratitis, and thermal injury infection models were performed as described (DiGiandomenico, A., et al., *Proc Natl Acad Sci USA* 104, 4624-4629 (2007)), with modifications. In the acute pneumonia model, BALB/c mice (The Jackson Laboratory) were infected with *P. aeruginosa* strains suspended in a 0.05 ml inoculum. In the thermal injury model, CF-1 mice (Charles River) received a 10% total body surface area burn with a metal brand heated to 92° C. for 10 seconds. Animals were infected subcutaneously with *P. aeruginosa* strain 6077 at the indicated dose. For organ burden experiments, acute pneumonia was induced in mice followed by harvesting of lungs, spleens, and kidneys 24 hours post-infection for determination of CFU.

Figure 6A:
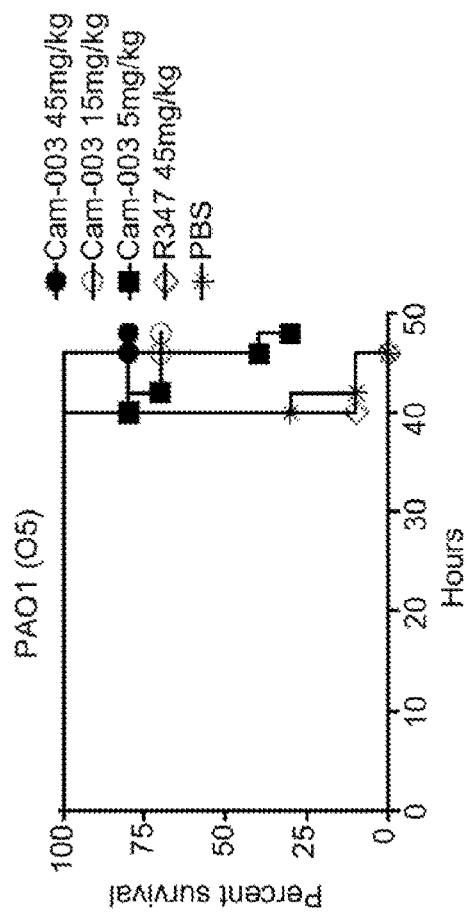
Figure 6B:
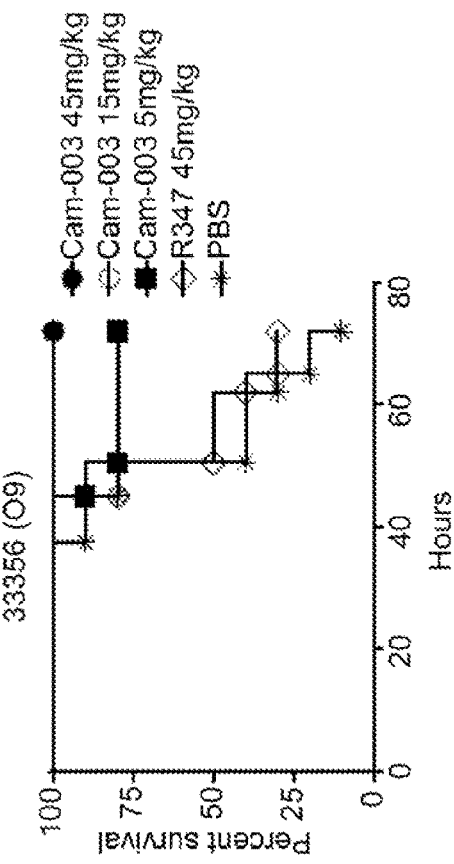
Figure 6C:
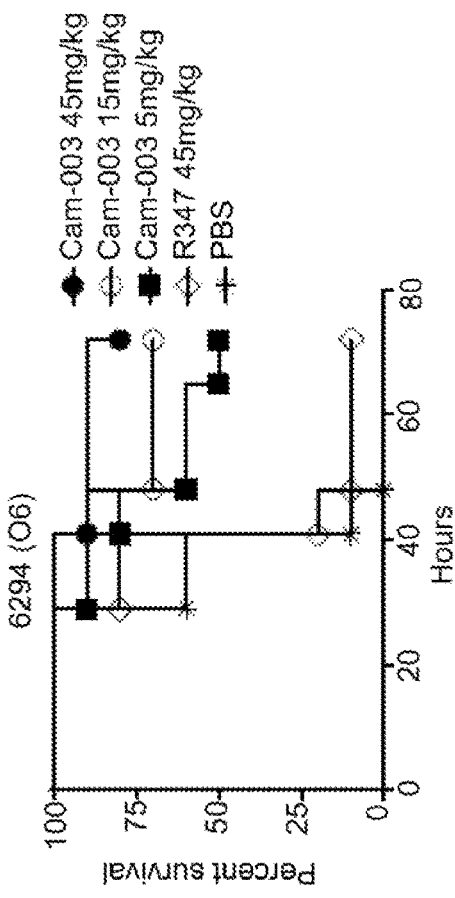
Figure 6D:
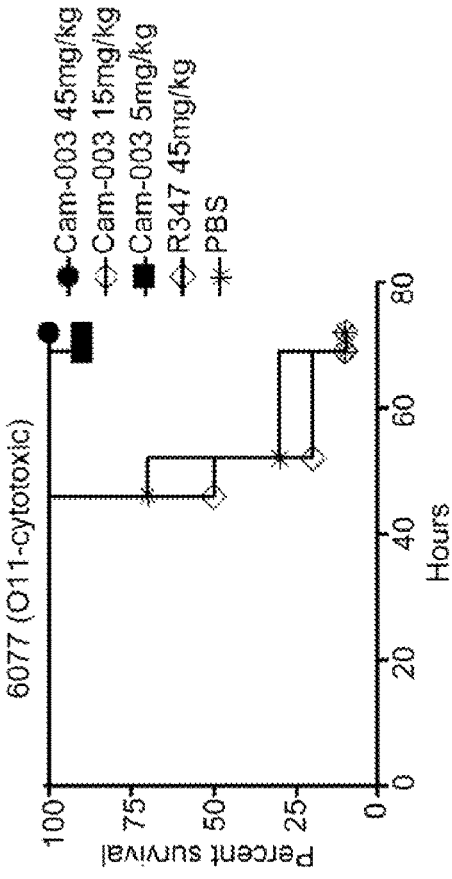
Figure 6E:
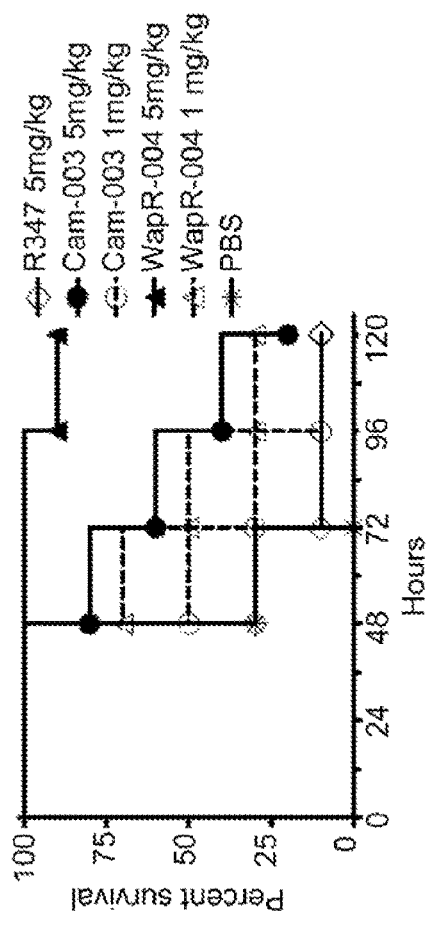
Figure 6F:
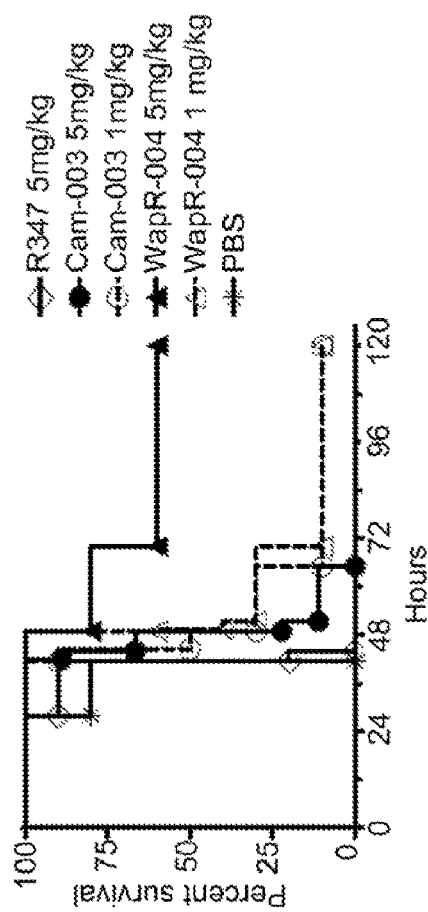
Figure 6G:
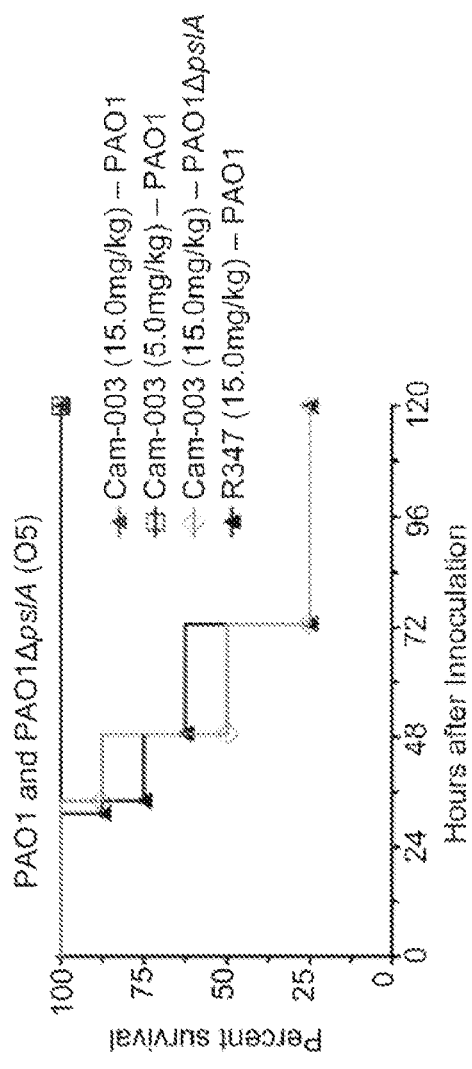

Monoclonal antibodies Cam-003 and WapR-004 were evaluated in an acute lethal pneumonia model against *P. aeruginosa* strains representing the most frequent serotypes associated with clinical disease. FIGS. 6A and 6C show significant concentration-dependent survival in Cam-003-treated mice infected with strains PAO1 and 6294 when compared to controls. FIGS. 6B and 6D show that complete protection from challenge with 33356 and cytotoxic strain 6077 was afforded by Cam-003 at 45 and 15 mg/kg while 80 and 90% survival was observed at 5 mg/kg for 33356 and 6077, respectively. FIGS. 6E and 6F show significant concentration-dependent survival in WapR-004-treated mice in the acute pneumonia model with strain 6077 (O11) ($8\times10^5$ CFU) (FIG. 6E), or 6077 (O11) ($6\times10^5$ CFU) (FIG. 6F). FIG. 6G shows that at 120 hours Cam-003 provided 100% survival following infection with strain PAO1. Increased survival was not observed against the Psl mutant strain, PAO1ΔpslA, used as a negative control in the PAO1 acute pneumonia study (FIG. 6G), confirming the lack of Cam-003 activity against strains deficient in Psl expression.

Figure 7B:
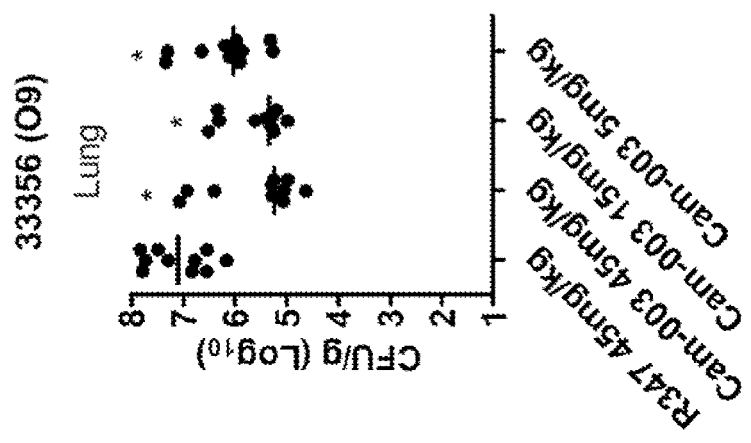
Figure 7A:
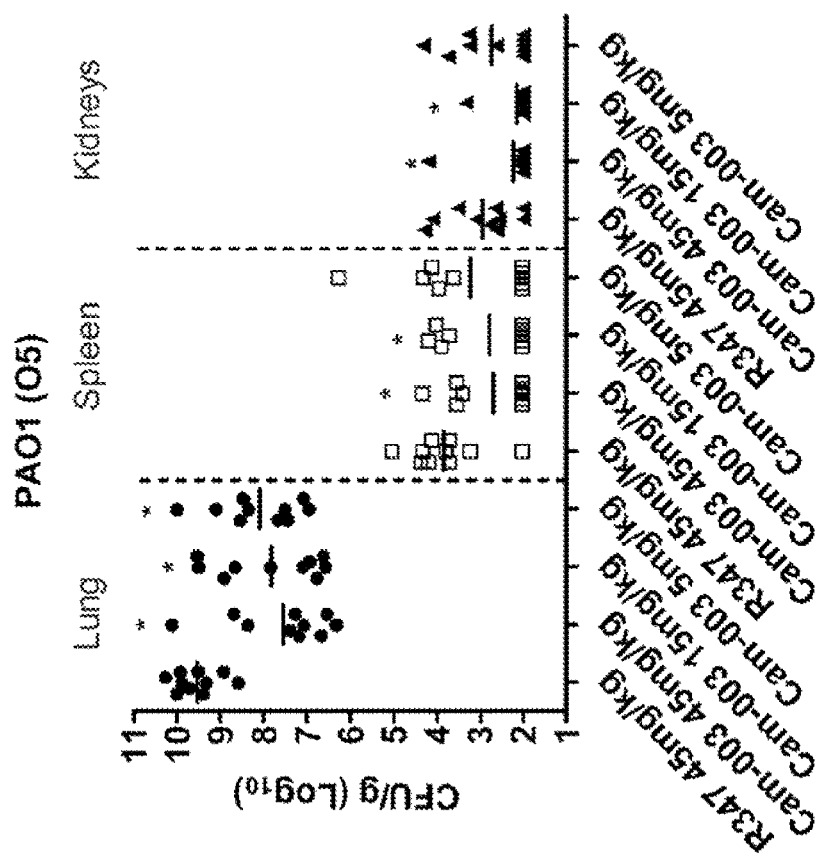
Figure 7C:
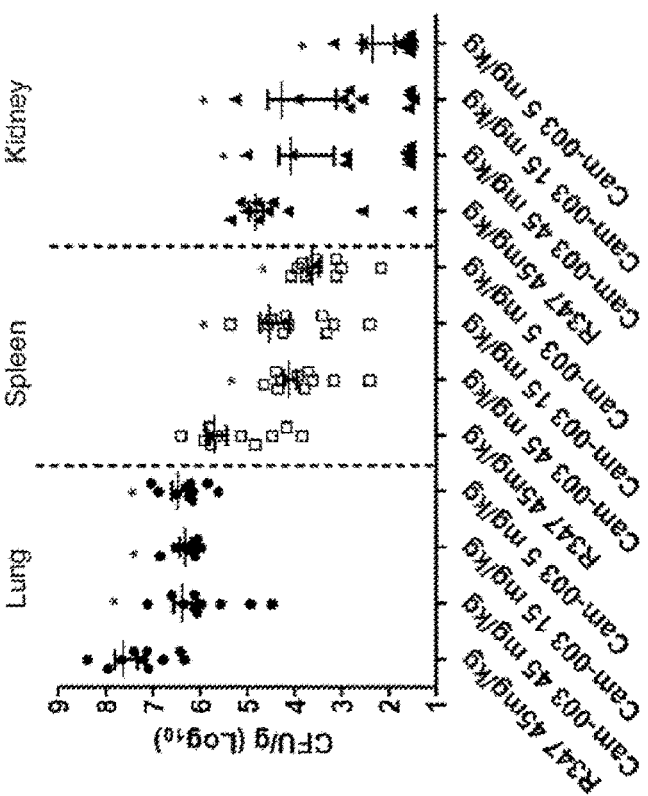
Figure 7D:
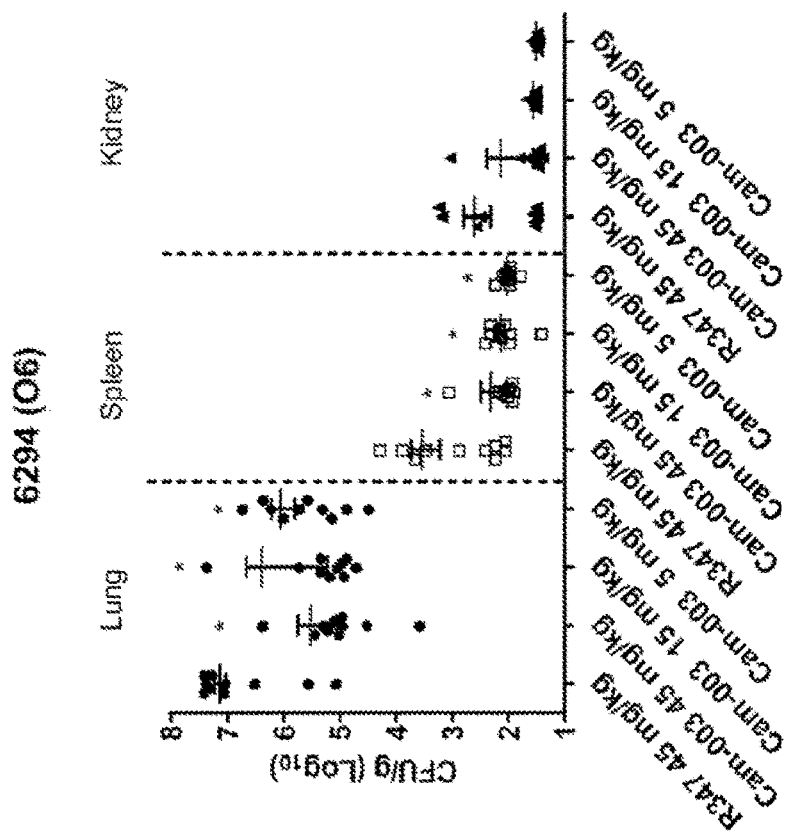
Figure 7E:
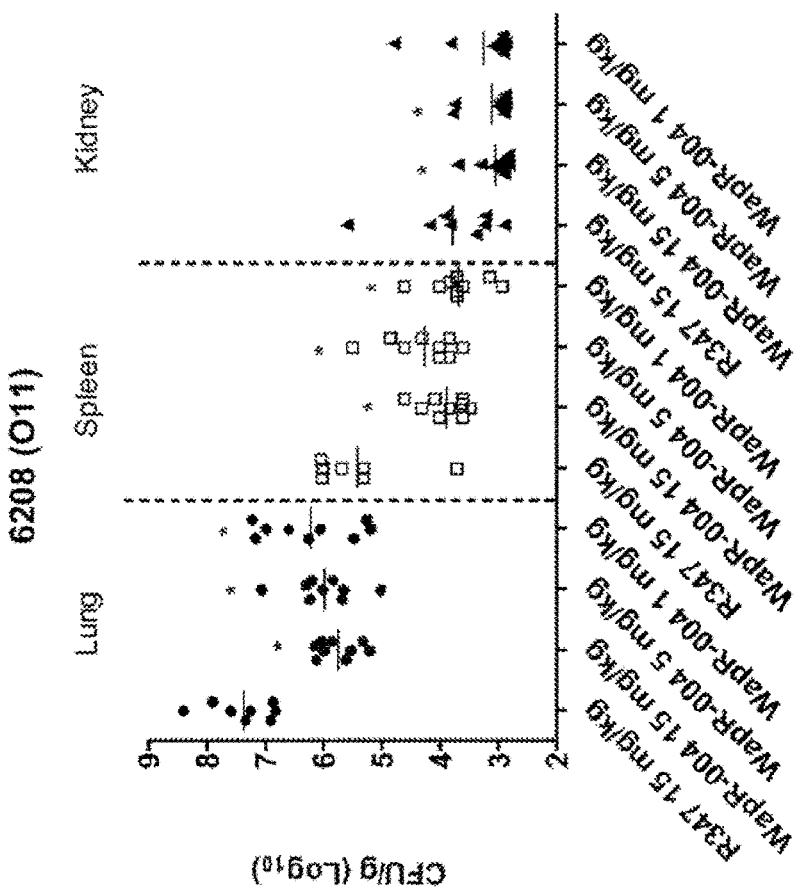
Figure 7F:
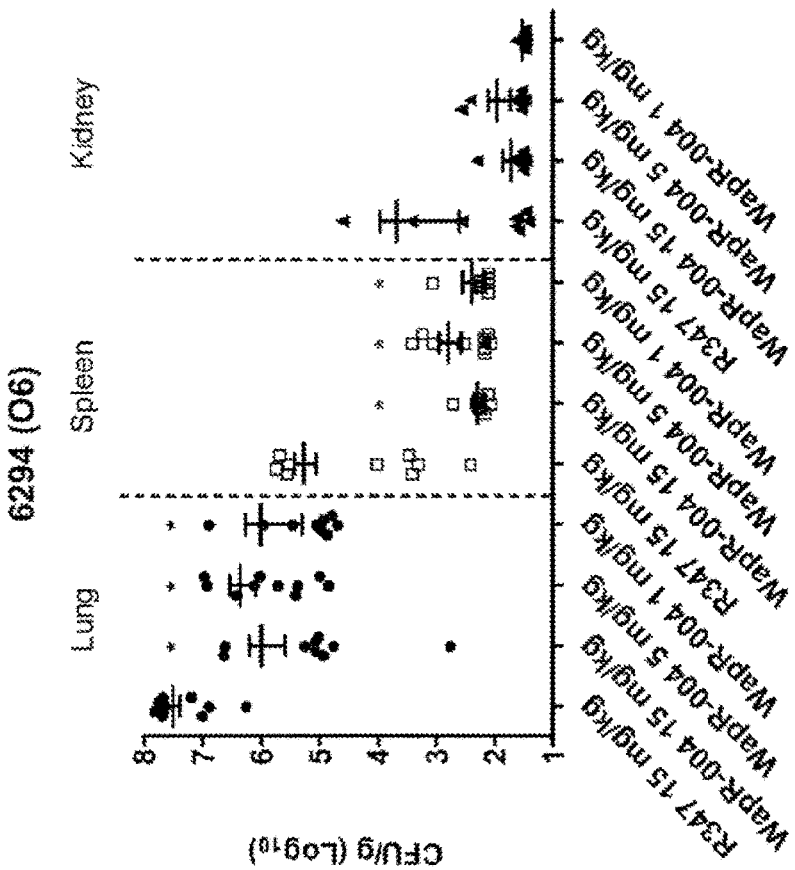

Cam-003 and WapR-004 were next examined for their ability to reduce *P. aeruginosa* organ burden in the lung and spread to distal organs, and later the animals were treated with various concentrations of WapR-004, Cam-003, or control antibodies at several different concentrations. Cam-003 was effective at reducing *P. aeruginosa* lung burden against all four strains tested. Cam-003 was most effective against the highly pathogenic cytotoxic strain, 6077, where the low dose was as effective as the higher dose (FIG. 7D). Cam-003 also had a marked effect in reducing dissemination to the spleen and kidneys in mice infected with PAO1 (FIG. 7A), 6294 (FIG. 7C), and 6077 (FIG. 7D), while dissemination to these organs was not observed in 33356 infected mice (FIG. 7B). FIGS. 7E and 7F show that similarly, WapR-004 reduced organ burden after induction of acute pneumonia with 6294 (O6) and 6206 (O11). Specifically, WapR-004 was effective at reducing *P. aeruginosa* dissemination to the spleen and kidneys in mice infected.

Example 7: Survival Rates for Animals Treated with Anti-Psl Monoclonal Antibodies Cam-003 and WapR-004 in a *P. aeruginosa* Corneal Infection Model Cam-003 and WapR-004 efficacy was next evaluated in a *P. aeruginosa* corneal infection model which emphasizes the pathogens ability to attach and colonize damaged tissue. FIGS. 8 A-D and 8 F-G show that mice receiving Cam-003 and WapR-004 had significantly less pathology and reduced bacterial counts in total eye homogenates than was observed in negative control-treated animals. FIG. 8E shows that Cam-003 was also effective when tested in a thermal injury model, providing significant protection at 15 and 5 mg/kg when compared to the antibody-treated control.

Figure 9B:
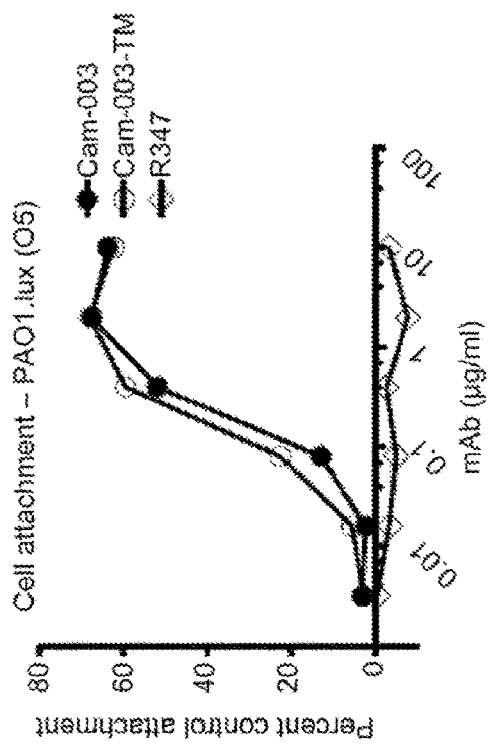
Figure 9A:
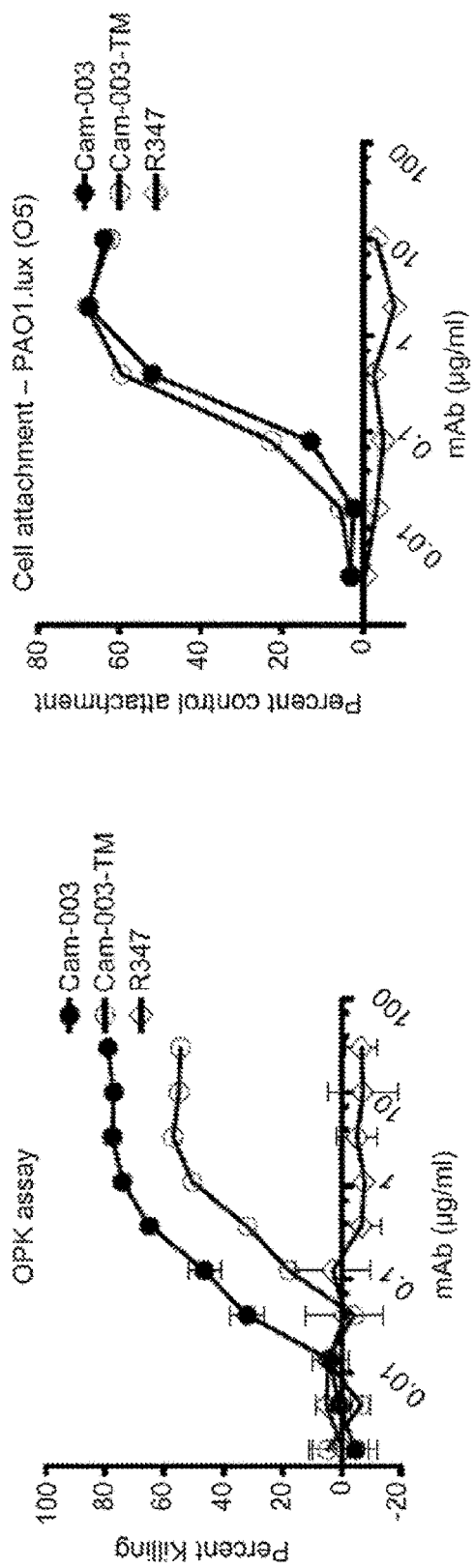
Figure 9C:
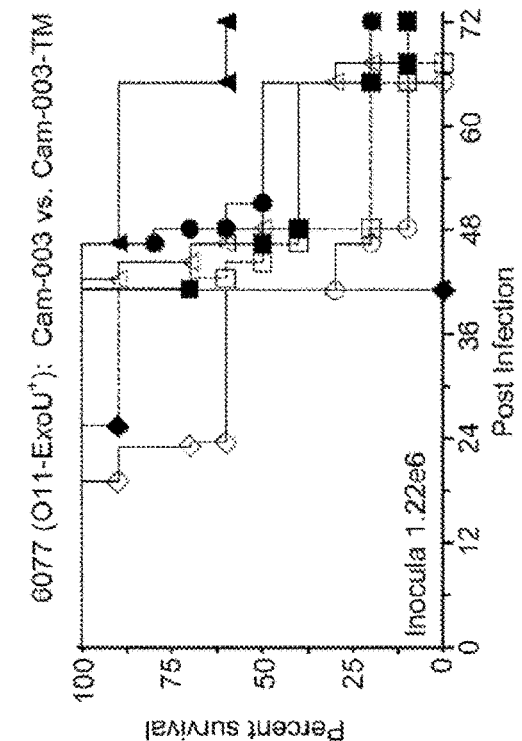
Figure 9D:
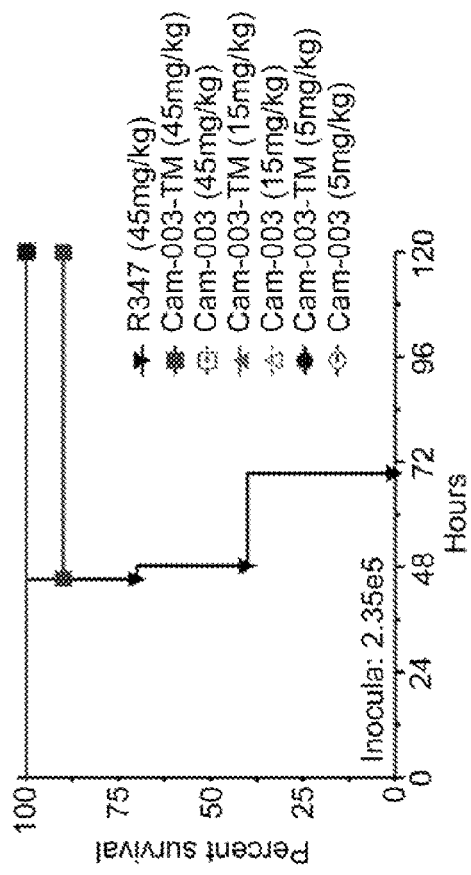
Figure 9E:
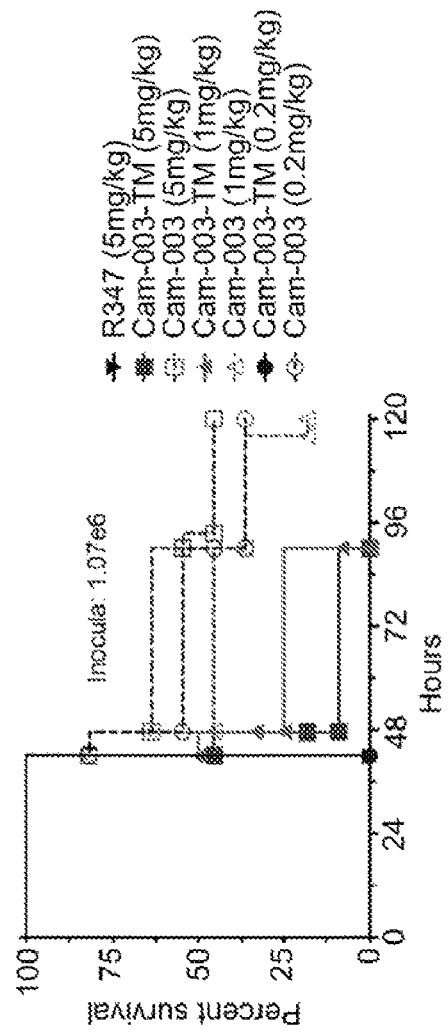
Figure 11A:
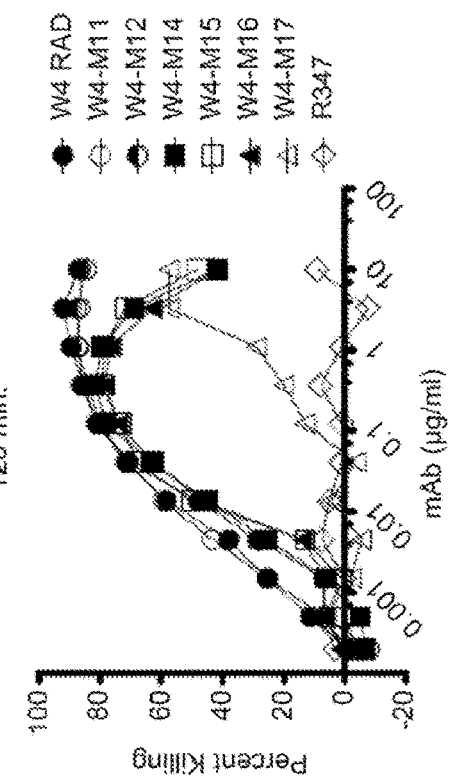
Figure 11B:
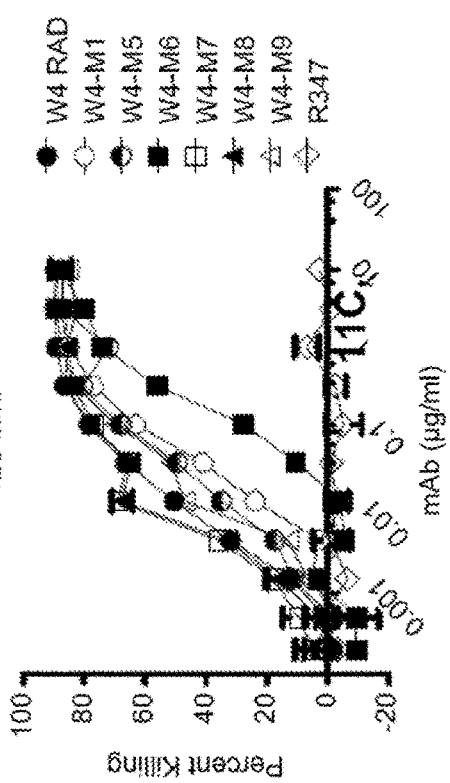
Figure 11C:
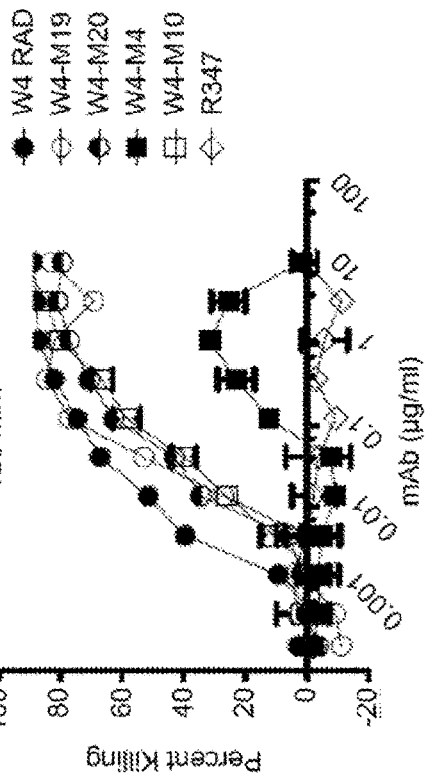
Figure 11D:
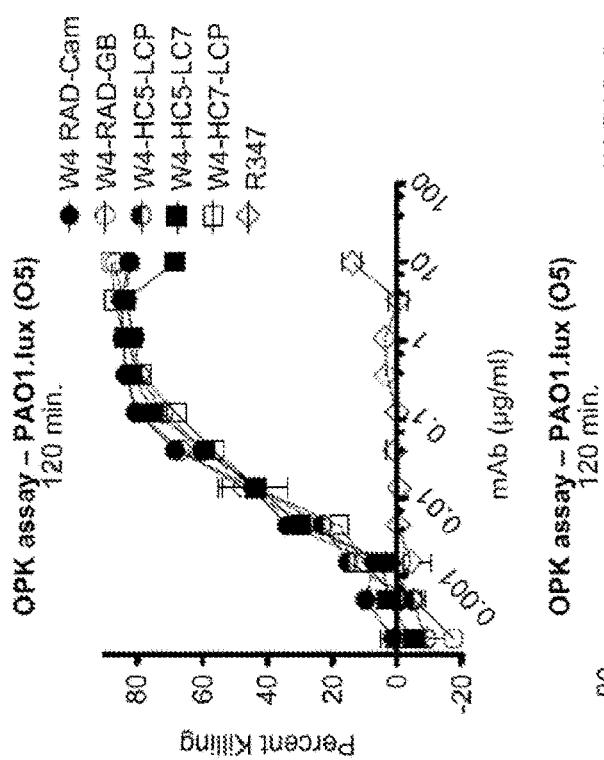
Figure 11E:
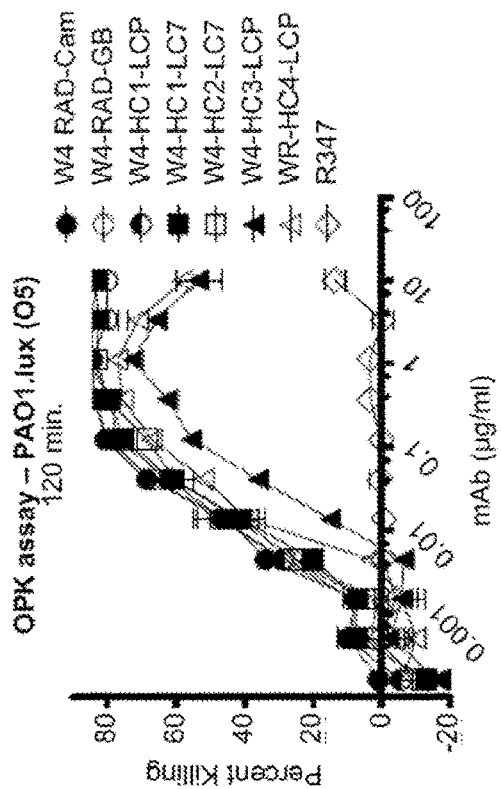
Figure 11F:
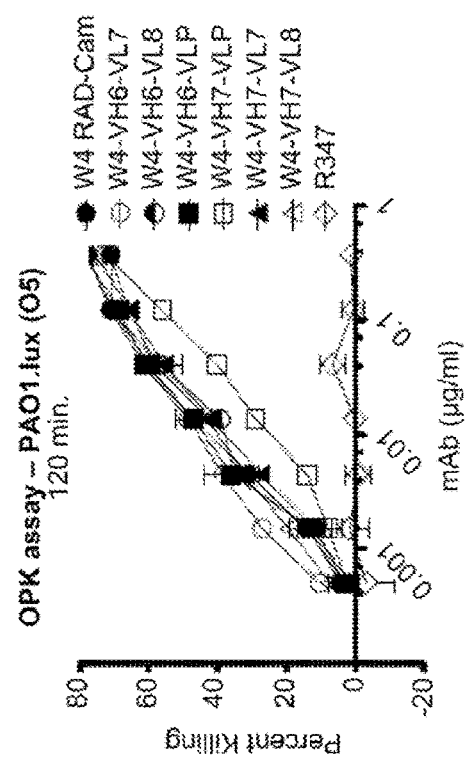
Figure 11G:
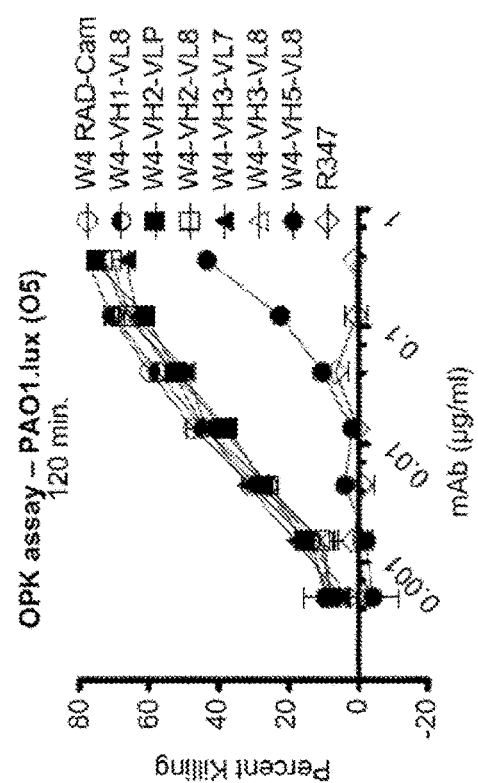
Figure 11I:
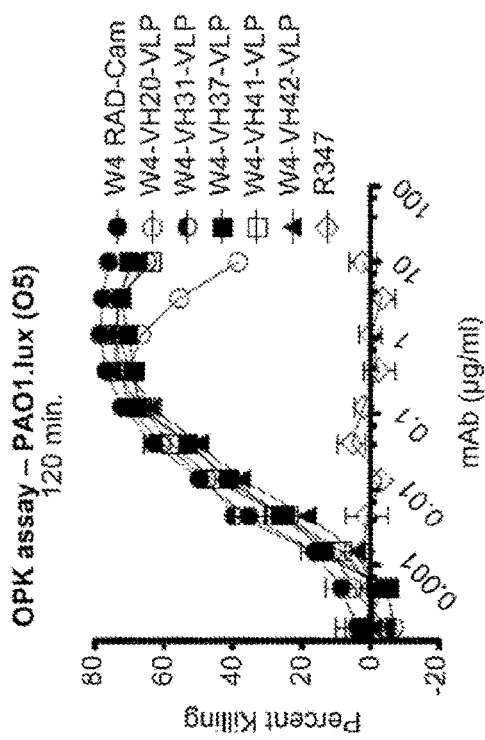
Figure 11H:
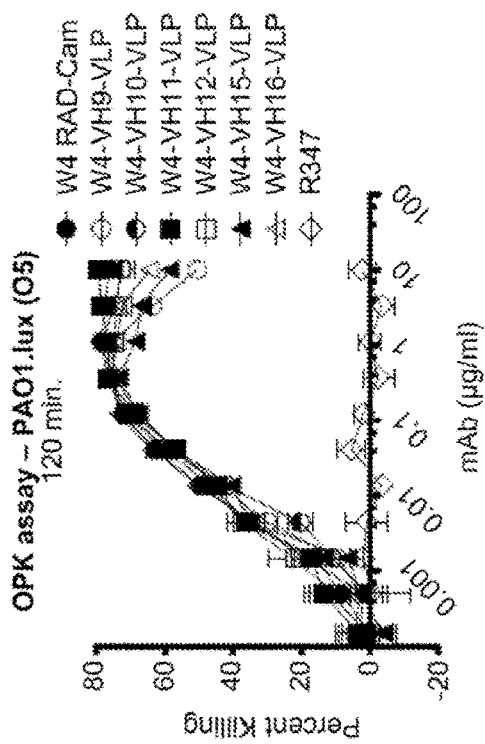
Figure 11K:
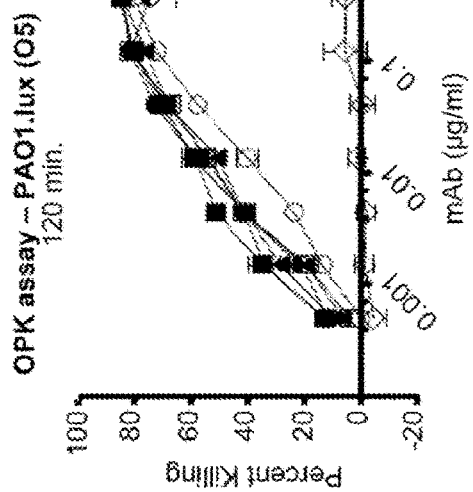
Figure 11J:
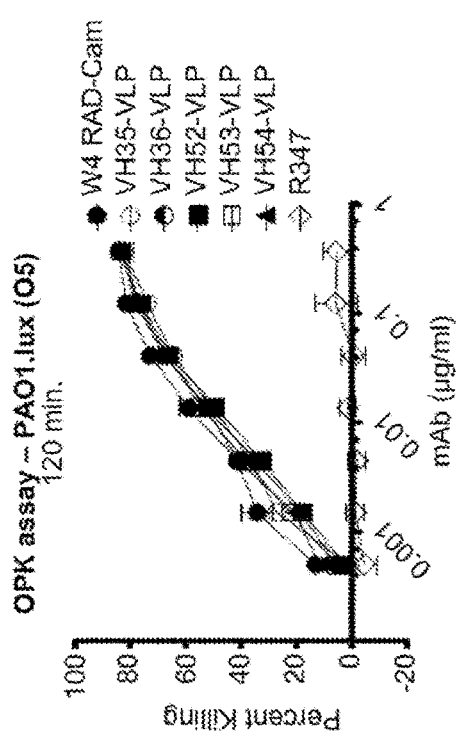

Example 8: A Cam-003 Fc Mutant Antibody, Cam-003-TM, has Diminished OPK and In Vivo Efficacy but Maintains Anti-Cell Attachment Activity Given the potential for dual mechanisms of action, a Cam-003 Fc mutant, Cam-003-TM, was created which harbors mutations in the Fc domain that reduces its interaction with Fcγ receptors (Oganesyan, V., et al., *Acta Crystallogr D Biol Crystallogr* 64, 700-704 (2008)), to identify if protection was more correlative to anti-cell attachment or OPK activity. *P. aeruginosa* mutants were constructed based on the allele replacement strategy described by Schweizer (Schweizer, H. P., *Mol Microbiol* 6, 1195-1204 (1992); Schweizer, H. D., *Biotechniques* 15, 831-834 (1993)). Vectors were mobilized from *E. coli* strain 517.1 into *P. aeruginosa* strain PAO1; recombinants were isolated as described (Hoang, T. T., et al., *Gene* 212, 77-86 (1998)). Gene deletion was confirmed by PCR. *P. aeruginosa* mutants were complemented with pUCP30T-based constructs harboring wild type genes. FIG. 9A shows that Cam-003-TM exhibited a 4-fold drop in OPK activity compared to Cam-003 (EC50 of 0.24 and 0.06, respectively) but was as effective in the cell attachment assay (FIG. 9B). FIG. 9C shows that Cam-003-TM was also less effective against pneumonia suggesting that optimal OPK activity is necessary for optimal protection. OPK and cell attachment assays were performed as previously described in Examples 2 and 4, respectively. When tested in the mouse acute pneumonia model, Cam-003-TM was similar in potency to Cam-003 at a low infectious inoculum of 6077 ($2.4 \times 10^5$ CFU) (FIG. 9D). However, further titration of the antibody dose followed by challenge with a larger infectious inoculum ($1.07 \times 10^6$) revealed Cam-003 activity was superior to Cam-003-TM, suggesting OPK activity significantly contributes to optimal protection in vivo (FIG. 9E).

Example 9: Epitope Mapping and Relative Affinity for Anti-Psl Antibodies

Epitope mapping was performed by competition ELISA and confirmed using an OCTET® flow system with Psl derived from the supernatant of an overnight culture of *P. aeruginosa* strain PAO1. For competition ELISA, antibodies were biotinylated using the EZ-Link Sulfo-NHS-Biotin and Biotinylation Kit (Thermo Scientific). Antigen coated plates were treated with the EC50 of biotinylated antibodies coincubated with unlabeled antibodies. After incubation with HRP-conjugated streptavidin (Thermo Scientific), plates were developed as described above. Competition experiments between anti-Psl mAbs determined that antibodies targeted at least three unique epitopes, referred to as class 1, 2, and 3 antibodies (FIG. 10A). Class 1 and 2 antibodies do not compete for binding, however the class 3 antibody, WapR-016, partially inhibits binding of the Class 1 and 2 antibodies.

Antibody affinity was determined by the OCTET® binding assays using Psl derived from the supernatant of overnight PAO1 cultures. Antibody $K_D$ was determined by averaging the binding kinetics of seven concentrations for each antibody. Affinity measurements were taken with a FORTEBIO® OCTET® 384 instrument using 384 slanted well plates. The supernatant from overnight PAO1 cultures±the pslA gene were used as the Psl source. Samples were loaded onto OCTET® AminoPropylSilane (hydrated in PBS) sensors and blocked, followed by measurement of anti-Psl mAb binding at several concentrations, and disassociation into PBS+1% BSA. All procedures were performed as described (Wang, X., et al., *J Immunol Methods* 362, 151-160). Association and disassociation raw ΔnM data were curve-fitted with GraphPad Prism. FIG. 10A shows the relative binding affinities of anti-Psl antibodies characterized above. Class 2 antibodies had the highest affinities of all the anti-Psl antibodies. FIG. 10A also shows a summary of cell attachment and OPK data experiments. FIG. 10B shows the relative binding affinities and OPK EC50 values of the Wap-004RAD (W4RAD) mutant as well as other W4 mutants prepared as described in Example 1.

Example 10: Binding of Polymyxin B (PMB)-mAb Conjugates to *P. aeruginosa* PAO1 Cells was Evaluated by FACS In this Example, PMB conjugated to an opsonic monoclonal antibody (mAb) that was capable of mediating bacterial clearance was evaluated to determine whether the conjugate would improve and/or expand mAb functionality, while also reducing the toxicity of PMB. CAM-003, a mAb targeting the *P. aeruginosa* Psl surface exopolysaccharide, which mediates potent opsonophagocytic killing (OPK) activity and protection in vivo, was selected for conjugate evaluation.

Figure 12:
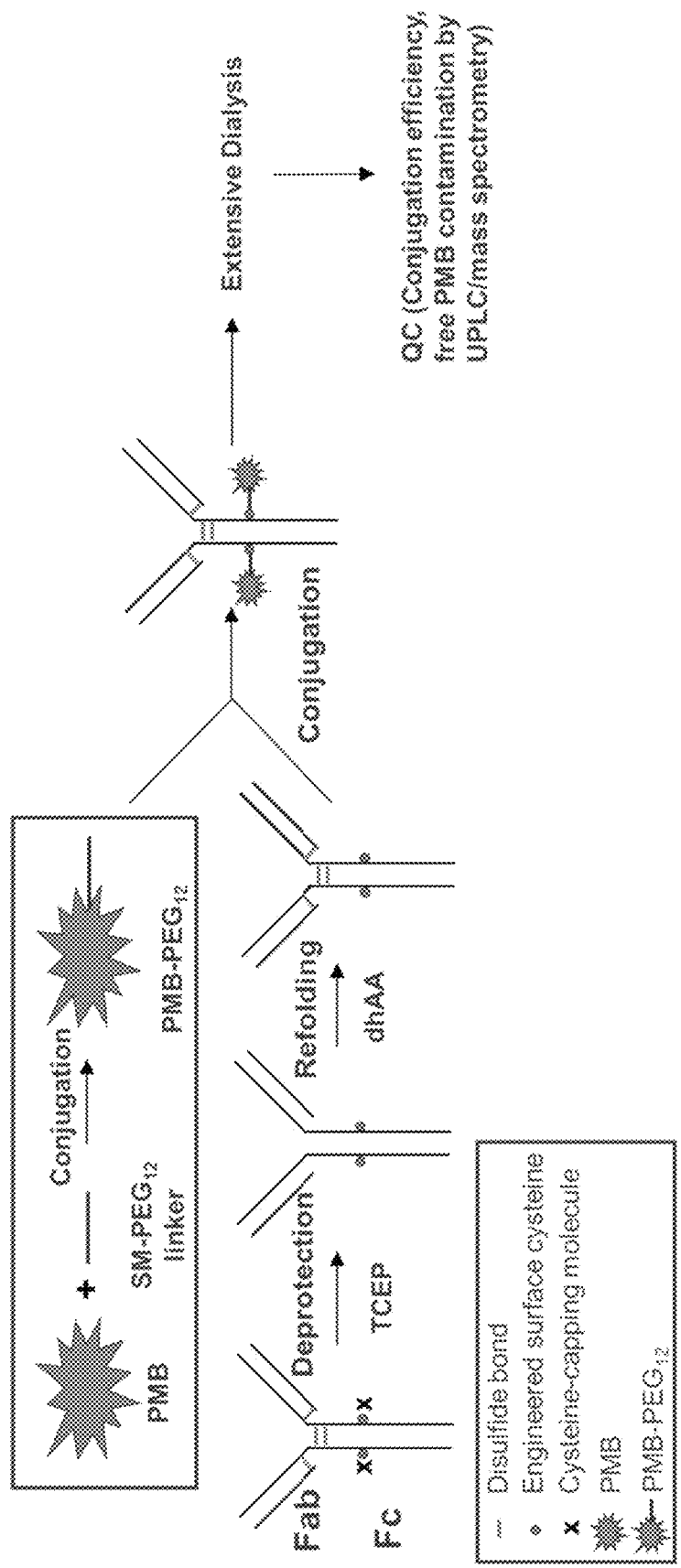

This example evaluates binding of various Polymyxin B (PMB)-mAbs conjugates to *P. aeruginosa* PAO1 cells. Using a two-step site-directed conjugation method (FIG. 12), Polymyxin B (PMB) was conjugated to the Cam-003 and A7 (hIgG1 control) mAb variants with either a single or double cysteine engineered into the Fc region. Cam-003 and A7 mAbs Fc variants were prepared using standard protocols as described in (Dimasi, N. et al., *J Mol Biol.* 393(3): 672-92 (2009)). The heterobifunctional SM(PEG)$_{12}$ linker (Pierce) was initially conjugated to one of the primary amines in PMB via the NHS group in the linker under conditions determined to favor conjugation of a single linker. Polymyxin B sulfate (Sigma) was dissolved in PBS pH 7.2 at 2 mg/ml and reacted with SM(PEG)$_{12}$ linker at a 4:1 PMB:linker ratio. The reaction was carried out at room temperature for 30 min and stopped with 50 mM glycine. The efficiency of SM(PEG)$_{12}$ linker conjugation to PMB was approximately 25%. Crude preparations of PMB-PEG$_{12}$ were then reacted with deprotected Fc cysteine mAb variants and conjugated via maleamide in the PEG$_{12}$ linker (see, e.g., WO 2011/005481 and WO 2009/092011). The PMB-mAb conjugates were purified by extensive dialysis. The conjugates were initially dialyzed in 3.3×PBS pH 7.2 with 0.7% CHAPS with four buffer exchanges, followed by dialysis in 1×PBS pH 7.2 with additional four buffer exchanges. Conjugation efficiency and levels free PMB-linker in the samples were determined by UPLC and mass spectrometry.

Figures 13A, 13B:
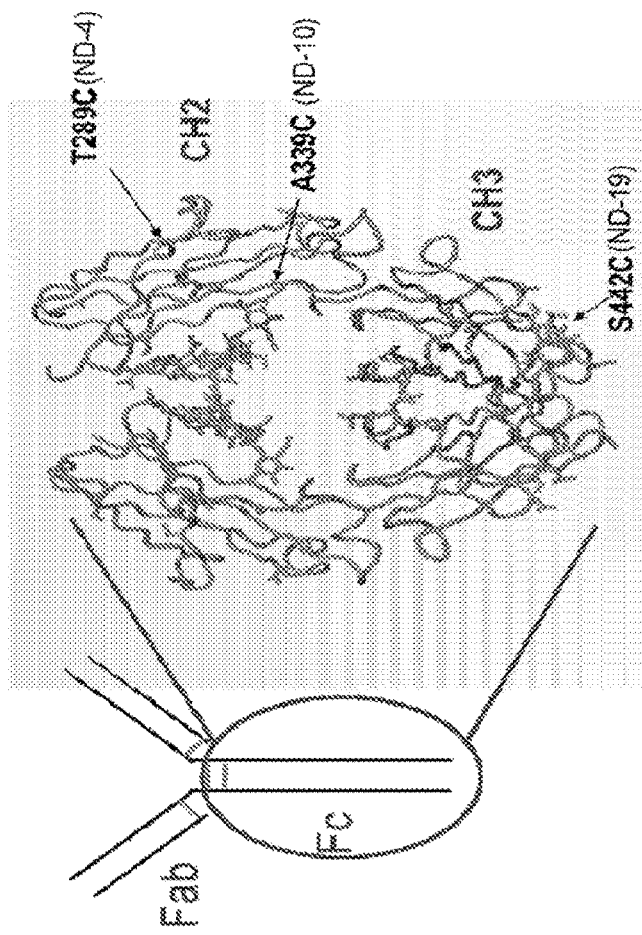
Figure 14A:
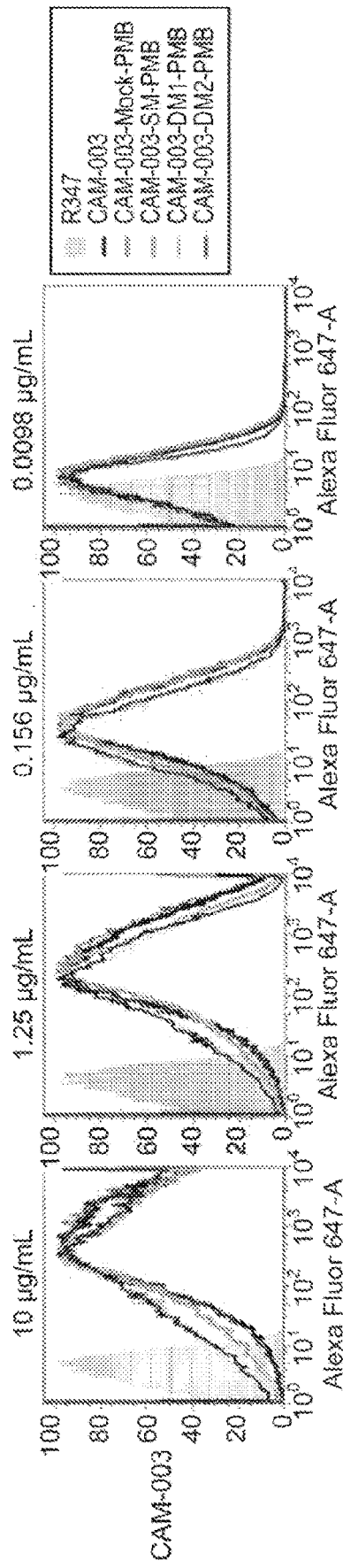
Figure 14B:
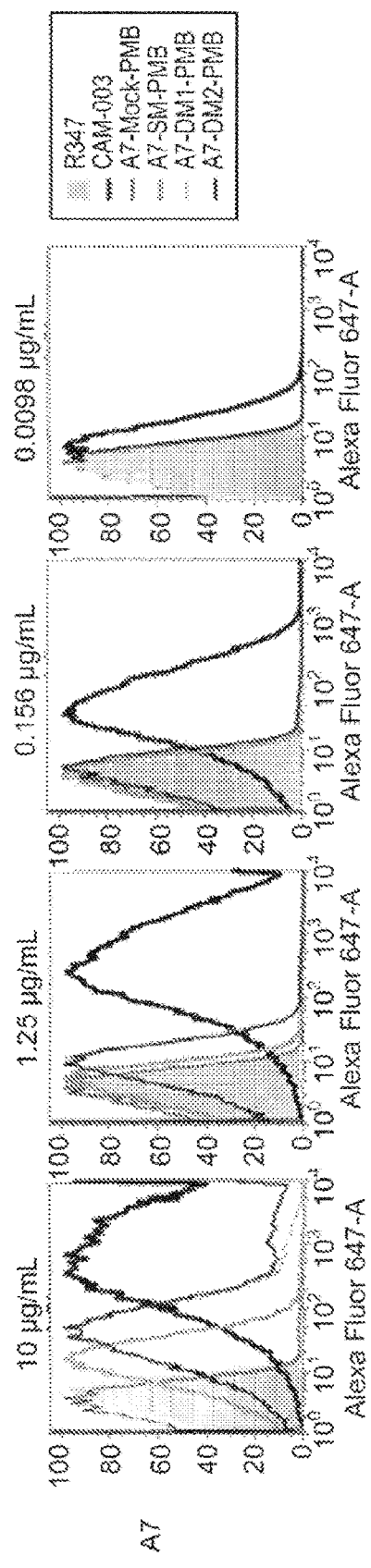

CAM-003 is specific for the *P. aeruginosa* Psl surface exopolysaccharide and mediates potent OPK activity and protection in multiple in vivo models. FIG. 13A shows Cam-003 and A7 Fc region mutated residues. SM (A339C), DM1 (T289C/A339C), DM2 (A339C/S442C). Conjugation efficiency of PMB-mAbs variants was determined by mass spectrometry analysis of heavy chains in purified conjugates. (see, e.g., WO 2011/005481 and WO 2009/092011). The overall conjugation efficiency was 75-85%. Purity of constructs was >95% relative to conjugated vs. free PMB-linker. FIG. 13B shows the average number of PMB in PMB-Cam-003 and PMB-A7 conjugates (double mutant 2 (DM2)>double mutant 1 (DM1)>single mutant (SM)). A7 conjugates exhibited greater conjugation efficiency compared to Cam-003 conjugates. Contamination with free PMB in the purified preparations was determined to be negligible. Binding of PMB-Cam-003 and PMB-A7 conjugates to *P. aeruginosa* PAO1 cells was evaluated by FACS. R347 was used as a negative control in all experiments. Samples were stained and analyzed as previously described in Example 1. No significant difference in binding of Cam-003 conjugates compared to unconjugated or mock-conjugated Cam-003 was observed (FIG. 14A). Binding of A7 control conjugates was proportional to the number of PMB molecules per conjugate (FIG. 14B). This analysis indicates that conjugation of PMB to Cam-003 does not significantly impact whole-cell binding and that conjugated PMB can mediate direct binding to cells, presumably by binding LPS.

Example 11: Evaluation of PMB-mAb Conjugates Promoting OPK of *P. aeruginosa*

This example describes two series of experiments evaluating the ability of PMB-mAb conjugates to promote OPK of *P. aeruginosa*. In the first experiments (FIGS. 15A-B), conjugate-mediated OPK activity by human HL-60 neutrophil cell line in the presence of rabbit complement was evaluated using *P. aeruginosa* strains expressing bacterial luciferase as described in Example 2. R347 was used as a negative control in these experiments. The CAM-003 conjugates retained potent OPK activity, although it diminished with increasing number of PMB per conjugate (SM>DM1>DM2) (FIG. 15A). The CAM-003 conjugates did not exhibit OPK activity against the ΔpslA *P. aeruginosa* strain which does not express the Psl target, indicating that mAb-mediated binding was required for killing (FIG. 15B). In the second series of experiments, reduction in luminescence following 2 h incubation relative to control lacking mAb was used to determine % killing. FIG. 18A shows that the CAM-003 conjugates retained OPK activity, although it diminished with increasing number of PMB per conjugate, particularly in DM and TM constructs (WT>SM>DM>TM). The CAM-003 conjugates did not exhibit OPK activity against the PAO! ΔpslA strain which does not express the Psl target (not shown). FIG. 18B shows that A7-PMB conjugates did not mediate OPK indicating that mAb-mediated binding was required for killing.

Example 12: Neutralization of *P. aeruginosa* LPS by PMB-mAb Conjugates

Figure 16B:
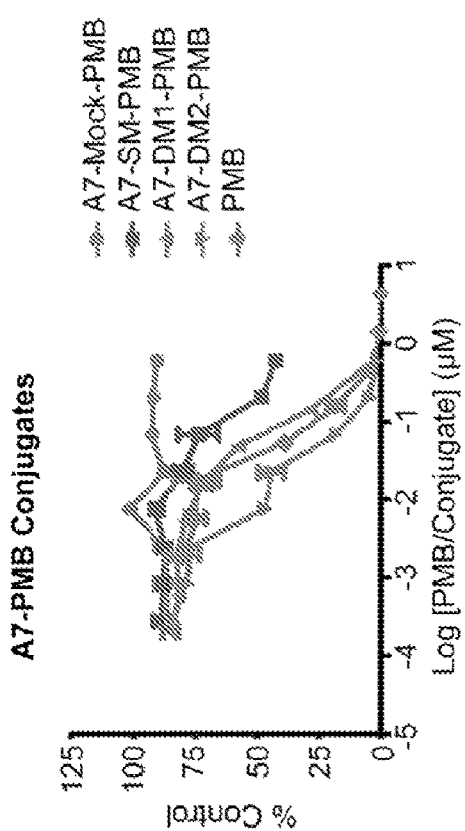
FIGS. 16A-16B show neutralization of *P. aeruginosa* LPS by PMB-mAb conjugates.
Figure 16A:
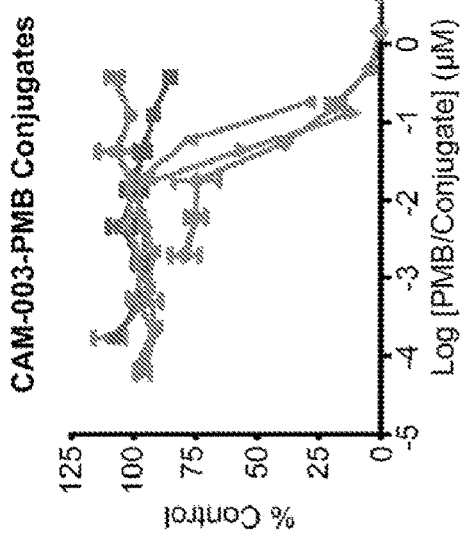

Neutralization of *P. aeruginosa* O10 LPS activity was evaluated by preincubating the PMB-mAb conjugates or PMB alone with LPS for 1 h, followed by stimulation of murine RAW 264.7 macrophages and quantification of TNF secretion. Final concentration of LPS was 2 ng/ml. TNF was quantified by the FACS-based BD™ Cytometric Bead Array (CBA) method (BD Biosciences) after 6 h stimulation. LPS neutralization was measured by a decrease in TNF production relative to the LPS maximal response. PMB-Cam-003 conjugates, but not mock-conjugated wild-type Cam-003 exhibited LPS neutralization. Efficiency of neutralization was directly proportional to the average number of PMB in the conjugate (DM2>DM1>SM) (FIG. 16A). PMB-A7 conjugates, but not mock-conjugated wild-type A7 exhibited LPS neutralization (FIG. 16B). A7 conjugates exhibited better neutralization than CAM-003 conjugates. A7 conjugates exhibited better neutralization than CAM-003 conjugates likely due to greater conjugation efficiency achieved with these molecules. Approximately 2 conjugated PMB molecules/mAb are required to neutralize the amount of LPS neutralized by a free PMB molecule.

Example 13: Evaluation of Cam-003-PMB Site-Directed Conjugates in Murine Models

The efficacy of Cam-003-PMB conjugates were evaluated in two types of murine models: 1) endotoxemia (LPS) challenge model, to determine the ability of the conjugates to neutralize and/or detoxify LPS in vivo; and 2) in *P. aeruginosa* sepsis model, to evaluate if Cam-003-PMB conjugates effect improved protection against bacterial challenge relative to the antibody alone through PMB-mediated LPS neutralization and/or clearance, in addition to the antibody-mediated bacterial clearance. Other *P. aeruginosa* challenge models can also be used to test the efficacy of Cam-003-PMB conjugates (see below).

A. Endotoxemia Model

It is well established that PMB can bind and neutralize LPS in vivo, and mediate protection against LPS challenge (Morrison, D C. et al. *J. Immunochemistry* 13(10):813-818 (1976), Drabick, J J. et al., *Antimicrob Agents Chemother.* 42(3):583-588 (1998)). In the endotoxemia model, Cam-003-PMB conjugates will be evaluated for their ability to protect animals from LPS challenge. Purified LPS from Gram-negative bacteria, including *P. aeruginosa* and *E. coli*, will be used to challenge mice at the established minimal lethal doses (LD100). As mice are relatively resistant to LPS, D-galactosamine may also be coadministered, as it greatly increases the sensitivity of mice to LPS to roughly that of humans (Galanos, C. et al., *Proc Natl Acad Sci USA.* 76(11):5939-5943 (1979)). Such models have been widely used for preclinical efficacy evaluation of LPS neutralizing molecules, including antibodies and polymyxin-protein conjugates (Bailat, S. et al., *Infect Immun.* 65(2):811-814 (1997), Birkenmeier, G. et al., *J Pharmacol Exp Ther.* 318(2):762-771 (2006), Drabick, J J. et al., *Antimicrob Agents Chemother.* 42(3):583-588 (1998)). Cam-003-PMB conjugates, control conjugates and unconjugated Cam-003 can be administered either therapeutically or prophylactically, and their ability to protect animals from LPS challenge can be evaluated. The extent of protection mediated by PMB conjugates can be correlated with levels of proinflammatory cytokines and chemokines measured in sera or plasma, including TNF, KC and IL-6.

B. *P. aeruginosa* Challenge Models

Several murine models of *P. aeruginosa* infection can be used to evaluate the ability of Cam-003-PMB conjugates to mediate protection. *P. aeruginosa* can be administered to mice intraperitoneally (sepsis model), intravenously (bacteremia model) or intranasally (pneumonia model) at the determined LD100 doses. These models have previously been used for preclinical efficacy studies of passive or active vaccines (Frank, D W. et al., *J Infect Dis.* 186(1):64-73. (2002), Secher, T. et al., *J Antimicrob Chemother.* 66(5): 1100-1109 (2011), Miyazaki, S. et al., *J Med Microbiol.* 43(3):169-175 (1995), Dunn, D L. et al., *Surgery* 96(2):440-446 (1984)).

As in the endotoxemia model, it may also be necessary to sensitize mice with D-galactosamine prior to bacterial challenge to overcome their innate resistance to LPS toxicity and to be able to evaluate the contribution of LPS neutralization and/or clearance to in vivo efficacy of the PMB conjugates. D-galactosamine has been demonstrated to reduce the LD100 of Gram-negative bacteria, likely by increasing sensitivity to LPS shed during infection (Bucklin, S E. et al., *J Infect Dis.* 172(6):1519-27 (1995)).

Cam-003-PMB conjugates, control conjugates and unconjugated Cam-003 can be administered either therapeutically or prophylactically. The ability of CAM-003 conjugates to effect increased protection over Cam-003 alone by neutralizing and/or clearing the bacterial LPS via the conjugated PMB moiety can be determined in survival studies. The efficacy of Cam-003-PMB conjugates in mediated bacterial clearance can also be evaluated by quantifying *P. aeruginosa* bacteria in serum and organs, including spleen, kidneys and lungs, following infection. Serum or plasma LPS levels can also be quantified to evaluate the extent of bacterial clearance and LPS clearance and/or neutralization by the Cam-003-PMB conjugates and compare it to those of unconjugated Cam-003 and control antibody-PMB conjugates.

C. Endotoxemia Model Data

In particular, C57Bl/6 mice (10 per group) were dosed i.p. with mAb or PMB-mAb conjugate 6 h prior to challenge with *P. aeruginosa* PAO10 LPS (Sigma) and D-galactosamine. PMB control was dosed i.p. 2 h prior to challenge at 0.2 mg/kg and typically provides 80-100% protection. Control mice dosed with unconjugated CAM-003 all died within 18 h. FIGS. 19A and B show that, at 45 mg/kg, DM and TM conjugates of CAM-003 and A7 provided 90-100% protection, while the SM conjugates were not protective.

TM conjugates were dosed at 45, 15 and 5 mg/kg. As shown in FIGS. 20A and B, loss of protective activity was more rapid with CAM-003-TM-PMB than with A7-TM-PMB, which retained 80% protection at 5 mg/kg. These differences suggest that unique structural features of a mAb can impact LPS neutralization activity of conjugated PMB, as previously seen in vitro.

D. Sepsis Model Data

C57Bl/6 mice (10 per group) were dosed with mAb or PMB-mAb conjugates i.p (10, 1 and 0.1 mg/kg) 6 h prior to i.p. challenge with $LD_{80-100}$ dose of *P. aeruginosa* strain 6294 (4E7 CFU). Data from two studies was combined in this analysis. Survival was monitored over 72 h. Combined results of two studies are shown in FIGS. 21A-C. Most control mice dosed with A7 or buffer died by 24 h. Unconjugated CAM-003 showed 50-90% protection. Protective activity appeared to be inversely correlated with dose. CAM-003-PMB conjugates conferred better protection than unconjugated mAb at the high dose of 10 mg/kg, suggesting that neutralization of LPS shed during infection contributed to survival. The A7-DM-PMB control conjugate exhibited 50% protective activity at 10 mg/kg, suggesting that LPS neutralization can provide a survival benefit. Conversely, the conjugates were less protective than CAM-003 at the low dose of 0.1 mg/kg, and protective activity correlated with in vitro OPK activity of the conjugates (WT>SM>DM>TM). Together the results indicate that conjugated PMB can confer added protective activity to an opsonic antibody by mediating neutralization of LPS and complement its bacterial clearance function.

High conjugation efficiency of PMB to engineered Fc cysteine residues was achieved using the SM-PEG$_{12}$ heterobifunctional linker. A series of site-directed PMB conjugates of CAM-003, a potent opsonic and protective mAb targeting *P. aeruginosa* Psl exopolysaccharide, was evaluated in vitro and in vivo. CAM-003-PMB conjugates retained in vitro OPK activity. However the OPK activity was impacted by the increase in the average number of PMB per mAb. DM and TM PMB-mAb conjugates conferred protection in mouse *P. aeruginosa* endotoxemia model, demonstrating that LPS neutralization function of PMB was conferred onto the mAb. CAM-003-PMB conjugates showed greater protective activity than unconjugated CAM-003 mAb in the *P. aeruginosa* sepsis model at high doses (10 mg/kg), and reduced activity at low dose (0.1 mg/kg). These data suggest that conjugated PMB can complement bacterial clearance mediated by the opsonic CAM-003 mAb and improve protection by LPS neutralization. The improvement in protective activity by CAM-003-PMB conjugates in the sepsis model is lost at lower doses, where levels of conjugated PMB are too low to neutralize LPS, and the primary mode of protection is likely mAb-mediated bacterial clearance. The loss of protective activity of the CAM-003-PMB conjugates at lower doses is consistent with the reduction in in vitro OPK activity as a result of PMB conjugation. These studies show that conjugated PMB on an opsonic mAb can confer LPS neutralization activity and result in increased protective activity in a systemic *P. aeruginosa* infection model. Optimization of conjugation sites to reduce the negative impact on OPK activity may further improve the protective activity of PMB conjugates relative to unconjugated opsonic mAb.

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated polynucleotide comprising a nucleic acid encoding an antibody or antigen-binding fragment thereof, wherein the antibody or antigen-binding fragment comprises a heavy chain variable region (VH), wherein the VH comprises a VH complementarity determining region-1 (VH-CDR1), VDCDR2, and VHCDR3 of amino acid sequences SEQ ID NO:47, 48, and 75, respectively, and the antibody or antigen-binding fragment comprises a light chain variable region (VL), wherein the VL comprises a VLCDR1, CDR2, and CDR3 of amino acids 50, 51, and 52, respectively.

2. A host cell comprising the polynucleotide of claim 1.

3. The polynucleotide of claim 1, wherein the antibody or fragment thereof comprises the VH and VL of SEQ ID NO:74 and SEQ ID NO:12, respectively.

4. A vector comprising the polynucleotide of claim 3.

5. A host cell comprising the polynucleotide of claim 3.

6. The polynucleotide of claim 3, wherein the antibody or antigen-binding fragment thereof is a scFv.

7. A vector comprising the polynucleotide of claim 6.

8. A host cell comprising the polynucleotide of claim 6.

9. The polynucleotide of claim 1 wherein the antibody or fragment thereof is a monoclonal antibody, a humanized antibody, a chimeric antibody, a human antibody, an Fab fragment, an Fab' fragment, an F(ab)2 fragment or a single chain Fv (scFv).

10. The polynucleotide of claim 9, wherein the antibody or antigen-binding fragment thereof is a scFv.

11. A vector comprising the polynucleotide of claim 10.

12. A host cell comprising the polynucleotide of claim 10.

13. A vector comprising the polynucleotide of claim 1.

14. The polynucleotide of claim 1, wherein the antibody or antigen-binding fragment thereof comprises a VH of SEQ ID NO:74.

15. A vector comprising the polynucleotide of claim 14.

16. The polynucleotide of claim 1, wherein the antibody or antigen-binding fragment thereof comprises a VH of SEQ ID NO:12.

17. A vector comprising the polynucleotide of claim 16.

18. An isolated polynucleotide comprising a nucleic acid encoding an antibody or antigen-binding fragment thereof that competitively inhibits *Pseudomonas* Psl binding by an antibody or antigen-binding fragment thereof comprising the heavy chain variable region (VH) and light chain variable region (VL) region of SEQ ID NO:74 and SEQ ID NO:12, respectively.

19. A vector comprising the polynucleotide of claim 18.

20. A host cell comprising the polynucleotide of claim 18.

21. A host cell comprising a polynucleotide encoding a VH comprising SEQ ID NO:74 and a polynucleotide encoding a VL comprising SEQ ID NO:12.

* * * * *

UNITED STATES PATENT AND TRADEMARK OFFICE
CERTIFICATE OF CORRECTION

PATENT NO. : 10,844,114 B2  
APPLICATION NO. : 16/400818  
DATED : November 24, 2020  
INVENTOR(S) : DiGiandomenico et al.

Page 1 of 1

It is certified that error appears in the above-identified patent and that said Letters Patent is hereby corrected as shown below:

In the Claims

In Claim 1, at Column 277, Line 54, change "VDCDR2" to --VHCDR2 --;
    At Column 277, Line 57, change "CDR2" to --VLCDR2--;
    At Column 277, Line 58, change "CDR3" to --VLCDR3--; and
    At Column 277, Line 58, change "amino acids 50, 51, and 52" to --amino acid sequences SEQ ID NO: 50, 51, and 52--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*